(12) United States Patent
Bucknor, Jr. et al.

(10) Patent No.: US 11,801,351 B2
(45) Date of Patent: Oct. 31, 2023

(54) CONCENTRATE ADAPTOR FOR VAPORIZER DEVICE

(71) Applicant: JUUL Labs, Inc., Washington, DC (US)

(72) Inventors: Franklyn Bucknor, Jr., San Francisco, CA (US); Philipe Manoux, Oakland, CA (US); Jace Martin, Alameda, CA (US); Alexander Ringrose, Oakland, CA (US); John Maxwell Ringrose, San Luis Obispo, CA (US); Daniel Sargent, San Francisco, CA (US); Ariel David Turgel, San Francisco, CA (US); Michael Chad Makay, Santa Clara, CA (US); Mark Edward Hearn, San Francisco, CA (US); Ricardo Verheul, Swifterbant (NL); Halle Ann Van De Hey, McKinney, TX (US)

(73) Assignee: JUUL Labs, Inc., Washington, DC (US)

( * ) Notice: Subject to any disclaimer, the term of this patent is extended or adjusted under 35 U.S.C. 154(b) by 356 days.

(21) Appl. No.: 16/932,548

(22) Filed: Jul. 17, 2020

(65) Prior Publication Data

US 2021/0016020 A1 Jan. 21, 2021

Related U.S. Application Data

(60) Provisional application No. 62/876,522, filed on Jul. 19, 2019, provisional application No. 62/876,527, (Continued)

(51) Int. Cl.
*A61M 11/04* (2006.01)
*A61M 15/00* (2006.01)
*A61M 39/10* (2006.01)

(52) U.S. Cl.
CPC ........ *A61M 11/041* (2013.01); *A61M 15/009* (2013.01); *A61M 39/10* (2013.01);
(Continued)

(58) Field of Classification Search
CPC ....... A24F 40/10; A24F 40/44; A61M 11/041; A61M 15/009; A61M 15/06; A61M 39/10;
(Continued)

(56) References Cited

U.S. PATENT DOCUMENTS

| 1,810,650 A | 6/1931 | Fay |
| 1,818,692 A | 8/1931 | Class |

(Continued)

FOREIGN PATENT DOCUMENTS

| CN | 101027091 A | 8/2007 |
| DE | 10212045 A1 | 10/2003 |

(Continued)

*Primary Examiner* — Colin W Stuart
*Assistant Examiner* — Matthew D Ziegler
(74) *Attorney, Agent, or Firm* — Mintz, Levin, Cohn, Ferris, Glovsky and Popeo, P.C.; Nicholas P. Mouton, Esq.

(57) ABSTRACT

A concentrate adaptor for a vaporizer device includes a reservoir and a base. The reservoir holds a concentrate. The reservoir is positioned within a vessel of the vaporizer device and is heated by a heating element of the vaporizer device to transfer heat to the concentrate, thereby generating an aerosol for inhalation by a user. The reservoir includes a sidewall surrounding an interior volume of the reservoir. The reservoir also includes a capillary structure positioned along the sidewall configured to direct the concentrate to the sidewall to be heated by the heating element.

20 Claims, 82 Drawing Sheets

Related U.S. Application Data filed on Jul. 19, 2019, provisional application No. 62/876,523, filed on Jul. 19, 2019, provisional application No. 62/899,626, filed on Sep. 12, 2019, provisional application No. 62/929,715, filed on Nov. 1, 2019, provisional application No. 62/962,887, filed on Jan. 17, 2020, provisional application No. 63/019,198, filed on May 1, 2020.

(52) U.S. Cl.
CPC ............... *A61M 2039/1077* (2013.01); *A61M 2205/582* (2013.01)

(58) Field of Classification Search
CPC .. A61M 2039/1077; A61M 2205/3606; A61M 2205/582
See application file for complete search history.

(56) References Cited

U.S. PATENT DOCUMENTS

| | | | |
|---|---|---|---|
| 1,900,956 A | 3/1933 | Somersall | |
| 2,235,879 A | 3/1941 | Hanks et al. | |
| 2,320,669 A | 6/1943 | Schmitt | |
| 2,443,417 A | 6/1948 | Duncan | |
| 2,522,718 A | 9/1950 | Huck | |
| 2,526,027 A | 10/1950 | Huck | |
| 2,533,794 A | 12/1950 | Hanks et al. | |
| 2,542,529 A | 2/1951 | Hunt | |
| 2,690,500 A | 9/1954 | Winberg et al. | |
| 2,847,547 A | 8/1958 | Gordon, Jr. | |
| 2,847,734 A | 8/1958 | Tauben | |
| 4,163,038 A | 7/1979 | Nishimura et al. | |
| 4,274,479 A * | 6/1981 | Eastman | F28D 15/046 29/890.032 |
| 4,571,485 A | 2/1986 | Spector | |
| 4,675,504 A | 6/1987 | Suhajda | |
| 6,285,829 B1 | 9/2001 | Smith | |
| 8,833,364 B2 * | 9/2014 | Buchberger | A61M 15/0021 128/200.14 |
| 9,623,205 B2 * | 4/2017 | Buchberger | A24F 40/44 |
| 10,463,077 B2 * | 11/2019 | Lau | F22B 1/284 |
| 10,617,834 B2 * | 4/2020 | Gould | A24F 40/50 |
| 2005/0253491 A1 | 11/2005 | Gilman | |
| 2007/0014549 A1 | 1/2007 | Demarest et al. | |
| 2008/0105257 A1 | 5/2008 | Klasek et al. | |
| 2009/0293892 A1 | 12/2009 | Williams et al. | |
| 2009/0302019 A1 | 12/2009 | Selenski et al. | |
| 2010/0236552 A1 | 9/2010 | Kwok et al. | |
| 2012/0255546 A1 | 10/2012 | Goetz et al. | |
| 2013/0039639 A1 | 2/2013 | Carney | |
| 2014/0133132 A1 | 5/2014 | Hsiao | |
| 2014/0133841 A1 | 5/2014 | Hsiao | |
| 2015/0101606 A1 | 4/2015 | White | |
| 2016/0015847 A1 | 1/2016 | Irvin et al. | |
| 2016/0287816 A1 | 10/2016 | Eksouzian | |
| 2016/0360790 A1 | 12/2016 | Calfee et al. | |
| 2017/0354186 A1 | 12/2017 | Johnson et al. | |
| 2017/0367402 A1 | 12/2017 | Lau et al. | |
| 2018/0043115 A1 | 2/2018 | Gould et al. | |
| 2018/0077967 A1 | 3/2018 | Hatton et al. | |
| 2018/0085551 A1 | 3/2018 | Krietzman | |
| 2019/0166913 A1 | 6/2019 | Trzecieski | |

FOREIGN PATENT DOCUMENTS

| | | |
|---|---|---|
| WO | WO-2007024130 A1 | 3/2007 |
| WO | WO-2014127446 A1 | 8/2014 |
| WO | WO-2016019353 A1 | 2/2016 |
| WO | WO-2017163046 A1 | 9/2017 |
| WO | WO-2018172765 A1 | 9/2018 |

* cited by examiner

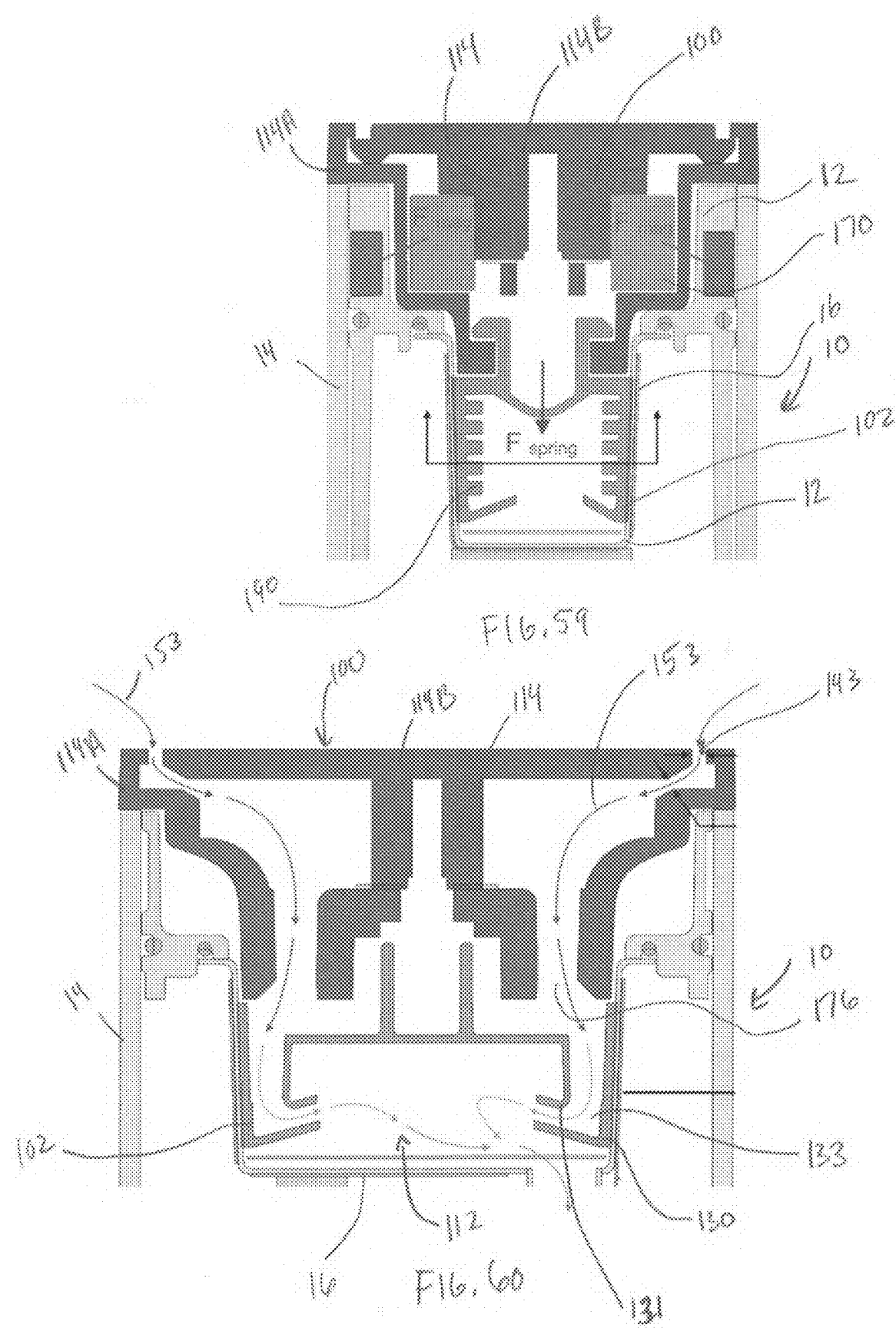

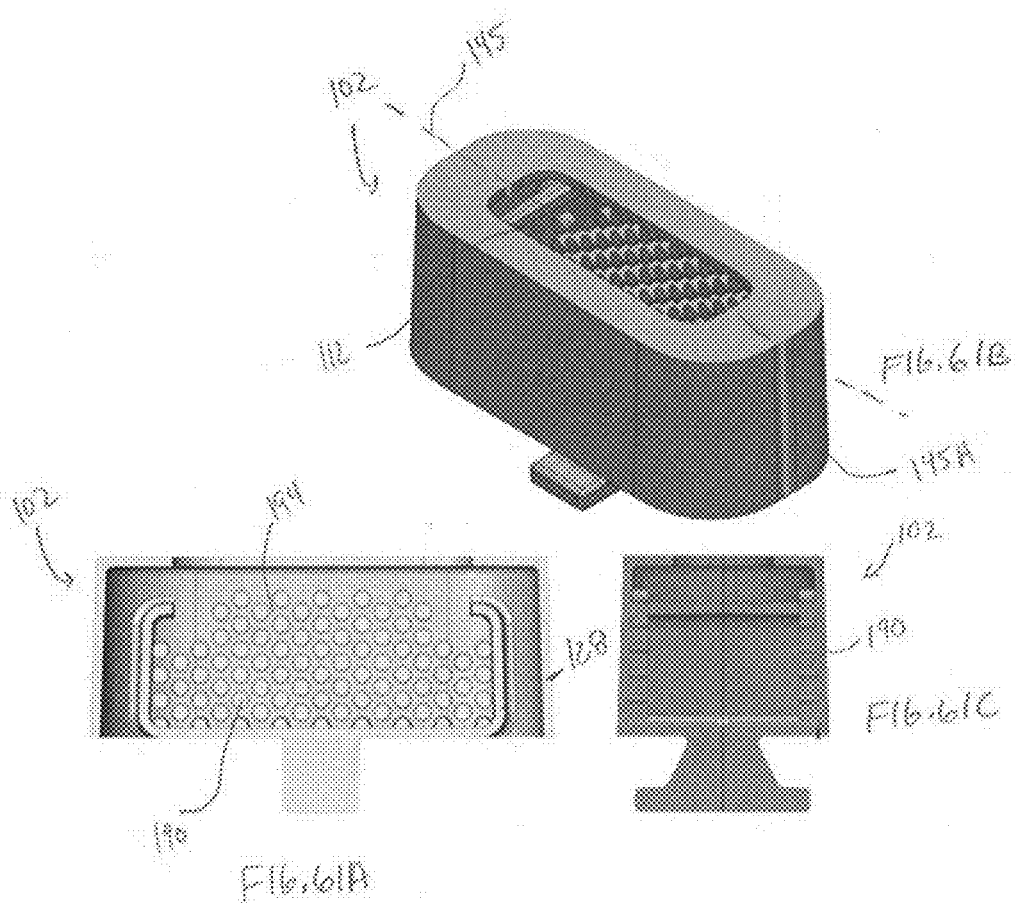

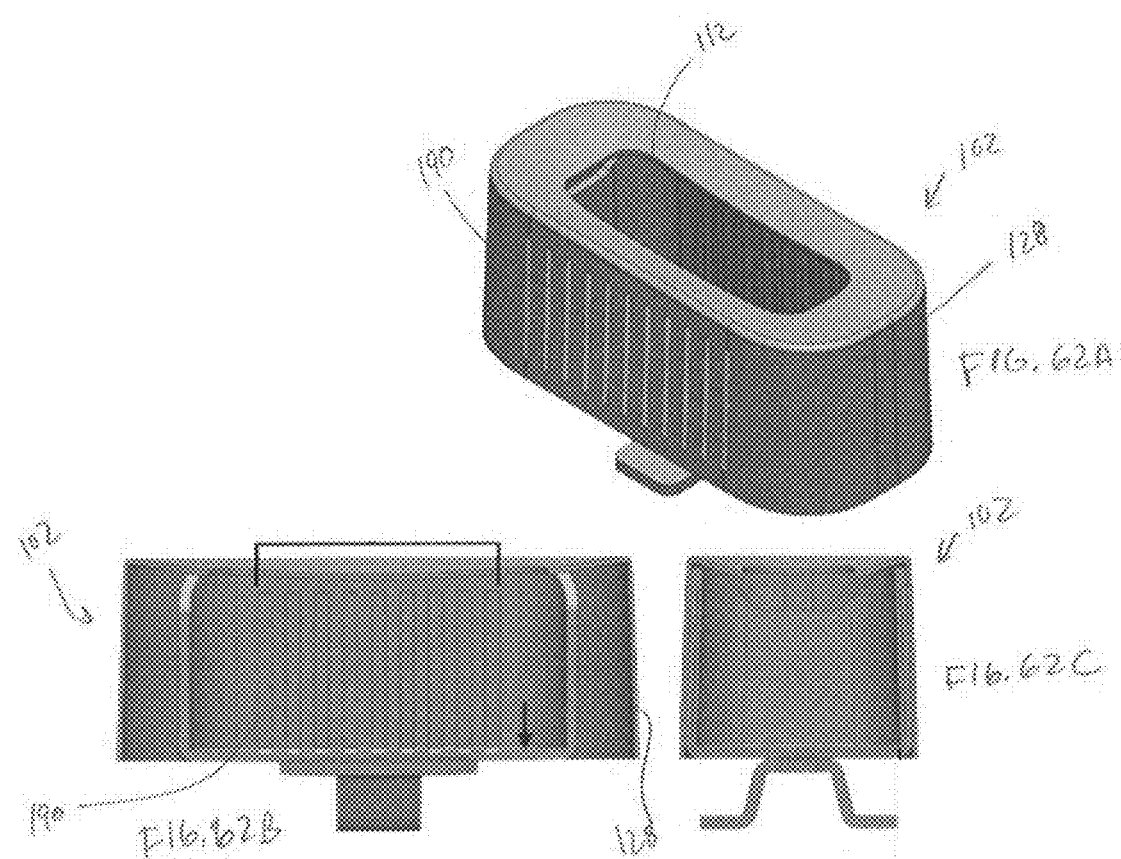

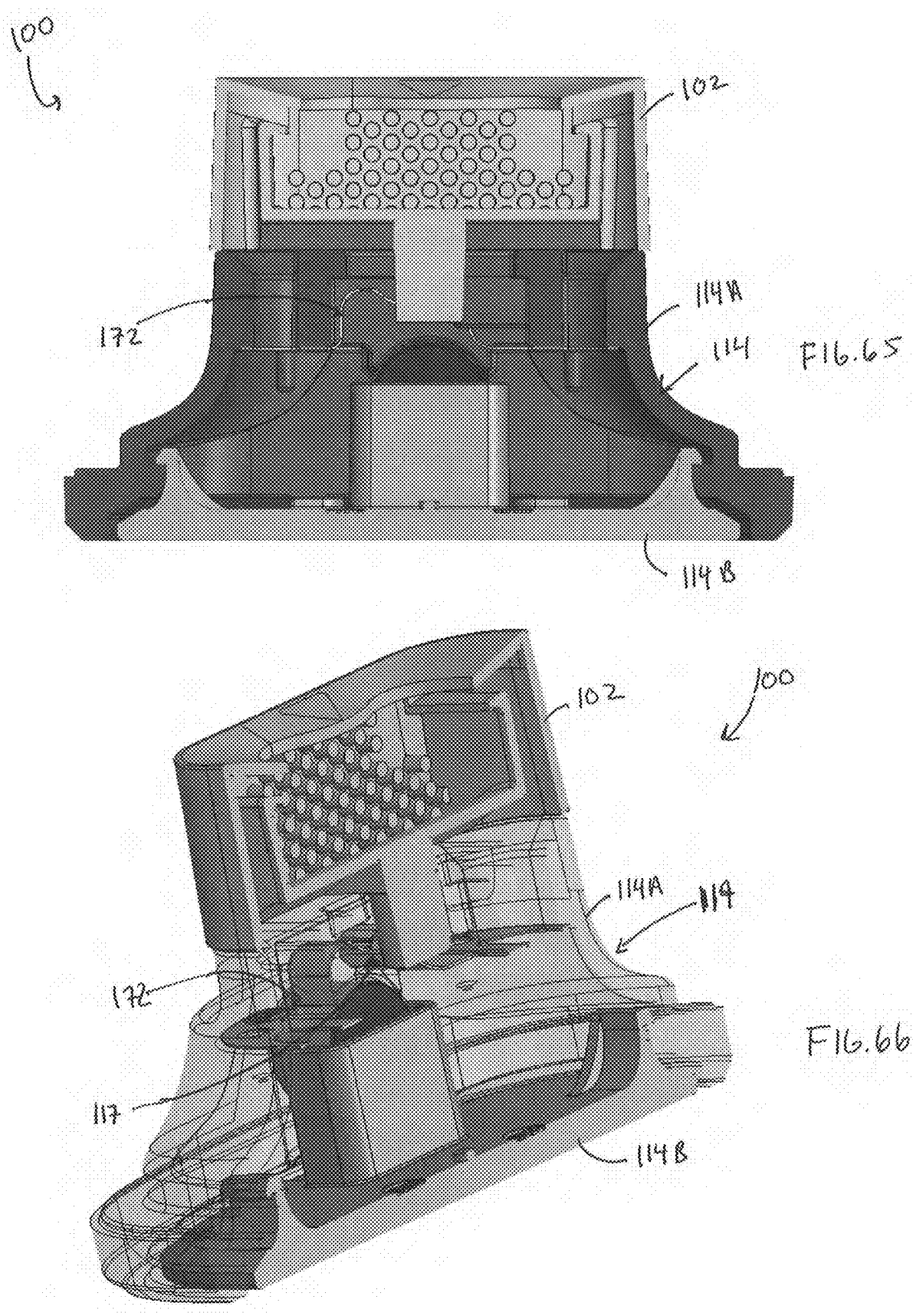

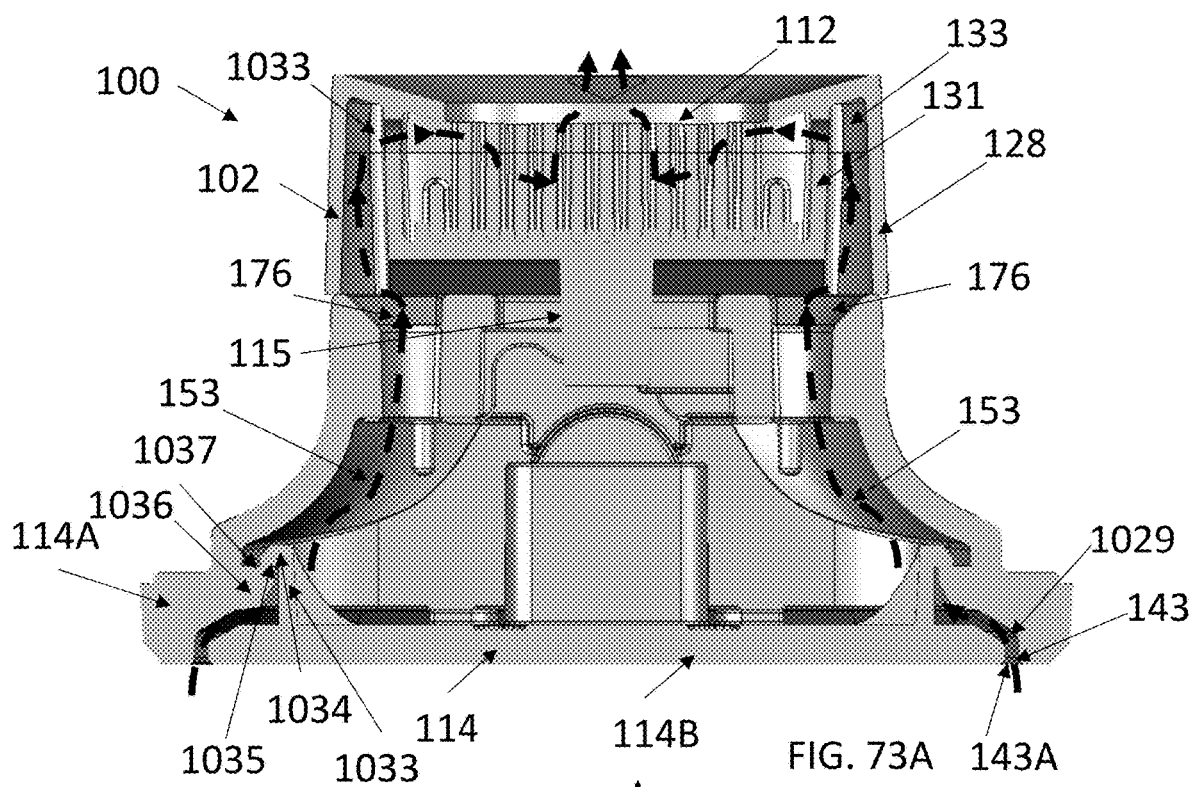
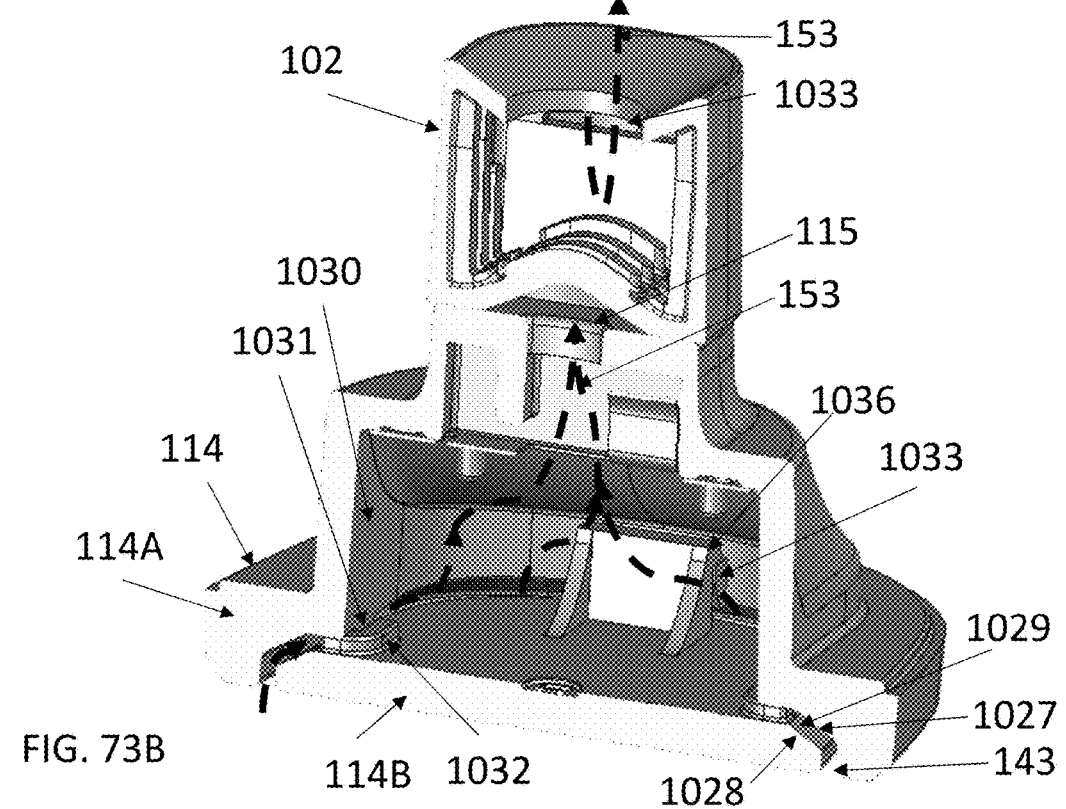

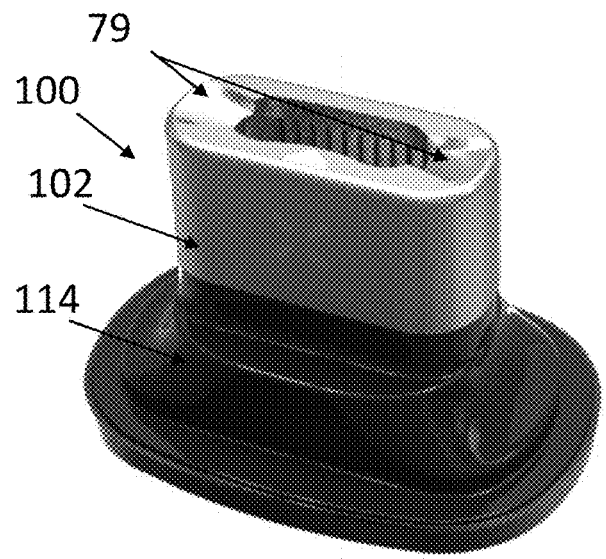
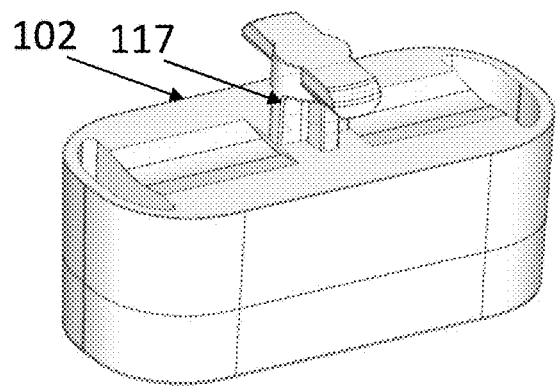
FIG. 81A FIG. 81B
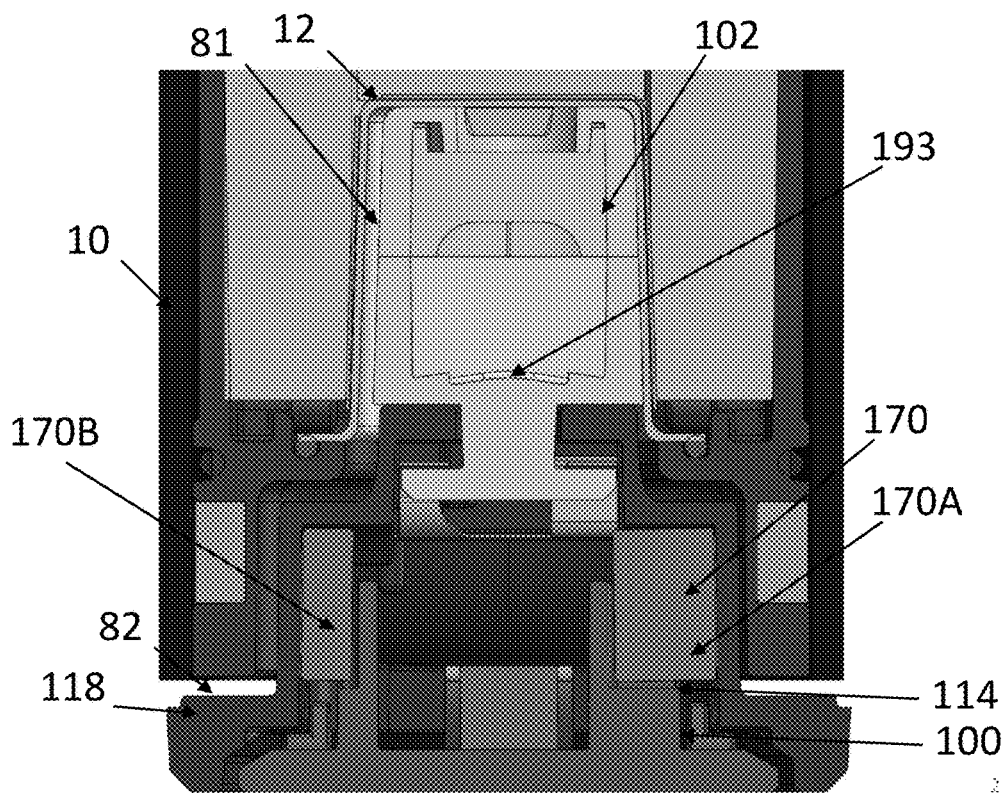
FIG. 81C

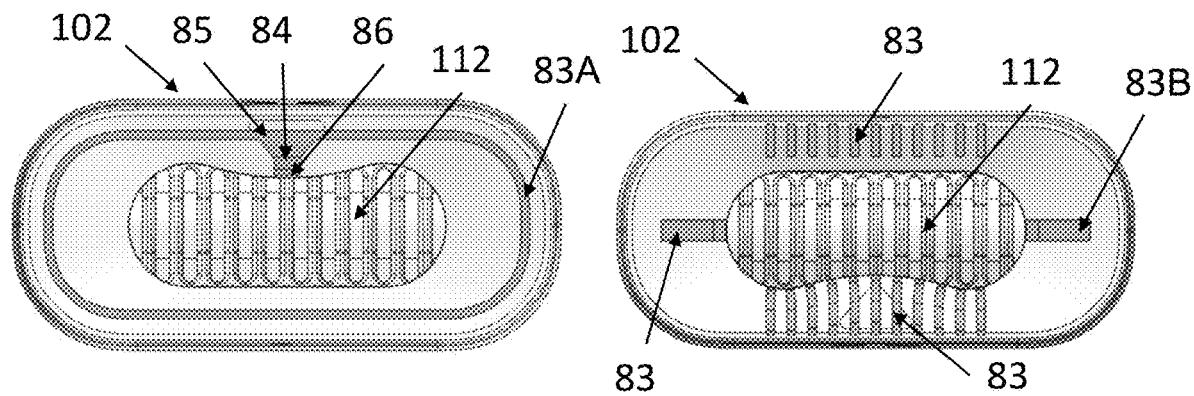
FIG. 83A
FIG. 83B
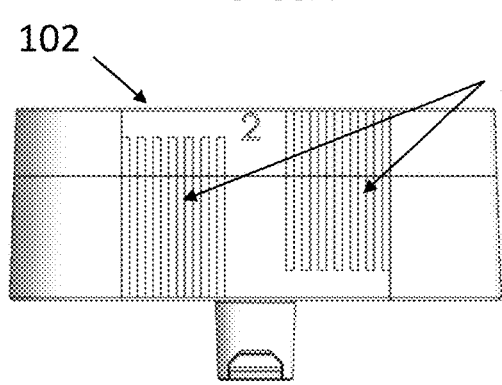
FIG. 83C
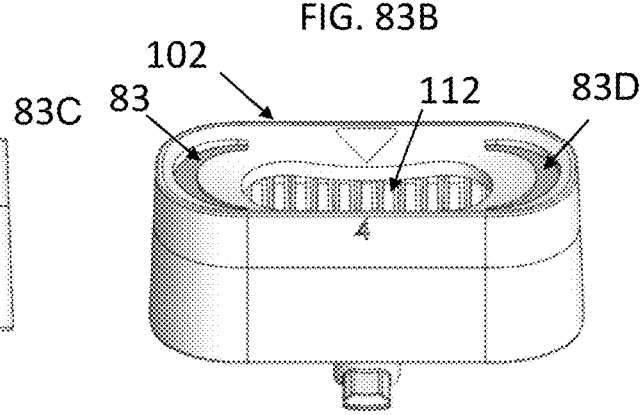
FIG. 83D
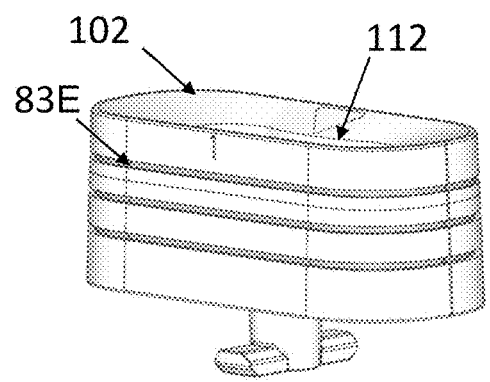
FIG. 83E
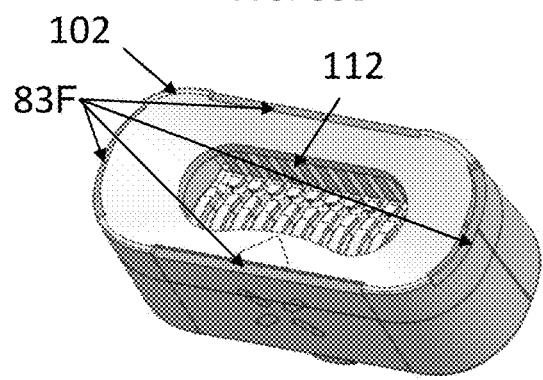
FIG. 83F

CONCENTRATE ADAPTOR FOR VAPORIZER DEVICE

CROSS-REFERENCE TO RELATED APPLICATIONS

The present application claims priority to U.S. Provisional Application No. 63/019,198, filed May 1, 2020, and titled "CONCENTRATE ADAPTOR FOR VAPORIZER DEVICE," U.S. Provisional Application No. 62/962,887, filed Jan. 17, 2020, and titled "CONCENTRATE ADAPTOR FOR VAPORIZER DEVICE," U.S. Provisional Application No. 62/929,715, filed Nov. 1, 2019, and titled "CONCENTRATE ADAPTOR FOR VAPORIZER DEVICE," U.S. Provisional Application No. 62/899,626, filed Sep. 12, 2019, and titled "CONCENTRATE ADAPTOR FOR VAPORIZER DEVICE," U.S. Provisional Application No. 62/876,523, filed Jul. 19, 2019, and titled "PERMANENT LID CONCENTRATE ADAPTOR FOR VAPORIZER DEVICE," U.S. Provisional Application No. 62/876,522, filed Jul. 19, 2019, and titled "GLASS CONCENTRATE ADAPTOR FOR VAPORIZER DEVICE," and U.S. Provisional Application No. 62/876,527, filed Jul. 19, 2019, and titled "CONCENTRATE ADAPTOR WITH INTEGRATED AIRFLOW PATH FOR VAPORIZER DEVICE," each of which are incorporated by reference herein in its entirety.

TECHNICAL FIELD

The current subject matter described herein relates generally to vaporizer devices, such as portable, personal vaporizer devices for generating and delivering an inhalable aerosol from one or more vaporizable materials, and more particularly relates to a concentrate adaptor for a vaporizer device.

BACKGROUND

Vaporizing devices, including electronic vaporizers or e-vaporizer devices, allow the delivery of vapor and aerosol containing one or more active ingredients by inhalation of the vapor and aerosol. Electronic vaporizer devices are gaining increasing popularity both for prescriptive medical use, in delivering medicaments, and for consumption of nicotine, tobacco, other liquid-based substances, and other plant-based smokeable materials, such as cannabis, including solid (e.g., loose-leaf or flower) materials, solid/liquid (e.g., suspensions, liquid-coated) materials, wax extracts, and prefilled pods (cartridges, wrapped containers, etc.) of such materials. Electronic vaporizer devices in particular may be portable, self-contained, and convenient for use.

SUMMARY

Aspects of the current subject matter relate to a concentrate adaptor for a vaporizer device.

According to some aspects, a concentrate adaptor for a vaporizer device includes a reservoir and a base. The reservoir may hold a concentrate. The reservoir may be positioned within a vessel of the vaporizer device and be heated by a heating element of the vaporizer device to transfer heat to the concentrate, thereby generating an aerosol for inhalation by a user. The reservoir may include a sidewall and a capillary structure. The sidewall may surround an interior volume of the reservoir. The capillary structure may be positioned along the sidewall configured to direct the concentrate to the sidewall to be heated by the heating element. The base may be coupled with the reservoir.

In some aspects, at least a portion of the base is positioned external to the vaporizer device.

In some aspects, the capillary structure includes one or more capillary channels formed across at least a portion of an interior of the sidewall. In some aspects, the one or more capillary channels extend in a first direction and a second direction that is perpendicular to the first direction. In some aspects, the one or more capillary channels are positioned along opposing portions of the interior of the sidewall. In some aspects, the one or more capillary channels are positioned along only a portion of the interior of the sidewall. In some aspects, the capillary structure further includes one or more capillary channels formed along a base wall of the reservoir. In some aspects, at least one capillary channel extends from a bottom of the interior of the sidewall to a top of the interior of the sidewall. In some aspects, at least one capillary channel extends from a bottom of the interior of the sidewall towards the top of the interior of the sidewall. In some aspects, the one or more capillary channels are formed as recesses between adjacent elongated bars and/or cylinders.

In some aspects, the capillary structure includes one or more capillary channels positioned on opposing long sides of the reservoir. In some aspects, the capillary structure does not include one or more capillary channels positioned on opposing short sides of the reservoir. In some aspects, the one or more capillary channels formed along the base wall are positioned offset from the one or more capillary channels formed along the interior of the sidewall. In some aspects, the one or more capillary channels formed along the base wall each comprise an equal depth. In some aspects, the one or more capillary channels formed along the base wall comprise varying depths.

In some aspects, the capillary structure includes one or more capillary openings. The capillary structure may be positioned within an interior volume of the reservoir.

In some aspects, the base and the reservoir are coupled via a quarter-turn mechanism.

In some aspects, the sidewall includes a first sidewall, a second sidewall opposing the first sidewall, a third sidewall joining the first sidewall to the second sidewall, and a fourth sidewall opposing the third sidewall and joining the first sidewall to the second sidewall. The first sidewall and the second sidewall may be longer than the third sidewall and the fourth sidewall. In some aspects, the reservoir further includes a connection feature. The base may include a base opening that receives the connection feature. Turning the reservoir relative to the base when the connection feature is positioned within the base opening may secure the reservoir to the base. In some aspects, the reservoir is secured to the base when the reservoir is moved from a first position to a second position. In the first position, the first sidewall and the second sidewall of the reservoir may be positioned approximately perpendicular to long sides of the base and the connection feature is positioned approximately perpendicular to the first sidewall and the second sidewall. In the second position, the first sidewall and the second sidewall of the reservoir may be positioned approximately parallel to the long sides of the base and the connection feature is positioned approximately perpendicular to the long sides of the base.

In some aspects, the base includes a base floor and a base housing. The base floor may include an outer base surface exposed external to the concentrate adaptor. The base housing may surround at least a portion of the base floor. In some aspects, the base floor includes a base floor connector. The base housing may include a slot. The base floor connector may be positioned within the slot to secure the base housing to the base floor.

In some aspects, the base housing includes an outer housing surface. The outer base surface may be spaced apart from the outer housing surface to define an inlet. The inlet may allow air to flow into the concentrate adaptor through the inlet.

In some aspects, the concentrate adaptor may also include an airflow path. The airflow path may extend between the base and the reservoir. The airflow path may be positioned entirely within the reservoir and the base of the concentrate adaptor between an inlet of the base and an outlet of the reservoir. The airflow path may be sealed within an interior of the concentrate adaptor. The airflow path may extend between the base and the reservoir. The airflow path may extend through an external opening into the base, out of the base, and into a reservoir opening in the reservoir.

In some aspects, the concentrate adaptor also includes a retention member. The retention member may provide tactile feedback to a user when the reservoir is coupled to the base. In some aspects, the retention member may provide a force that pulls the reservoir towards the base to form a seal between the reservoir and the base.

In some aspects, the reservoir includes a reservoir top and a reservoir base, and the capillary structure is positioned on the reservoir base.

In some aspects, the reservoir comprises a reservoir top and a reservoir base. A first portion of the capillary structure may be positioned on the reservoir base, and a second portion of the capillary structure may be positioned on the reservoir top.

In some aspects, a vaporizer device may include a housing with a vessel, a heating element, and a concentrate adaptor.

In some aspects, a method of vaporizing a concentrate held within a concentrate adaptor coupled to a vaporizer device may include heating at least a portion of the concentrate adaptor. The portion of the concentrate adaptor may be positioned within the vaporizer device. The portion of the concentrate adaptor may include a capillary structure. The capillary structure may cause at least a portion of the concentrate to flow towards a sidewall of the concentrate adaptor.

In some aspects, the method also includes inserting the concentrate into the concentrate adaptor.

In some aspects, the method also includes assembling the concentrate adaptor. The assembling may include coupling a reservoir to a base.

In some aspects, the coupling includes inserting a portion of the reservoir into an opening in the base, and turning the reservoir with respect to the base by 90 degrees. In some aspects, the method also includes causing tactile feedback when the concentrate adaptor is assembled.

In some aspects, the method also includes turning the reservoir relative to the base when the connection feature is positioned within the base opening is configured to secure the reservoir to the base.

In some aspects, the turning comprises moving the reservoir from a first position to a second position. In the first position, the first sidewall and the second sidewall of the reservoir are positioned approximately perpendicular to long sides of the base and the connection feature is positioned approximately perpendicular to the first sidewall and the second sidewall. In the second position, the first sidewall and the second sidewall of the reservoir are positioned approximately parallel to the long sides of the base and the connection feature is positioned approximately perpendicular to the long sides of the base.

In some aspects, the method also includes coupling the concentrate adaptor to the vaporizer device.

In some aspects, the method also includes activating the vaporizer device. The activating may include one or more of inhaling on a mouthpiece of the vaporizer device and causing power to be supplied to the vaporizer device.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings:

FIG. 59 illustrates an example airflow path in a concentrate adaptor consistent with implementations of the current subject matter;

FIG. 60 illustrates an example airflow path in a concentrate adaptor consistent with implementations of the current subject matter;

FIGS. 61A-61C illustrate an example reservoir of a concentrate adaptor consistent with implementations of the current subject matter;

FIGS. 62A-62C illustrate an example reservoir of a concentrate adaptor consistent with implementations of the current subject matter;

FIG. 65 illustrates a side cross-sectional view of a concentrate adaptor consistent with implementations of the current subject matter;

FIG. 66 illustrates a perspective cross-sectional view of a concentrate adaptor consistent with implementations of the current subject matter;

FIGS. 67-71 illustrate an example reservoir of a concentrate adaptor consistent with implementations of the current subject matter;

FIGS. 72-78 illustrate an example reservoir of a concentrate adaptor consistent with implementations of the current subject matter;

FIGS. 81A-81C illustrate an example concentrate adaptor and vaporizer device consistent with implementations of the current subject matter;

FIGS. 83A-83F illustrate an example reservoir of a concentrate adaptor consistent with implementations of the current subject matter;

DETAILED DESCRIPTION

Figure 1:
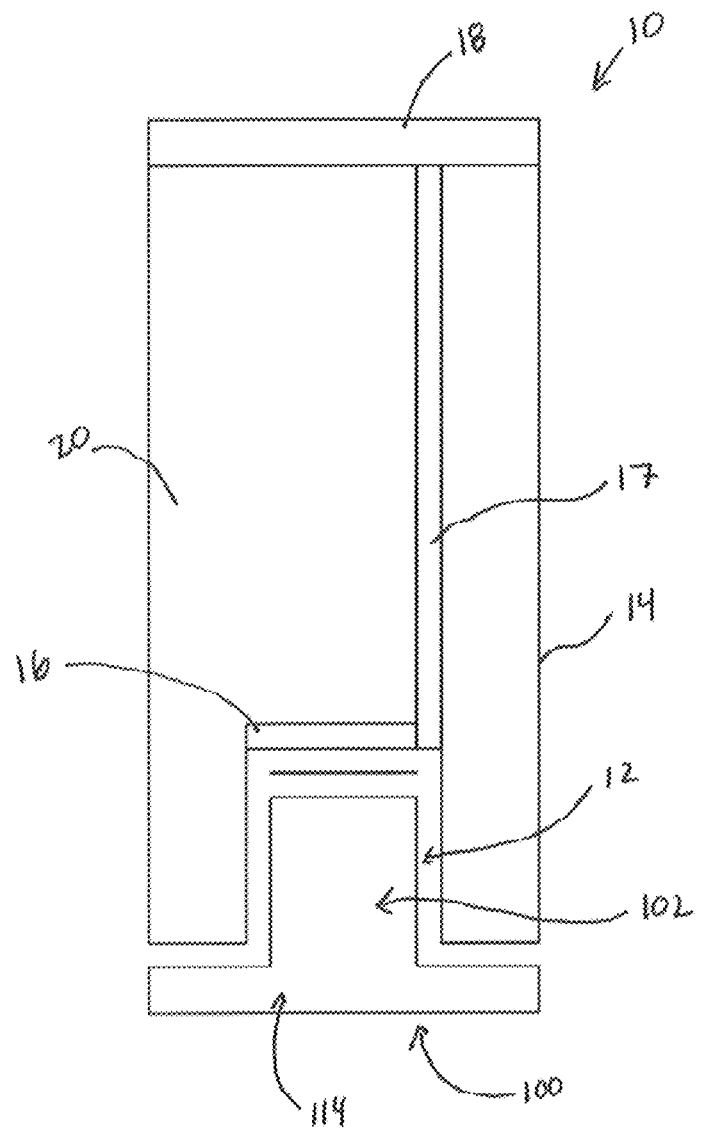
FIG. 1 schematically illustrates an example vaporizer device consistent with implementations of the current subject matter.

The following descriptions are meant to be exemplary, and aspects related to the concentrate adaptor consistent with the current subject matter are not limited to the example vaporizer devices described herein.

Implementations of the current subject matter include devices relating to vaporizing of one or more materials for inhalation by a user. The term "vaporizer" may be used generically in the following description and may refer to a vaporizer device, such as an electronic vaporizer. Vaporizers consistent with the current subject matter may be referred to by various terms such as inhalable aerosol devices, aerosolizers, vaporization devices, electronic vaping devices, electronic vaporizers, vape pens, etc. Examples of vaporizers consistent with implementations of the current subject matter include electronic vaporizers, electronic cigarettes, e-cigarettes, or the like. In general, such vaporizers are often portable, hand-held devices that heat a vaporizable material to provide an inhalable dose of the material. The vaporizer may include a heater configured to heat a vaporizable material which results in the production of one or more gas-phase components of the vaporizable material. A vaporizable material may include liquid and/or oil-type plant materials, or a semi-solid like a wax, or plant material such as leaves or flowers, either raw or processed. The gas-phase components of the vaporizable material may condense after being vaporized such that an aerosol is formed in a flowing air stream that is deliverable for inhalation by a user. The vaporizers may, in some implementations of the current subject matter, be particularly adapted for use with an oil-based vaporizable material, such as cannabis-derived oils although other types of vaporizable materials may be used as well.

Aspects of the current subject matter relate to a vaporizer device that vaporizes concentrates (e.g., cannabis concentrates including wax, shatter, budder, butane hash oil, and the like) contained or otherwise provided in the concentrate adaptor. The concentrate adaptor may include one or more capillary structures. The capillary structure may be integrally formed in the concentrate adaptor and/or may be coupled to the concentrate adaptor. The capillary structure may be positioned within the concentrate adaptor. For example, the capillary structure may be positioned within the concentrate adaptor, along all and/or a portion of interior side walls of the concentrate adaptor. The capillary structure may include one or more capillary openings and/or capillary channels that may be formed as recesses between various geometric configurations, bars, cylinders, or shapes, and the recesses themselves may have various geometric configurations or shapes. For example, the capillary openings and/or capillary channels may be formed between mostly-vertically extending bars or cylinders with varying profiles that extend from or near a top end of the capillary structure to or near a bottom end of the capillary structure, formed between various shapes that are formed on the sidewalls and/or base walls of the capillary structure and/or the like. As another example, two or more geometric configurations or shapes may be combined to form the capillary channels and/or capillary openings of the capillary structure. Vertically and horizontally oriented capillary channels and/or capillary openings allow for the concentrate to flow in various directions, providing for improved heating performance.

The capillary openings and/or capillary channels serve to guide the concentrate upward, inwards, outwards, and/or along or near the sidewalls of the reservoir. This provides for the concentrate being nearer to the source of heat (e.g., the heating element) when the reservoir is contained within the vessel of the vaporizer device (thereby maximizing the ratio of heat applied per unit volume of the concentrate, resulting in faster vaporization). This may additionally and/or alternatively provide for the concentrate to be autonomously distributed as the concentrate adaptor is heated, the distribution being independent from an initial placement of the concentrate. Moreover, the capillary openings and/or capillary channels help to retain the concentrate and prevent or reduce leakage. Additionally, the capillary openings and/or capillary channels can be designed to contain or accommodate a known volume, which influences guidelines related to filling for the user.

For example, as the vaporizable material (e.g., the concentrate) is heated, the vaporizable material may liquefy. The liquefied vaporizable material may be drawn to the capillary channels and/or capillary openings due to, for example, capillary action caused by adjacent shapes formed on the sidewalls of the capillary structure. The adjacent structures (e.g., shapes, bars, and/or the like) formed on the sidewalls of the capillary structure may allow fluid, such as the liquefied vaporizable material, to be held between and/or drawn into the space between the adjacent shapes, bars, and/or the like in various orientations. For example, the adjacent structures can be desirably spaced to allow for fluid (e.g., vaporizable material) to be transported from and/or drawn from a center or other portion of the reservoir of the concentrate adaptor to the capillary structure (in which the fluid is heated and/or vaporized to generate an aerosol), for example, via capillary action.

The size (e.g., length, width, etc.) of the space between adjacent structures of the capillary structure can be desirably narrow to maintain strong and/or sufficient capillary forces to draw and/or otherwise retain the fluid between the structures. Example widths and/or depths of adjacent structures (e.g., capillary channels) formed within the capillary structure are described with respect to FIGS. 67-78, but may be applicable to the various examples of the concentrate adaptor described herein. For example, the size of the space may control the rate at which the fluid is drawn within the space. In some implementations, the size of the space and/or the shape and/or size of the structures of the capillary structure can be desirably selected and/or sized to limit or prevent the vaporizable material from draining into or out of the capillary structure too quickly, and/or secure the vaporizable material within the capillary structure. In some implementations, the size of the space and/or the shape and/or size of the structures of the capillary structure can be desirably selected and/or sized to allow the space to hold a sufficient amount of vaporizable material.

Thus, the capillary structure (and concentrate adaptor) described herein consistent with implementations of the current subject matter may efficiently control an amount of vaporizable material heated and vaporized by the vaporizer device. The capillary structure may also help to limit and/or prevent leaking of the vaporizable material out of the capillary structure.

FIG. 1 schematically illustrates an example of a vaporizer device 10, consistent with implementations of the current subject matter. The vaporizer device 10 includes a vessel 12 contained within a housing 14, and further includes a heating element 16 that is configured to elevate a temperature within the vessel 12 to a level and/or range that is suitable for vaporizing concentrates. The vessel 12 may be positioned within a cavity of the housing 14 of the vaporizer device 10.

As shown in FIG. 1, the vaporizer device 10 may include or be coupled with a concentrate adaptor 100. The concentrate adaptor 100 includes a reservoir 102 that holds one or more portions of a concentrate. The reservoir 102 may include one or more materials, such as stainless steel, aluminum, glass, ceramic, titanium, copper, diamond-like carbon, and/or a conductive metal or a combination thereof. The reservoir 102 may also include a plating material that coats the material of the reservoir 102.

The concentrate adaptor 100 further includes a base 114 configured to accept or connect to the reservoir 102. The reservoir 102 may be removable coupled to the base 114. In some embodiments, however, the reservoir 102 may be permanently coupled to and/or integrally formed with the base 114, such as via over molding. When the reservoir 102 of the concentrate adaptor 100 is fitted within the vessel 12, the base 114 closes and/or fits over at least a portion of an open end of the housing 14 of the vaporizer device that includes the vessel 12, forming an air chamber. When the heating element 16 is activated, the vaporizer device 10 heats and vaporizes the concentrate when the reservoir 102 is deposited or otherwise placed within the vessel 12. Heat transfer occurs between the vessel 12 and the reservoir 102 and the concentrate contained therein. For example, upon contact with the heated interior surface of the vessel 12, the concentrate may rapidly vaporize and mix with air in the air chamber to form an aerosol. The aerosol travels through an air path 17 through the housing 14 and exits from the vaporizer device through a mouthpiece 18. The mouthpiece 18 is configured to enable a user to draw, for example through inhalation, the aerosol from the vaporizer device. The vaporizer device 10 may have an elongated cylindrical shape, with the vessel 12 at a distal end of the vaporizer device 10 and the mouthpiece 18 at a proximal end of the vaporizer device 10, the proximal end opposite the distal end.

The concentrate adaptor 100 includes a plurality of apertures configured to allow the passage of air. For example, the reservoir 102 and/or the base 114 may include one or more first apertures configured to allow air to exit the reservoir 102. The reservoir 102 and/or the base 114 may include one or more second apertures configured to allow air to enter into the reservoir 102 from, for example, outside of the vaporizer device 10. A user inhaling from the mouthpiece 18 of the vaporizer device 10 causes an intake of air into the reservoir 102. The incoming air mixes with the vapor generated by the vaporization of the contents of the reservoir 102 to form an aerosol. The resulting air flow carries the aerosol out of the reservoir 102 through the one or more first apertures. The aerosol travels through the air path 17 to the mouthpiece 18 where the aerosol is delivered to the user.

The base 114 and/or housing 14 may include one or more mechanisms, for example, snaps, latches, grooves, threading, magnets, clips, quick connect, sliding mechanisms, quarter turn release, friction fit, and the like, configured to position and/or secure the base 114 against the housing 14.

In some implementations, the reservoir 102 includes sidewalls having opposing first and second sides 119A, 119B, which are joined by opposing third and fourth sides 119C, 119D (see for example, FIGS. 36-42). At least the first and second sides 119A, 119B are approximately parallel to one another. The first and second sides 119A, 119B may be longer than the third and fourth sides 119C, 119D. In some implementations, the first and second sides 119A, 119B of the reservoir 102 may have a length of approximately 18 mm. In some implementations, the length of the first and second sides 119A, 119B ranges from approximately 16.0 mm to 17.0 mm, 17.0 mm to 18.0 mm, 18.0 mm to 19.0 mm, and/or other ranges therebetween. In some implementations, the third and fourth sides 119C, 119D of the reservoir 102 may have a length of approximately 8 mm. In some implementations, the length of the third and fourth sides 119C, 119D ranges from approximately 6.0 mm to 7.0 mm, 7.0 mm to 8.0 mm, 8.0 mm to 9.0 mm, and/or other ranges therebetween. The reservoir 102 may be desirably shaped to fit within a corresponding opening in the vaporizer device 10.

An outer shell 20 (which may include all or a portion of the housing 14) or cover of the vaporizer device 10 may be made of various types of materials, including for example aluminum (e.g., AL6063, AL6061), stainless steel, glass, ceramic, titanium, plastic (e.g., Acrylonitrile Butadiene Styrene (ABS), Nylon, Polycarbonate (PC), Polyether Sulfone (PESU), and the like), fiberglass, carbon fiber, and any hard, durable material.

Referring to FIG. 2-FIG. 17, aspects of the concentrate adaptor 100 consistent with implementations of the current subject matter are illustrated.

As described, the concentrate adaptor 100 includes the reservoir 102 and the base 114. An exterior surface of the reservoir 102 may conform to dimensions, shapes, and/or contours of an interior surface of the vessel 12 in which the reservoir 102 fits. In some implementations, contact between the reservoir 102 and the vessel 12 may be maximized to increase heat transfer therebetween.

Figure 2:
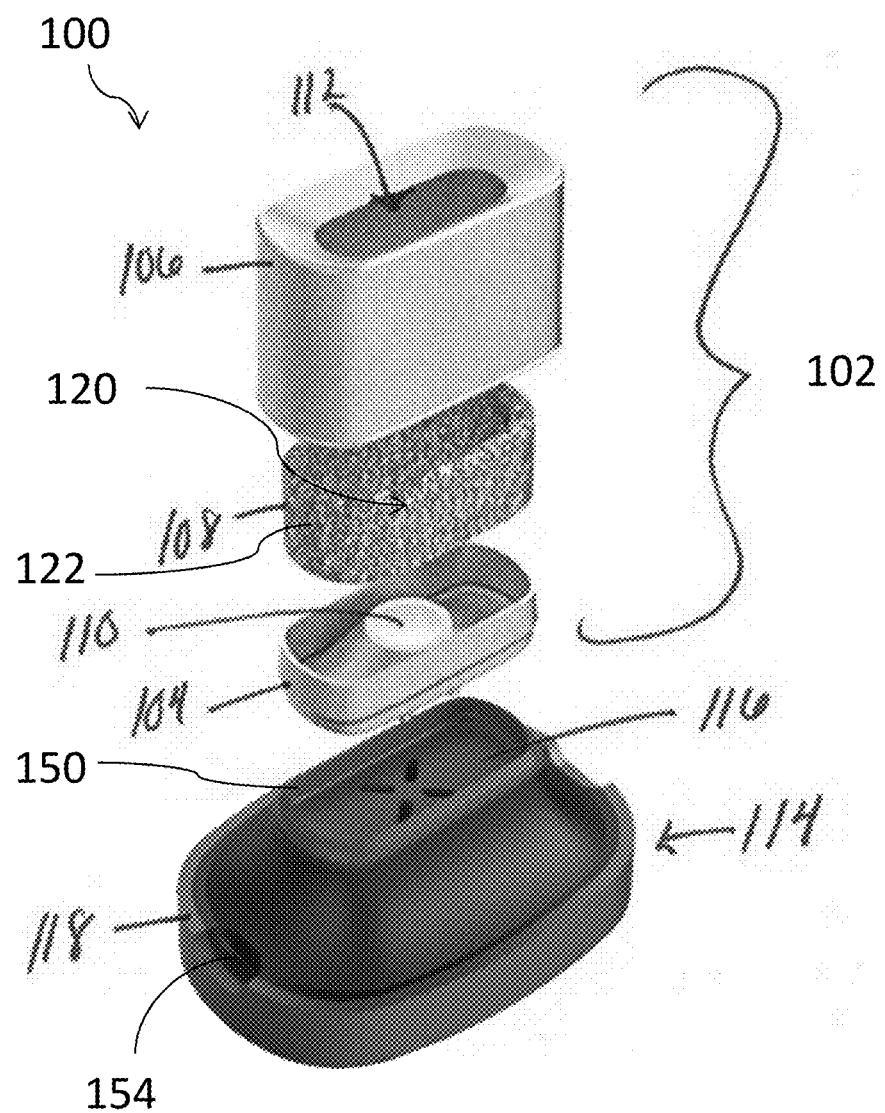
FIG. 2 illustrates an exploded view of a concentrate adaptor consistent with implementations of the current subject matter.
Figure 6:
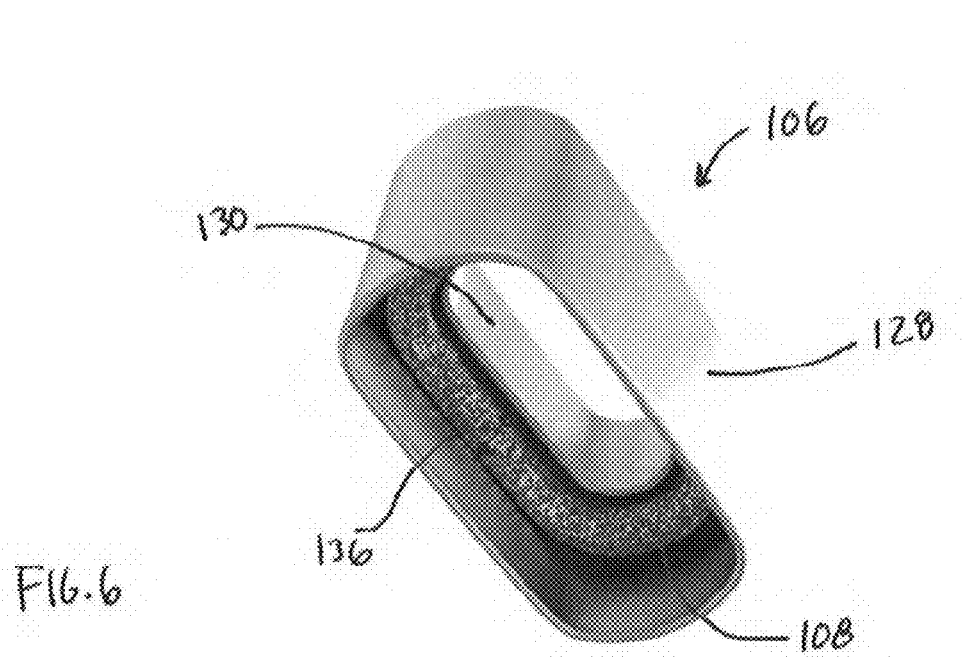
FIG. 6 illustrates a perspective view of a reservoir of a concentrate adaptor consistent with implementations of the current subject matter.
Figure 7:
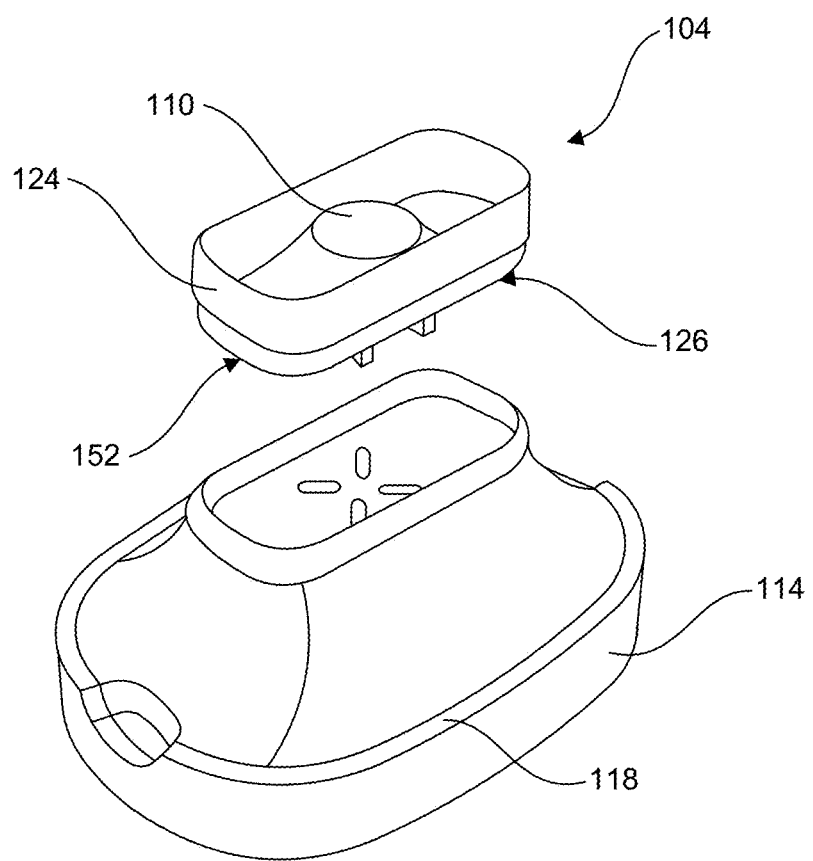
FIG. 7 illustrates a partial exploded view of a concentrate adaptor consistent with implementations of the current subject matter.
Figure 8:
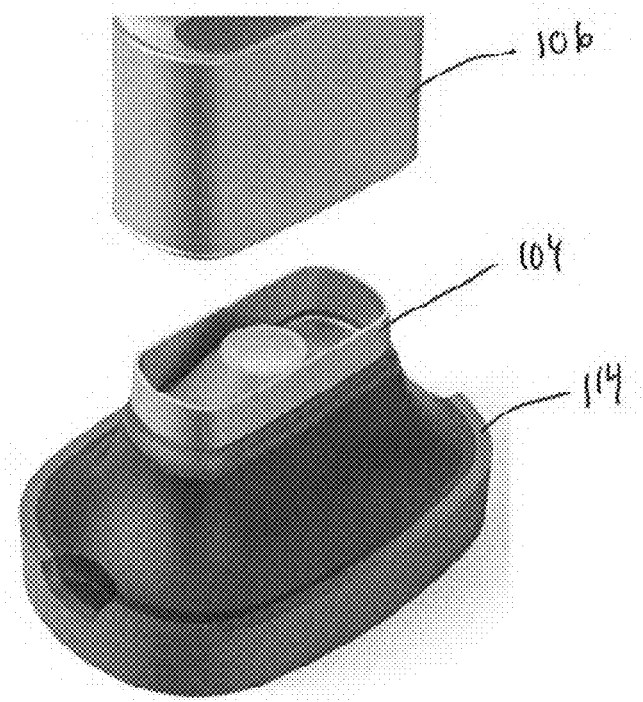
FIG. 8 illustrates a partial exploded view of a concentrate adaptor consistent with implementations of the current subject matter.
Figure 9:
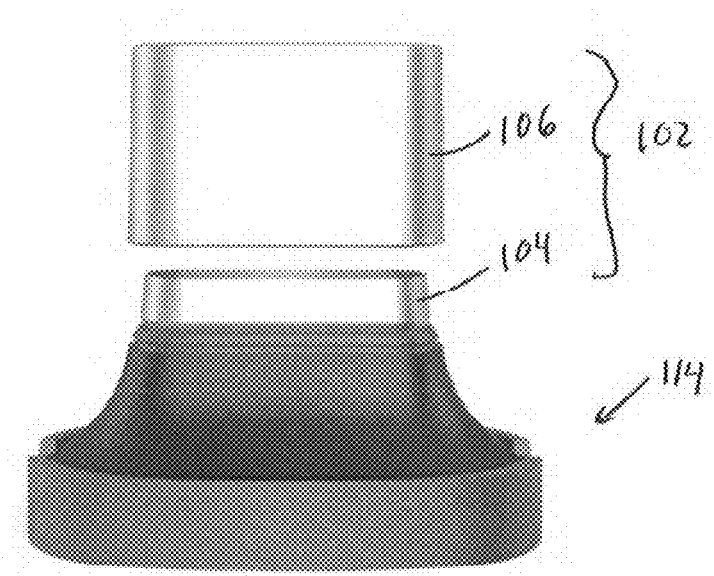
FIG. 9 illustrates a partial exploded view of a concentrate adaptor consistent with implementations of the current subject matter.
Figure 16:
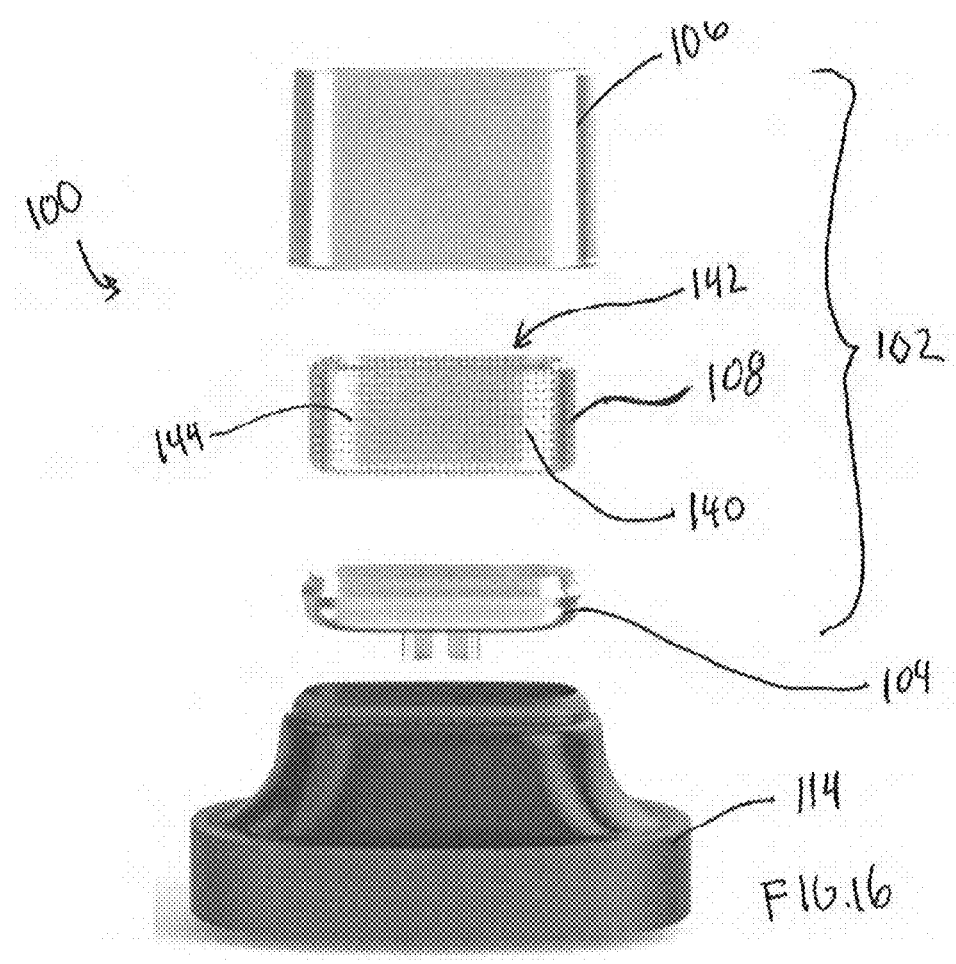
FIG. 16 illustrates an exploded view of a concentrate adaptor consistent with implementations of the current subject matter.

The reservoir 102 includes a reservoir base 104 and a reservoir top 106. As shown in FIGS. 2, 6, and 16, the reservoir 102 may also include a capillary loop 108. The reservoir base 104 and the reservoir top 106 may be formed from metal (e.g., aluminum or stainless steel), although other resilient materials capable of withstanding heat from the heating element and not reacting with the concentrates may be used. The reservoir base 104, the reservoir top 106, and the capillary loop 108 may be, in an implementation, of an elongated cylindrical shape with an oval or near oval cross-section, in which a first pair of opposing sides 120 are longer than a second pair of opposing sides 122 (see FIG. 2). The second pair of opposing sides 122 may form an arc between the first pair of opposing sides 120, or may otherwise be curved. This shape may conform to the interior surface of the vessel 12. The reservoir base 104, the reservoir top 106, and the capillary loop 108 may take other forms, such as a cylinder with a circular cross-section, a square cross-section, a rectangular cross-section, or any type of polygonal cross-section.

The reservoir base 104 has a bottom plate 126 with sidewalls 124 extending therefrom. The sidewalls 124 define at least a portion of an interior portion into which the concentrate is placed. A plate 110 extending upward from the bottom plate 126 within the interior portion of the reservoir base 104 may be provided as a target to guide the user for placement of the concentrate. For example, portions of the bottom plate 126 may extend upward to a flat surface that defines the plate 110. The flat surface that defines the plate 110 may be circular, oval, elliptical, or any polygonal shape.

The reservoir top 106 has a first outer wall 128 and a second inner wall 130 internal to the first outer wall 128 (see FIG. 6). The first outer wall 128 and the second inner wall 130 may have oval or near oval cross-sections or cross-sections of various forms. Moreover, the cross-sections of the first outer wall 128 and the second inner wall 130 need not be the same general shape. The first outer wall 128 and the second inner wall 130 are joined at a top surface 132 that defines a top portion of the reservoir top 106. The positioning of the first outer wall 128 and the second inner wall 130 defines a gap 136 therebetween. The gap 136 is open (e.g., accessible) from the side opposite the top portion of the reservoir top 106. The length of the first outer wall 128 may be greater than that of the second inner wall 130, such that the first outer wall 128 extends farther from the top portion than the second inner wall 130. An opening 112 is formed in the top portion of the reservoir top 106. A shape of the opening 112 may generally correspond to the cross-sectional shape of the second inner wall 130. A surface of the top portion of the reservoir top 106 may be angled downwardly and inwardly from its outer edge to an outer perimeter of the opening 112. The surface of the top portion of the reservoir top 106 may instead be flat, substantially flat, or angled upward. In an implementation, the surface of the top portion of the reservoir top 106 is not required to be of a constant form (e.g., one portion may be angled and another portion flat). The opening 112 is provided to provide access to an interior portion of the reservoir.

The reservoir base 104 and the reservoir top 106 are configured to connect to one another to form the assembled reservoir 102. The sidewalls of the reservoir base 104 and the first outer wall 128 of the reservoir top 106 may generally and/or substantially correspond to one another in size and shape to allow for engagement between the reservoir base 104 and the reservoir top 106. For example, the reservoir base 104 and the reservoir top 106 may fit together by engagement of the sidewalls of the reservoir base 104 with the first outer wall 128 of the reservoir top 106 (see FIG. 5, FIG. 8, FIG. 9). A diameter of the first outer wall 128 may be slightly larger than that of the sidewalls of the reservoir base 104 to allow for the sidewalls of the reservoir base 104 to fit snugly within an interior region of the first outer wall 128. In an implementation, the reservoir base 104 and the reservoir top 106 may be welded together in a permanent or near-permanent connection. In some implementations, the reservoir base 104 and the reservoir top 106 are integrally formed. In an implementation, an 0-ring may be provided around the circumference of the sidewalls of the reservoir base 104 to provide a tight fit within the interior region of the first outer wall 128. Once connected, the opening 112 in the top portion of the reservoir top 106 provides access to the interior portion of the reservoir base 104 (see FIG. 3).

The capillary loop 108 may be positioned within the gap 136 defined by the first outer wall 128 and the second inner wall 130 (see FIG. 6). The capillary loop 108 may be a mesh formed from steel, other metal, any porous material (e.g., ceramic, cotton, silica fibers, etc.), or combinations thereof. The capillary loop 108 acts to prevent or reduce leakage of the concentrate from the opening 112 in the top portion of the reservoir top 106. Due to its positioning within the gap 136 defined by the first outer wall 128 and the second inner wall 130, and when the reservoir 102 is assembled, the capillary loop 108 may capture concentrate that is leaking from the reservoir base 104 (e.g., if the vaporizer device is disturbed or turned on its side or upside down).

In an implementation, the capillary loop 108 is a screen with an outer wall 140 and an inner wall 142. The outer wall 140 and the inner wall 142 may be connected at top and bottom portions (see FIG. 16). The screen may be formed from steel or other metal or porous materials.

In an implementation, the capillary loop 108 may be a metal material (e.g., copper or stainless steel) in which porous features 144 are formed using, for example, chemical etching, laser drilling, and the like. The capillary loop 108 may be modeled and manufactured through additive manufacturing methods with ceramic or metal or any material capable of withstanding high temperatures (or the temperature that allows for vaporization). The capillary loop 108 may also be formed by sheet metal and chemically etched, laser drilled, etc. for intentional pore size and shape.

The base 114 of the concentrate adaptor 100 may be formed from plastic, metal, or another resilient material. For example, the base 114 may be made from an elastomeric material to ensure a sealed fit of the concentrate adaptor 100 within the vessel 12 of the housing 14 of the vaporizer device 10. The base 114 has a top surface 150 that interfaces with a bottom surface 152 of the reservoir 102 for connection or engagement between the base 114 and the reservoir 102 (FIG. 2-FIG. 4 and FIG. 7-FIG. 9). For example, a top engagement surface 116 of the base 114 may be defined by a rib (e.g., an over-molded seal) that extends upward from the top surface of the base 114. A circumference of the rib may generally and/or substantially correspond in size and shape to the bottom surface 152 of the reservoir 102. In particular, the sidewalls of the reservoir base 104 may be sized and shaped such that when the bottom surface 152 of the reservoir 102 is placed against or adjacent the top engagement surface of the base 114, the rib encircles the sidewalls of the reservoir base 104 in a tight and secure engagement. A bottom portion of the sidewalls of the reservoir base 104 may be recessed and aligned or substantially aligned with the rib when engaged. In an implementation, the reservoir 102 and the base 114 may be laser welded together in a permanent or near-permanent connection. In other implementations, as discussed in more detail below, the reservoir 102 and the base 114 may be connected via other means, such as a locking mechanism (see FIGS. 40-42 and 47-49).

Figure 10:
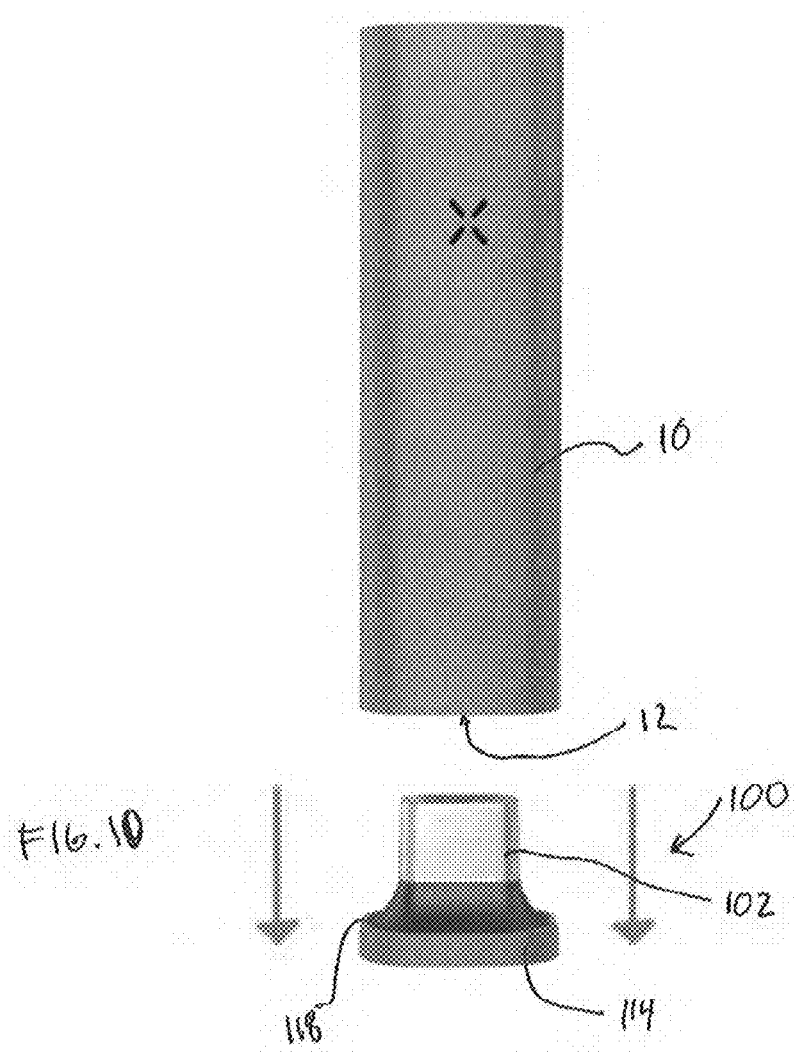
FIG. 10 illustrates a concentrate adaptor and a vaporizer device consistent with implementations of the current subject matter.
Figure 11:
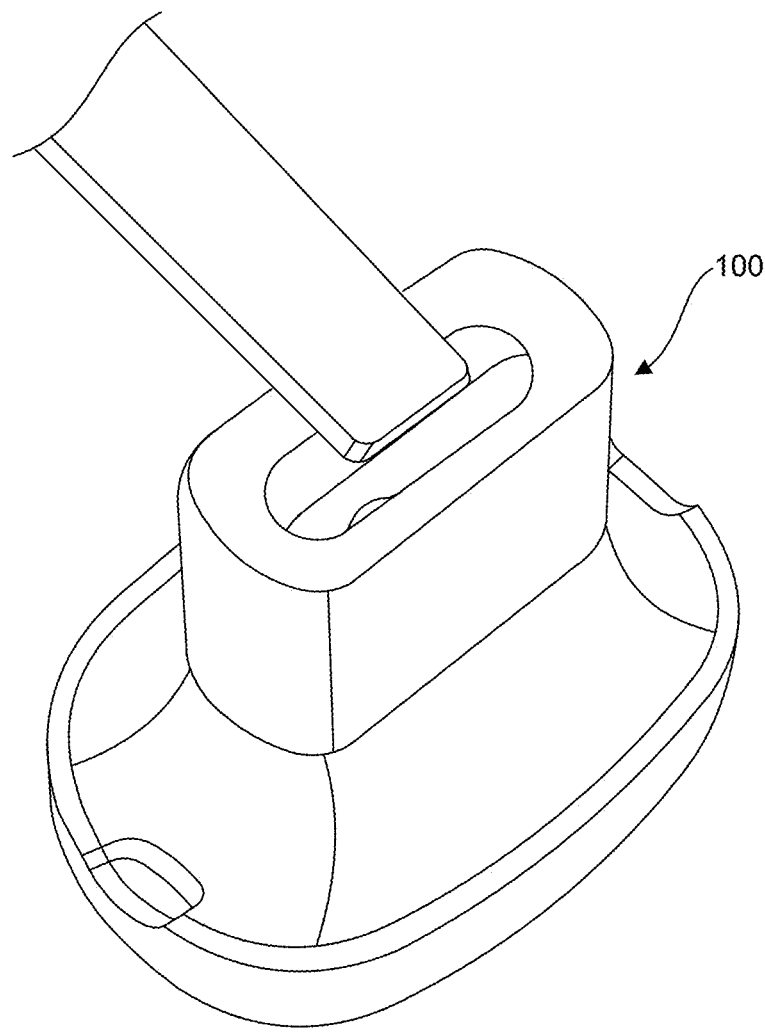
FIG. 11 illustrates a concentrate adaptor consistent with implementations of the current subject matter.
Figure 12:
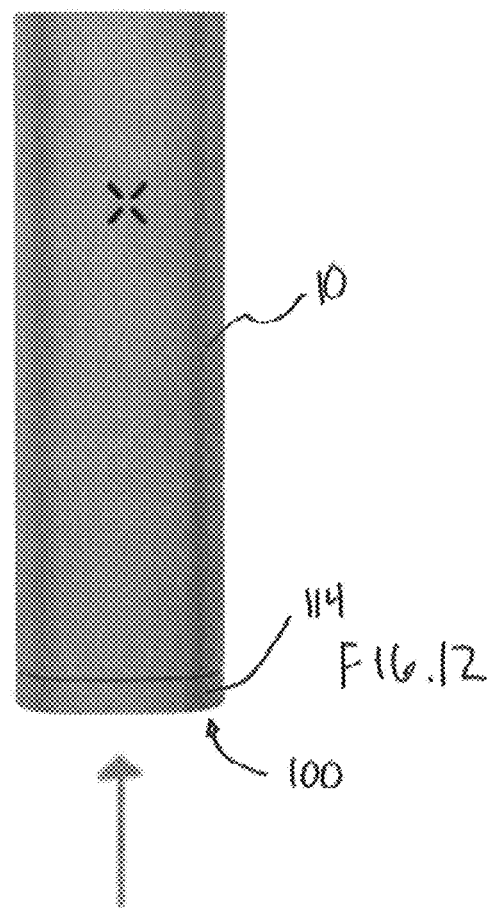
FIG. 12 illustrates a vaporizer device and a concentrate adaptor consistent with implementations of the current subject matter.
Figure 13:
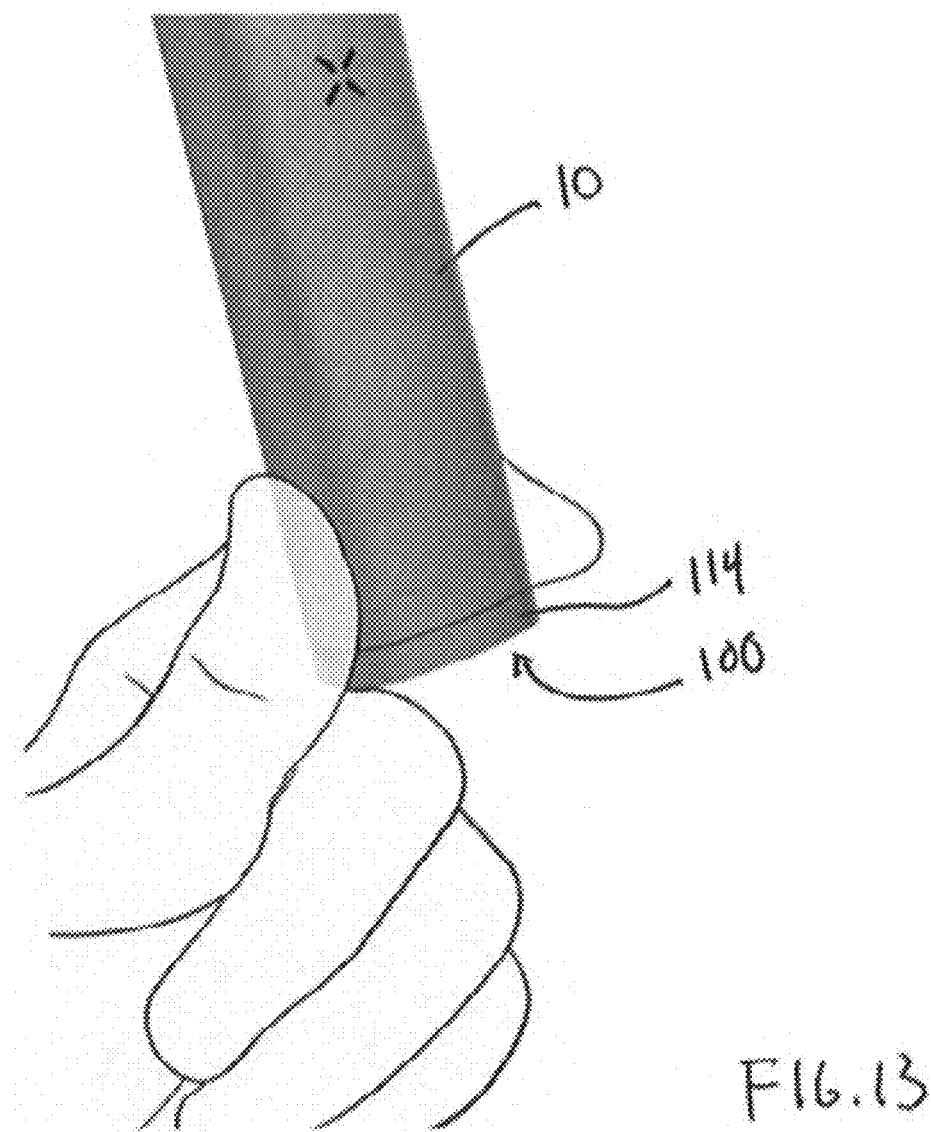
FIG. 13 illustrates a vaporizer device and a concentrate adaptor consistent with implementations of the current subject matter.
Figure 14:
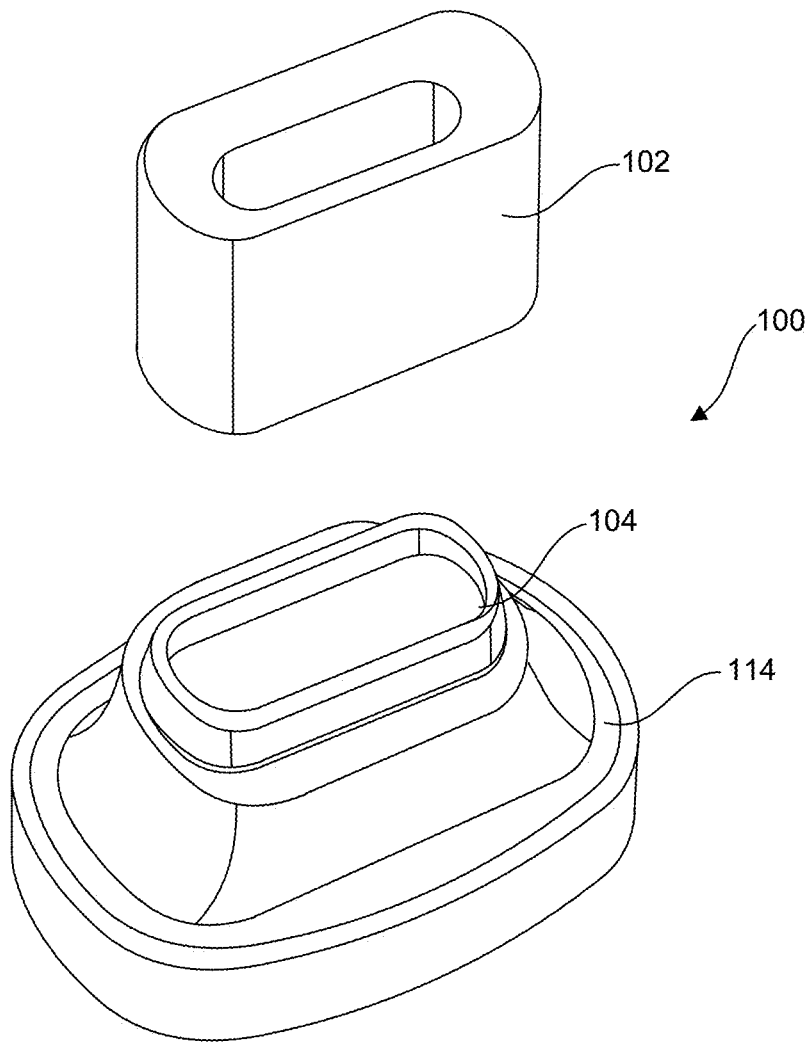
FIG. 14 illustrates an exploded view of a concentrate adaptor consistent with implementations of the current subject matter.
Figure 15:
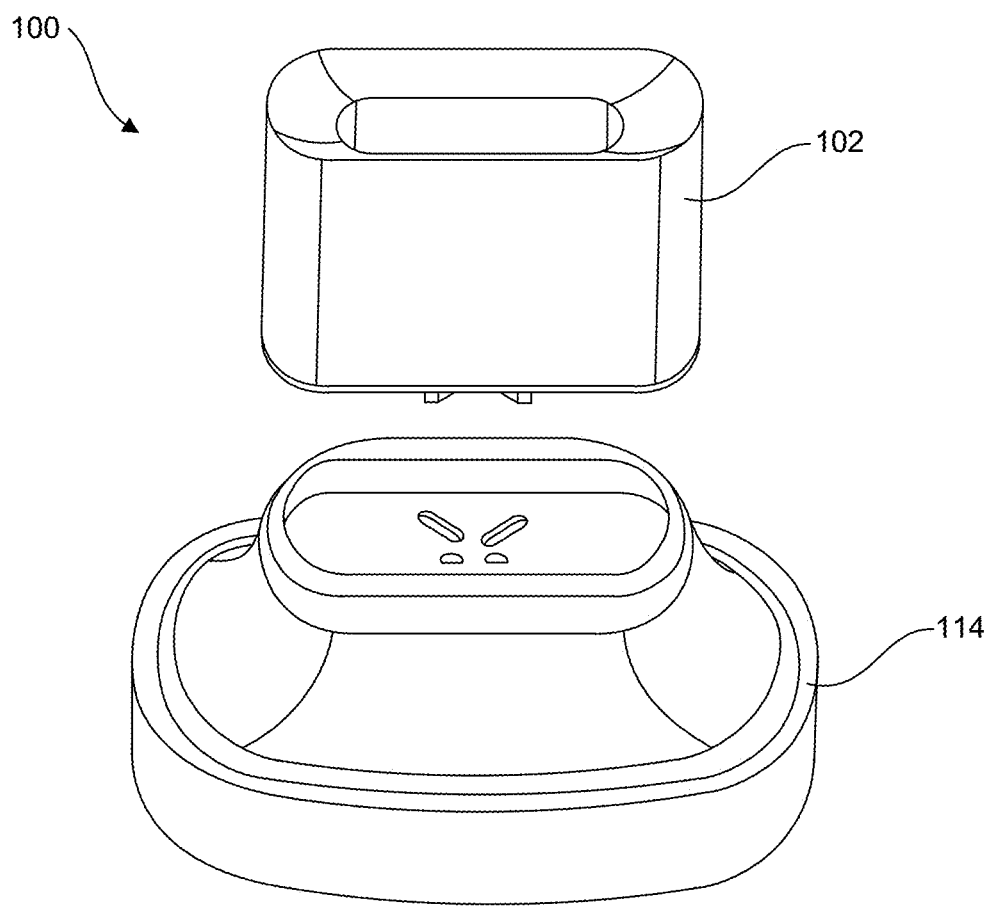
FIG. 15 illustrates an exploded view of a concentrate adaptor consistent with implementations of the current subject matter.

When the reservoir 102 and the base 114 are connected to one another, the concentrate adaptor 100 may be inserted into the vaporizer device 10 such that the reservoir 102 is fitted within the vessel 12 of the housing 14 (see FIG. 10, FIG. 12, FIG. 13, FIG. 59, FIG. 60, FIGS. 79A-79B, FIGS. 80A-80B, FIG. 81C, FIG. 82, FIG. 84C, FIG. 85C, FIG. 86D, FIG. 87B). A bottom portion of the base 114 may include a ledge 118 (e.g., a cylindrical ledge) that interfaces with the open end of the housing 14 of the vaporizer device. For example, an upper surface of the cylindrical ledge 118 of the base 114 may contact a complimentary bottom surface of the housing 14 of the vaporizer device (FIG. 10, FIG. 12, FIG. 13). As explained in more detail below, the cylindrical ledge 118 may, in some implementations, be spaced apart from the complimentary bottom surface of the housing 14 of the vaporizer device 10 to allow air to flow into the vaporizer device and/or the concentrate adaptor. When the reservoir 102 of the concentrate adaptor 100 is fitted within the vessel 12 of the vaporizer device, the base 114 closes and fits over at least a portion of the open end of the housing 14 of the vaporizer device that includes the vessel 12. As previously described, when the heating element 16 is activated, the vaporizer device 10 heats and vaporizes the concentrate when the reservoir 102 is deposited or otherwise placed within the vessel 12.

Figure 3:
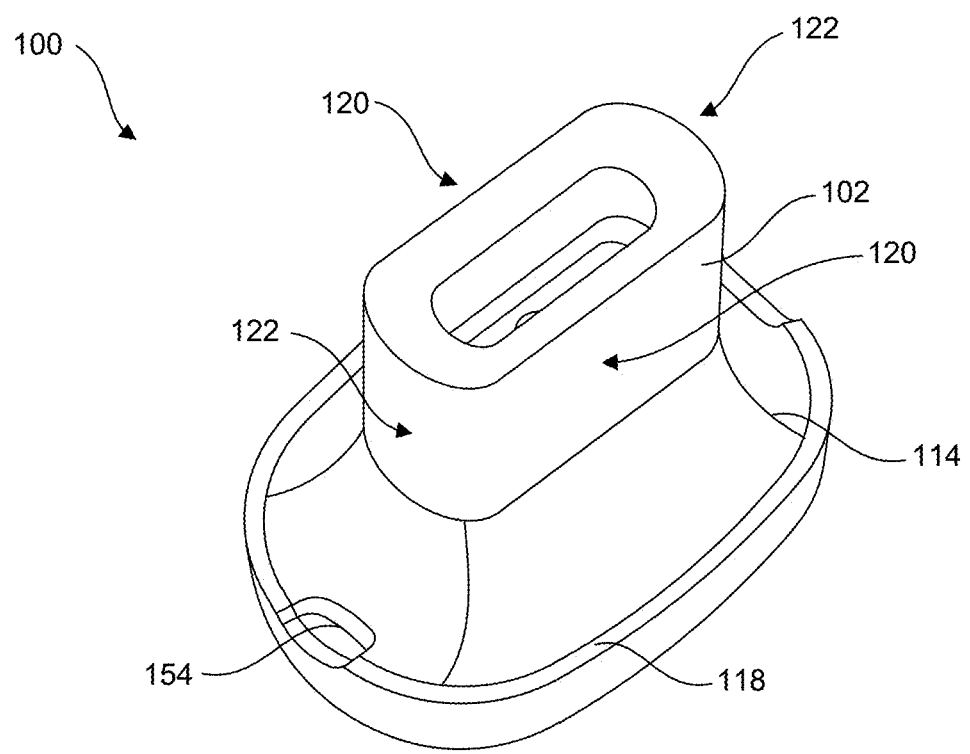
FIG. 3 illustrates a perspective view of a concentrate adaptor consistent with implementations of the current subject matter.
Figure 4:
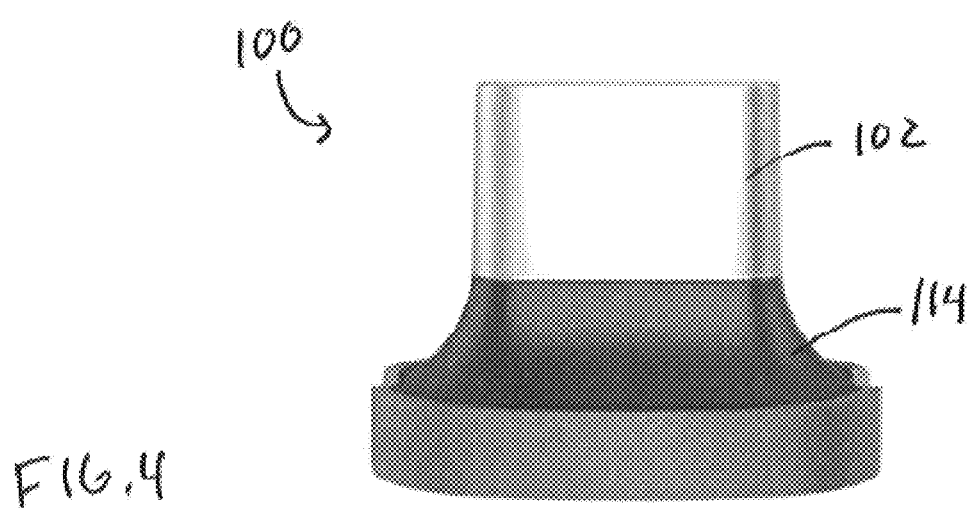
FIG. 4 illustrates a side view of a concentrate adaptor consistent with implementations of the current subject matter.
Figure 5:
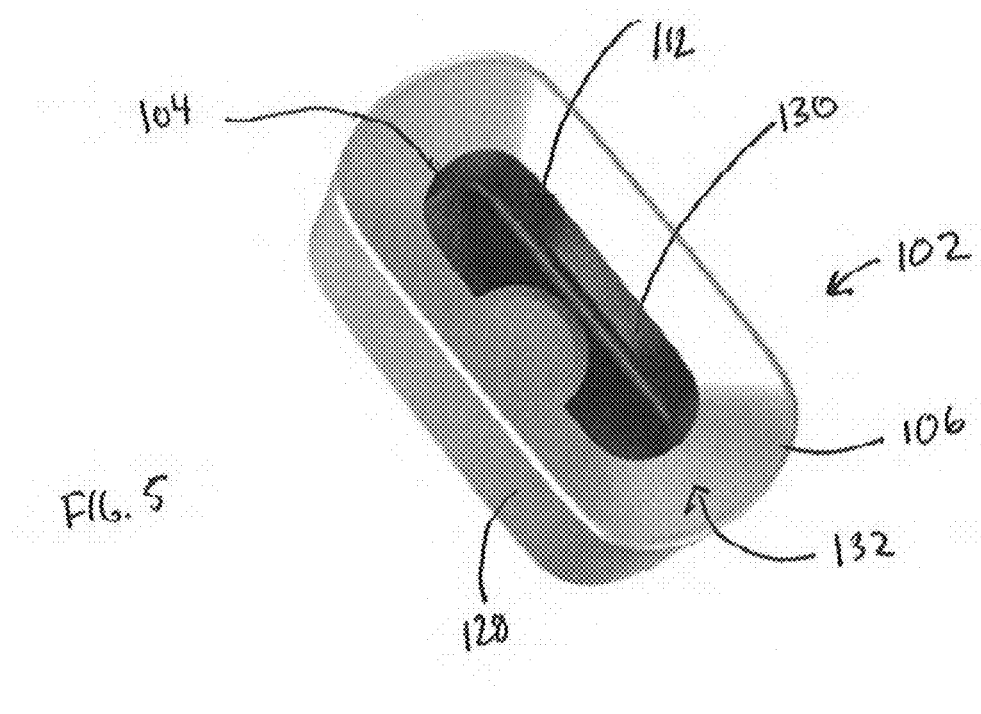
FIG. 5 illustrates a perspective view of a reservoir of a concentrate adaptor consistent with implementations of the current subject matter.

As noted, the concentrate adaptor 100 may include a plurality of apertures configured to allow for the passage of air. As shown in FIGS. 2 and 3, for example, the base 114 includes several apertures 154 for airflow. One or more apertures 154 may be cut-out regions of at least the cylindrical ledge 118 of the base 114, where the cut-out regions may be of various shapes and sizes. When the concentrate adaptor 100 is fitted within the vessel 12 of the vaporizer device, the user may adjust airflow by covering one or more portions of the cut-out regions (see FIG. 13). FIG. 31-FIG. 35, FIGS. 44-46, FIGS. 59-60, FIG. 84F, FIG. 84I, and FIG. 84K, illustrate additional and/or alternative airflow paths through various apertures and profiles formed in the reservoir 102 and/or the base 114. With respect to FIG. 31-FIG. 35, one or more slots may be formed along edges of the circumference of the top portion of the reservoir top 106, allowing the airflow to enter into the reservoir 102.

Figure 31:
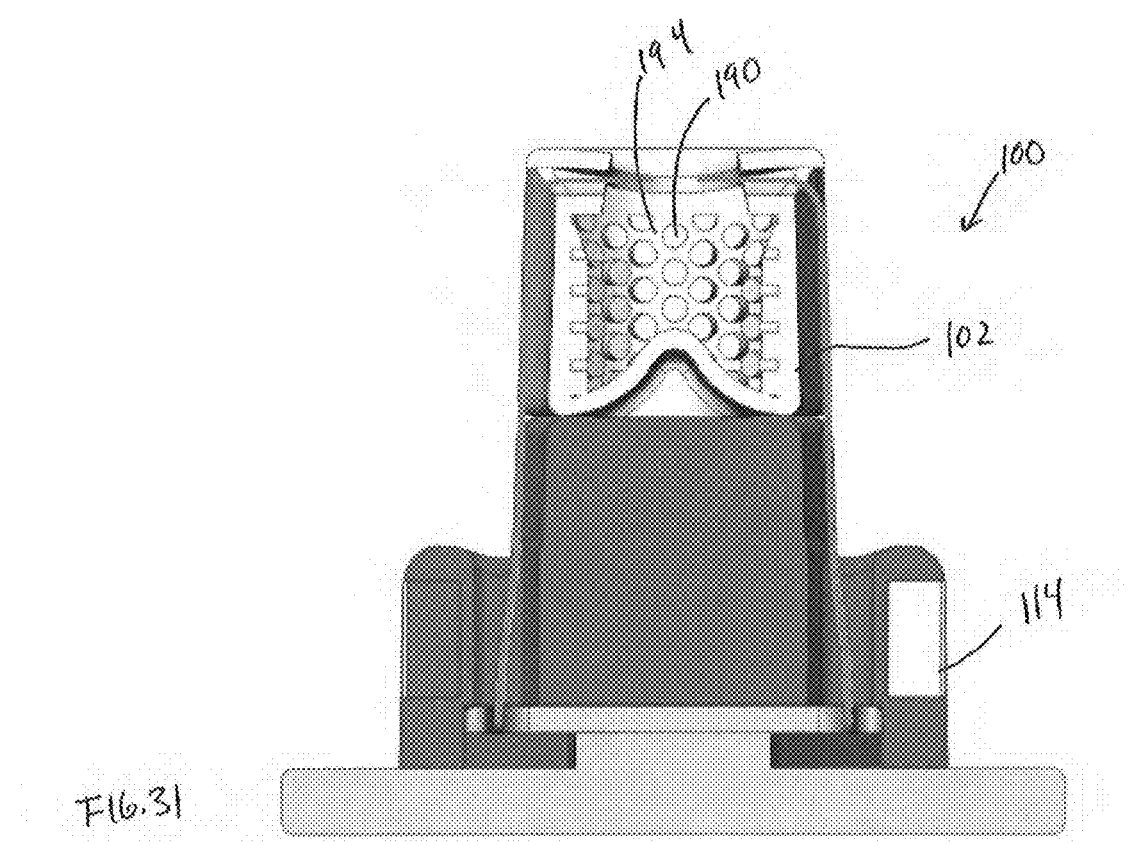
FIG. 31 illustrates an example airflow path in a concentrate adaptor consistent with implementations of the current subject matter.
Figure 32:
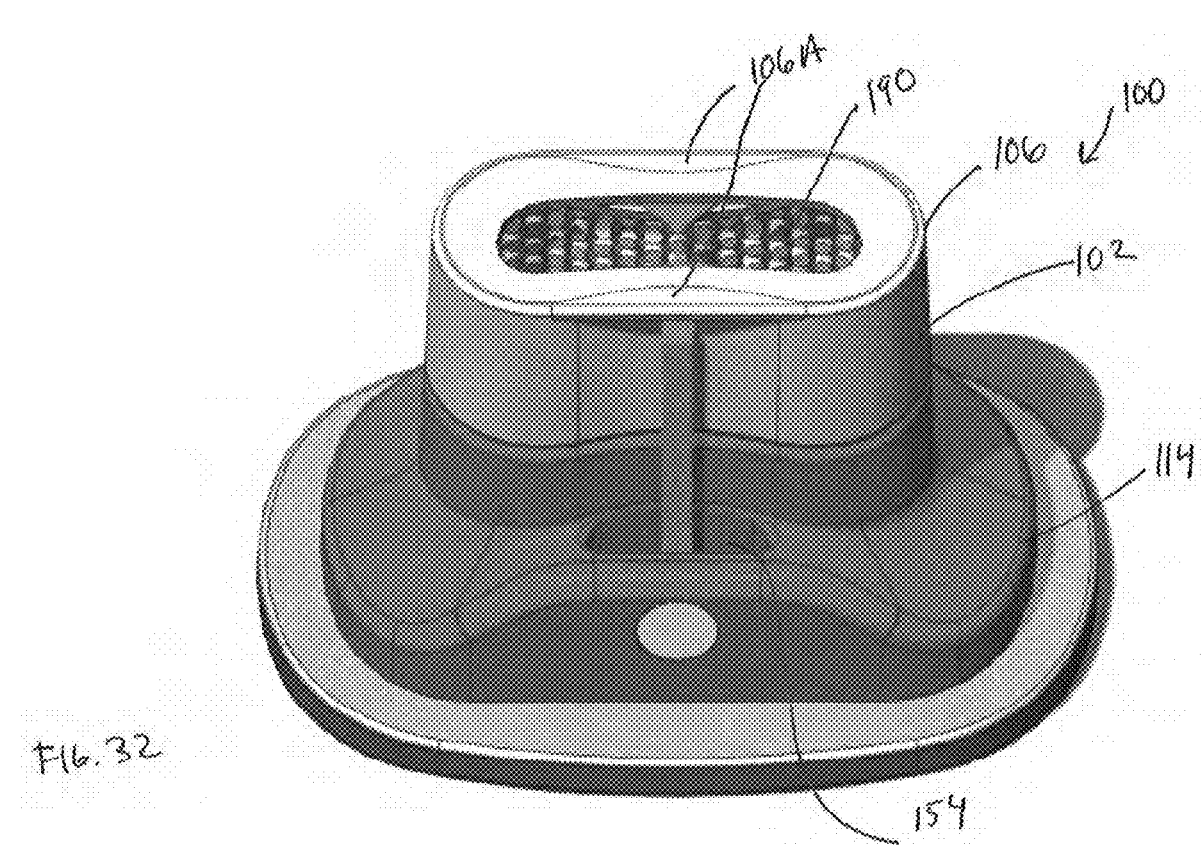
FIG. 32 illustrates an example airflow path in a concentrate adaptor consistent with implementations of the current subject matter.
Figure 33:
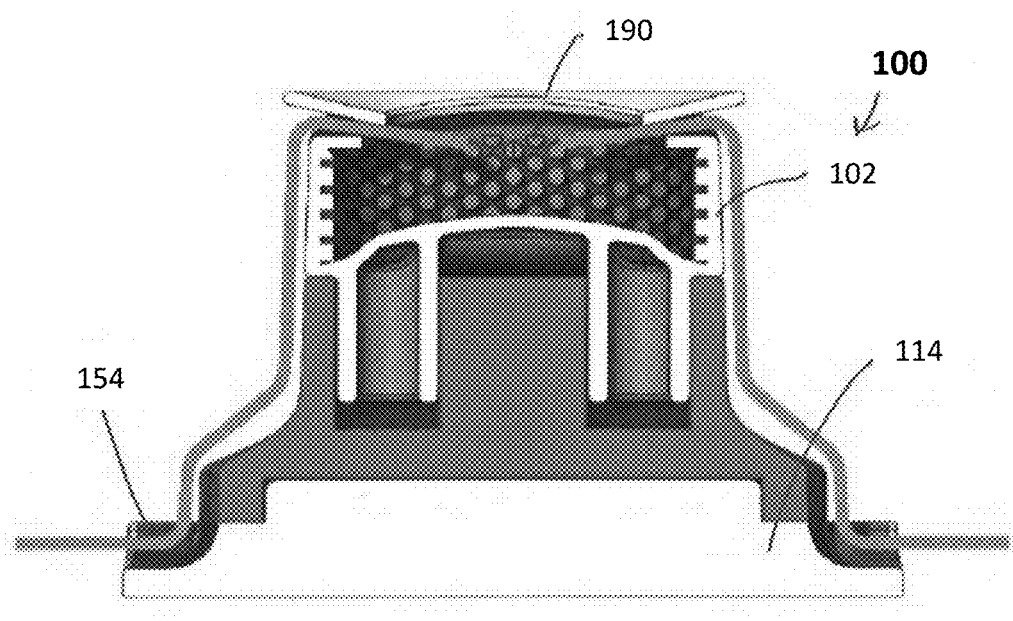
FIG. 33 illustrates an example airflow path in a concentrate adaptor consistent with implementations of the current subject matter.
Figure 34:
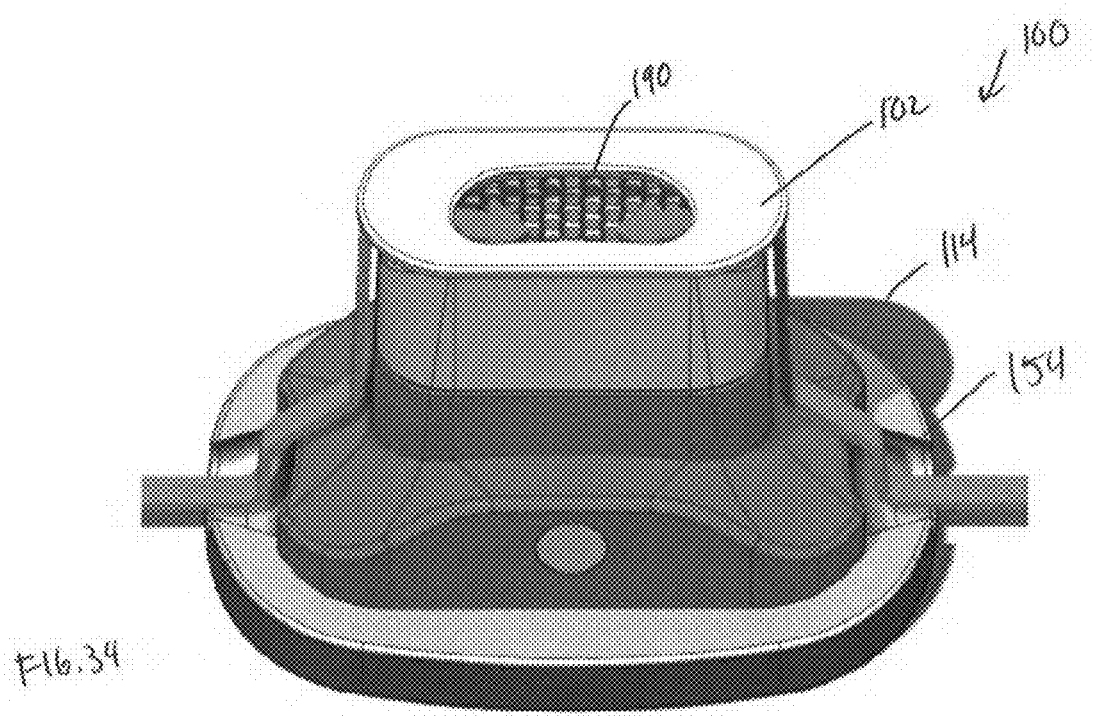
FIG. 34 illustrates an example airflow path in a concentrate adaptor consistent with implementations of the current subject matter.
Figure 35:
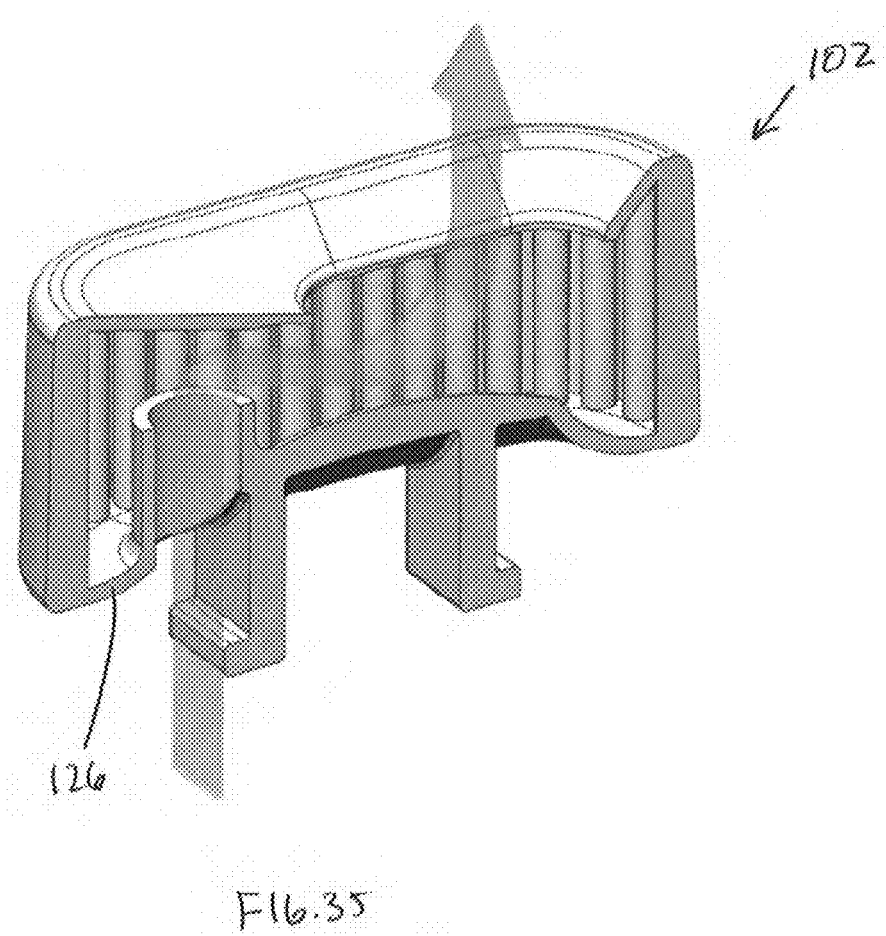
FIG. 35 illustrates an example airflow path in a concentrate adaptor consistent with implementations of the current subject matter.

In an implementation, a guide or overhang 106A at the top portion of the reservoir top 106 may be aligned with a respective slot to direct the airflow into the reservoir 102 of the concentrate adaptor 100. The airflow may be directed from the cut-out regions of the cylindrical ledge of the base 114 (FIG. 33 and FIG. 34). The airflow may be directed from apertures formed through the top surface of the base 114 (FIG. 31 and FIG. 32). In an implementation, one or more apertures may be formed through the bottom plate 126 of the reservoir base 104 and may be aligned with respective apertures formed through a corresponding surface of the base 114, providing for airflow to be directed up and into the reservoir 102 before leaving through the opening 112 in the top portion of the reservoir top 106 (FIG. 35). The apertures may capitalize on the difference in velocity of air flowing into the concentrate adaptor 100 relating to air in other parts of the concentrate adaptor 100 and/or the vessel 12, and may similarly capitalize on the difference in pressure of those apertures.

Figure 17:
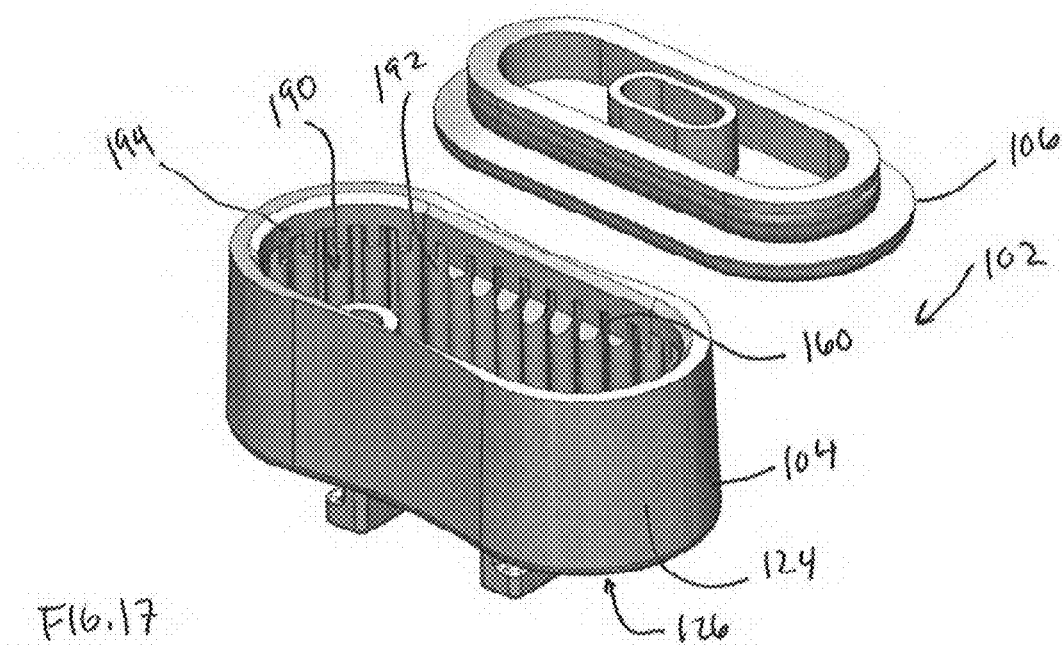
FIG. 17 illustrates an exploded view of a reservoir of a concentrate adaptor consistent with implementations of the current subject matter.

Referring to FIG. 17, capillary channels 160 may be formed within interior portions of the reservoir base 104 (e.g., the bottom plate 126 and the sidewalls 124). The capillary channels 160 may also be formed within internal walls of the reservoir top 106. Features of the capillary channels 160 are described with reference to FIG. 17-FIG. 30.

Referring to FIG. 17-FIG. 30, aspects of various capillary structures 190 that may be employed with the concentrate adaptor 100 consistent with implementations of the current subject matter are illustrated.

A capillary structure 190 may be provided or formed within the concentrate adaptor 100. For example, a capillary structure 190 may fit or be formed within the reservoir 102 of the concentrate adaptor 100 such that at least one of the sidewalls 192 of the capillary structure generally and/or substantially conform to or are aligned with the sidewalls 124 of the reservoir 102 (see FIG. 23-FIG. 25). The capillary structure 190 may be a cylindrical component with an open top and an open bottom. The sidewalls 192 may have one or more capillary openings 196 extending through the sidewalls of the capillary structure and/or one or more capillary channels 194 formed on an interior surface of the sidewalls 192 of the capillary structure 190. For example, the capillary structure 190 may be a thin metal sleeve, cut such that capillary openings 196 are formed through the sleeve. The capillary structure 190 may be formed on interior sidewalls 124 of the reservoir 102 in varying thicknesses such that the variations in thickness form capillary channels 194. The capillary structure 190 may be formed from aluminum or another metal or any other suitable material that is resilient and able to withstand the temperature of vaporization. The capillary structure 190 may be formed using metal injection molding, a combination of metal injection molding and computer numerical control, or metal injection co-molding. The capillary channels 194 may be formed by metal injection molding, chemical etching, laser drilling, and/or knurling. Individual capillary channels may be formed from metal injection molding or computer numerical control.

The shape and size of the capillary openings 196 and/or capillary channels 194 may take various forms and combinations of forms, and as noted below, may be positioned across all of the sidewalls 192 of the capillary structure 190, or only some of the side walls 192 of the capillary structure 190, such as across at least a portion of each of the side walls 124. For example, the capillary channels 194 may be formed as recesses between various geometric configurations or shapes, and the recesses themselves may have various geometric configurations or shapes. Various examples of capillary channels 194 are shown in FIG. 17-FIG. 22 and FIG. 26-FIG. 35. The capillary channels 194 may be formed between mostly-vertically extending bars or cylinders with varying profiles that extend from or near a top end of the capillary structure 190 to or near a bottom end of the capillary structure 190 (FIG. 17-FIG. 22, FIG. 67-71, FIGS. 72-78). As another example, the capillary channels 194 may be formed between various shapes that are formed on the sidewalls 192 of the capillary structure 190 (e.g., hexagons as in FIG. 26 and FIG. 28, ellipses as in FIG. 27, circles as in FIG. 31-FIG. 34, FIG. 47-FIG. 60, and FIG. 61A-FIG. 61C). As another example, two or more geometric configurations or shapes may be combined to form the capillary channels 194 of the capillary structure 190 (e.g., two sets of noncontiguous bars as in FIG. 29-FIG. 30 formed on respective halves of the capillary structure 190 that may be laser welded together; or the capillary structure 190 may be formed from multiple parts split along any or multiple axes). Vertically and horizontally oriented channels 194 allow for the concentrate to flow in various directions, providing for improved heating performance as further described below. The capillary structure consistent with implementations of the current subject matter is not limited to the particular configurations shown. Other geometric configurations and/or shapes in various combinations may be used (e.g., ovals, squares, any type of polygon, any type of irregular shape, etc.).

Figure 23:
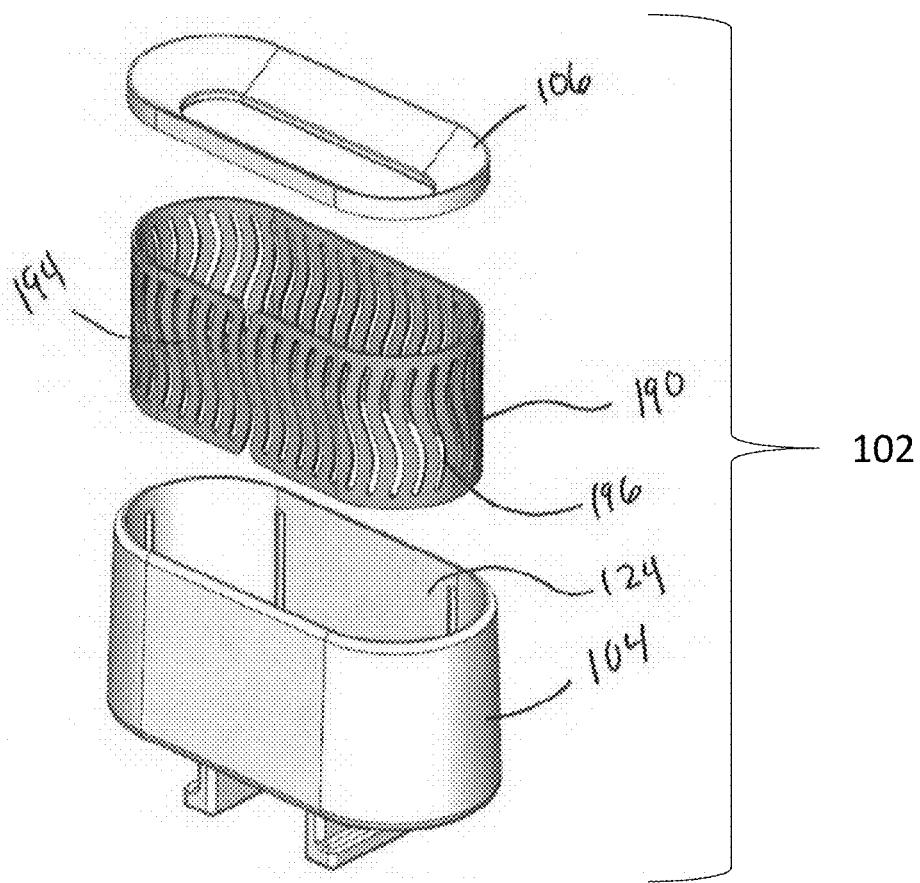
FIG. 23 illustrates an exploded view of a reservoir of a concentrate adaptor consistent with implementations of the current subject matter.
Figure 24:
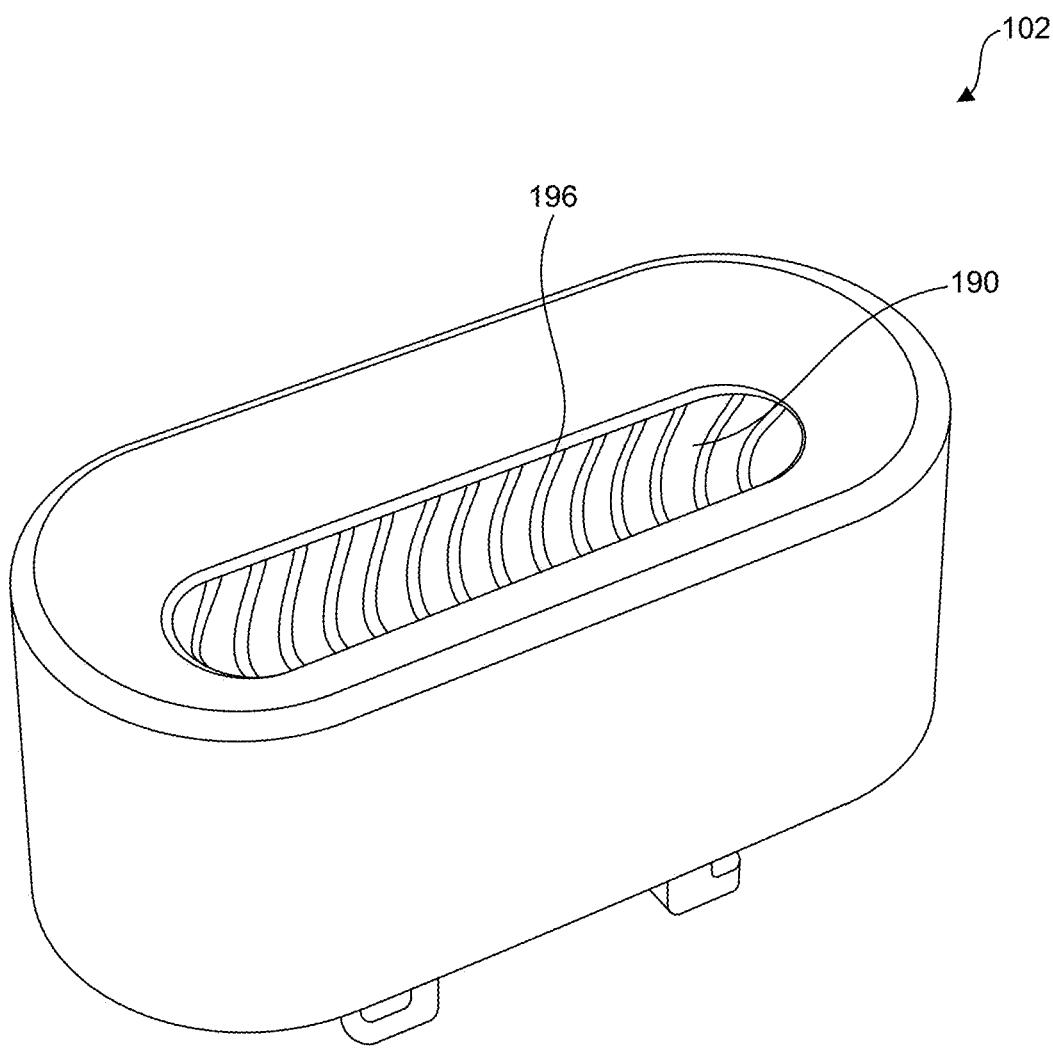
FIG. 24 illustrates a reservoir of a concentrate adaptor consistent with implementations of the current subject matter.
Figure 25:
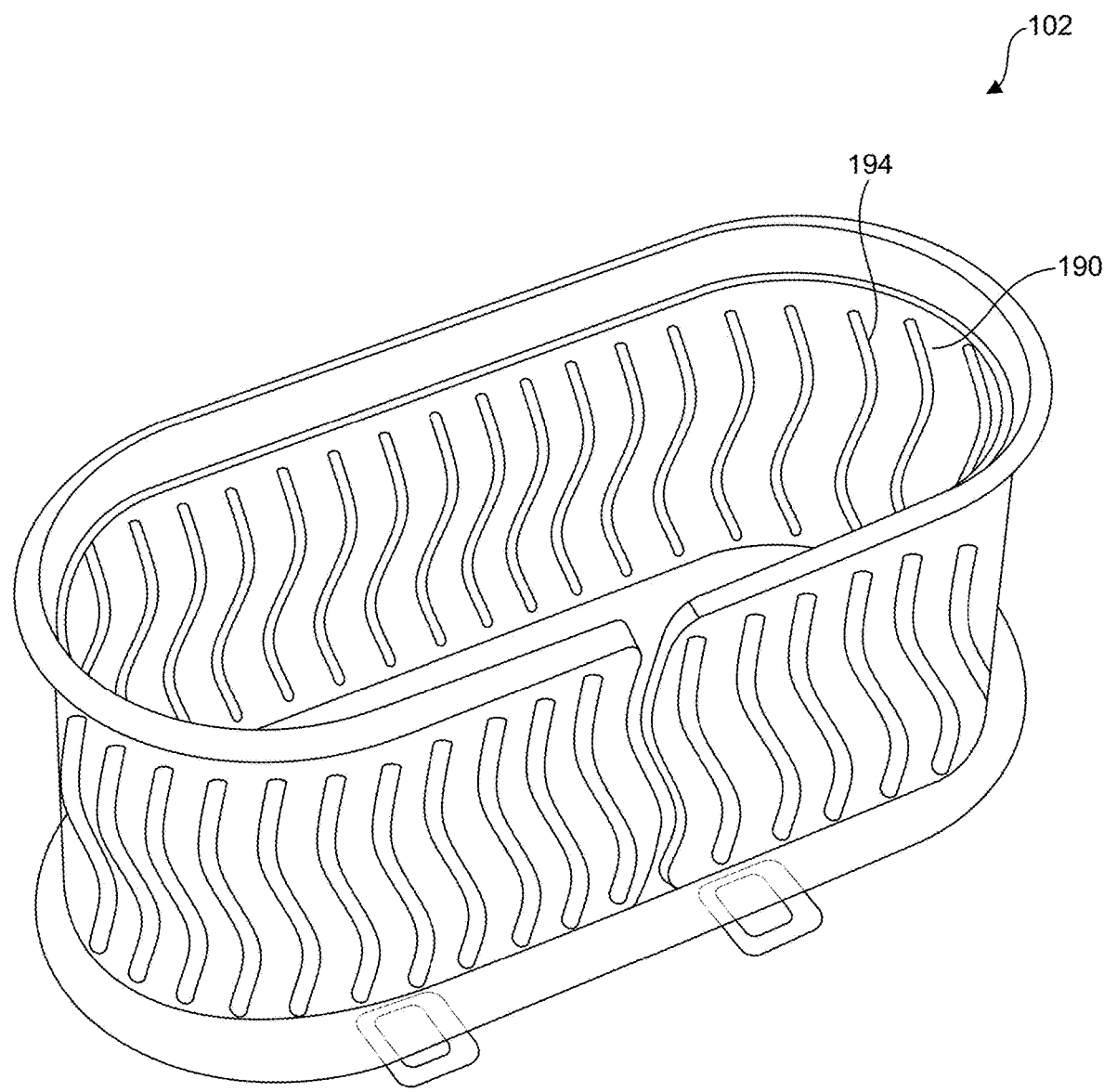
FIG. 25 illustrates a reservoir of a concentrate adaptor consistent with implementations of the current subject matter.
Figure 26:
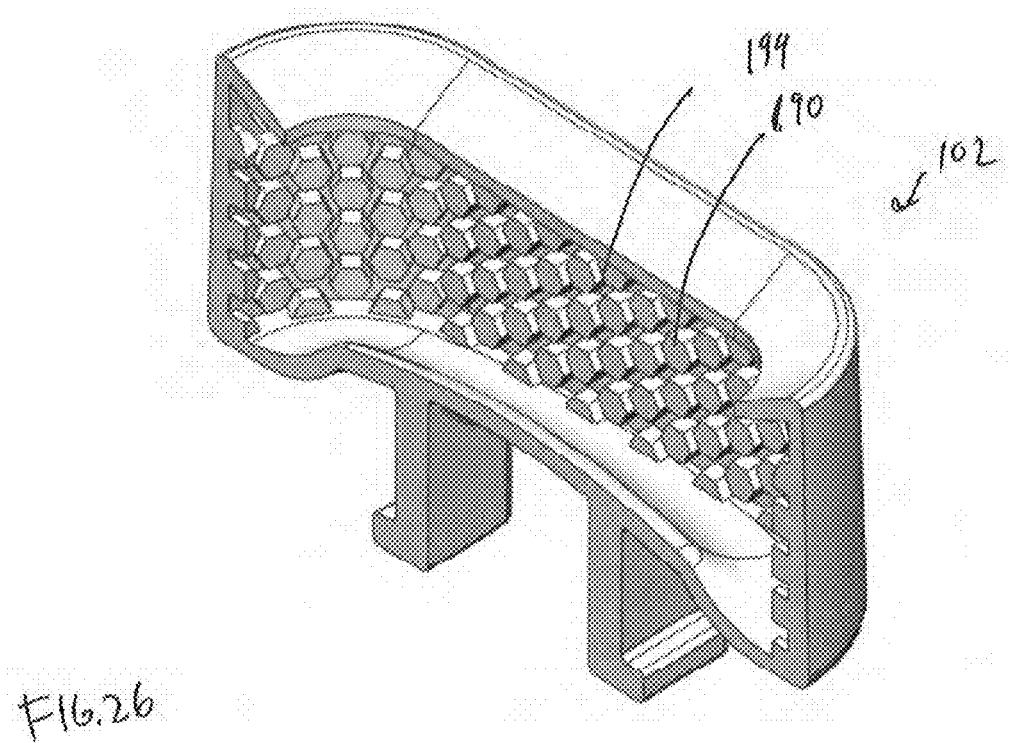
FIG. 26 illustrates a cross-sectional view of a reservoir of a concentrate adaptor consistent with implementations of the current subject matter.
Figure 27:
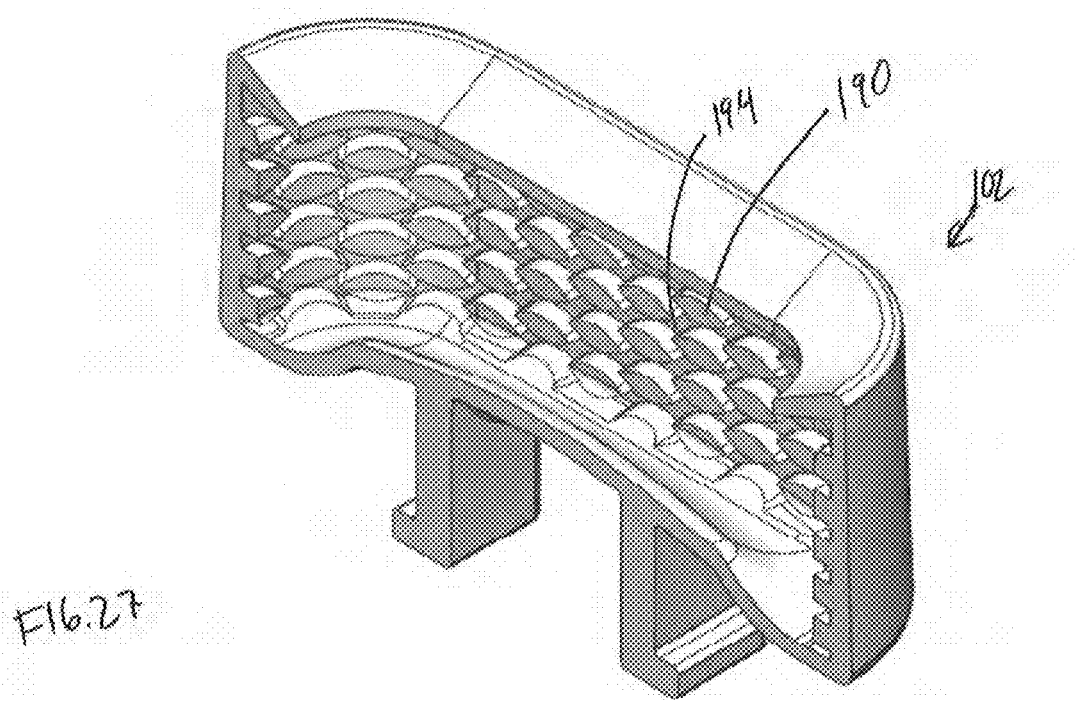
FIG. 27 illustrates a cross-sectional view of a reservoir of a concentrate adaptor consistent with implementations of the current subject matter.
Figure 28:
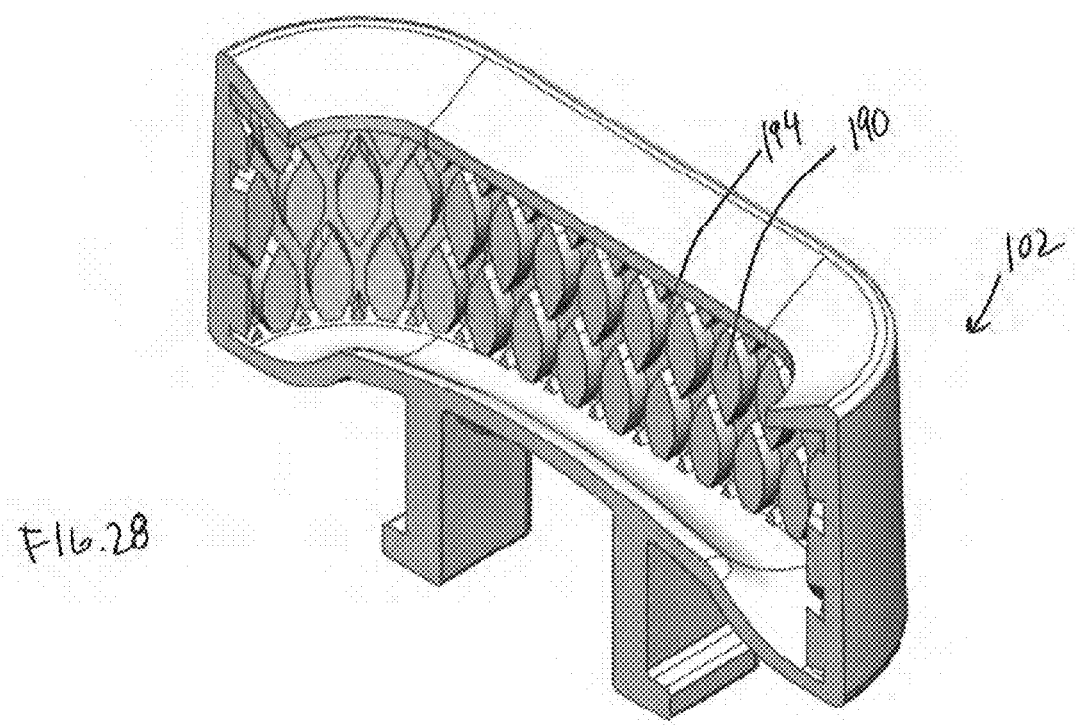
FIG. 28 illustrates a cross-sectional view of a reservoir of a concentrate adaptor consistent with implementations of the current subject matter.
Figure 29:
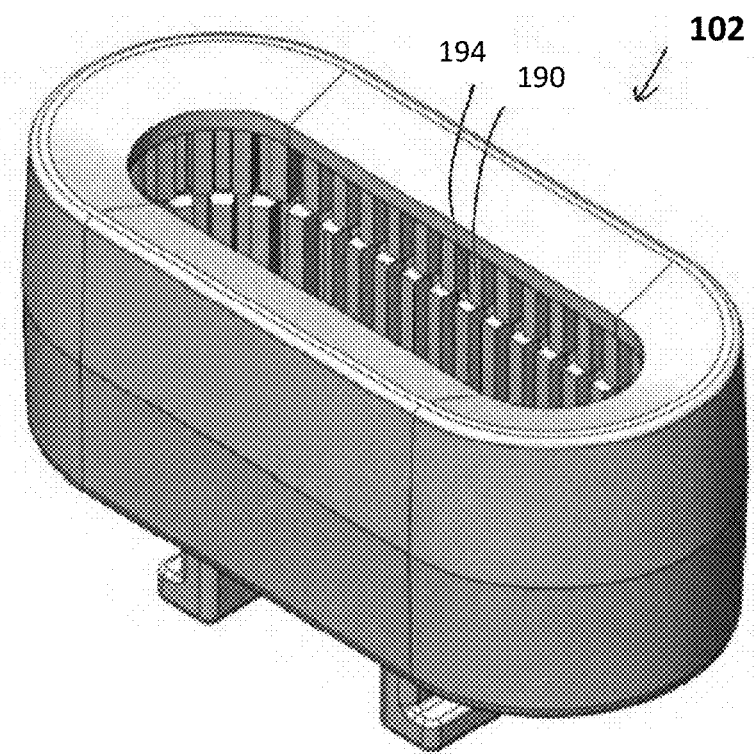
FIG. 29 illustrates a reservoir of a concentrate adaptor consistent with implementations of the current subject matter.
Figure 30:
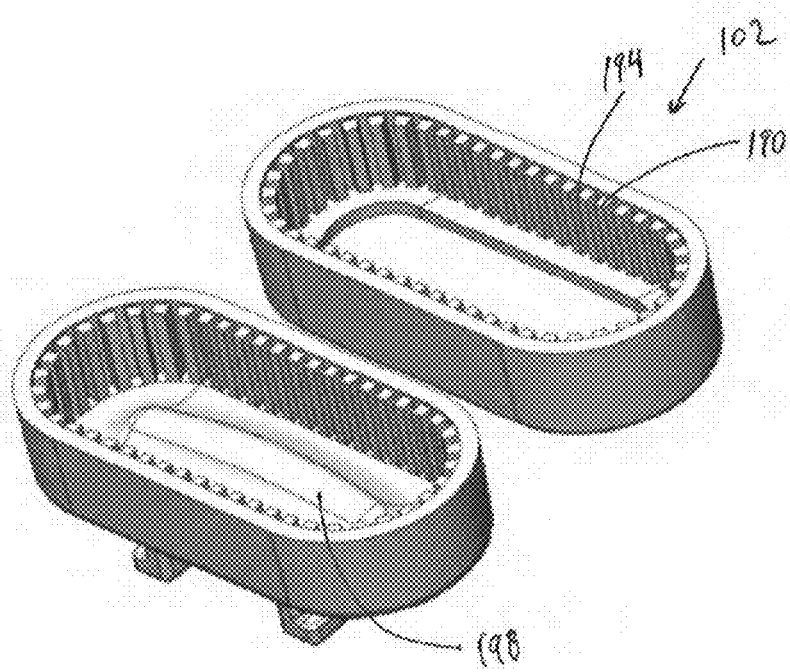
FIG. 30 illustrates an exploded view of a reservoir of a concentrate adaptor consistent with implementations of the current subject matter.

FIG. 23-FIG. 25 provides an example of a capillary structure 190 with one type of capillary opening 196 (e.g., vertically extending rectangles or bars that extend from near the top end of the capillary structure 190 to near the bottom end of the capillary structure 190) formed through the sidewalls 192. In an implementation, the capillary openings 194 may be angular-V shapes and the like. The capillary structure 190 may be flat or substantially flat with respect to a vertical orientation from the top end to the bottom end, or the capillary structure 190 may be curved. As shown, the capillary structure 190 is nested within the reservoir 102 of the concentrate adaptor 100. A lid covering a portion (e.g., a portion of the outer perimeter) of the open portion of the reservoir 102 may be added The capillary openings 196 and/or capillary channels 194 serve to guide the concentrate upward, outwards, and/or along or near the sidewalls 124 of the reservoir 102. This provides for the concentrate being nearer to the source of heat (e.g., the heating element) when the reservoir 102 is contained within the vessel 12 of the vaporizer device 10 (thereby maximizing the ratio of heat applied per unit volume of the concentrate, resulting in faster vaporization), and also provides for the concentrate to be autonomously distributed as the concentrate adaptor 100 is heated, the distribution being independent from an initial placement of the concentrate. Moreover, the capillary openings 196 and/or capillary channels 194 help to retain the concentrate and prevent or reduce leakage. Additionally, the capillary openings 196 and/or capillary channels 194 can be designed to contain or accommodate a known volume, which influences guidelines related to filling for the user.

Figure 18:
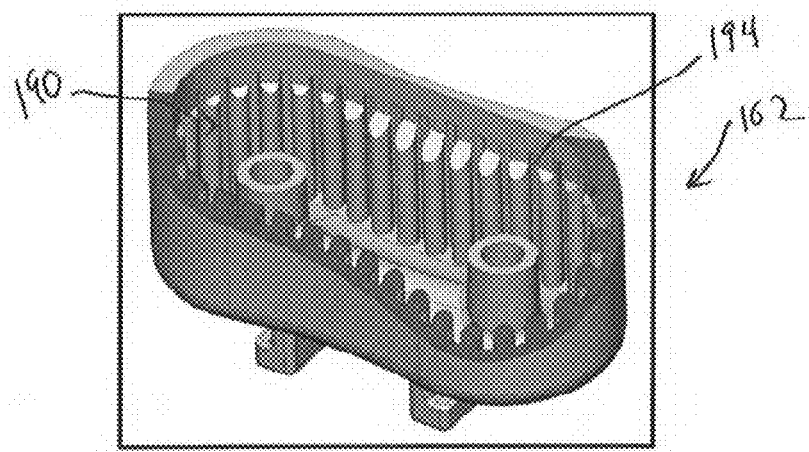
FIG. 18 illustrates a cross-sectional view of a reservoir of a concentrate adaptor consistent with implementations of the current subject matter.
Figure 19:
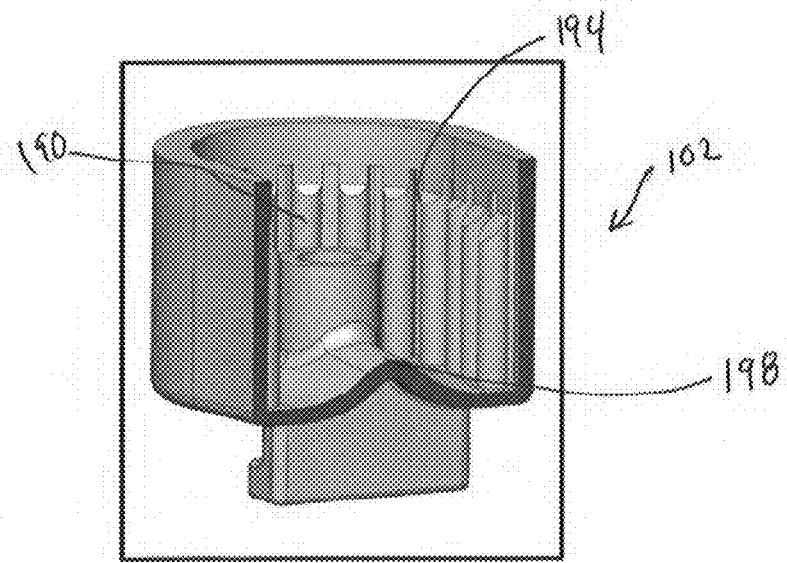
FIG. 19 illustrates a cross-sectional view of a reservoir of a concentrate adaptor consistent with implementations of the current subject matter.
Figure 20:
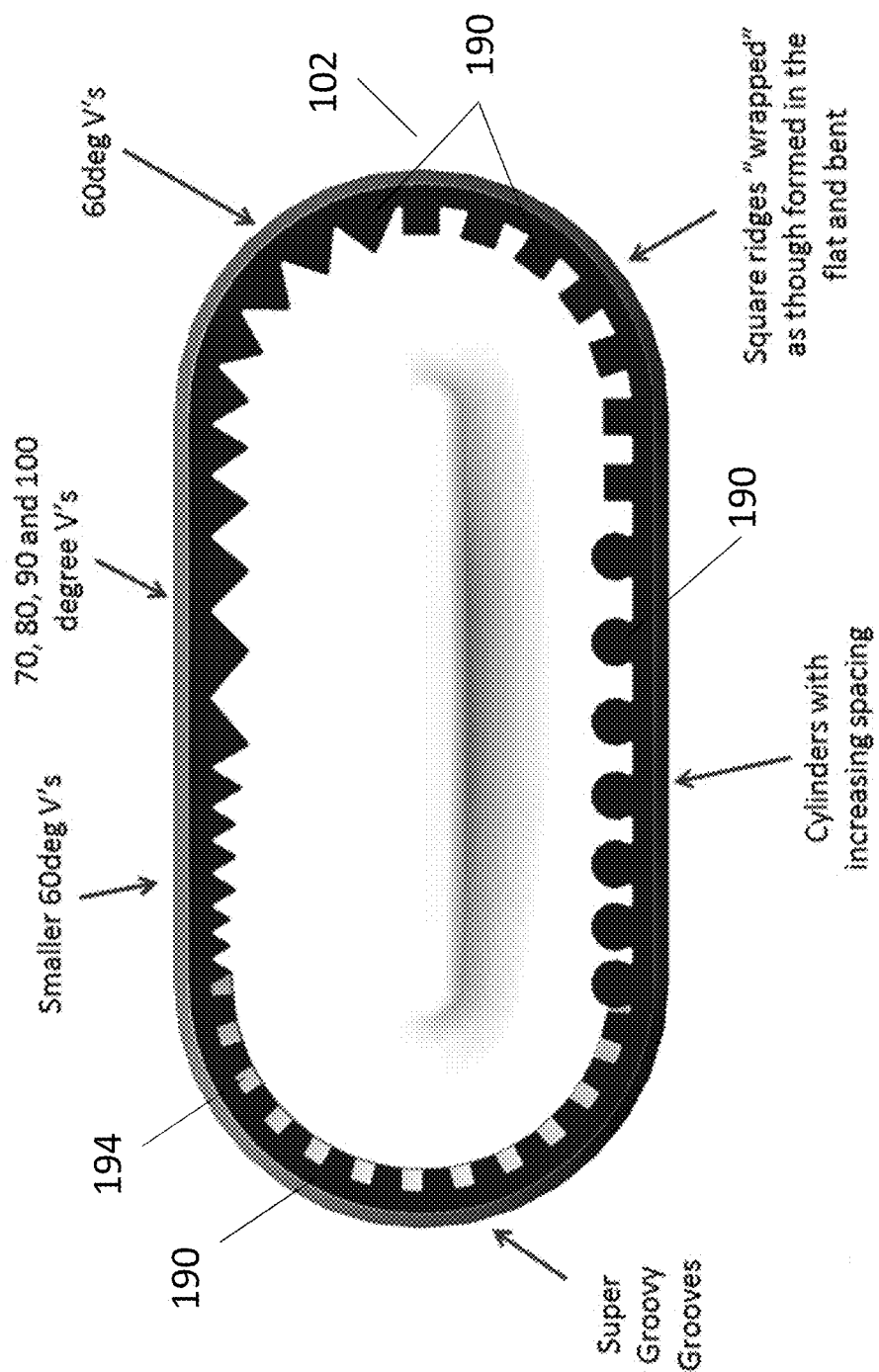
FIG. 20 illustrates a cross-sectional view of a reservoir of a concentrate adaptor consistent with implementations of the current subject matter.
Figure 21:
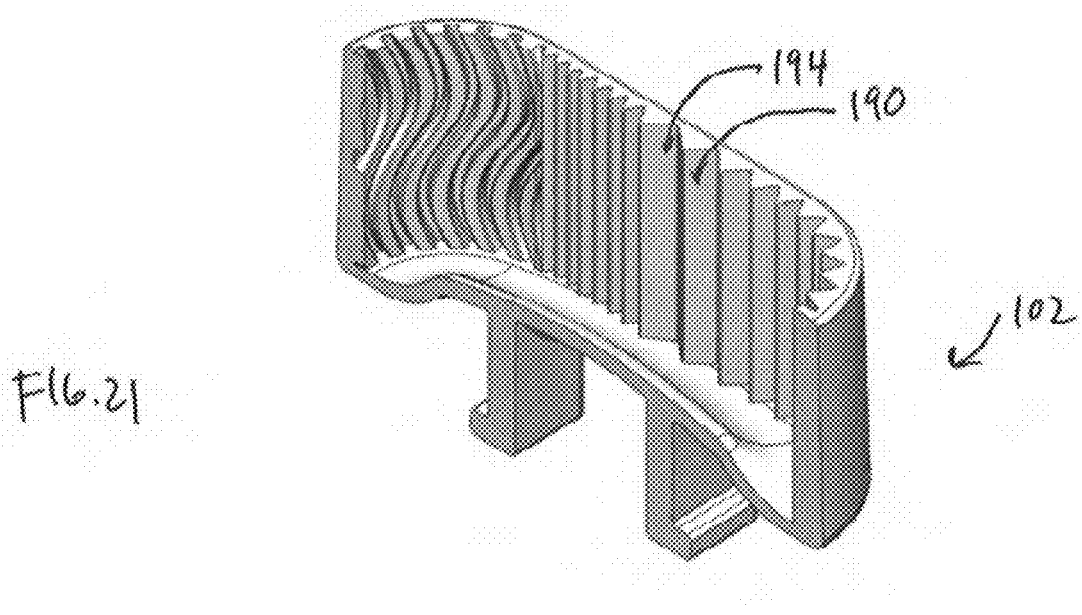
FIG. 21 illustrates a cross-sectional view of a reservoir of a concentrate adaptor consistent with implementations of the current subject matter.
Figure 22:
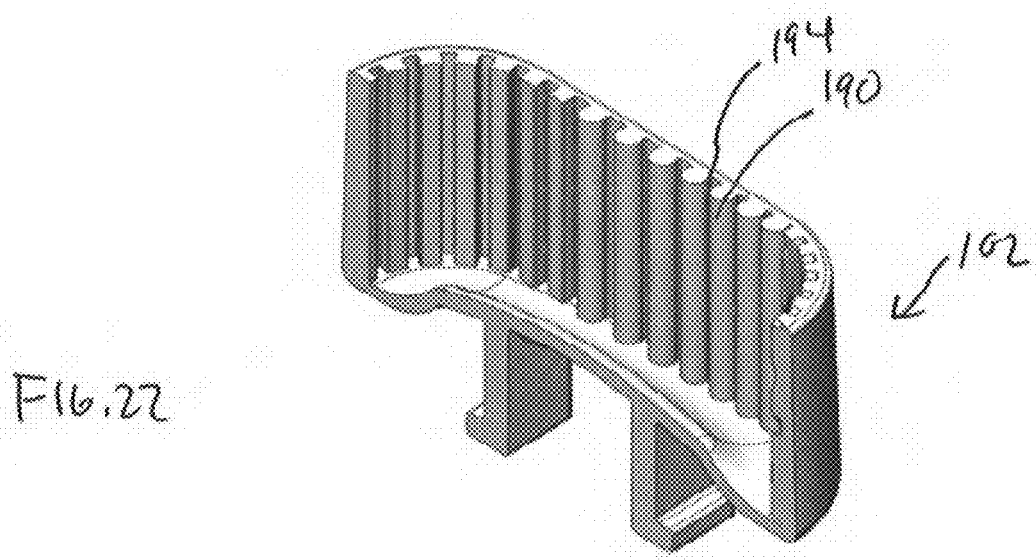
FIG. 22 illustrates a cross-sectional view of a reservoir of a concentrate adaptor consistent with implementations of the current subject matter.

As shown in FIG. 18 and FIG. 19, the bottom side of the reservoir 102 may include a domed surface 198. As heat is applied to the vessel 12, viscosity of the concentrate lowers. The incorporation of the domed surface 198 provides for the concentrate to naturally move down the domed surface 198 toward the sidewalls 124 of the reservoir 102. This provides for the concentrate to move to and be distributed along the sidewalls 124 of the reservoir 102, and also influences autonomous, predictable movement of the concentrate as the concentrate adaptor 100 is being heated, the movement being independent from the initial placement of the concentrate.

FIGS. 36-46 illustrate another example of the concentrate adaptor 100. The concentrate adaptor 100 shown in FIGS. 36-46 includes the same or similar features to the features described above with respect to the concentrate adaptors shown in FIGS. 1-35. For example, the concentrate adaptor may include the reservoir 102, which holds one or more portions of a concentrate, and the base 114, which may accept or connect to the reservoir 102. A user inhaling from the mouthpiece 18 of the vaporizer device 10 causes an intake of air into the reservoir 102. The incoming air mixes with the vapor generated by the vaporization of the contents of the reservoir 102 to form an aerosol. The resulting air flow carries the aerosol out of the reservoir 102 through the one or more first apertures. The aerosol travels through the air path 17 to the mouthpiece 18 where the aerosol is delivered to the user.

Referring to FIGS. 36-42, the reservoir 102 includes a reservoir base 104 and a reservoir top 106. In this example, the reservoir base 104 and the reservoir top 106 may be integrally formed or may be separately coupled (e.g., by placing the reservoir top 106 over a top end of the reservoir base 104). The reservoir base 104 has a bottom plate 126 (from which the connection feature 117 extends) with sidewalls 124 extending therefrom towards the reservoir top 106. The sidewalls 124 define at least a portion of an interior portion into which the concentrate is placed. The sidewalls 124 include opposing first and second sides 119A, 119B, which are joined by opposing third and fourth sides 119C, 119D. At least the first and second sides 119A, 119B are approximately parallel to one another. The first and second sides 119A, 119B may be longer than the third and fourth sides 119C, 119D.

Figure 39:
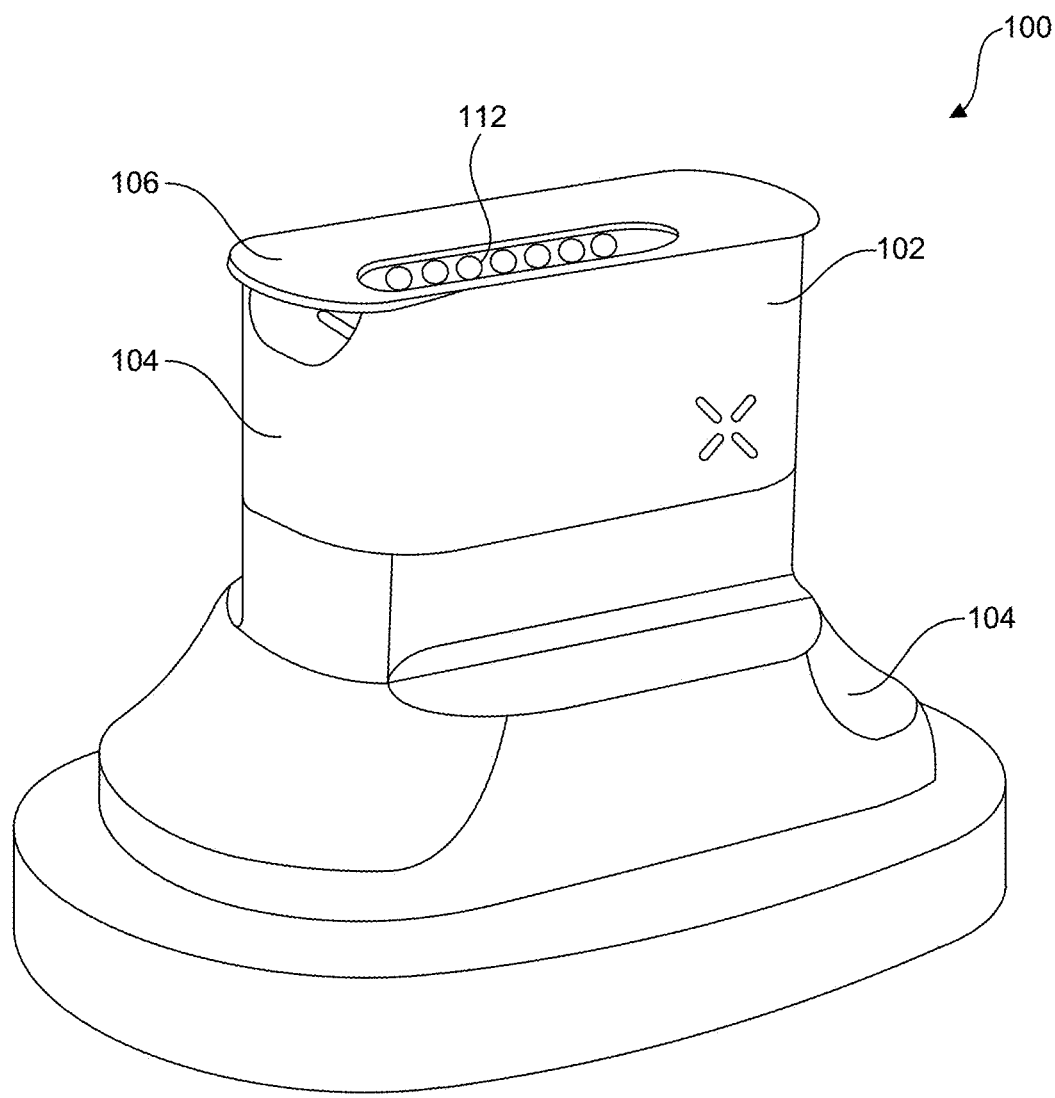
FIG. 39 illustrates a concentrate adaptor consistent with implementations of the current subject matter.

An opening 112 is formed in the top portion of the reservoir top 106 (see FIG. 39). A shape of the opening 112 may generally correspond to the cross-sectional shape of the second inner wall 130. A surface of the top portion of the reservoir top 106 may be angled downward from its outer edge to an outer perimeter of the opening 112, which may direct the concentrate into the interior portion of the reservoir 102. The surface of the top portion of the reservoir top 106 may instead be flat, substantially flat, or angled upward. In an implementation, the surface of the top portion of the reservoir top 106 is not required to be of a constant form (e.g., one portion may be angled and another portion flat). The opening 112 is provided to provide access to an interior portion of the reservoir.

Figure 36:
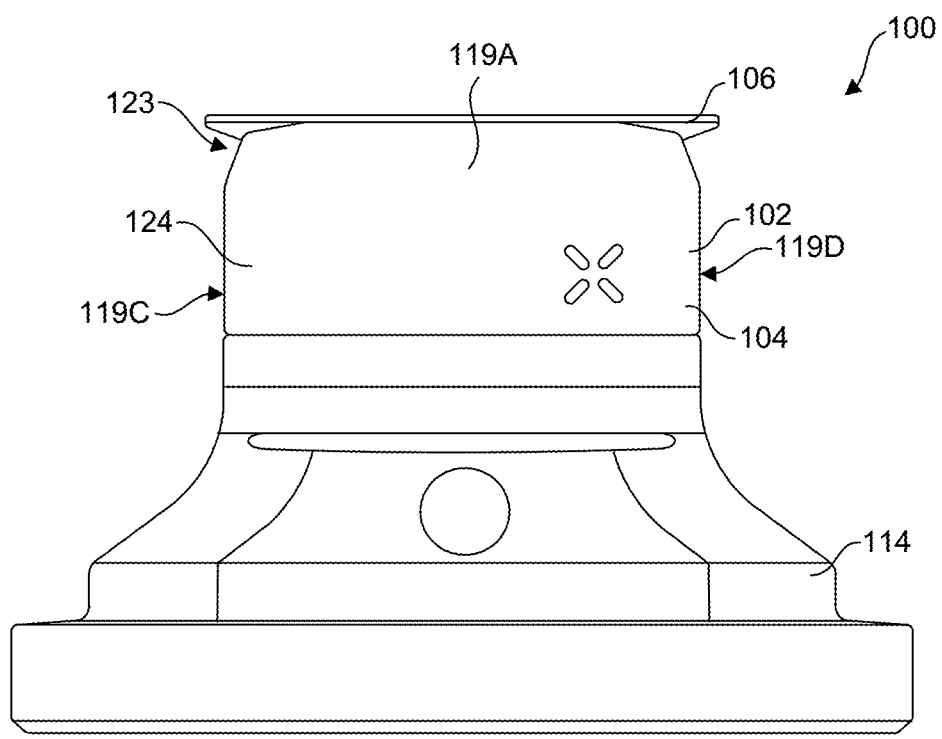
FIG. 36 illustrates a concentrate adaptor consistent with implementations of the current subject matter.
Figure 37:
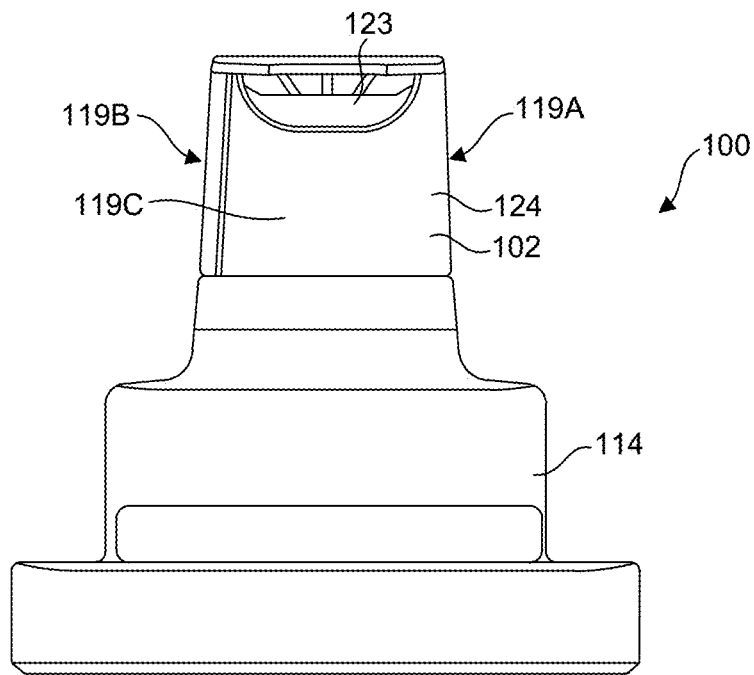
FIG. 37 illustrates a concentrate adaptor consistent with implementations of the current subject matter.
Figure 38:
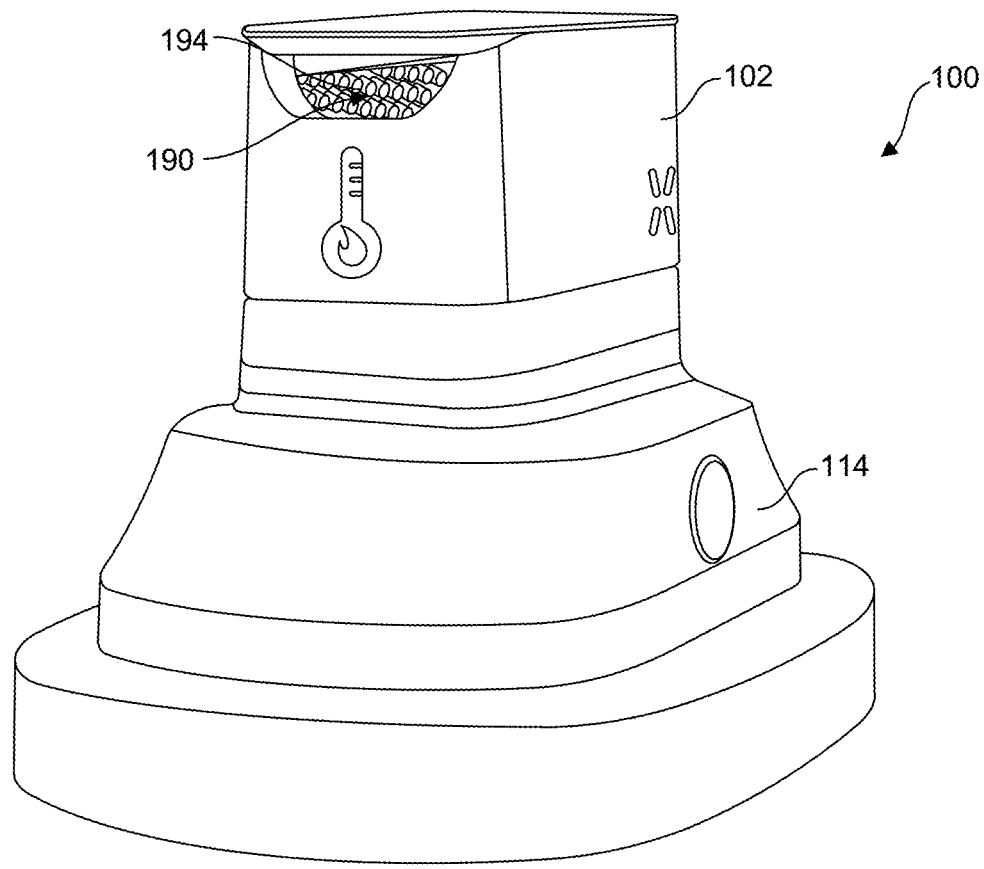
FIG. 38 illustrates a concentrate adaptor consistent with implementations of the current subject matter.

In some implementations, the reservoir 102 includes side wall openings 123 formed at the junction between the reservoir top 106 and the reservoir base 104 along at least the third and fourth sides 119C, 119D (see FIGS. 36-38). The side wall openings 123 may provide an airflow passage for air to flow into and out of the interior volume of the reservoir 102.

As noted above, the reservoir 102 may include the one or more capillary openings 196 (see FIG. 23) and/or capillary channels 194 positioned across all or a portion of the inner side walls of the reservoir 102. In the example shown in FIGS. 36-38, the capillary openings 196 and/or capillary channels 194 may be positioned across only the interior of the first and second sides 119A, 119B (e.g., the long sides).

This configuration may help to maximize heat transfer and heating efficiency of the concentrate, and also help to reduce leaking of the concentrate from the interior portion of the reservoir 102. For example, the third and fourth sides 119C, 119D of the reservoir are shorter than the first and second sides 119A, 119B of the reservoir 102. Because the third and fourth sides 119C, 119D are shorter, the heat transfer from the heating element to the concentrate is less efficient along the third and fourth sides 119C, 119D. Thus, it may be desirable to direct the heated and/or liquefied concentrate towards the first and second sides 119A, 119B, which are longer and have a greater surface area than the third and fourth sides 119C, 119D. Additionally and/or alternatively, it may be desirable for the first and second sides 119A, 119B to be flat and/or otherwise planar, rather than having a curved surface. The longer and/or flatter surfaces may provide more effective surface area to provide better heating to the vaporizable material.

Additionally, in some implementations, the vaporizer device 10 may be held and/or otherwise rest along the first and second sides 119A, 119B (which may be longer and/or flatter than the third and fourth sides 119C, 119D). Since side wall openings 123 may be introduced to the side walls 124 of the reservoir 102, it may be desirable to position the side wall openings 123 along portions of the side walls 124 that are not along the surfaces upon which the vaporizer device 10 rests and are not along the sidewalls having the capillary channels and/or capillary openings to which the concentrate is directed. In other words, it may be desirable for the side wall openings 123 to be positioned along portions of the side walls 124 away from the surfaces upon which the vaporizer device 10 rests or is likely to be held. It may also be desirable to direct the concentrate away from the side walls 124 that include the side wall openings 123 (e.g., towards the capillary openings and/or channels in the first and second sides 119A, 119B). This may help to eliminate or reduce the likelihood that the concentrate will leak out of the side wall openings 123.

In some implementations, positioning the capillary openings 196 and/or the capillary channels 194 along the first and second sides 119A, 119B of the reservoir 102 rather than the third and fourth sides 119C, 119D, helps to improve manufacturability of the reservoir 102 of the concentrate adaptor 100. For example, by removing the capillary openings 196 and/or the capillary channels 194 from the third and fourth sides 119C, 119D, it is less likely that these structures will break during manufacturing, such as at the corners of the reservoir 102.

In some implementations, the shorter third and fourth sides 119C, 119D may be relatively flat, so the third and fourth sides 119C, 119D are spaced from the corresponding side walls of the vessel of the vaporizer device 10 when the concentrate adaptor 100 is coupled to the vaporizer device 10. This allows concentrate to travel between the reservoir 102 and the vessel in the case of a leak, without forming an additional capillary channel.

The base 114 of the concentrate adaptor 100 may be formed from plastic, metal, or another resilient material. For example, the base 114 may be made from an elastomeric material to ensure a sealed fit of the concentrate adaptor 100 within the vessel 12 of the housing 14 of the vaporizer device 10. The base 114 may include one or more coupling elements 170, such as magnets for coupling the base 114 to the vaporizer device 10. In some implementations, the magnets 170 may magnetically couple the base 114 to one or more magnetic elements or materials of the vaporizer device 10. In some implementations, the magnets 170 are positioned along an outer surface of the base 114 (see FIGS. 36-38). In some implementations, the magnets are nested within the base 114, such that the magnets are not exposed (see FIG. 39 and FIG. 49).

Figure 40:
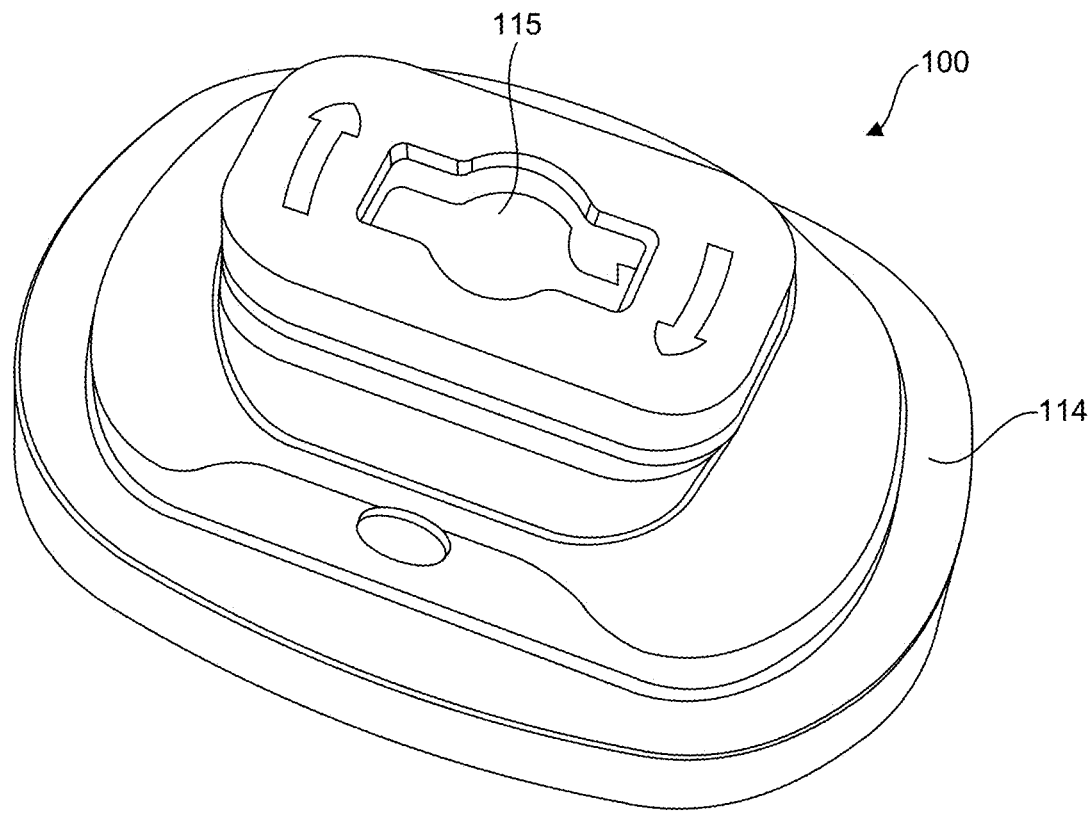
FIG. 40 illustrates a locking mechanism of a concentrate adaptor consistent with implementations of the current subject matter.
Figure 41:
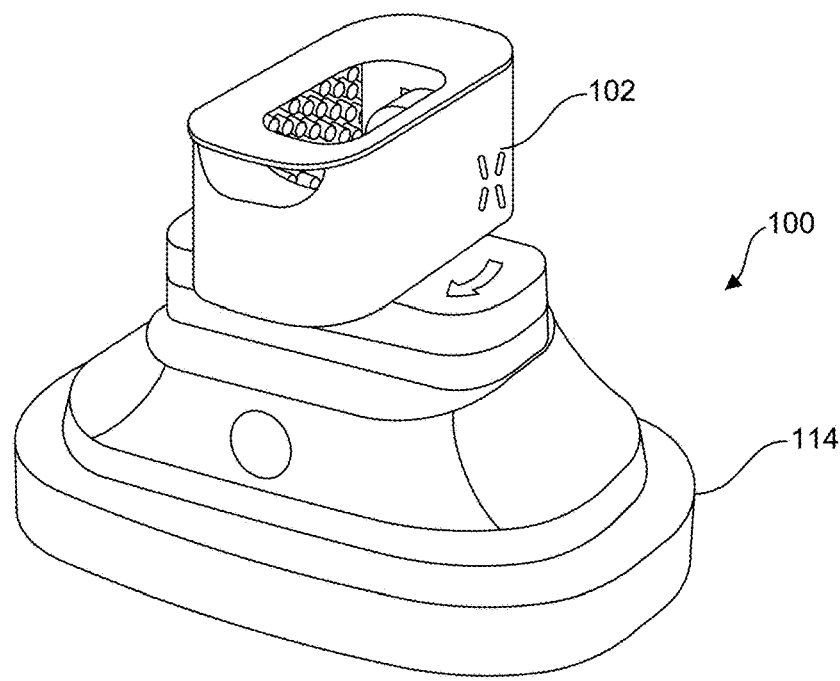
FIG. 41 illustrates a locking mechanism of a concentrate adaptor consistent with implementations of the current subject matter.
Figure 42:
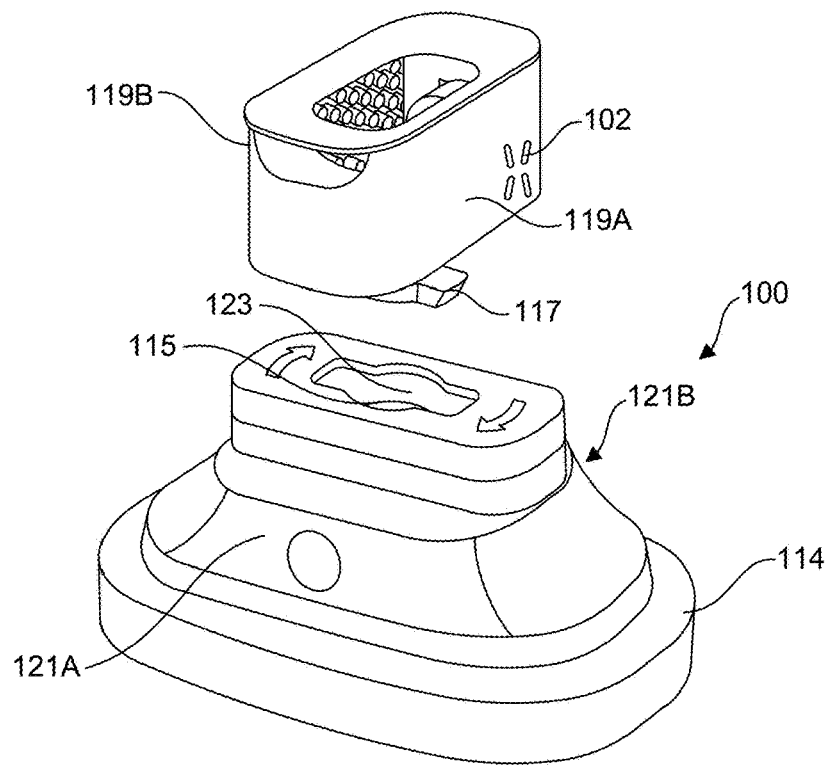
FIG. 42 illustrates a locking mechanism of a concentrate adaptor consistent with implementations of the current subject matter.

The base 114 and/or housing 14 may include one or more mechanisms, for example, snaps, latches, grooves, threading, magnets, clips, quick connect, sliding mechanisms, quarter turn release, friction fit, and the like, configured to position and/or secure the base 114 against the housing 14. The example concentrate adaptor 100 shown in FIGS. 40-42 includes a locking mechanism, such as a quarter turn or other turn release mechanism, snap-fit mechanism, press and release mechanism, and/or another locking mechanism that couples the base 114 to the reservoir 102. In particular, FIG. 40 shows an example of the base 114 consistent with implementations of the current subject matter. The base 114 includes a base opening 115. The base opening 115 may be shaped and/or keyed to correspond to a corresponding connection feature 117 on the reservoir 102. The base opening 115 may be circular, rectangular, triangular, or have another shape. For example, the base opening 115 may include a circular central portion with a rectangular lateral portion positioned on opposing sides of the circular central portion.

The corresponding connection feature 117 may have the same or similar shape as the base opening 115 and may extend from a bottom of the reservoir 102. For example, the connection feature 117 of the reservoir 102 may be configured to fit within the base opening 115 when the connection feature 117 is aligned with the base opening 115. In some implementations, the connection feature 117 is aligned with the base opening 115 when the opposing first and second sides 119A, 119B (e.g., the long sides of the reservoir) of the reservoir 102 are positioned approximately perpendicular to the first and second sides 121A, 121B of the base 114 (e.g., the long sides of the base). To couple (e.g., lock) the reservoir 102 to the base 114, the connection feature 117 may be inserted through the base opening 115, beyond inner walls of the base 114, and be positioned within an interior volume of the base 114. The reservoir 102 may then be rotated (e.g., by approximately 90 degrees) to lock the reservoir 102 into place. When the reservoir 102 is rotated relative to the base 114 (or vice versa), the reservoir 102 may be properly locked into place with respect to the base 114 when the first and second sides 119A, 119B of the reservoir 102 are aligned with and/or are positioned approximately parallel to the first and second sides 121A, 121B of the base 114. To release the reservoir 102 from the base 114, the reservoir 102 may be turned in the opposite direction relative to the base 114.

In some implementations, the connection feature 117 and/or the base 114 includes one or more detents (e.g., ball detents). The detents may provide tactile feedback to the user to indicate when the reservoir 102 is properly coupled to the base 114.

In some implementations, the coupling mechanisms described above, such as the quarter-turn mechanism, helps to ensure that the concentrate adaptor 100 remains intact in case of a leak event, drop, and the like. Generally, when using a concentrate adaptor, a vaporizer device 10 may experience a leak event, in which concentrate leaks out of the reservoir 102. In such instances, a user may not remove the adapter until a certain amount of time has passed, thereby allowing the liquefied concentrate to cool and solidify. This may undesirably seal the reservoir to the base. The coupling mechanisms between the reservoir 102 and the base 114 described herein help to reduce the likelihood that the reservoir will be sealed to the base in the case of a leak. These configurations also help the user to separate the reservoir 102 from the base 114. For example, the force that secures the reservoir 102 to the base 114 is greater than the force it would take to overcome the force of the solidified concentrate. Additionally, the force a user would apply to remove the reservoir 102 from the base 114 is perpendicular to the force that locks the reservoir 102 into the base 114. This minimizes the possibility for breakage of the concentrate adaptor 100.

When the reservoir 102 and the base 114 are connected to one another, the concentrate adaptor 100 may be inserted into the vaporizer device 10 such that the reservoir 102 is fitted within the vessel 12 of the housing 14.

When the reservoir 102 of the concentrate adaptor 100 is fitted within the vessel 12 of the vaporizer device, the base 114 closes and fits over at least a portion of the open end of the housing 14 of the vaporizer device that includes the vessel 12. (see FIG. 43). As previously described, when the heating element 16 is activated, the vaporizer device 10 heats and vaporizes the concentrate when the reservoir 102 is deposited or otherwise placed within the vessel 12.

In some implementations, the cylindrical ledge 118 of the base 114 is spaced apart from the complimentary bottom surface of the housing 14 of the vaporizer device 10 to allow air to flow through a gap between the base 114 and the housing 14 into the vaporizer device and/or the concentrate adaptor. Additionally and/or alternatively, air may flow through a bottom end portion of the base 114.

Figure 43:
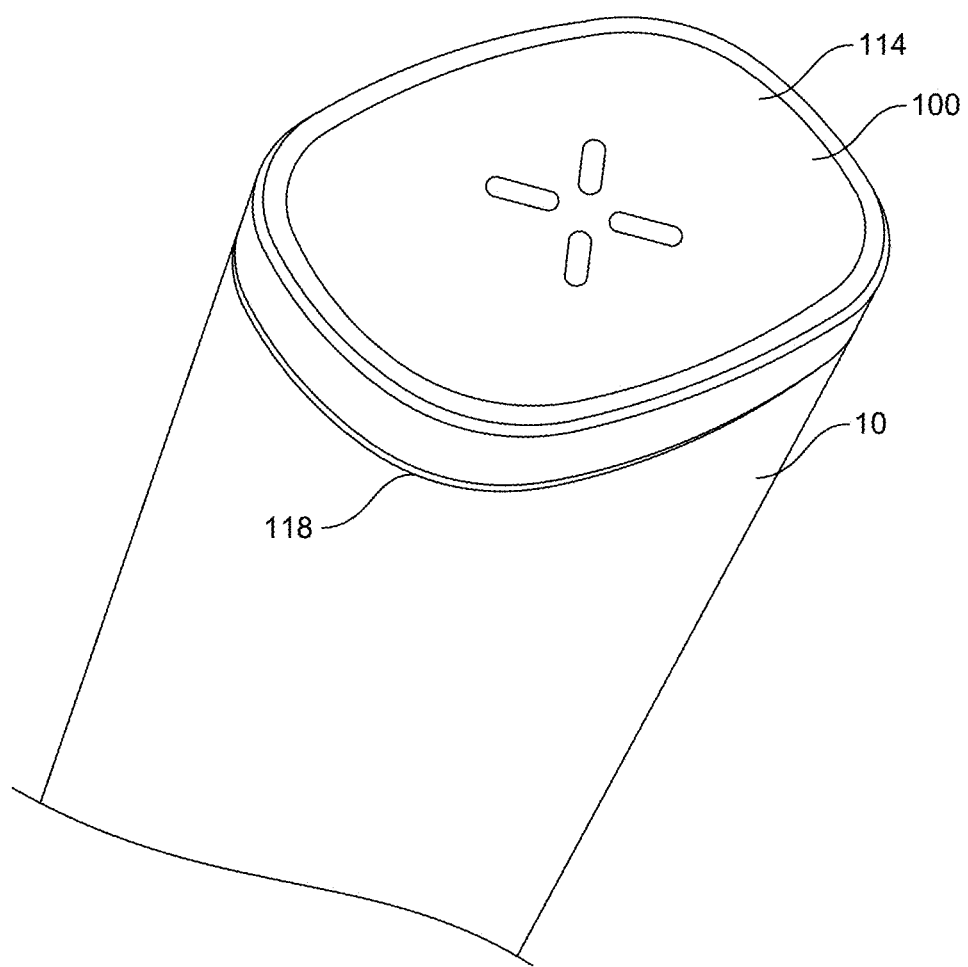
FIG. 43 illustrates a concentrate adaptor coupled to a vaporizer device consistent with implementations of the current subject matter.

FIG. 43 illustrates a bottom end portion of the base 114 of the concentrate adaptor 100. The bottom end portion may include chamfered edges. The bottom end portion may include a bumper that extends along an outer perimeter of the bottom end portion. The bumper may include an elastomeric material, such as thermoplastic polyurethane (TPU), or other materials that provide for shock absorption to limit damage to the vaporizer device 10 when the vaporizer device 10 is dropped and/or contacts a rigid surface.

Figure 44:
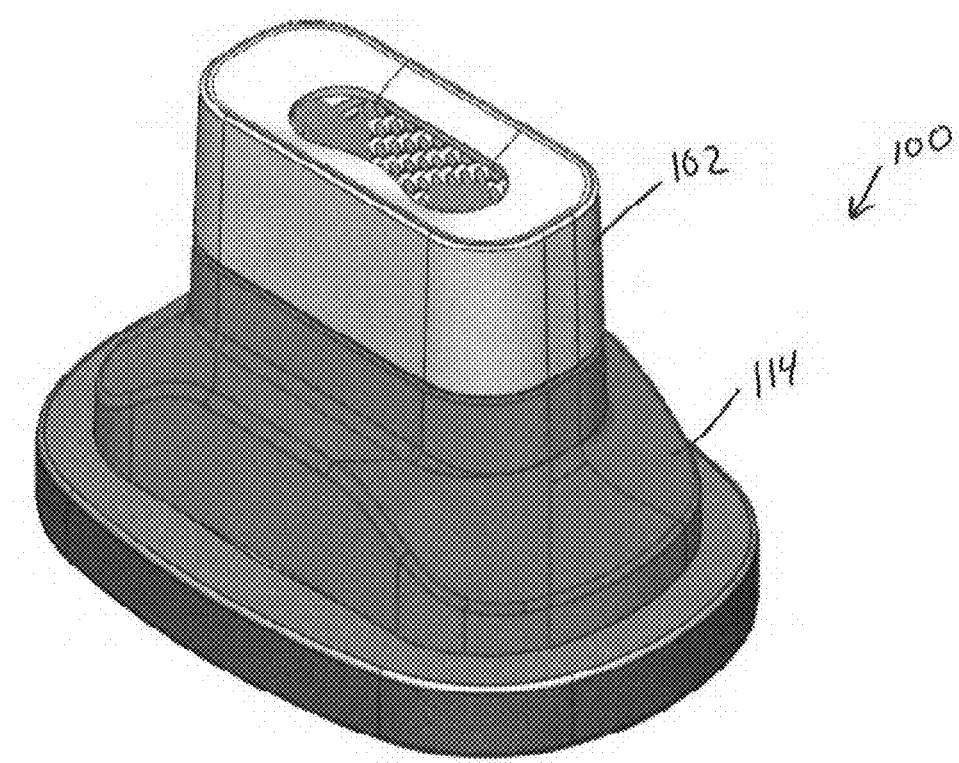
FIG. 44 illustrates an example airflow path in a concentrate adaptor consistent with implementations of the current subject matter.
Figure 45:
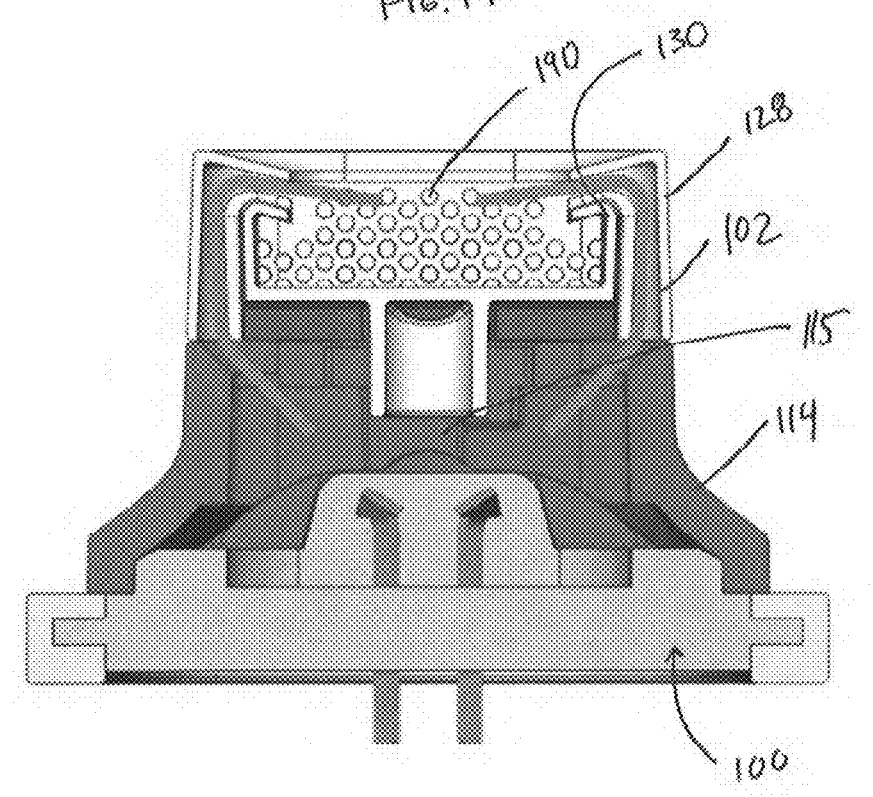
FIG. 45 illustrates an example airflow path in a concentrate adaptor consistent with implementations of the current subject matter.
Figure 46:
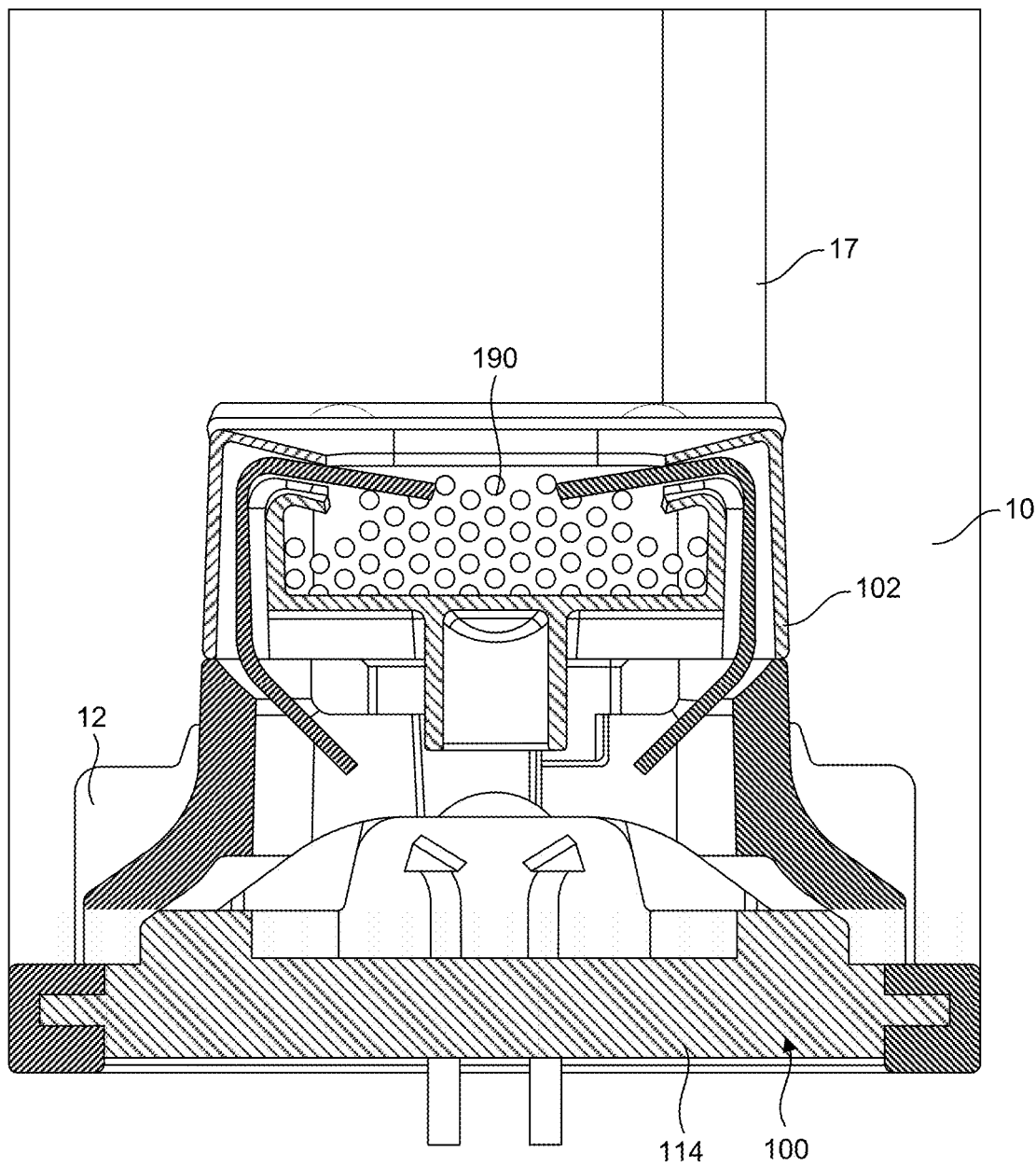
FIG. 46 illustrates an example airflow path in a concentrate adaptor consistent with implementations of the current subject matter.
Figure 47:
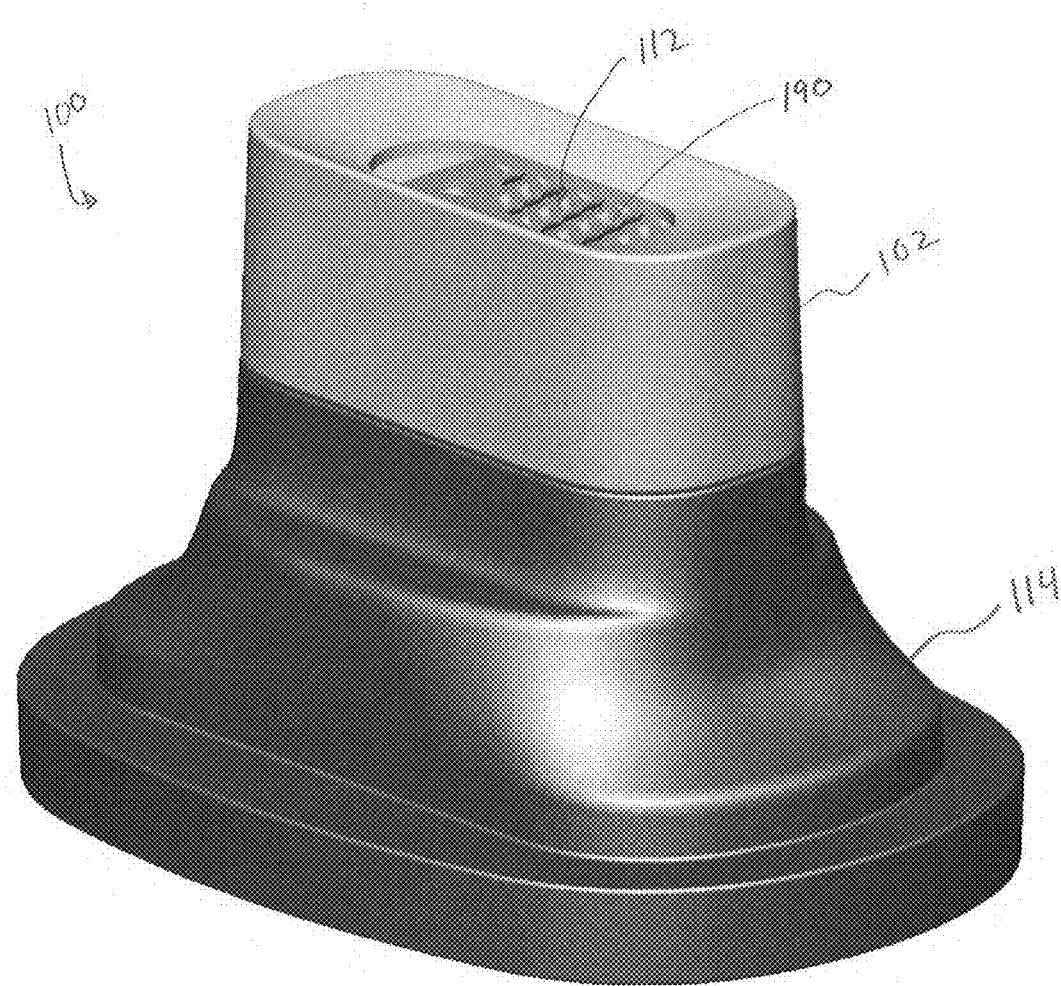
FIG. 47 illustrates an example concentrate adaptor consistent with implementations of the current subject matter.

As noted, the concentrate adaptor 100 may include a plurality of apertures configured to allow for the passage of air. As shown in FIGS. 44-46, for example, the base 114 includes several apertures may include one or more apertures for airflow and/or the gap formed between the base and the housing may provide for airflow. FIGS. 44-46 illustrate example airflow paths through various apertures and profiles formed in the reservoir 102 and/or the base 114. As shown in FIGS. 44-46, the airflow path between the base 114 and the reservoir 102 may be internal, entirely within the concentrate adaptor 100. This configuration may maximize airflow by retaining all (or most) of the air that passes into the concentrate adaptor 100. As shown, the airflow path may extend through the interior portion of the base 114, through an opening in the base 114 (such as the base opening 115), and between outer and inner walls 128, 130 of the reservoir 102, and into the interior portion of the reservoir 102.

FIGS. 47-60 illustrate another example of the concentrate adaptor 100. The concentrate adaptor 100 shown in FIGS. 47-60 includes the same or similar features to the features described above with respect to the concentrate adaptors described herein. For example, the concentrate adaptor 100 may include the reservoir 102, which holds one or more portions of a concentrate, and the base 114, which may accept or connect to the reservoir 102. A user inhaling from the mouthpiece 18 of the vaporizer device 10 causes an intake of air into the reservoir 102. The incoming air mixes with the vapor generated by the vaporization of the contents of the reservoir 102 to form an aerosol. The resulting air flow carries the aerosol out of the reservoir 102 through the opening 112. The aerosol travels through the air path 17 to the mouthpiece 18 where the aerosol is delivered to the user.

Figure 48:
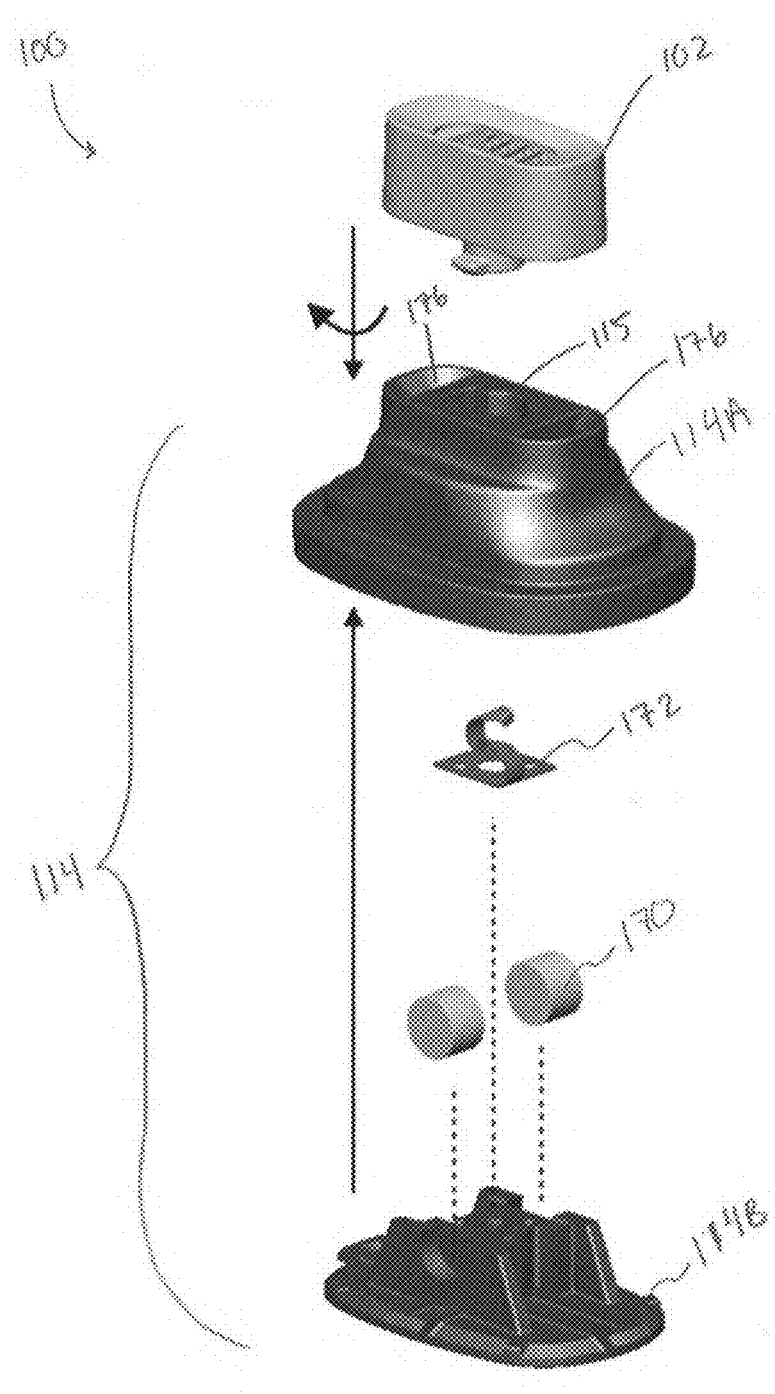
FIG. 48 illustrates an exploded view of an example concentrate adaptor consistent with implementations of the current subject matter.
Figure 49:
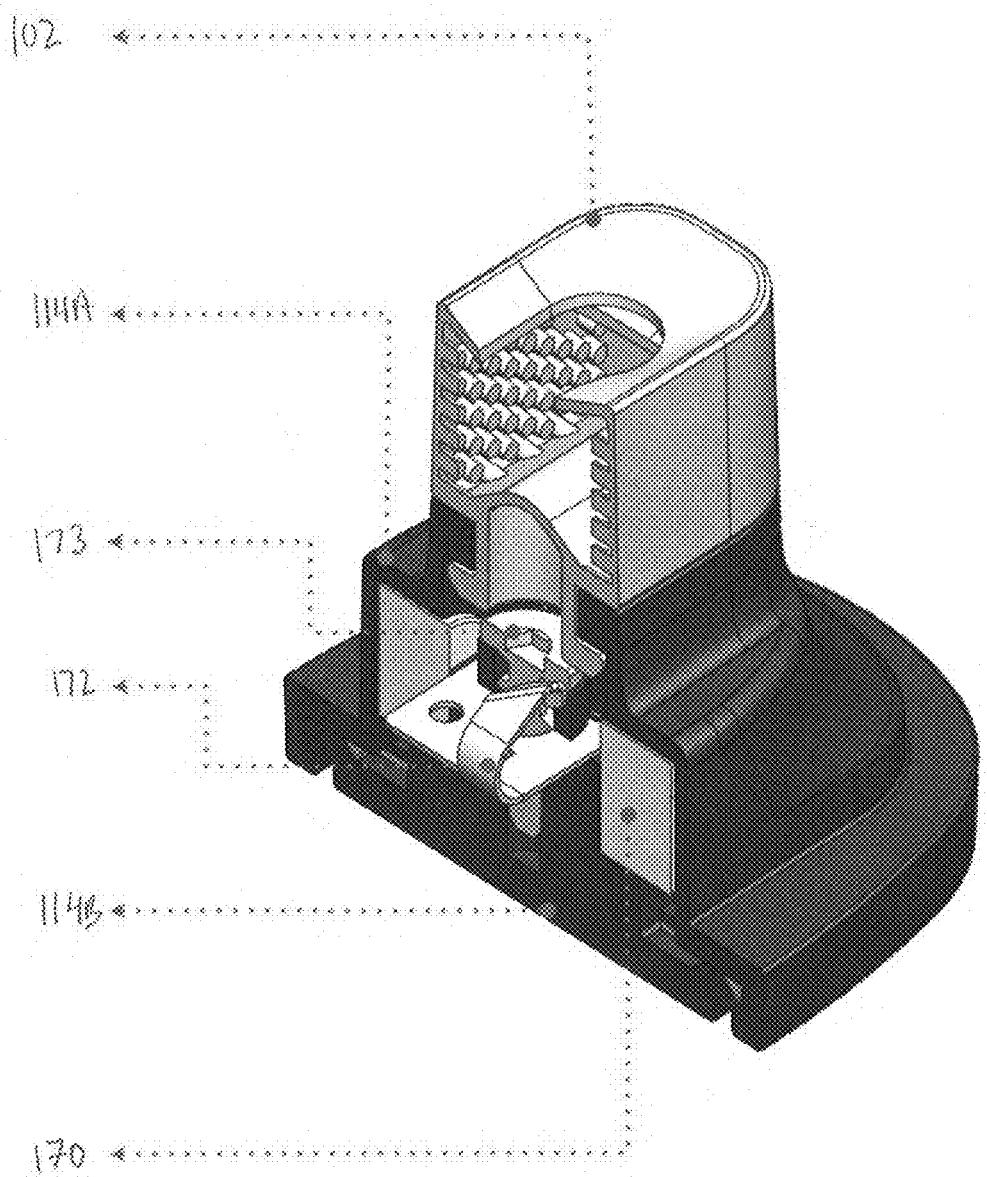
FIG. 49 illustrates cross-sectional view of an example concentrate adaptor consistent with implementations of the current subject matter.
Figure 50:
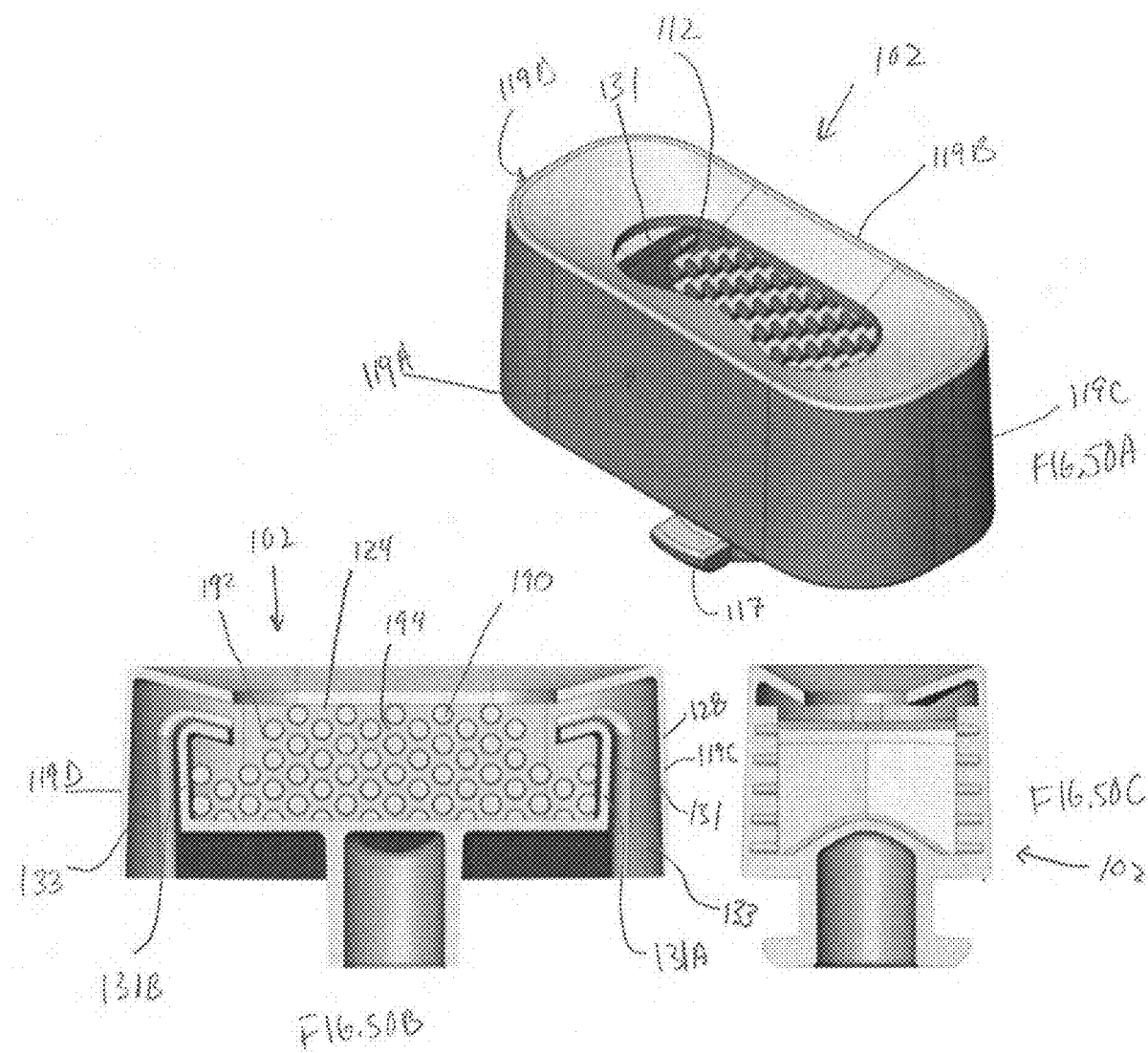
FIG. 50A-50C illustrates an example reservoir of a concentrate adaptor consistent with implementations of the current subject matter.

FIG. 48 illustrates an exploded view of the concentrate adaptor 100 and FIG. 49 illustrates a cross-sectional view of the concentrate adaptor 100, consistent with implementations of the current subject matter. As noted above, the concentrate adaptor 100 includes the reservoir 102 and the base 114. In some implementations, the base 114 may include a base housing 114A, a base floor 114B, a retention member 172, and one or more coupling elements 170. The base floor 114B may support the retention member 172 and/or the one or more coupling elements 170 and may be at least partially positioned within the base housing 114A.

FIGS. 50A-50C illustrate an example of the reservoir 102. The reservoir 102 includes an outer wall 128 that surrounds an interior volume of the reservoir 102. The outer wall 128 may include a first side 119A, a second side 119B, a third side 119C, and a fourth side 119D. An opening 112 is formed in the top portion of the reservoir 102 (see FIGS. 50A-50C). A surface of the top portion of the reservoir 102 may be angled downwardly and/or inwardly from its outer edge to an outer perimeter of the opening 112, which may direct the concentrate into the interior portion of the reservoir 102. The surface of the top portion of the reservoir 102 may instead be flat, substantially flat, or angled upward. In an implementation, the surface of the top portion of the reservoir top 106 is not required to be of a constant form (e.g., one portion may be angled and another portion flat). The opening 112 is provided to provide access to an interior portion of the reservoir.

The reservoir 102 may include the capillary structure 190. For example, as discussed herein, the capillary structure 190 may be formed on interior sidewalls 124 of the reservoir 102 in varying thicknesses such that the variations in thickness form capillary channels 194. The capillary structure 190 may be formed from aluminum, or another metal, ceramic, plastic, polyetheretherketone, or any other suitable material that is resilient and able to withstand the temperature of vaporization. The capillary structure 190 may be coated and/or otherwise finished with a finishing material, including aluminum, anodized aluminum, and/or the like. The capillary structure 190 may be formed using metal injection molding, a combination of metal injection molding and computer numerical control, metal injection co-molding, laser welding, and/or the like. The capillary channels 194 may be formed by metal injection molding, chemical etching, laser drilling, and/or knurling. Individual capillary channels may be formed from metal injection molding or computer numerical control.

The shape and size of the capillary channels 194 may take various forms and combinations of forms, and as noted below, may be positioned across all of the sidewalls 192 of the capillary structure 190, or only some of the side walls 192 of the capillary structure 190, such as across at least a portion of each of the interior sidewalls 124. For example, the capillary channels 194 may be formed as recesses between various geometric configurations or shapes, and the recesses themselves may have various geometric configurations or shapes. Various examples of capillary channels 194 are shown and described herein. Vertically and horizontally oriented channels 194 allow for the concentrate to flow in various directions, providing for improved heating performance as further described below. The capillary structure consistent with implementations of the current subject matter is not limited to the particular configurations shown. Other geometric configurations and/or shapes in various combinations may be used (e.g., ovals, squares, any type of polygon, any type of irregular shape, etc.).

The reservoir 102 may include the one or more capillary channels 194 positioned across all or a portion of the interior sidewalls 124 of the reservoir 102. In the example shown in FIGS. 47-60, the capillary channels 194 may be positioned across the interior of first and second sides 119A, 119B (e.g., the long sides) of the reservoir 102. In some implementations, the capillary channels 194 may be positioned across only the interior of first and second sides 119A, 119B of the reservoir 102. This configuration may help to maximize heat transfer and heating efficiency of the concentrate, and also help to reduce leaking of the concentrate from the interior portion of the reservoir 102. For example, the third and fourth sides 119C, 119D of the reservoir 102 may be shorter than the first and second sides 119A, 119B of the reservoir 102. Because the third and fourth sides 119C, 119D are shorter, the heat transfer from the heating element to the concentrate is less efficient along the third and fourth sides 119C, 119D. Thus, it may be desirable to direct the heated and/or liquefied concentrate towards the first and second sides 119A, 119B, which are longer and have a greater surface area than the third and fourth sides 119C, 119D.

In some implementations, positioning the capillary channels 194 along the interior of the first and second sides 119A, 119B of the reservoir 102 rather than the interior of the third and fourth sides 119C, 119D, helps to improve manufacturability of the reservoir 102 of the concentrate adaptor 100. For example, by removing the capillary channels 194 from the third and fourth sides 119C, 119D, it is less likely that these structures will break during manufacturing, such as at the corners of the reservoir 102.

In some implementations, the shorter third and fourth sides 119C, 119D may be relatively flat, so the third and fourth sides 119C, 119D are spaced from the corresponding side walls of the vessel of the vaporizer device 10 when the concentrate adaptor 100 is coupled to the vaporizer device 10. This allows concentrate to travel between the reservoir 102 and the vessel in the case of a leak, without forming an additional capillary channel.

In some implementations, the reservoir 102 includes an inner wall 131. The inner wall 131 may be positioned internal (e.g., within an interior volume of the reservoir 102) relative to the outer wall 128. The inner wall 131 may be spaced apart from at least a portion of the outer wall 128. For example, the inner wall 131 may be positioned within the interior volume of the reservoir 102 and spaced apart from at least the third and fourth sides 119C, 119D of the reservoir 102. In some implementations, the inner wall 131 includes separate portions 131A, 131B (e.g., two separate portions). Each of the separate portions may be positioned within the interior volume of the reservoir 102 and spaced apart from at least the third and fourth sides 119C, 119D of the reservoir 102. The space between the inner wall 131 and the outer wall 128, such as between the first portion 131A and the third side 119C and/or between the second portion 131B and the fourth side 119D, forms an interior channel 133. The interior channel 133 may define an airflow path within the reservoir 102. For example, the air entering the reservoir may flow through the interior channel into the interior volume of the reservoir 102. The incoming air mixes with the vapor generated by the vaporization of the contents of the reservoir 102 to form an aerosol. The resulting air flow carries the aerosol out of the reservoir 102 through the opening 112.

In some implementations, as described above, the reservoir 102 includes a connection feature 117. The connection feature 117 extends from a bottom surface of the reservoir 102. The connection feature 117 may be used to couple the reservoir 102 to the base 114.

Figure 51:
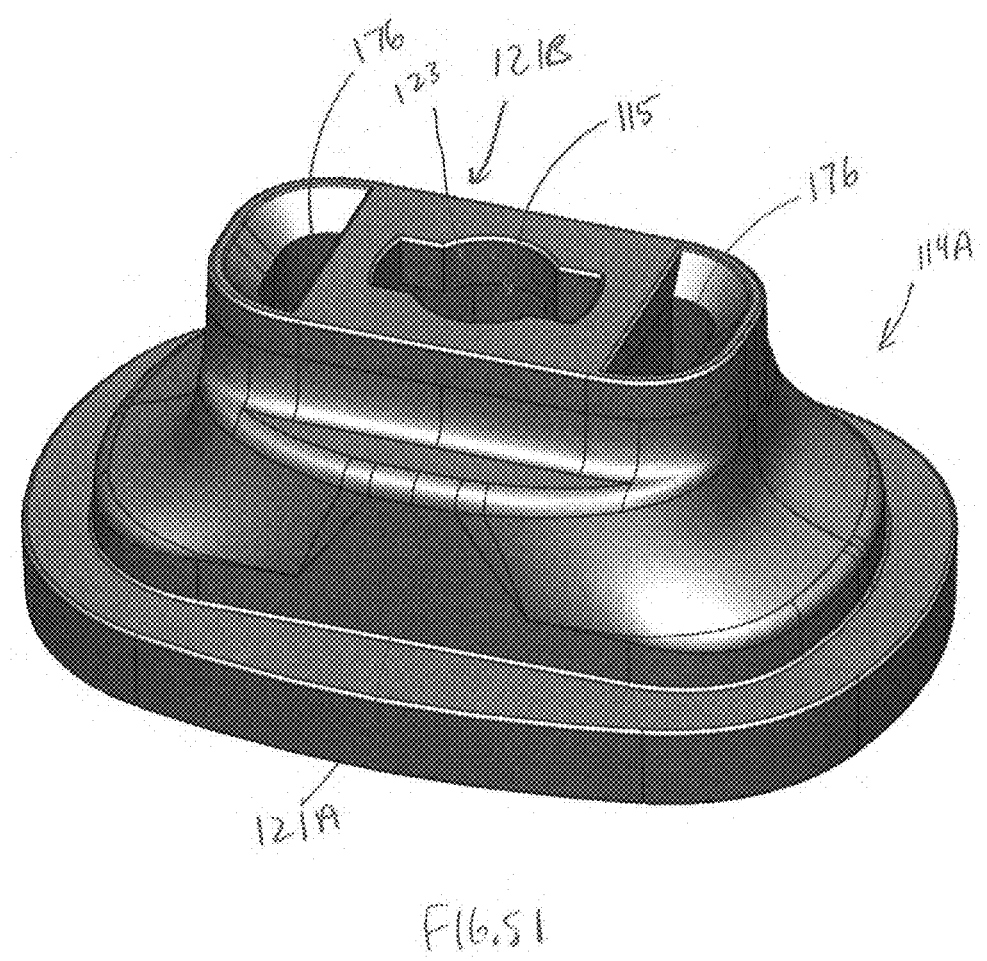
FIG. 51 illustrates an example base housing of a concentrate adaptor consistent with implementations of the current subject matter.

FIGS. 51-52C illustrate an example of the base housing 114A of the base 114. The base 114 (e.g., the base housing 114A) may include one or more mechanisms, for example, snaps, latches, grooves, threading, magnets, clips, quick connect, sliding mechanisms, quarter turn release, friction fit, and the like, configured to position and/or secure the base 114 to the reservoir 102. The example concentrate adaptor 100 shown in FIGS. 47-60 includes a locking mechanism, such as a quarter turn or other turn release mechanism, snap-fit mechanism, press and release mechanism, and/or another locking mechanism that couples the base 114 to the reservoir 102. The locking mechanism described herein may assist in reducing gaps formed between the reservoir 102 and the base 114. The locking mechanism described herein may reduce and/or eliminate movement of the concentrate adaptor 100 within the vaporizer device 10 and/or may reduce and/or eliminate movement of the reservoir 102 relative to the base 114 (or vice versa).

Figure 52A:
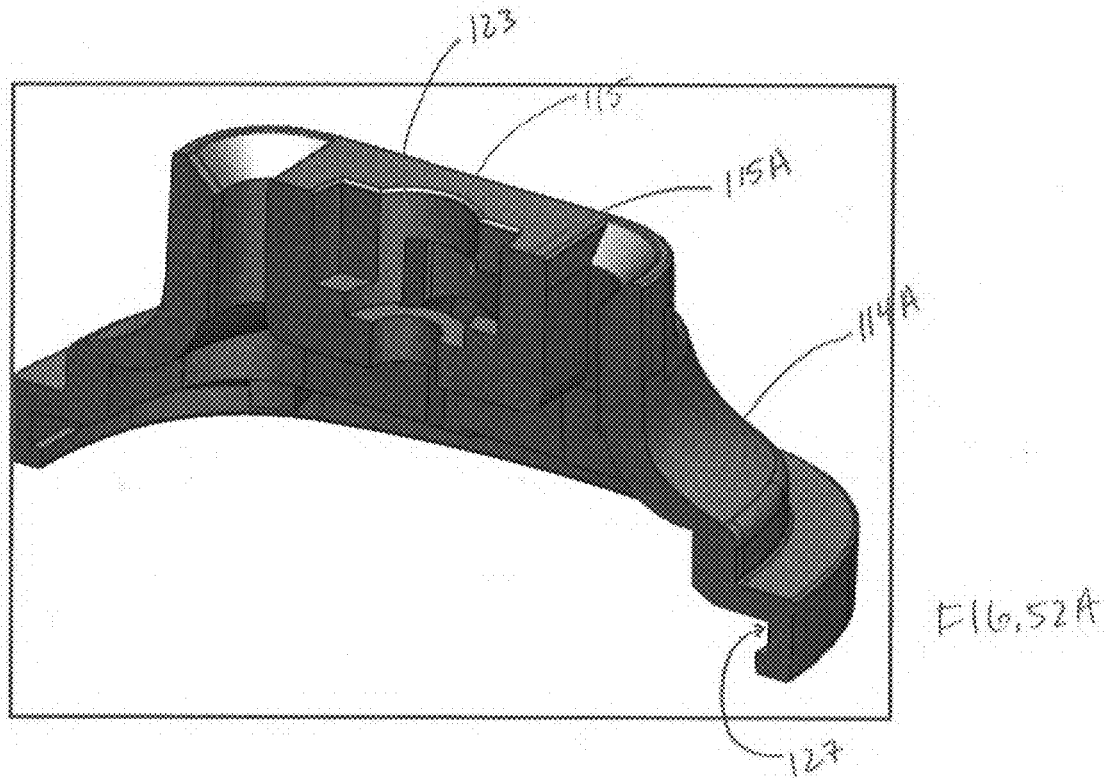
FIG. 52A-52B illustrate cross-sectional view of an example base housing of a concentrate adaptor consistent with implementations of the current subject matter.
Figure 52B:
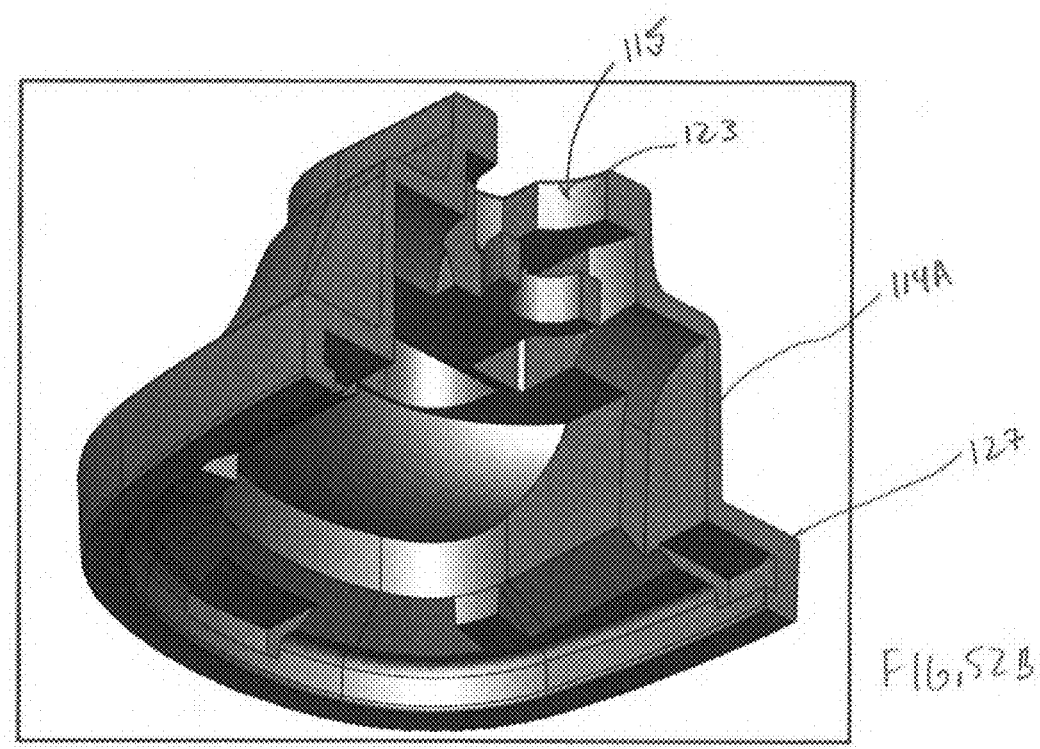

In particular, FIG. 51 shows an example of the base housing 114A consistent with implementations of the current subject matter, and FIGS. 52A and 52B illustrate cross-sectional views of the base housing 114A. The base housing 114A of the base 114 includes a base opening 115. The base opening 115 may be shaped and/or keyed to correspond to the connection feature 117 of the reservoir 102. The base opening 115 may be circular, rectangular, triangular, or have another shape. For example, the base opening 115 may include a circular central portion with a rectangular lateral portion positioned on opposing sides of the circular central portion.

The base opening 115 may have the same or similar shape as the connection feature 117. For example, the connection feature 117 of the reservoir 102 may be configured to fit within the base opening 115 when the connection feature 117 is aligned with the base opening 115. As shown in FIG. 52A, the base housing 114A includes a connection feature receiving portion 115A. The base opening 115 leads to the connection feature receiving portion 115A. The connection feature receiving portion 115A defines a separated interior volume within the base housing 114A that may receive the connection feature 117.

In some implementations, the connection feature 117 is aligned with the base opening 115 when the opposing first and second sides 119A, 119B (e.g., the long sides of the reservoir) of the reservoir 102 are positioned approximately perpendicular to the first and second sides 121A, 121B of the base housing 114A (e.g., the long sides of the base). To couple (e.g., lock) the reservoir 102 to the base 114, the connection feature 117 may be inserted through the base opening 115, beyond inner walls of the base housing 114A, and be positioned within an the connection feature receiving portion 115A. The reservoir 102 may then be rotated (e.g., by approximately 90 degrees or another amount) to lock the reservoir 102 into place. When the reservoir 102 is rotated relative to the base housing 114A (or the base 114) (or vice versa), the reservoir 102 may be properly locked into place with respect to the base 114 when the first and second sides 119A, 119B of the reservoir 102 are aligned with and/or are positioned approximately parallel to the first and second sides 121A, 121B of the base 114. To release the reservoir 102 from the base 114, the reservoir 102 may be turned in the opposite direction relative to the base 114.

In some implementations, the locking mechanisms described above, such as the quarter-turn mechanism, help to ensure that the concentrate adaptor 100 remains intact in case of a leak event, drop, and the like. Generally, when using a concentrate adaptor, a vaporizer device 10 may experience a leak event, in which concentrate leaks out of the reservoir 102. In such instances, a user may not remove the adapter until a certain amount of time has passed, thereby allowing the liquefied concentrate to cool and solidify. This may undesirably seal the reservoir to the base. The locking mechanisms between the reservoir 102 and the base 114 described herein help to reduce the likelihood that the reservoir will be sealed to the base in the case of a leak. These configurations also help the user to separate the reservoir 102 from the base 114. For example, the force that secures the reservoir 102 to the base 114 is greater than the force it would take to overcome the force of the solidified concentrate. Additionally, the force a user would apply to remove the reservoir 102 from the base 114 is perpendicular to the force that locks reservoir 102 into the base 114. This minimizes the possibility for breakage of the concentrate adaptor 100.

Figure 55:
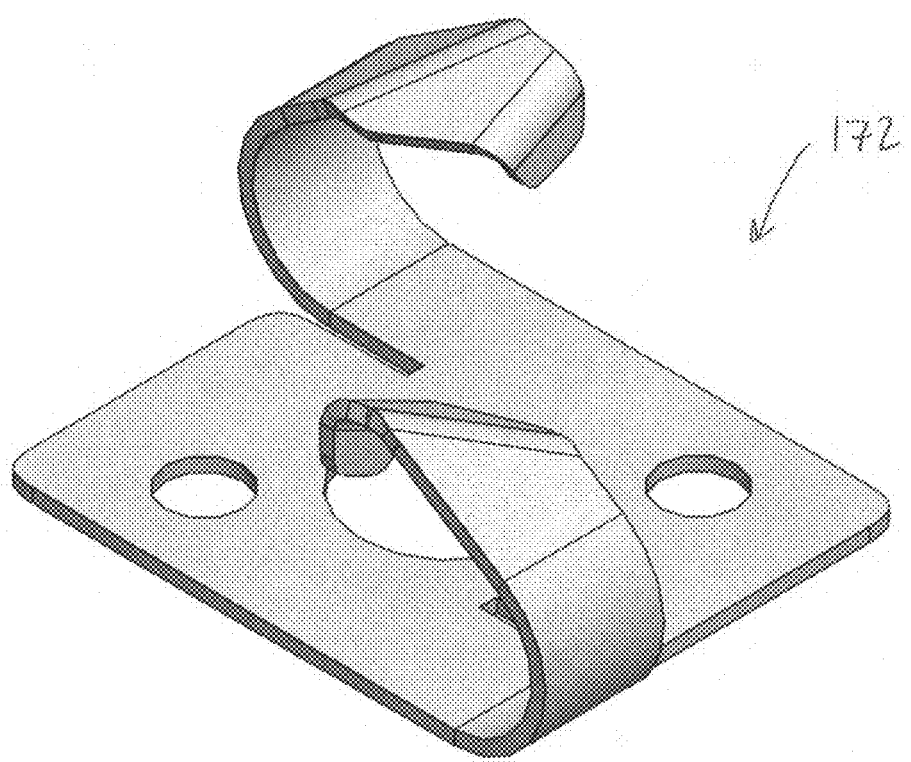
FIG. 55 illustrates an example retention member of a concentrate adaptor consistent with implementations of the current subject matter.
Figure 56:
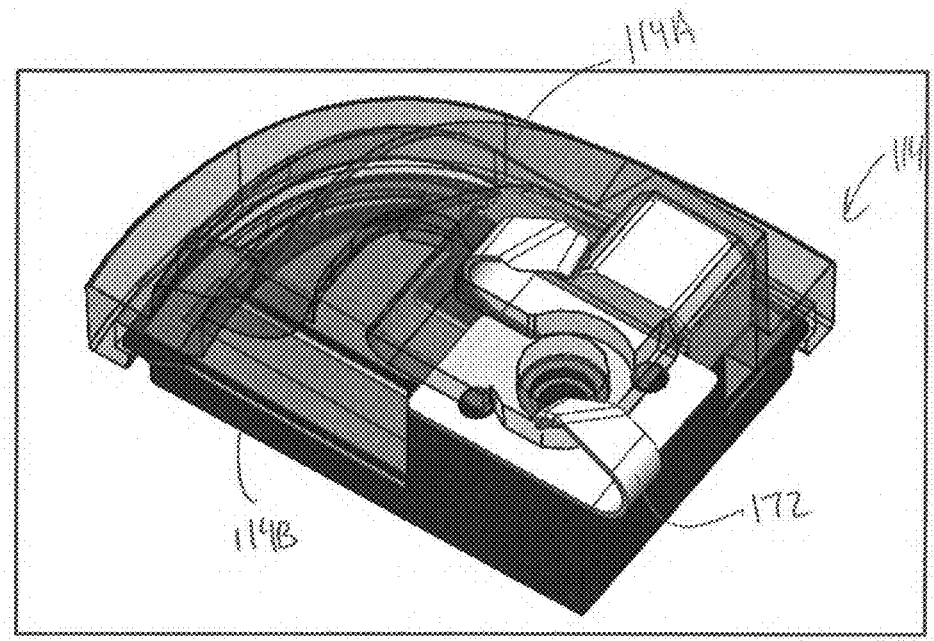
FIG. 56 illustrates an example retention member in a base of a concentrate adaptor consistent with implementations of the current subject matter.
Figure 57:
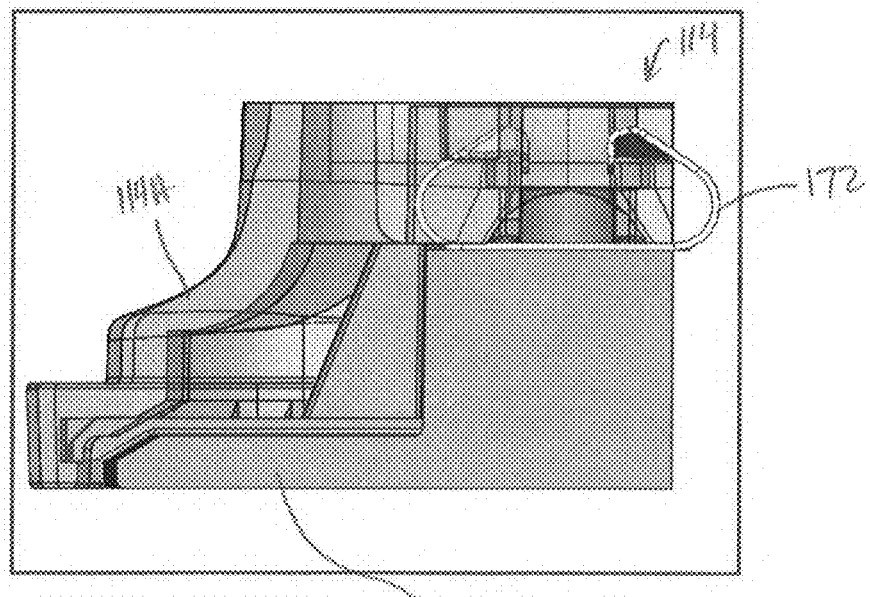
FIG. 57 illustrates an example retention member in a base of a concentrate adaptor consistent with implementations of the current subject matter.

In some implementations, the base 114 includes one or more retention members 172. The retention member 172 may include a spring, such as a detent spring, or other mechanical feature. The retention member 172 may provide tactile feedback to the user to indicate when the reservoir 102 is properly coupled to the base 114 (e.g., the base housing 114A). For example, as the reservoir 102 (and connection feature 117) is turned relative to the base housing 114A, the connection feature 117 may contact (either directly or via another component, such as the fastener 173) the retention member 172. The retention member 172 may provide a counter-force on the connection feature 117. In some implementations, the retention member 172 provide feedback, such as tactile feedback that indicates to the user that the reservoir 102 is locked into place with respect to the base 114. An example of the retention member 172 is shown in FIGS. 55-57 and another example of the retention member 172 is shown in FIGS. 63-66 and FIGS. 72-78.

Referring to FIGS. 52A and 52B, the base housing 114A may include a slot 127. The slot 127 may receive and/or otherwise couple to the base floor 114B. For example, a portion of the base floor 114B may slide into, snap into, and/or otherwise be retained within the slot 127.

Figure 53:
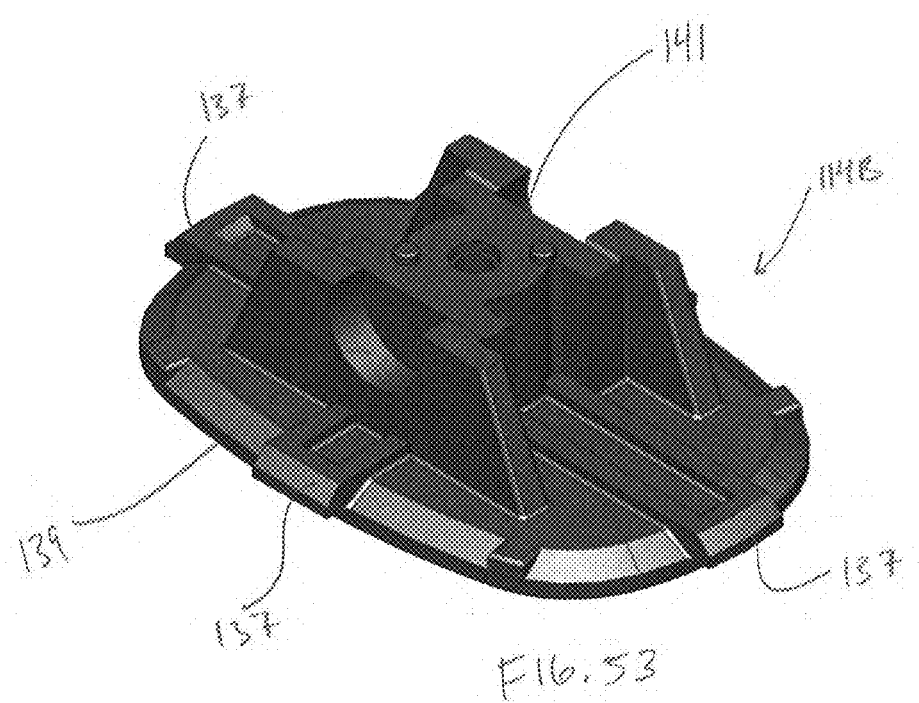
FIG. 53 illustrates an example base floor of a concentrate adaptor consistent with implementations of the current subject matter.
Figure 54:
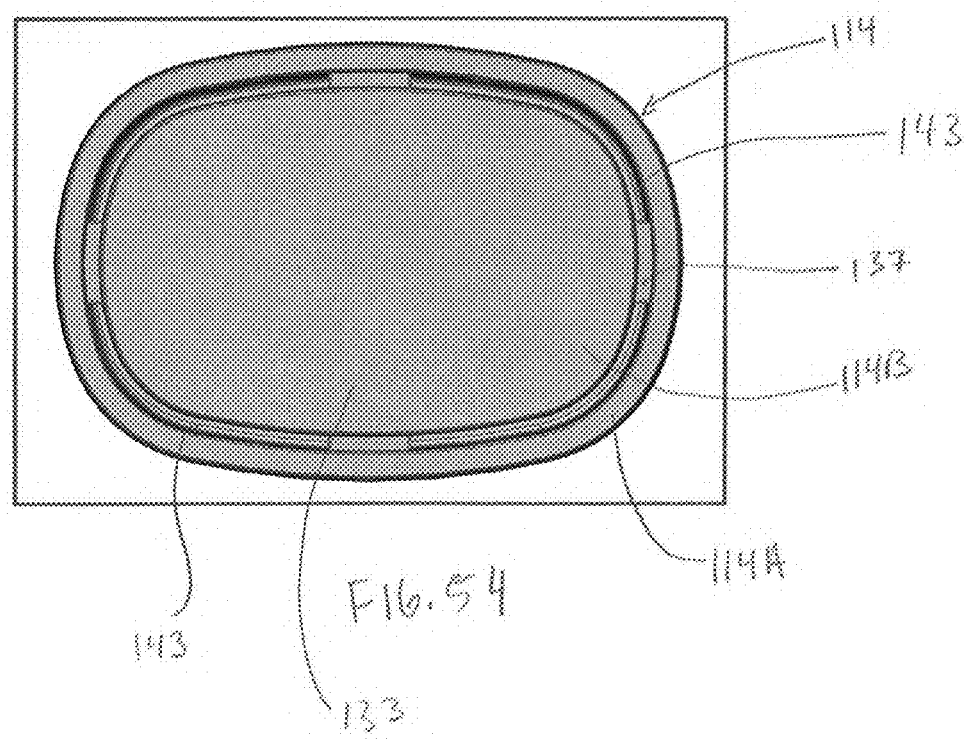
FIG. 54 illustrates an example base floor of a concentrate adaptor consistent with implementations of the current subject matter.

FIGS. 53 and 54 illustrate an example of the base floor 114B of the base 114. The base floor 114B includes a bottom surface 135, a base floor connector 137, a coupling element receiver 139, and a retention member support 141.

The base floor connector 137 may extend radially outwardly from a base of the base floor 114B. The base floor connector 137 may extend about at least a portion of the base floor 114B. The base floor connector 137 may include at least four base floor connectors 137. In other implementations, the base floor connector 137 includes at least one, two, three, five, six, seven, eight, or more base floor connectors 137. Each of the base floor connectors 137 may be spaced apart from one another about a perimeter of the base floor 114B. The base floor connector 137 may secure the base floor 114B to the base housing 114A. For example, the base floor connector 137 may slide into, snap into, and/or otherwise be positioned within the slot 127 of the base housing 114A. In some implementations, the base floor connector 137 may permanently secure the base floor 114B to the base housing 114A. The base floor connector 137 also spaces the bottom surface 135 from a bottom of the base housing 114A to define bottom base opening 143 therebetween. The bottom base opening 143 forms an inlet that allows air to flow into the base 114 of the concentrate adaptor 100. A size (e.g., a length) of the bottom base opening 143 formed between the bottom surface 135 and the bottom of the base housing 114A defines the surface area of the initial air inlet of air passing into the concentrate adaptor 100, improving draw resistance and/or overall airflow within the concentrate adaptor 100 and vaporizer device 10.

Referring to FIG. 53, the base floor 114B may include the coupling element receiver 139. The coupling element receiver 139 may be shaped to receive the one or more coupling elements 170. For example, the shape of the coupling element receiver 139 may correspond to the shape of the one or more coupling elements 170. As shown, the coupling element receiver 139 may have a curved shape to correspond to the curved shape of the one or more coupling elements 170. The corresponding shapes of the coupling element receiver 139 and the one or more coupling elements 170 more securely retains the coupling element 170 within the coupling element receiver 139. The coupling element receiver 139 may support the one or more coupling elements 170 within the interior volume of the base 114.

Also referring to FIG. 53, the base floor 114B may include the retention member support 141. The retention member support 141 may support and/or retain the retention member 172 within the base 114.

Figure 63:
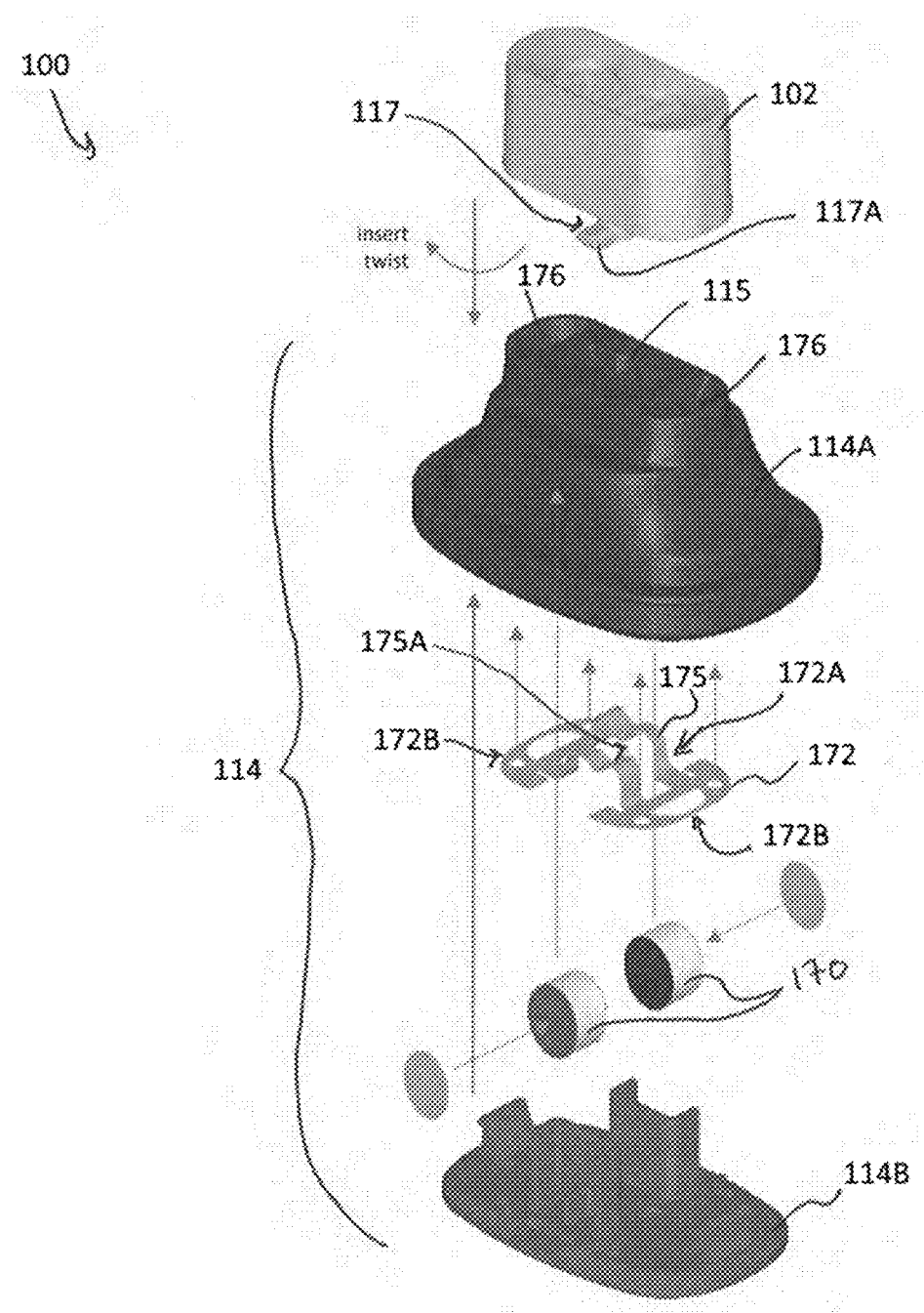
FIG. 63 illustrates an exploded view of an example concentrate adaptor consistent with implementations of the current subject matter.
Figure 64:
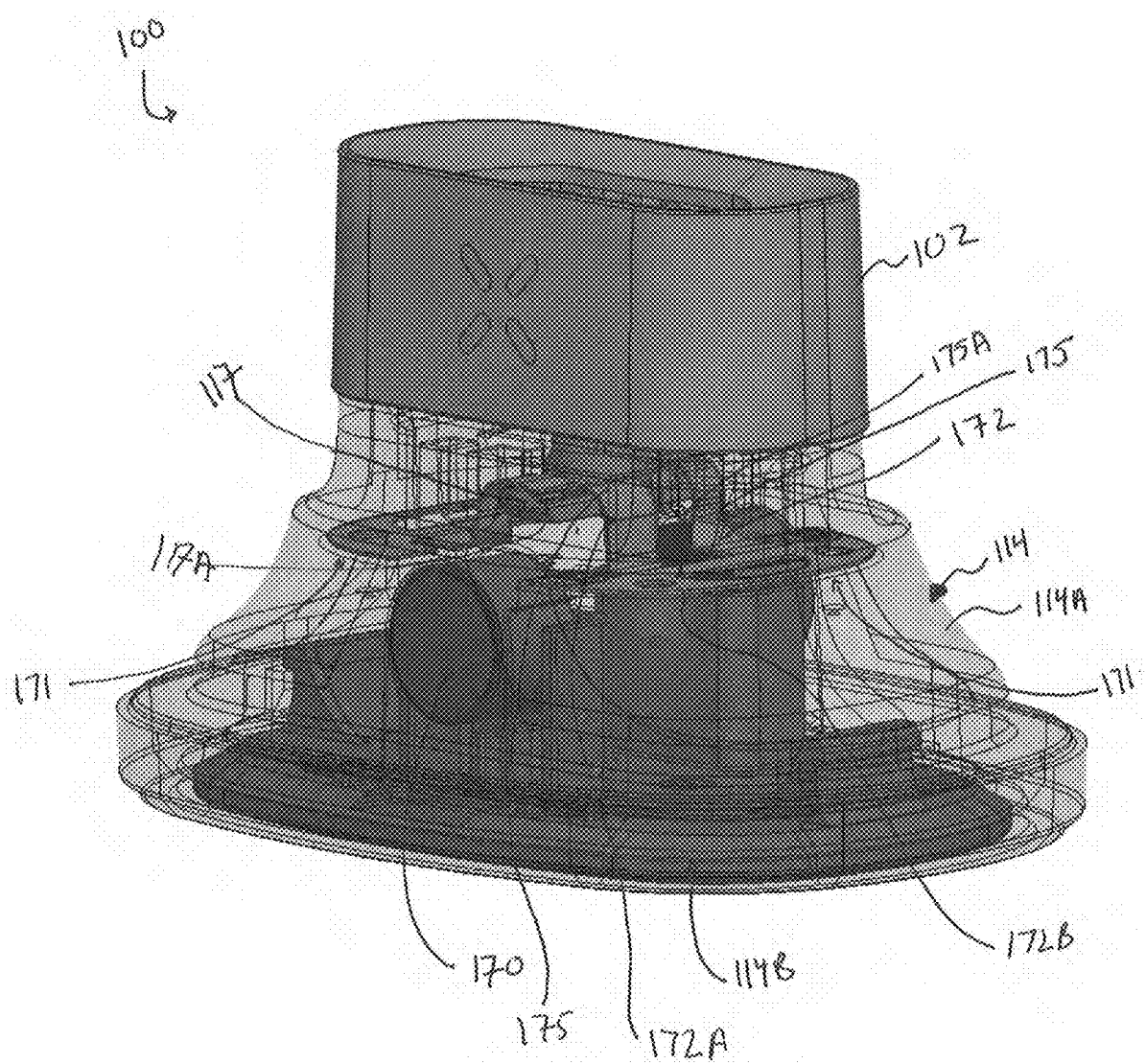
FIG. 64 illustrates a perspective view of a concentrate adaptor consistent with implementations of the current subject matter.

FIGS. 63-66 illustrate another example of the retention member 172. For example, FIG. 63 illustrates an exploded view of the concentrate adaptor 100, FIG. 64 illustrates an example of the concentrate adaptor 100 with the base housing 114A shown as transparent for clarity, and FIGS. 65-66 are cross-sectional views of the concentrate adaptor 100, consistent with implementations of the current subject matter. As noted above, the concentrate adaptor 100 includes the reservoir 102 and the base 114. In some implementations, the base 114 may include a base housing 114A, a base floor 114B, a retention member 172, and one or more coupling elements 170. In the example concentrate adaptor 100 shown in FIGS. 63-66, the base housing 114A supports the retention member 172 and the base floor 114B supports the one or more coupling elements 170. The base floor 114B may be at least partially positioned within the base housing 114A. The base housing 114A may receive and/or otherwise couple to the base floor 114B. For example, a portion of the base floor 114B may slide into, snap into, and/or otherwise be retained within the base housing 114A.

As noted above with respect to FIGS. 47-60, the base 114 (e.g., the base housing 114A) may include one or more mechanisms, for example, snaps, latches, grooves, threading, magnets, clips, quick connect, sliding mechanisms, quarter turn release, friction fit, and the like, configured to position and/or secure the base 114 to the reservoir 102. Similar to the example concentrate adaptor 100 shown in FIGS. 47-60, the concentrate adaptor 100 shown in FIGS. 63-66 includes a locking mechanism, such as a quarter turn or other turn release mechanism, snap-fit mechanism, press and release mechanism, and/or another locking mechanism that couples the base 114 to the reservoir 102. The locking mechanism described herein may assist in reducing gaps formed between the reservoir 102 and the base 114, which in turn seal the airflow path formed within the concentrate adaptor 100 (e.g., between the base 114 and the reservoir 102). The locking mechanism described herein may reduce and/or eliminate movement of the concentrate adaptor 100 within the vaporizer device 10 and/or may reduce or eliminate movement of the reservoir 102 relative to the base 114 (or vice versa).

Referring to FIG. 63, the locking mechanism includes the connection feature 117 (which extends from a bottom of the reservoir 102 and includes two opposing tabs 117A) and the retention member 172. The retention member 172 shown in FIGS. 63-66 helps to secure the reservoir 102 to the base 114 via a quarter turn locking mechanism, for example. The retention member 172 includes a central retention portion 172A and base retention portions 172B positioned on opposite sides of the central retention portion 172A. The base retention portions 172B are configured to rest on or otherwise be coupled to inner platforms 171 of the base housing 114A of the base 114. The inner platforms 171 are configured to support each of the base retention portions 172B of the retention member 172.

In some implementations, the base retention portions 172B may be positioned such that the central retention portion 172A is under compression. For example, the engagement between the base retention portions 172B with the inner platforms 171 may provide a compressive force to either or both sides of the central retention portion 172A, which is raised with respect to the base retention portions 172B. In some implementations, the central retention portion 172A of the retention member 172 applies a force towards the base 114 (e.g., towards the base floor 114B) and/or away from the reservoir 102 (e.g., away from the connection feature 117).

As shown in FIGS. 63-66, the central retention portion 172A may include two central retention members 175. The central retention members 175 may be spaced apart by a retention opening 175A. When the reservoir 102 is coupled with the base 114, the connection feature 117 (with the tabs 117A) passes from an outer side of the retention member 172, at least partially through the retention opening 175A, and at least partially to an inner side of the retention member 172. Thus, as the reservoir 102 is turned to lock into place with respect to the base 114, the tabs 117A of the connection feature 117 slide along the inner side of the retention member 117 such that a surface of the tabs 117A (e.g., an outer surface) contacts a corresponding surface of the retention member 172, such as a surface of one or more of the central retention members 175 (e.g., an inner surface). As a result, the retention member 172, such as at the central retention portion 172A applies a force or other load on (or away from) the reservoir 102 that pulls the reservoir 102 into the proper position relative to the base 114 (e.g., such that the long sides of the reservoir align with the long sides of the base and/or the short sides of the reservoir align with the short sides of the base). This configuration may help to reduce air gaps between the reservoir 102 and the base 114 and may help to seal the airflow path within the concentrate adaptor 100.

Figure 58:
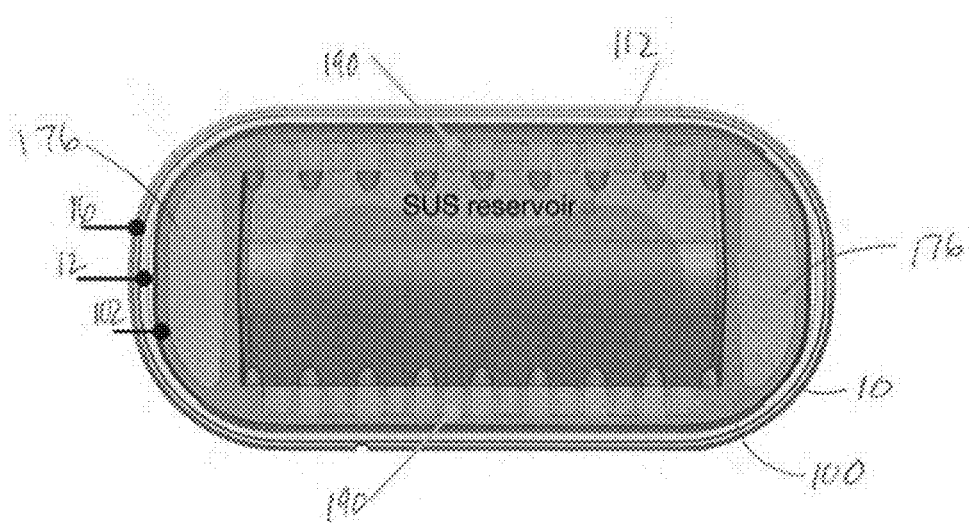
FIG. 58 illustrates a cross-sectional view of a concentrate adaptor inserted into a vaporizer device consistent with implementations of the current subject matter.

Referring to FIGS. 58-60, FIGS. 58-60 illustrate example cross-sectional views of the vaporizer device 10 and the concentrate adaptor 100, with the concentrate adaptor 100 inserted into the vaporizer device 10 such that the reservoir 102 is fitted within the vessel 12 of the housing 14. FIGS. 59-60 illustrate example airflow paths 153 through various apertures and profiles formed in the reservoir 102, the base 114 and/or the vessel 12. As shown in FIGS. 58-60, air from outside the concentrate adaptor 100 may enter the interior of the concentrate adaptor 100 via the bottom base opening 143 and through a channel formed between the base housing 114A and the base floor 114B. Once air enters the concentrate adaptor 100, such as into the interior of the base 114, the airflow path 153 between the base 114 and the reservoir 102 may be internal, entirely within the concentrate adaptor 100 and/or vaporizer device 10. For example, as noted above, the reservoir 102 may be locked into place with respect to the base 114. Locking the reservoir 102 into place with respect to the base 114 may seal the reservoir 102 with the base 114 to form a sealed internal volume of the concentrate adaptor 100. Thus, the airflow path 153 may be contained entirely within the concentrate adaptor 100 until the air exits the concentrate adaptor 100 via an outlet, such as the opening 112 of the reservoir 102. This configuration may maximize airflow by retaining all (or most) of the air that passes into the concentrate adaptor 100 and along the airflow path 153.

For example, air may flow into the concentrate adaptor 100 through the bottom base opening 143 and along the airflow path 153. The airflow path 153 may extend from the bottom base opening 143 (e.g., an inlet), through the interior portion of the base 114 (e.g., between the base housing 114A and the base floor 114B). The airflow path 153 may extend through one or more outlets 176 (e.g., two or more outlets 176 positioned on opposing sides of the base opening 115) in the base 114 (see FIG. 52A). The airflow path 153 may then extend from the outlets 176 into the reservoir 102, such as along channel 133 of the reservoir 102 formed between the outer and inner walls 128, 131. In some implementations, the airflow path may then extend into the interior portion of the reservoir 102. The incoming air mixes with the vapor generated by the vaporization of the contents of the reservoir 102 to form an aerosol. For example, the vaporizable material may be heated, and travel towards the sides of the reservoir 102 via the capillary structure 190. The incoming air may mix with the heated vaporizable material from within the capillary structure 190. The resulting air flow carries the aerosol out of the reservoir 102 through the opening 112. The aerosol travels through the air path 17 to the mouthpiece 18 where the aerosol is delivered to the user.

FIGS. 61A-61C illustrate another example of the reservoir 102, consistent with implementations of the current subject matter. The reservoir 102 shown in FIGS. 61A-61C may include the same or similar features or components to the features described above with respect to the concentrate adaptors shown in FIGS. 1-60.

For example, the reservoir 102 includes an outer wall 128 that surrounds an interior volume of the reservoir 102. The reservoir 102 includes an opening 112 formed in the top portion of the reservoir 102. A surface of the top portion of the reservoir 102 may be flat from its outer edge to an outer perimeter of the opening 112, which may direct the concentrate into the interior portion of the reservoir 102.

The reservoir 102 may include the capillary structure 190. For example, as discussed above with respect to FIGS. 1-60, the capillary structure 190 may be formed on interior sidewalls of the reservoir 102 in varying thicknesses such that the variations in thickness form capillary channels 194. The shape and size of the capillary channels 194 may take various forms and combinations of forms, and as noted below, may be positioned across all of the sidewalls of the capillary structure 190, or only some of the side walls of the capillary structure 190, such as across at least a portion of each of the interior sidewalls. For example, the capillary channels 194 may be formed as recesses between various geometric configurations or shapes (such as circles or cylinders), and the recesses themselves may have various geometric configurations or shapes. Vertically and horizontally oriented channels 194 allow for the concentrate to flow in various directions, providing for improved heating performance.

The example reservoir 102 shown in FIGS. 61A-61C may be formed by coupling two halves of the reservoir 102. For example, the reservoir 102 may include a first half and a second half. The first half and the second half may be positioned on opposite sides of a lateral axis 145. The first half and the second half of the reservoir 102 may be coupled along coupling line 145A formed in the reservoir 102 along the lateral axis 145. For example, the first half and the second half of the reservoir 102 may be welded, adhered, fastened, and the like. This configuration helps to improve manufacturability of the reservoir 102.

FIGS. 62A-62C illustrate another example of the reservoir 102, consistent with implementations of the current subject matter. The reservoir 102 shown in FIGS. 62A-62C may include similar features to the features described above with respect to the concentrate adaptors shown in FIGS. 1-61C.

For example, the reservoir 102 includes an outer wall 128 that surrounds an interior volume of the reservoir 102. The reservoir 102 includes an opening 112 formed in the top portion of the reservoir 102. A surface of the top portion of the reservoir 102 may be angled downwardly and/or inwardly from its outer edge to an outer perimeter of the opening 112, which may direct the concentrate into the interior portion of the reservoir 102.

The reservoir 102 may include the capillary structure 190. For example, as discussed above with respect to FIGS. 1-61C, the capillary structure 190 may be formed on interior sidewalls of the reservoir 102 in varying thicknesses such that the variations in thickness form capillary channels 194. In some implementations, such as the example reservoir 102 shown in FIGS. 62A-62C, the capillary structure 190 may be exposed external to the reservoir 102. The shape and size of the capillary channels 194 may take various forms and combinations of forms, and as noted below, may be positioned across all of the sidewalls of the capillary structure 190, or only some of the side walls of the capillary structure 190, such as across at least a portion of each of the interior sidewalls. For example, the capillary channels 194 may be formed as slots formed within the outer wall 128 of the reservoir 102. The capillary channels 194 shown in FIGS. 62A-62C may be chemically etched and/or sealed (e.g., along an exterior surface exposed external to the reservoir) via laser welding.

FIGS. 67-71 illustrate another example of the reservoir 102, consistent with implementations of the current subject matter. The reservoir 102 shown in FIGS. 67-71 may include the same or similar features and/or components to the features described above with respect to the concentrate adaptors shown in FIGS. 1-66.

For example, the reservoir 102 includes an outer wall that surrounds an interior volume of the reservoir 102. The reservoir 102 includes an opening 112 (see FIG. 67) formed in the top portion of the reservoir 102. A surface of the top portion of the reservoir 102 may direct the concentrate into the interior portion of the reservoir 102.

The reservoir 102 may include the capillary structure 190. For example, as discussed above with respect to FIGS. 1-66, the capillary structure 190 may be formed on interior sidewalls of the reservoir 102 in varying thicknesses such that the variations in thickness form capillary channels 194. The shape and size of the capillary channels 194 may take various forms and combinations of forms, and may be positioned across all of the sidewalls of the capillary structure 190, or only some of the side walls of the capillary structure 190, such as across at least a portion of each of the interior sidewalls. As shown in FIGS. 67-71, the capillary channels 194 may be positioned across the interior of first and second sides (e.g., the long sides) of the reservoir 102. In some implementations, the capillary channels 194 may be additionally and/or alternatively positioned across a base wall 193 of the reservoir 102. This configuration may help to maximize heat transfer and heating efficiency of the concentrate, and also help to reduce leaking of the concentrate from the interior portion of the reservoir 102. For example, third and fourth sides of the reservoir 102 may be shorter than the first and second sides of the reservoir 102. Because the third and fourth sides are shorter, the heat transfer from the heating element to the concentrate may be less efficient along the third and fourth sides. Thus, it may be desirable to direct the heated and/or liquefied concentrate towards the first and second sides, which are longer and have a greater surface area than the third and fourth sides. Additionally and/or alternatively, the capillary channels 194 positioned along the base wall 193 of the reservoir may help to improve leak prevention along the base wall 193 of the reservoir 102. Forming capillary channels 194 along the base wall 193 may also help to increase carrying capacity (e.g., a volume of vaporizable material capable of being held and/or suspending within the capillary channels) of the capillary channels 194. Forming capillary channels 194 along the base wall 193 may also help to direct the vaporizable material towards the side walls of the reservoir 102 to be heated.

For example, the capillary channels 194 may be formed as recesses between various geometric configurations or shapes (such as circles, cylinders, elongated bars, elongated protrusions, and/or the like), and the recesses themselves may have various geometric configurations or shapes. Vertically and horizontally oriented channels 194 allow for the concentrate to flow in various directions, providing for improved heating performance. As shown in FIGS. 67-71, the capillary channels 194 may be formed between elongated bars or cylinders that extend from or near a top end of the interior sidewalls of the reservoir 102 (such as at or near a top end of the reservoir base 104) to or near a bottom end of the interior sidewalls of the reservoir 102 (such as at or near the base wall 193). The capillary channels 194 may additionally and/or alternatively be formed between elongated bars or cylinders that extend across the bottom wall 193 of the reservoir from one side wall to the opposing side wall.

The capillary channels 194 as described herein, such as the capillary channels 194 shown in FIGS. 67-71 may have a width of approximately 0.3 mm to 0.6 mm, 0.3 mm to 0.4 mm, or 0.5 mm to 0.6 mm. Such width of the capillary channels 194 may be desirably sized to capture and/or retain a sufficient amount of vaporizable material within the capillary channels 194 and to allow the liquefied vaporizable material to flow towards the sidewalls of the reservoir 102 via capillary action. As described herein, the width of the capillary channels 194 may be desirably sized so that the capillary forces provided by the capillary channels 194 is sufficient to retain and direct the flow of vaporizable material. Such width of the capillary channels 194 may additionally and/or alternatively help to reduce flooding of the vaporizable material towards the sidewalls of the reservoir 102 and/or out of the reservoir 102. For example, width of the capillary channels 194 that are too wide may result in flooding or leakage of the vaporizable material out of the reservoir 102. In some implementations, the width of the capillary channels 194 described herein ranges from approximately 0.2 mm to 0.3 mm, 0.3 mm to 0.4 mm, 0.4 mm to 0.5 mm, 0.5 mm to 0.6 mm, 0.6 mm to 0.7 mm, and/or other ranges therebetween.

In some implementations, the depth of the capillary channels 194 may also help to apply a sufficient capillary force to retain and/or direct the flow of a sufficient amount of vaporizable material. For example, the depth of the capillary channels 194 may desirably range from approximately 0.7 mm to 0.8 mm. In some implementations, the depth of the capillary channels 194 may range from approximately 0.4 mm to 0.5 mm, 0.5 mm to 0.6 mm, 0.6 mm to 0.7 mm, 0.8 mm to 0.9 mm and/or other ranges therebetween.

In some implementations, the capillary channels 194 may be spaced apart from the elongated bars and/or cylinders. The elongated bars and/or cylinders may have a width that ranges from approximately 0.5 mm to 0.6 mm, which may help to improve performance of the reservoir 102. For example, the width of the elongated bars and/or cylinders may space each adjacent capillary channel 194 away from one another to provide a desired capillary force within each capillary channel 194. In some implementations, the width of the elongated bars and/or cylinders may range from approximately 0.4 mm to 0.5 mm, 0.6 mm to 0.7 mm, 0.7 mm to 0.8 mm, 0.8 mm to 0.9 mm and/or other ranges therebetween.

As noted above, the capillary structure 190 may be positioned on one or more sidewalls of the reservoir 102. In some implementations, the side walls of the reservoir 102 may include a wall thickness of approximately 0.3 mm, or a range of thicknesses of approximately 0.2 mm to 0.3 mm, 0.1 to 0.3 mm, 0.3 mm to 0.5 mm, and/or ranges therebetween. The thickness of the side walls of the reservoir 102 may be desirably thin to improve and/or speed up heat transfer between the vaporizer device 10 and the reservoir 102, and thus the heat transfer between the reservoir 102 and vaporizable material. Thus, such configurations may help to delivery vapor (e.g., vaporized vaporizable material) to the user at a faster rate.

The capillary structure 190 composed of elongated bars or cylinders helps to control the direction of flow of vaporizable material towards the side walls of the reservoir 102. The capillary structure 190 shown in FIGS. 67-71 may also help to reduce or prevent leakage of vaporizable material since the direction of the flow of vaporizable may be better controlled. In some implementations, lateral movement and/or vertical movement (along the channels 194 and/or perpendicular relative to the channels 194) of the vaporizable material may be desired to help prevent leaks, as the direction of flow may be better distributed along multiple axes. Additionally and/or alternatively, the capillary channels 194 formed along the side walls of the reservoir 102 may be separated from the capillary channels 194 formed along the base wall 193 by a capillary gap 195. In other words, the capillary channels 194 may not extend between the side walls of the reservoir 102 and the base wall 193. The capillary gap 195 allows at least some of the vaporizable material to travel in multiple directions, such as directions perpendicular to the direction of the capillary channels 194 formed between the elongated bars or cylinders. This configuration helps to improve efficiency of heating the vaporizable material by encouraging the vaporizable material to travel towards the side walls of the reservoir 102 in more than one direction.

Figure 67:
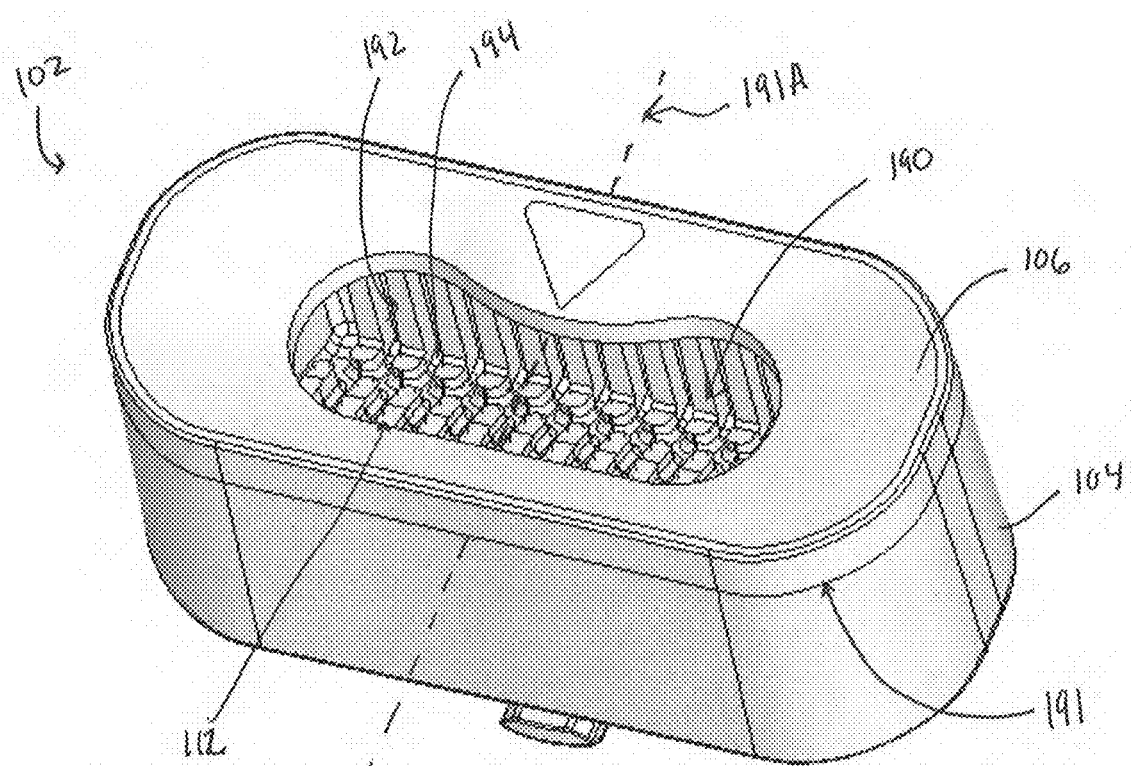
Figure 68:
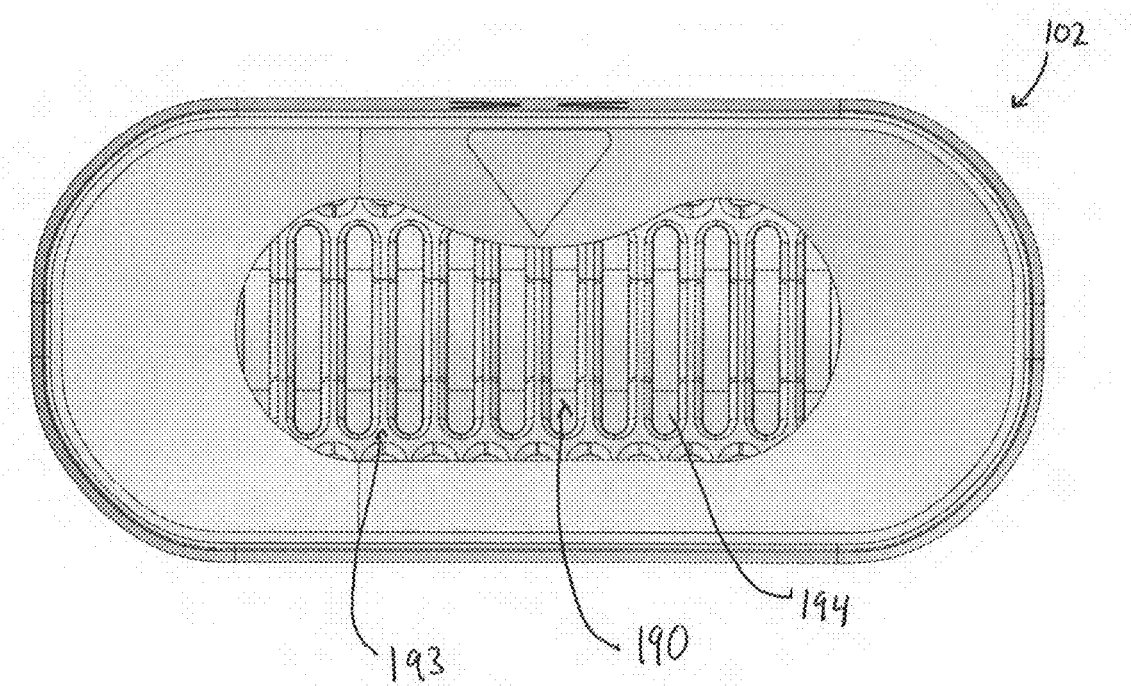
Figure 69:
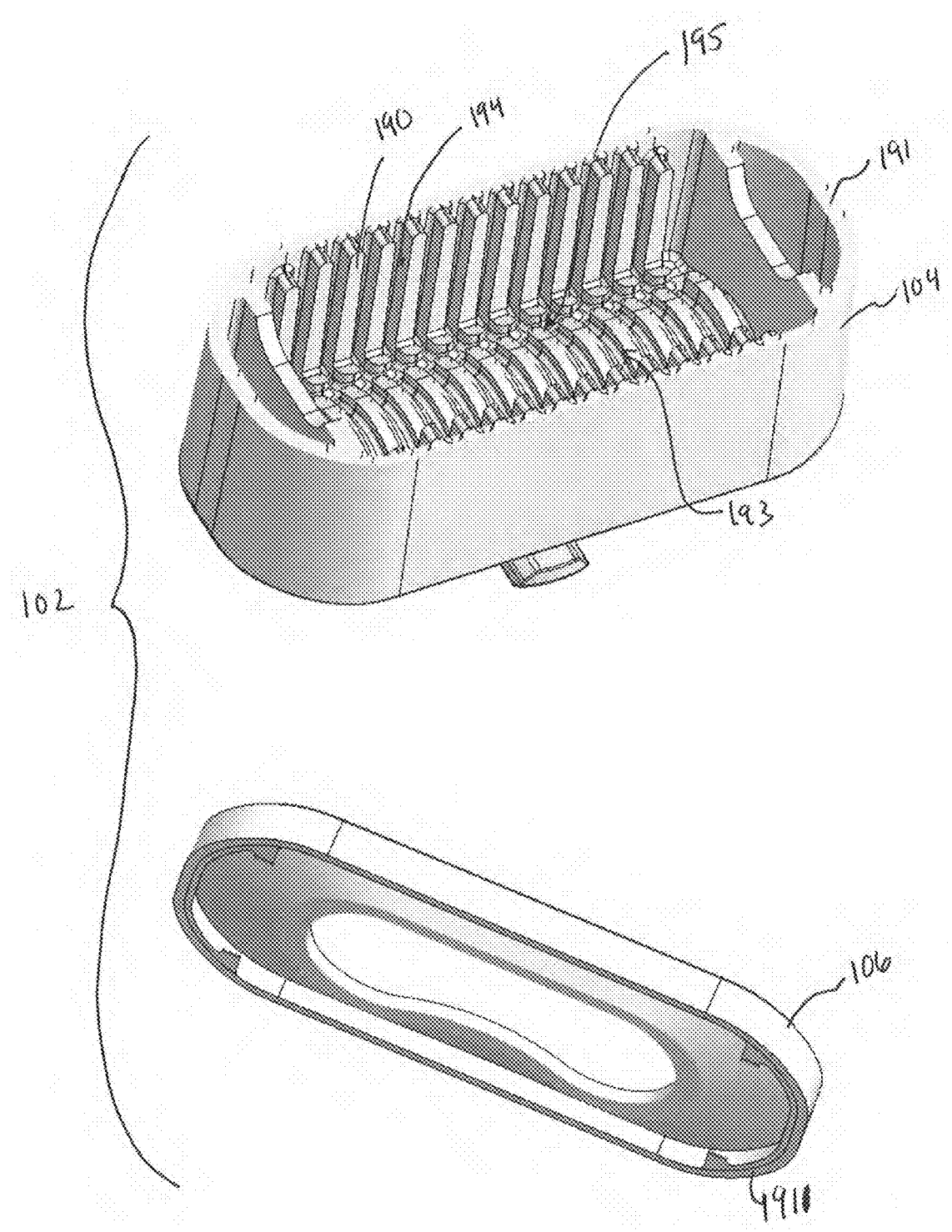
Figure 90:
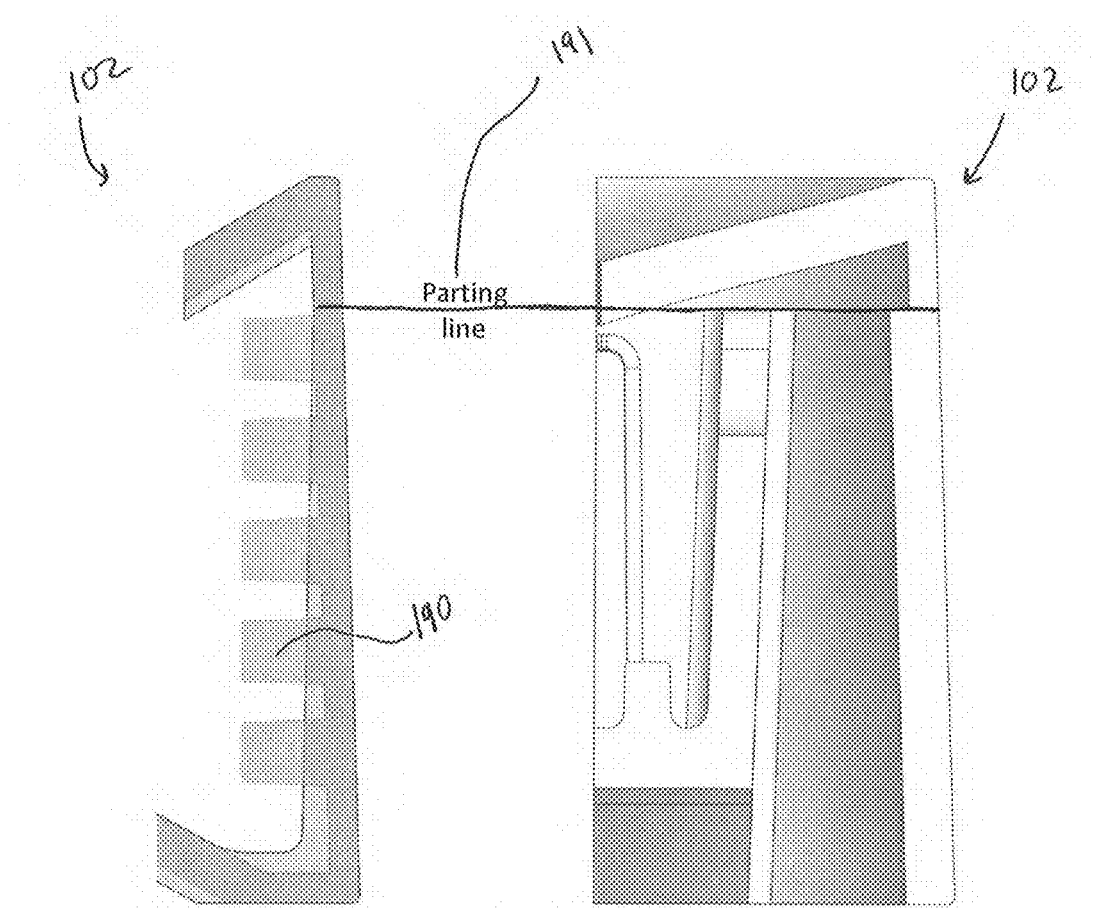
FIGS. 90A-90C illustrate an example case for a concentrate adaptor consistent with implementations of the current subject matter.
Figure 71:
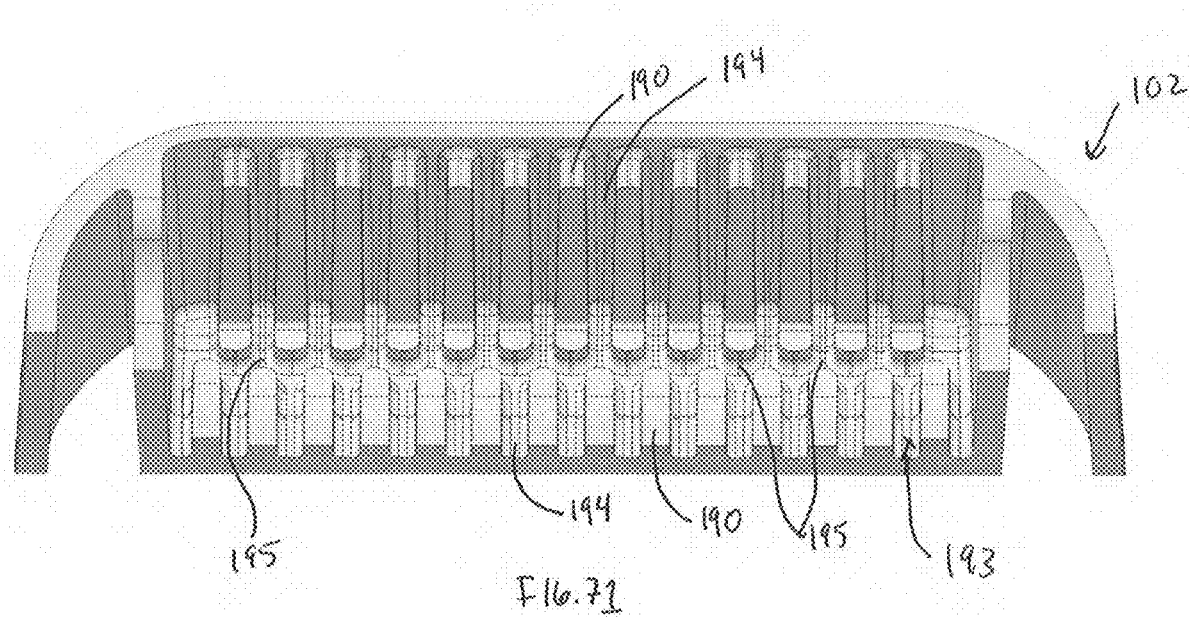

Referring to FIG. 69, the reservoir 102 may be formed by coupling one or more components. For example, the reservoir 102 may include a reservoir top 106 and a reservoir base 104. The reservoir base 104 may have a larger height than a height of the reservoir top 106. As shown in FIGS. 67, the reservoir top 106 may be joined to the reservoir base 104 along parting line 191 (e.g., along axis 191A) (see FIG. 67 and FIGS. 69-70). In some implementations, the reservoir top 106 may be coupled to the reservoir base 104 via various manufacturing methods. For example, the reservoir top 106 may be joined to the reservoir base 104 via laser welding, sintering, die casting, adhering, fastening and/or the like. The multi-component construction of the reservoir 102 may improve the manufacturability of the concentrate adaptor 100 (e.g., the reservoir 102) and/or improve the efficiency of the manufacturing of the concentrate adaptor 100. For example, the reservoir base 104 may include the capillary structure 190. In some implementations, the reservoir top 106 does not include the capillary structure 190. This improves the manufacturability of the reservoir base 104, for example, by allowing the reservoir base 104, which includes the capillary structure 190, to be molded, extruded, and/or otherwise manufactured more easily. This configuration may also help to reduce the likelihood that the capillary structure 190 will break or become damaged during manufacturing.

In some implementations, the reservoir 102 described herein, such as the reservoir 102 shown in FIGS. 67-71 may be made of one or more materials. For example, the reservoir 102 may include stainless steel, aluminum, and/or another type of conductive metal or combination thereof. In some implementations, the reservoir 102 may desirably be made at least in part of aluminum, which would improve the thermal conductivity of the reservoir 102, thereby heating the vaporizable material within the reservoir 102 at a faster rate, and providing the vaporized vaporizable material to the user at a faster rate. This may improve the user experience when using the concentrate adaptor 100.

FIGS. 72-78 illustrate another example of the concentrate adaptor 100, consistent with implementations of the current subject matter. The concentrate adaptor 100 illustrated in FIGS. 72-78 includes the same and/or similar properties and/or components as the concentrate adaptor 100 illustrated in FIGS. 1-71.

Figure 72:
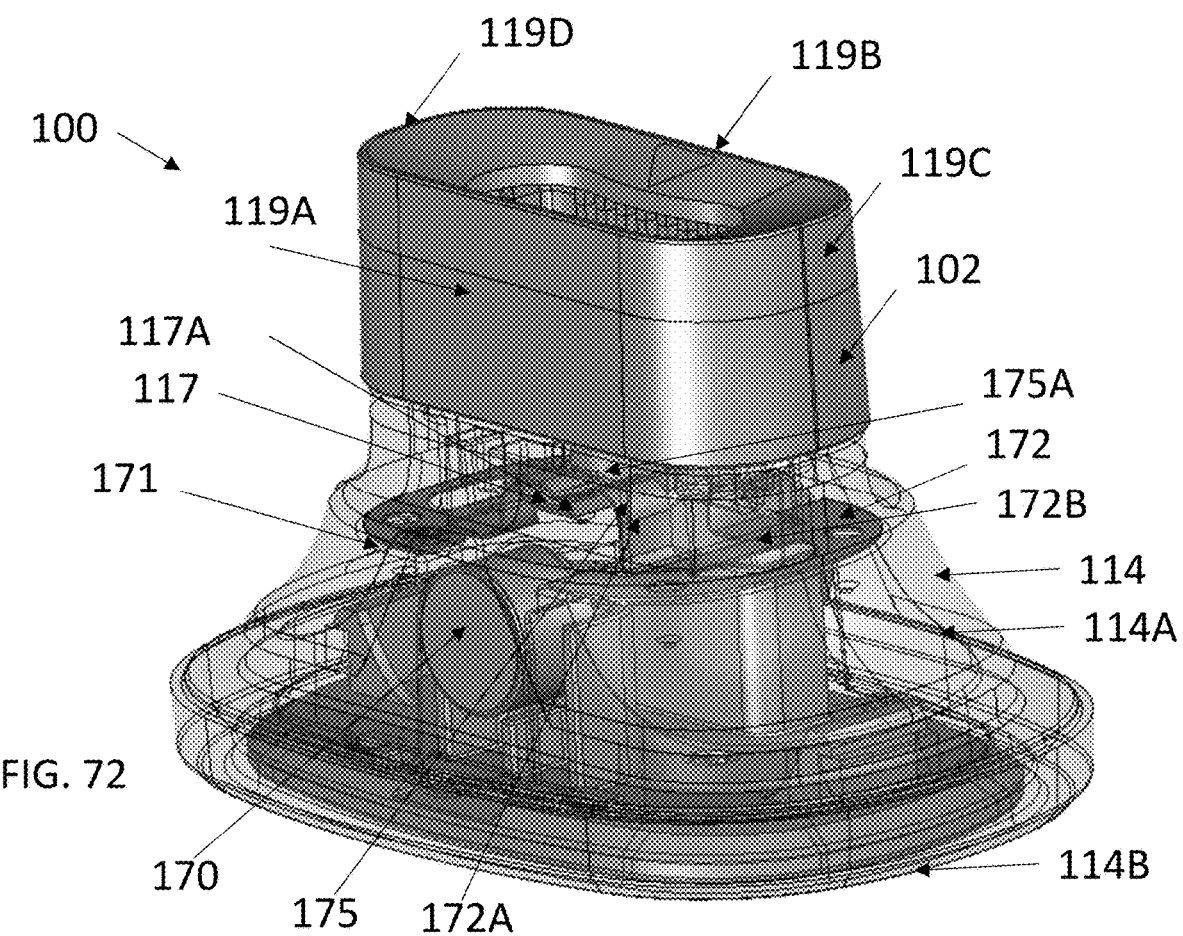

FIG. 72 illustrates an example of the concentrate adaptor 100 with the base housing 114A shown as transparent for clarity. FIG. 73A is a cross-sectional view of the concentrate adaptor 100, consistent with implementations of the current subject matter. FIG. 73B is another cross-sectional view of the concentrate adaptor 100, consistent with implementations of the current subject matter. As shown in FIGS. 72, 73A, and 73B, the concentrate adaptor includes the reservoir 102 and the base 114. In some implementations, the base 114 may include a base housing 114A, a base floor 114B, a retention member 172, and one or more coupling elements 170.

Similar to the concentrate adaptor 100 shown in FIGS. 63-66, in the concentrate adaptor 100 shown in FIGS. 72-78, the base housing 114A supports the retention member 172 and the base floor 114B supports the one or more coupling elements 170. As shown in FIGS. 72-73B, the base floor 114B is coupled to the base housing 114A and is at least partially positioned within the base housing 114A. In other words, the base housing 114A may receive and/or otherwise couple to the base floor 114B. In some implementations, at least a portion of the base floor 114B may slide into, snap into, and/or otherwise be retained within the base housing 114A. Additionally and/or alternatively, at least a portion of the base housing 114A may slide into, snap into, and/or otherwise be coupled to the base floor 114B.

Referring to FIGS. 73A and 73B, the base housing 114A may include a recess 1027, formed along a perimeter of an interior end portion of the base housing 114A. The recess 1027 may receive and/or otherwise couple to a portion of the base floor 114B. For example, the base floor 114B may include a radial extension 1028 that extends along a perimeter of the base floor 114B. A shape of the recess 1027 may correspond to a shape of the radial extension 1028 such that a surface of the recess 1027 is positioned approximately parallel to a surface of the radial extension 1028.

A channel 1029 may be formed between the radial extension 1028 and the recess 1027 to allow air to pass through the channel 1029 into the interior of the base 114 of the concentrate adaptor 100. The channel 1029 may radially extend about all or a portion of the bottom of the base 114. The channel 1029 may be positioned proximate to an outer edge of the bottom of the base 114. The channel 1029 may be positioned offset from the outer edge of the bottom of the base 114. In some implementations, the base 114 includes a bottom base opening 143. The bottom base opening 143 is positioned at the end of the channel 1029 and defines an inlet that allows air to flow into the base 114 of the concentrate adaptor 100. The bottom base opening 143 may be desirably sized to allow a desirable amount of air to pass into the concentrate adaptor 100 in use. For example, a width of the bottom base opening 143 may be approximately 0.4 mm to 1.0 mm. In some implementations, the width of the bottom base opening 143 is approximately 0.3 mm, 0.4 mm, 0.5 mm, 0.6 mm, 0.7 mm, 0.8 mm, 0.9 mm, 1.0 mm, 1.1 mm, 1.2 mm, 1.3 mm, and/or the like. In some implementations, the bottom base opening 143 includes a tapered portion 143A. The tapered portion 143A may have a width that is wider at an outer end of the tapered portion 143A than a width at an inner end of the tapered portion 143A. For example, the width at the outer end of the tapered portion 143A may be approximately 1.0 mm and the width at the inner end of the tapered portion 143B may be approximately 0.5 mm. This configuration may allow air to more easily enter the channel 1029 via the bottom base opening 143. The size and/or shape of the bottom base opening 143 (and/or the tapered portion 143A) may therefore reduce draw resistance and/or improve overall airflow into the concentrate adaptor 100 and vaporizer device 10, leading to more efficient vaporization of the vaporizable material and an improved user experience.

Referring to FIGS. 73A and 73B, the channel 1029 may extend from the bottom base opening 143 to the interior of the base housing 114A of the base 114 to deliver outside air to the interior of the concentrate adaptor 100. The channel 1029 may be desirably sized to allow a desirable amount of air to pass into the concentrate adaptor 100 in use. For example, a width of the channel 1029 may be approximately 0.4 mm to 0.5 mm. In some implementations, the width of the channel 1029 is approximately 0.3 mm, 0.4 mm, 0.5 mm, 0.6 mm, 0.7 mm, 0.8 mm, 0.9 mm, 1.0 mm, 1.1 mm, 1.2 mm, 1.3 mm, and/or the like. The size and/or shape of the channel 1029 may reduce draw resistance and/or improve overall airflow into the concentrate adaptor 100 and vaporizer device 10, leading to more efficient vaporization of the vaporizable material and an improved user experience.

As noted above, the base housing 114A may be coupled to the base floor 114B and the recess 1027 of the base housing 114A may be spaced apart from the radial extension 1028 of the base floor 114B to define the channel 1029. The base 114 may include one or more coupling mechanisms to secure the base housing 114A to the base floor 114B and to maintain the channel 1029 formed between the base housing 114A and the base floor 114B. For example, the one or more coupling mechanisms may include one, two, three, four, five, six, or more coupling mechanisms, such as a protrusion 1031 and corresponding slot 1032 and/or a base coupler 1034 and corresponding inner wall ledge 1036.

Referring to FIGS. 73A and 73B, an inner wall 1030 of the base 114 may include a protrusion 1031 that extends from the inner wall 1030 away from the base opening 115 and/or towards the base floor 114B. The base floor 114B may include a corresponding slot 1032 that is configured to receive the protrusion 1031 to secure the base housing 114A to the base floor 114B. In some implementations, the protrusion 1031 and the corresponding slot 1032 includes one, two, three, four or more protrusions 1031 and corresponding slots 1032. In some implementations, the protrusion 1031 and the corresponding slot 1032 are positioned on opposing sides of the base 114. In some implementations, two protrusions 1031 and two corresponding slots 1032 are positioned on opposing sides of the base 114. For example, at least one protrusion 1031 and corresponding slot 1032 may be positioned on a long side of the base 114 and at least one opposing protrusion 1031 and corresponding slot 1032 is positioned on the opposing long side of the base 114. Additionally and/or alternatively, at least one protrusion 1031 and corresponding slot 1032 may be positioned on a short side of the base 114 and at least one opposing protrusion 1031 and corresponding slot 1032 is positioned on the opposing short side of the base 114. The protrusion 1031 may couple to the corresponding slot 1032 via a snap-fit arrangement, friction fit, adhesive, a mechanical fastener, and/or the like.

In some implementations, the base floor 114B includes an inwardly extending member 1033 that extends towards the interior of the base 114. The inwardly extending member 1033 may include a base coupler 1034 positioned at an end of the inwardly extending member 1033. The base coupler 1034 may extend from the inwardly extending member 1033 outwardly towards the base housing 114A. The base coupler 1034 may include a face 1035 that faces away from the interior of the base 114. The base housing 114A includes an inner wall ledge 1036 that extends inwardly towards the interior of the base 114 from the inner wall of the base housing 114A. The inner wall ledge 1036 includes a face 1037 that faces towards the base opening 115 and is configured to contact the face 1035 of the base coupler 1034. The inner wall ledge 1036 may be secured to the base coupler 1034 via a snap-fit arrangement, friction fit, adhesive, a mechanical fastener, and/or the like to secure the base floor 114B to the base housing 114A. For example, during assembly of the base 114, the base coupler 1034 may snap over the inner wall ledge 1036 to securely couple the base floor 114B to the base housing 114A. In some implementations, the base 114 includes one, two, three, four or more base couplers 1034 and corresponding inner wall ledges 1036. In some implementations, the base 114 includes one base coupler 1034 and corresponding inner wall ledge 1036 on one side (e.g., the short side and/or the long side) of the base 114, and a second base coupler 1034 and corresponding inner wall ledge 1036 on the opposite side (e.g., the opposite short side and/or the long side) of the base 114. In some implementations, the base 114 includes at least one protrusion 1031 and corresponding slot 1032 on one or both long sides of the base 114 and at least one base coupler 1034 and corresponding inner wall ledge 1036 on one or both short sides of the base 114. The one or more coupling mechanisms securely couple the base floor 114B to the base housing 114A yet still allow air to pass through the channel 1029 formed between the base floor 114B and the base housing 114A.

Similar to the example concentrate adaptor 100 shown in FIGS. 47-60 and 63-66, the concentrate adaptor 100 shown in FIGS. 72-78 includes a locking mechanism, such as a quarter turn or other turn release mechanism, snap-fit mechanism, press and release mechanism, and/or another locking mechanism that couples the base 114 to the reservoir 102. The locking mechanism described herein may assist in reducing gaps formed between the reservoir 102 and the base 114, which in turn seal the airflow path formed within the concentrate adaptor 100 (e.g., between the base 114 and the reservoir 102). The locking mechanism described herein may reduce and/or eliminate movement of the concentrate adaptor 100 within the vaporizer device 10 and/or may reduce or eliminate movement of the reservoir 102 relative to the base 114 (or vice versa). The locking mechanism of the concentrate adaptor 100 may be the same or similar to the locking mechanism of the concentrate adaptor 100 shown and described with respect to the concentrate adaptor of FIGS. 63-66 and may include one or more of the same components. For example, the locking mechanism shown in FIGS. 72-28 may include the connection feature 117 (which extends from a bottom of the reservoir 102 and includes two opposing tabs 117A) and the retention member 172. Similar to the retention member 172 shown in FIGS. 63-66, the retention member 172 shown in FIGS. 72-73B helps to secure the reservoir 102 to the base 114 via a quarter turn locking mechanism, for example. The retention member 172 includes a central retention portion 172A and base retention portions 172B positioned on opposite sides of the central retention portion 172A. The base retention portions 172B are configured to rest on or otherwise be coupled to inner platforms 171 of the base housing 114A of the base 114. The inner platforms 171 are configured to support each of the base retention portions 172B of the retention member 172.

FIGS. 72-78 illustrate another example of the reservoir 102, consistent with implementations of the current subject matter. The reservoir 102 shown in FIGS. 72-78 may include the same or similar features to the features described above with respect to the concentrate adaptors shown in FIGS. 1-71. For example, the reservoir 102 shown in FIGS. 72-78 may include one or more components that are the same as and/or are interchangeable with one or more components of the reservoir 102 shown and/or described with respect to FIGS. 1-71.

For example, the reservoir 102 includes an outer wall 128 that surrounds an interior volume of the reservoir 102. The reservoir 102 may also include an inner wall 131. A channel 133 may be formed between the inner wall 131 and the outer wall 128. The reservoir 102 includes an opening 112 formed in the top portion of the reservoir 102.

The reservoir 102 may include the capillary structure 190. For example, as discussed above with respect to FIGS. 1-71, the capillary structure 190 may be formed on one or more interior sidewalls of the reservoir 102 in varying thicknesses such that the variations in thickness form capillary channels 194. The shape and size of the capillary channels 194 may take various forms and combinations of forms, and may be positioned across all of the walls of the capillary structure 190, or only some of the walls of the capillary structure 190, such as across at least a portion of one or more of the interior sidewalls and/or the base wall. As shown in FIGS. 72-78, the capillary channels 194 may be positioned across the interior of first and second sides (e.g., the long sides) of the reservoir 102. In some implementations, the capillary channels 194 may be additionally and/or alternatively positioned across a base wall 193 of the reservoir 102. This configuration may help to maximize heat transfer and heating efficiency of the concentrate. This configuration may also reduce leaking of the concentrate from the interior portion of the reservoir 102.

For example, third and fourth sides 119C, 119D of the reservoir 102 may be shorter than first and second sides 119A, 119B of the reservoir 102 (see FIG. 72). Because the third and fourth sides 119C, 119D are shorter, the heat transfer from the heating element to the vaporizable material stored within the reservoir 102 may be less efficient along the third and fourth sides 119C, 119D. Thus, it may be desirable to direct the heated and/or liquefied vaporizable material towards the first and second sides 119A, 119B, which are longer and have a greater surface area than the third and fourth sides 119C, 119D. As described herein, the first and second sides 119A, 119B of the reservoir 102 may have a length of approximately 18 mm. In some implementations, the length of the first and second sides 119A, 119B ranges from approximately 16.0 mm to 17.0 mm, 17.0 mm to 18.0 mm, 18.0 mm to 19.0 mm, and/or other ranges therebetween. In some implementations, the third and fourth sides 119C, 119D of the reservoir 102 may have a length of approximately 8 mm. In some implementations, the length of the third and fourth sides 119C, 119D ranges from approximately 6.0 mm to 7.0 mm, 7.0 mm to 8.0 mm, 8.0 mm to 9.0 mm, and/or other ranges therebetween.

Additionally and/or alternatively, the capillary channels 194 positioned along the base wall 193 of the reservoir may help to improve leak prevention along the base wall 193 of the reservoir 102. For example, the capillary channels 194 positioned along the base wall 193 may help to retain the vaporizable material within the reservoir 102. Forming capillary channels 194 along the base wall 193 may also help to increase carrying capacity (e.g., a volume of vaporizable material capable of being held and/or suspending within the capillary channels) of the capillary channels 194. For example, the capillary structure 190 including the capillary channels 194 may have a carrying capacity of approximately 40 mg of vaporizable material. In some implementations, the concentrate adaptor 100 has a carrying capacity of approximately 0 to 10 mg, 10 mg to 20 mg, 20 mg to 30 mg, 30 mg to 40 mg, 40 mg to 50 mg, 50 mg to 60 mg, 60 mg to 70 mg, 70 mg to 80 mg, 80 mg to 90 mg, and/or other ranges therebetween. Forming capillary channels 194 along the base wall 193 may also help to direct the vaporizable material towards the side walls of the reservoir 102 to be heated. Thus, the concentrate adaptor 100 may more efficiently and quickly vaporize the vaporizable material, leading to an improved user experience.

In some implementations, the capillary channels 194 may be formed as recesses between various geometric configurations or shapes (such as circles, cylinders, elongated bars, elongated protrusions, and/or the like), and the recesses themselves may have various geometric configurations or shapes. Vertically and horizontally oriented channels 194 allow for the concentrate to flow in various directions, providing for improved heating performance. As shown in FIGS. 72-78, the capillary channels 194 may be formed between elongated bars or cylinders that extend from or near a top end of the interior sidewalls of the reservoir 102 (such as at or near a top end of the reservoir base 104) to or near a bottom end of the interior sidewalls of the reservoir 102 (such as at or near the base wall 193). Forming the channels 194 between adjacent elongated bars or cylinders helps to create an elongated pathway that is sized, as described below, so that the capillary forces provided by the capillary channels 194 is sufficient to retain the vaporizable material and direct the flow of vaporizable material. As shown in at least FIG. 77, at least some of the capillary channels 194 extend from the bottom end of the interior sidewalls to the top end of the interior side walls of the reservoir 102, on at least the first and second sides 119A, 119B. The capillary channels 194 may additionally and/or alternatively be formed between elongated bars or cylinders that extend across the bottom wall 193 of the reservoir from one side wall to the opposing side wall.

The capillary structure 190 including the capillary channels 194 described herein may more efficiently control the rate at which the fluid is drawn within the space. In some implementations, the size and/or shape of the capillary channels 194 formed between the adjacent elongated bars and/or cylinders limits or prevents the vaporizable material from draining into or out of the capillary structure too quickly. The size and/or shape of the capillary channels 194 may additionally and/or alternatively secure the vaporizable material within the capillary structure 190 to prevent leakage of the vaporizable material out of the reservoir 102 and/or into other portions of the concentrate adaptor 100. As described herein, the capillary structure 190 may also be sized and/or shaped to direct the flow of heated and/or liquefied vaporizable material towards the sides (e.g., the long sides) of the reservoir 102, where the vaporizable material may be heated more efficiently and/or quickly. This may help to improve the vapor quality and/or improve the user experience when using the vaporizer device 10 and/or the concentrate adaptor 100.

In some implementations, the reservoir 102 may include twelve capillary channels 194 along the interior side wall on each of the at least the first and second sides 119A, 119B. In some implementations, the reservoir 102 includes at least one, two, three, four, five, six, seven, eight, nine, ten, eleven, twelve, thirteen, fourteen, fifteen, sixteen, seventeen, eighteen, nineteen, twenty, or more capillary channels 194 along the interior side wall on at least one or both of the first and second sides 119A, 119B. In some implementations, the capillary channels 194 have the same dimensions (e.g., length, width, and/or depth). In some implementations, the capillary channels 194 may have various shapes and/or sizes. For example, the capillary structure 190 on the interior side wall on at least one or both of the first and second sides 119A, 119B includes a first capillary channel 194A or group of capillary channels 194A (and corresponding elongate bars) that extend from the bottom end of the interior side wall to the top end of the interior side wall, and a second capillary channel 194B or group of capillary channels 194B (and corresponding elongate bars) that extend from the bottom end of the interior side wall along a length of the interior side wall that does not reach the top end of the interior side wall. In this example, the first group of capillary channels 194A may include one, two, three, four, five, six, seven, eight, nine, ten, or more capillary channels 194. The first group of capillary channels 194A may be formed along a center of an interior side wall of the reservoir 102. The second group of capillary channels 194B may include one, two, three, four or more capillary channels 194. The second group of capillary channels 194B may be formed along opposing sides of the first group of capillary channels 194. Such configurations help to direct the heated and/or liquefied vaporizable material towards the bottom and center of the interior sidewalls of the reservoir 102. This may increase vaporization efficiency of the vaporizable material within the reservoir 102. In some implementations, the first group of capillary channels 194A (and/or the corresponding elongate bars) may have a length of approximately 5 mm to 6 mm. In some implementations, the second group of capillary channels 194B (and/or the corresponding elongate bars) has a length of approximately 3 mm to 4 mm. In some implementations, the first group of capillary channels 194A, such as the capillary channels 194 that extend along the length of the interior sidewalls, helps to improve the rigidity of the walls of the reservoir 102.

The capillary channels 194 as described herein, such as the capillary channels 194 shown in FIGS. 72-78 may have a width of approximately 0.3 mm to 0.6 mm, 0.3 mm to 0.4 mm, or 0.5 mm to 0.6 mm. Such width of the capillary channels 194 may be desirably sized to capture and/or retain a sufficient amount of vaporizable material within the capillary channels 194 and to allow the liquefied vaporizable material to flow towards the sidewalls of the reservoir 102 via capillary action. As described herein, the width of the capillary channels 194 may be desirably sized so that the capillary forces provided by the capillary channels 194 is sufficient to retain and direct the flow of vaporizable material. Such width of the capillary channels 194 may additionally and/or alternatively reduce flooding of the vaporizable material towards the sidewalls of the reservoir 102 and/or out of the reservoir 102. For example, a width of the capillary channels 194 that is too wide may result in flooding or leakage of the vaporizable material out of the reservoir 102. In some implementations, the width of the capillary channels 194 described herein ranges from approximately 0.2 mm to 0.3 mm, 0.3 mm to 0.4 mm, 0.4 mm to 0.5 mm, 0.5 mm to 0.6 mm, 0.6 mm to 0.7 mm, and/or other ranges therebetween.

In some implementations, the depth of the capillary channels 194 may also help to apply a sufficient capillary force to retain and/or direct the flow of a sufficient amount of vaporizable material. For example, the depth of the capillary channels 194 may desirably range from approximately 0.7 mm to 0.8 mm. In some implementations, the depth of the capillary channels 194 may range from approximately 0.4 mm to 0.5 mm, 0.5 mm to 0.6 mm, 0.6 mm to 0.7 mm, 0.8 mm to 0.9 mm and/or other ranges therebetween.

As noted above, the reservoir 102 may include one or more capillary channels 194 positioned along the base wall 193. The reservoir 102 may include one, two, three, four, five, six, seven, eight, nine, ten, eleven, twelve, thirteen, fourteen, fifteen, sixteen, seventeen, eighteen, nineteen, twenty, or more capillary channels 194 formed along the base wall 193. The capillary channels 194 may extend along a width of the base wall 193 between the first and second sides 119A, 119B of the reservoir 102. In some implementations, the capillary channels 194 along the base wall 193 (and/or the side wall) each have the same dimensions (e.g., depth, length, and/or width). In some implementations, the capillary channels 194 formed along the base wall 193 have varying dimensions, such as a varying depth. For example, the capillary channels 194 may include two outer capillary channels 194C positioned on opposing ends of the row of capillary channels 194 formed along the base wall 193. The two outer capillary channels 194C (and/or adjacent elongate bars) may include a depth that is greater than the depth of the capillary channels 194 (and/or adjacent elongate bars) formed between the two outer capillary channels 194C (and/or adjacent elongate bars). For example, the depth of the outer capillary channels 194C (and/or adjacent elongate bars) may be approximately 0.7 mm while the depth of the remaining capillary channels 194 therebetween may be approximately 0.5 mm. The greater depth of the outer capillary channels 194C may desirably help to reduce leaking of the vaporizable material out of the reservoir.

In some implementations, the capillary channels 194 positioned along the base wall 193 of the reservoir 102 may be positioned offset from the capillary channels 194 formed along the sidewalls of the reservoir 102. For example, one or more of the capillary channels 194 and/or adjacent elongate bars along the base wall 193 may be positioned between adjacent pairs of the capillary channels 194 positioned along the sidewalls of the reservoir 102. This helps to encourage flow of vaporizable material towards the side walls to be more efficiently heated.

As described herein, the capillary channels 194 may be spaced apart by the elongated bars and/or cylinders. The elongated bars and/or cylinders may each have a width that ranges from approximately 0.5 mm to 0.6 mm, which improves performance of the reservoir 102. For example, the width of the elongated bars and/or cylinders may space each adjacent capillary channel 194 away from one another to provide a desired capillary force within each capillary channel 194. In some implementations, the width of the elongated bars and/or cylinders may range from approximately 0.4 mm to 0.5 mm, 0.6 mm to 0.7 mm, 0.7 mm to 0.8 mm, 0.8 mm to 0.9 mm and/or other ranges therebetween. In some implementations, at least some of the elongated bars and/or cylinders have rounded ends. The rounded ends of the elongated bars and/or cylinders helps to encourage flow of the vaporizable material towards the side walls of the reservoir and helps to reduce leakage of the vaporizable material from the reservoir 102.

As noted above, the capillary structure 190 may be positioned on one or more sidewalls of the reservoir 102. In some implementations, the side walls of the reservoir 102 may include a wall thickness of approximately 0.3 mm, or a range of thicknesses of approximately 0.2 mm to 0.3 mm, 0.1 to 0.3 mm, 0.3 mm to 0.5 mm, and/or ranges therebetween. The thickness of the side walls of the reservoir 102 may be desirably thin to improve and/or speed up heat transfer between the vaporizer device 10 and the reservoir 102, and thus the heat transfer between the reservoir 102 and vaporizable material. Thus, such configurations may help to delivery vapor (e.g., vaporized vaporizable material) to the user at a faster rate.

The capillary structure 190 composed of elongated bars or cylinders helps to control the direction of flow of vaporizable material towards the side walls of the reservoir 102. The capillary structure 190 shown in FIGS. 72-78 may also help to reduce or prevent leakage of vaporizable material since the direction of the flow of vaporizable may be better controlled. In some implementations, lateral movement and/or vertical movement (along the channels 194 and/or in a direction perpendicular relative to the capillary channels 194) of the vaporizable material may be desired to help prevent leaks, as the direction of flow may be better distributed along multiple axes. Additionally and/or alternatively, the capillary channels 194 formed along the side walls of the reservoir 102 may be separated from the capillary channels 194 formed along the base wall 193 by a capillary gap 195. In other words, the capillary channels 194 may not extend between the side walls of the reservoir 102 and the base wall 193. The capillary gap 195 allows at least some of the vaporizable material to travel in multiple directions, such as directions perpendicular to the direction of the capillary channels 194 formed between the elongated bars or cylinders. This configuration helps to improve efficiency of heating the vaporizable material by encouraging the vaporizable material to travel towards the side walls of the reservoir 102 in more than one direction.

Figure 76:
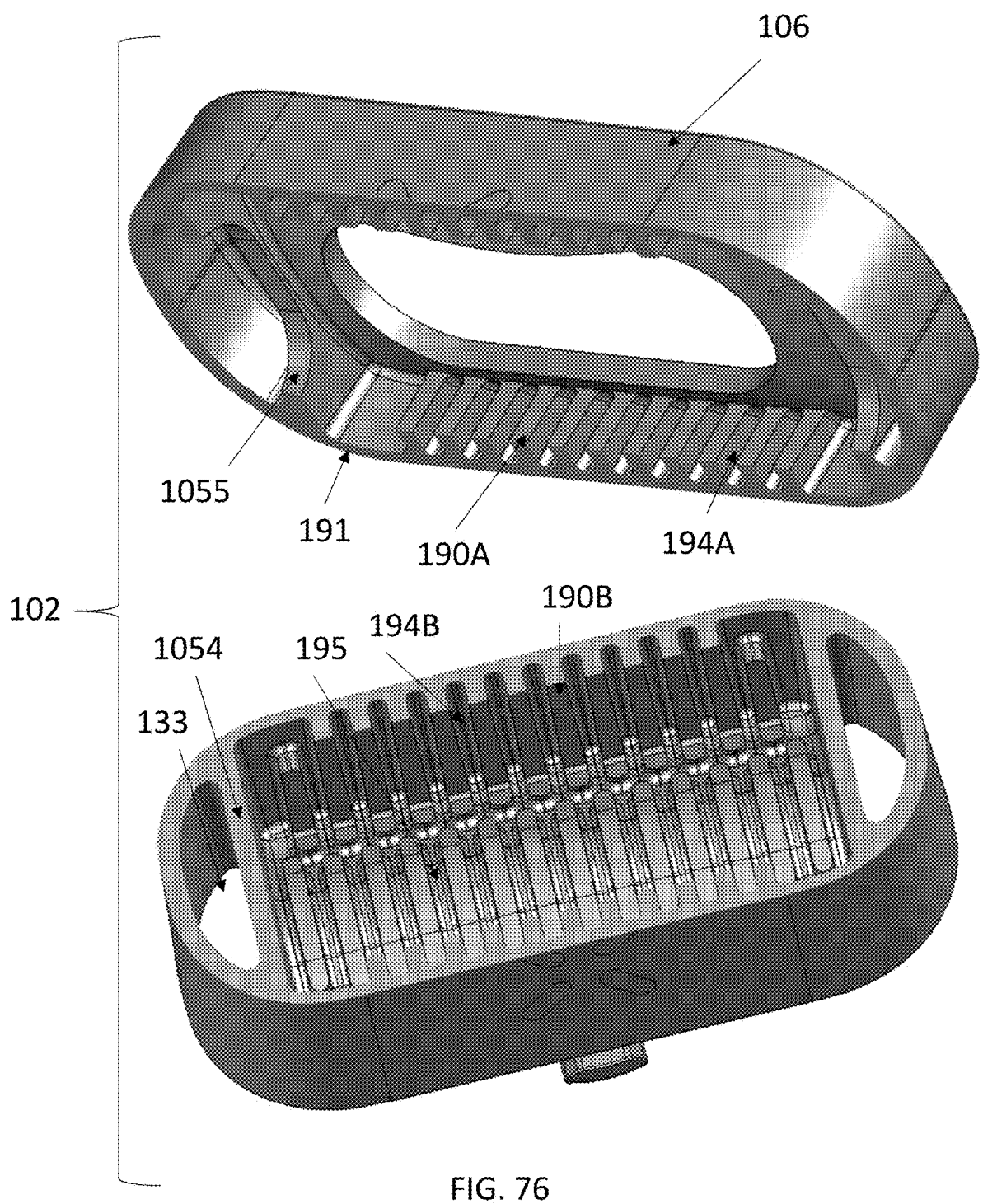
Figure 77:
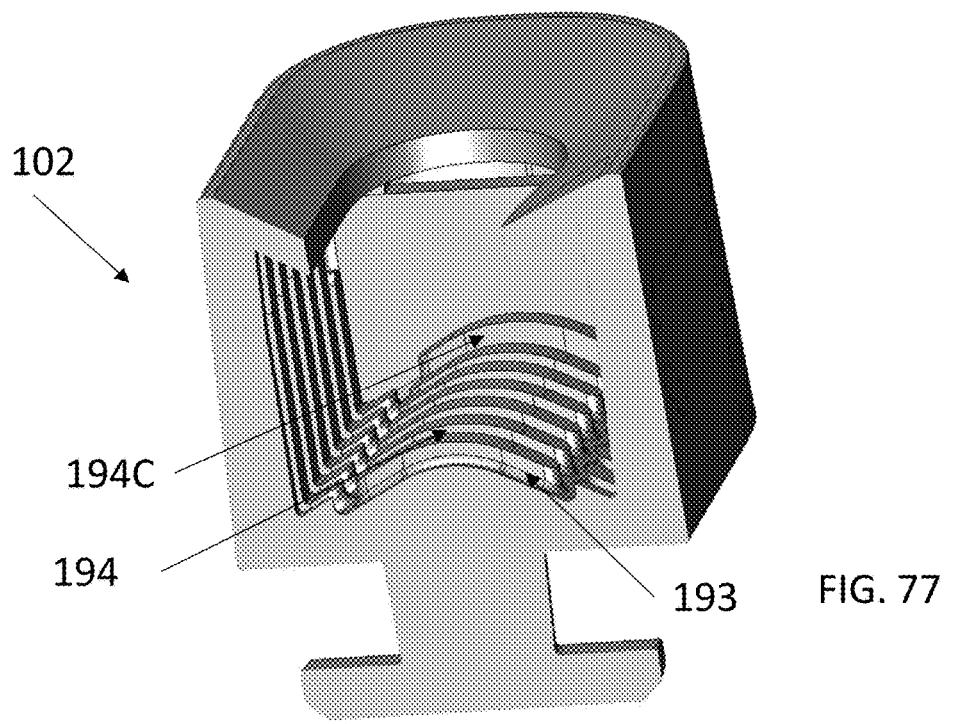
Figure 78:
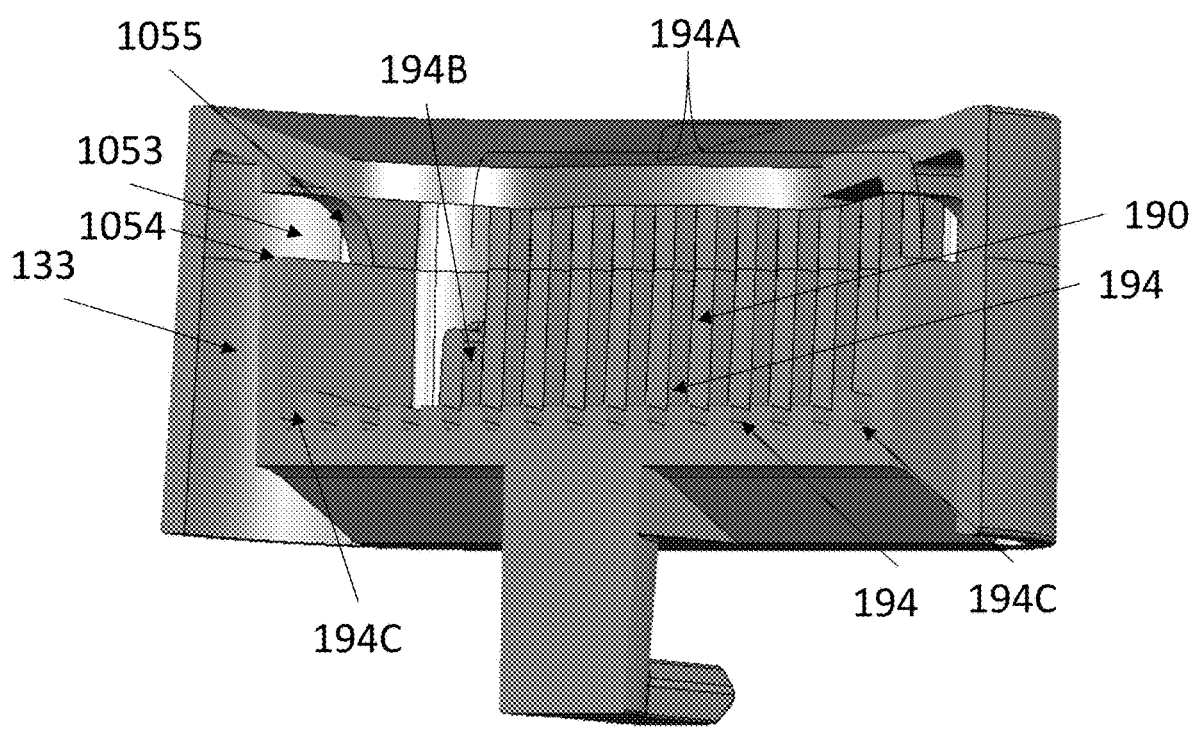

Referring to FIG. 76, the reservoir 102 shown in FIGS. 72-78 may be formed by coupling one or more components. For example, the reservoir 102 may include a reservoir top 106 and a reservoir base 104. The reservoir base 104 may have a larger height than a height of the reservoir top 106. For example, the reservoir base 104 may have a height of approximately 4 mm to 5 mm and the reservoir top 106 may have a height of approximately 2 mm to 3 mm. In some implementations, the reservoir base 104 has a height of approximately 1 mm to 2 mm, 2 mm to 3 mm, 3 mm to 4 mm, 4 mm to 5 mm, 5 mm to 6 mm, 6 mm to 7 mm, t mm to 8 mm, 8 mm to 9 mm, 9 mm to 10 mm, 1 mm to 10 mm, 5 mm to 20 mm, and/or other ranges therebetween, and the reservoir top 106 has a height of approximately 1 mm to 2 mm, 2 mm to 3 mm, 3 mm to 4 mm, 4 mm to 5 mm, 5 mm to 6 mm, 6 mm to 7 mm, t mm to 8 mm, 8 mm to 9 mm, 9 mm to 10 mm, 1 mm to 10 mm, 5 mm to 20 mm, and/or other ranges therebetween. In some implementations, a ratio of the height of the reservoir base 104 to the height of the reservoir top 106 is approximately 5:3, 5:2, 2:1, 4:3, 10:1, 5:1, 4:1, 3:1, 7:4, 9:4, 11:4, 20:1, 15:1, and/or other ranges therebetween.

Figure 74:
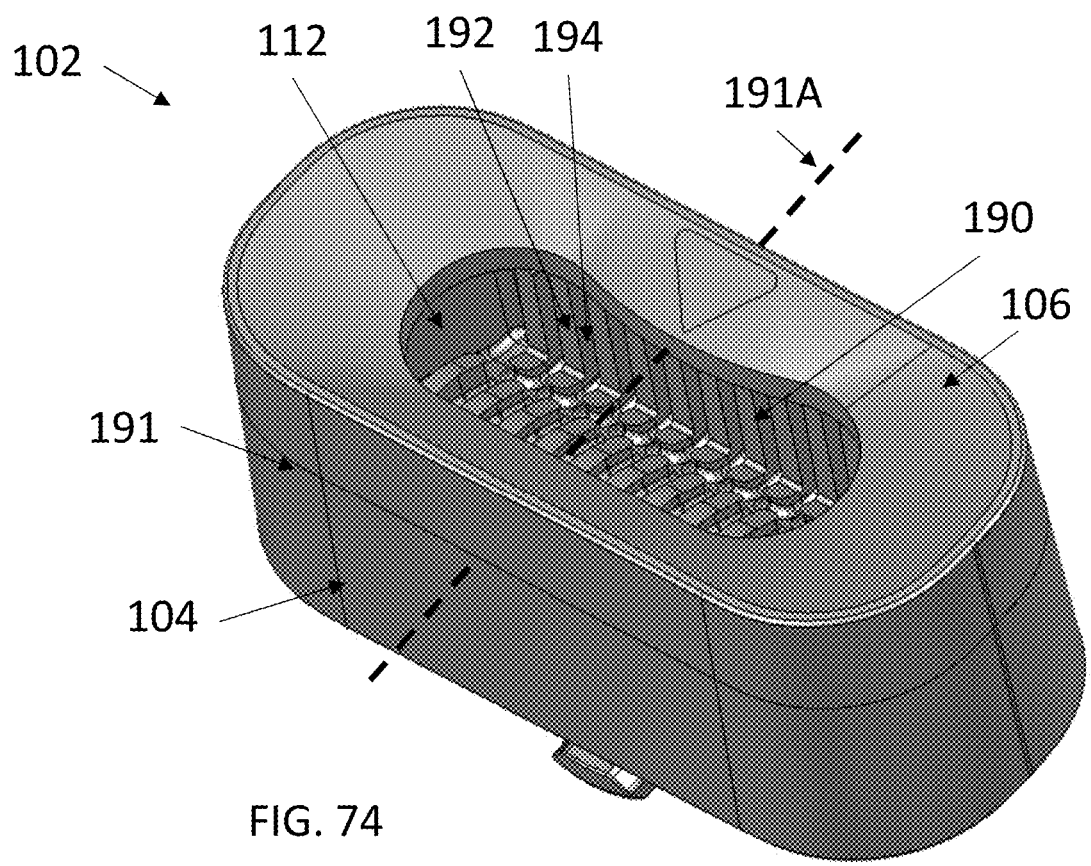
Figure 75:
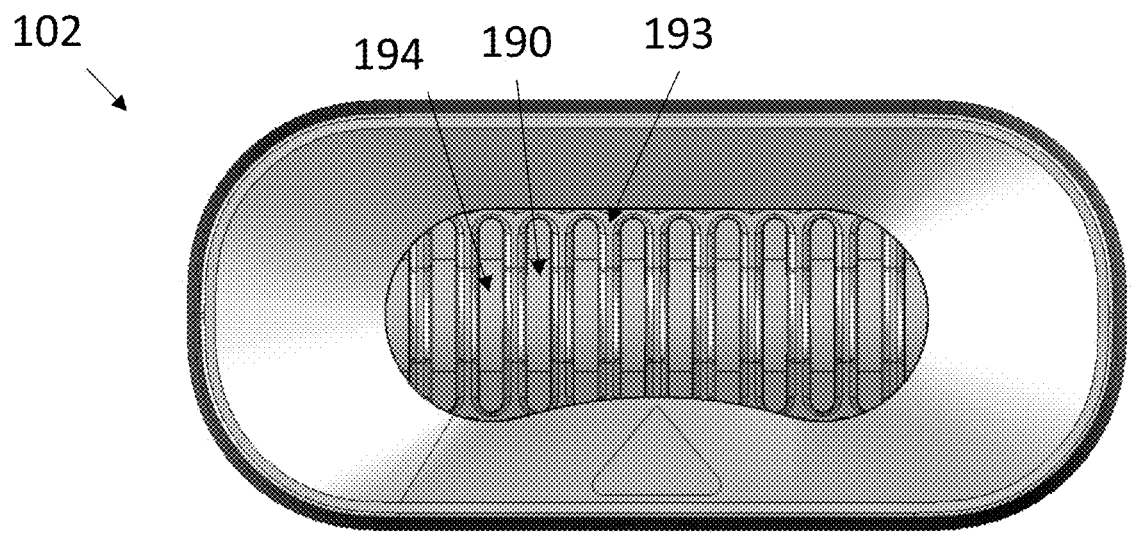

As shown in FIGS. 72-78, the reservoir top 106 may be joined to the reservoir base 104 along parting line 191 (e.g., along axis 191A) (see FIG. 74 and FIG. 76). In some implementations, the reservoir top 106 may be coupled to the reservoir base 104 via various manufacturing methods. For example, the reservoir top 106 may be joined to the reservoir base 104 via laser welding, sintering, die casting, adhering, fastening and/or the like. The multi-component construction of the reservoir 102 may improve the manufacturability of the concentrate adaptor 100 (e.g., the reservoir 102) and/or improve the efficiency of the manufacturing of the concentrate adaptor 100.

In some implementations, the reservoir base 104 may include at least a portion of the capillary structure 190 (e.g., the capillary channels 194 formed along one or more sidewalls) and the reservoir top 106 may also include at least a portion of the capillary structure 190 (e.g., the capillary channels 194 formed along one or more sidewalls). In some implementations, the reservoir base 104 includes at least a portion of the first group of capillary channels 194A and at the second group of capillary channels 194B. In some implementations, the reservoir top 106 includes at least a portion of the first group of capillary channels 194B. In some implementations, the reservoir top 106 does not include the second group of capillary channels 194B. The two-piece construction described herein may improve the manufacturability of the reservoir base 104, for example, by strengthening the side walls of the reservoir 102 and allows the side walls to be more easily molded, extruded, and/or otherwise manufactured. This configuration may also reduce the likelihood that the capillary structure 190 will break or become damaged during manufacturing.

In some implementations, the reservoir 102 includes a channel 133 formed between the outer and inner walls 128, 131 of the reservoir 102 to allow air to pass into the interior of the reservoir 102 from the base 114, as described in more detail herein. The channel 133 may include a channel opening 1053. The channel opening 1053 forms an air inlet into the interior of the reservoir 102 through which the air travels from the channel 133. The channel opening 1053 may be formed by a portion 1054 of the inner wall 131 on the reservoir base 104 and a curved wall 1055 on the reservoir top 106 (see FIGS. 76 and 78). The curved wall 1055 positioned on the reservoir top 106 helps to reduce back leakage of the vaporizable material from the interior of the reservoir 102 into the channel 133, while still allowing a sufficient amount of air to pass through the channel opening 1053 into the interior of the reservoir 102 to mix with the vaporizable material. The curved wall 1055 positioned on the reservoir top 106 may also help to improve manufacturability of the reservoir 102.

In some implementations, the reservoir 102 described herein, such as the reservoir 102 shown in FIGS. 72-78 may be made of one or more materials. For example, the reservoir 102 may include stainless steel, aluminum, and/or another type of conductive metal or combination thereof. In some implementations, the reservoir 102 may desirably be made at least in part of aluminum, which improves the thermal conductivity of the reservoir 102, thereby heating the vaporizable material within the reservoir 102 at a faster rate, and providing the vaporized vaporizable material to the user at a faster rate. This may improve the user experience when using the concentrate adaptor 100 by delivering the aerosol to the user more quickly and more consistently.

Referring back to FIGS. 73A and 73B, FIGS. 73A and 73B illustrate example airflow paths 153 through various apertures and profiles formed in the reservoir 102 and/or the base 114 of the concentrate adaptor 100. As shown in FIGS. 73A and 73B, air from outside concentrate adaptor 100 may enter the interior of the concentrate adaptor 100 via the bottom base opening 143 and through the channel 1029 formed between the base housing 114A and the base floor 114B. In some implementations, the air may flow through the channel 1029 and around the one or more coupling mechanisms into the interior of the base 114. Once the air enters the concentrate adaptor 100, such as into the interior of the base 114, the airflow path 153 may be contained entirely within the concentrate adaptor 100 until the air exits the concentrate adaptor 100 via an outlet, such as the opening 112 of the reservoir 102. For example, as described herein, the reservoir 102 may be locked into place with respect to the base 114. Locking the reservoir 102 into place with respect to the base 114 may seal the reservoir 102 with the base 114 to form a sealed internal volume of the concentrate adaptor 100. This configuration may maximize airflow by retaining all (or most) of the air that passes into the concentrate adaptor 100. For example, air may flow into the concentrate adaptor 100 through the bottom base opening 143 and along the airflow path 153. The airflow path 153 may extend from the bottom base opening 143 (e.g., an inlet), through the channel 1029, into the interior of the base 114 (e.g., between the base housing 114A and the base floor 114B).

From the interior of the base 114, the air may travel along the airflow path through one or more outlets 176 in the base 114 (see FIG. 73A). For example, the base 114 may include two or more outlets 176 positioned on opposing sides of the base opening 115). The air may continue to travel along the airflow path 153 from the outlets 176 into the reservoir 102, such as along channel 133 of the reservoir 102 formed between the outer and inner walls 128, 131 of the reservoir 102. In some implementations, the air may continue to travel along the airflow path 153 through a channel opening 1053 into the interior portion of the reservoir 102. The incoming air mixes with the vapor generated by the vaporization of the contents of the reservoir 102 (e.g., the vaporizable material) to form an aerosol. For example, the vaporizable material may be heated, and travel towards the sides of the reservoir 102 via the capillary structure 190. The incoming air may mix with the heated vaporizable material from within the capillary structure 190. The resulting air flow carries the aerosol out of the reservoir 102 through an outlet of the reservoir 102, such as the opening 112 of the reservoir 102. In some implementations, the aerosol exits the reservoir 102 of the concentrate adaptor, through the air path 17 of the vaporizer device 10, to the mouthpiece 18 where the aerosol is delivered to the user when the user draws on the vaporizer device 10.

Consistent with implementations of the current subject matter, the reservoir 102 of the concentrate adaptor 100 described herein may be modified to improve performance of the concentrate adaptor 100. For example, the reservoir 102 may be modified to increase the surface area of the reservoir 102 in direct contact with the vessel 12 and/or the heating element of the vaporizer device 10 and/or reduce the overall mass of the concentrate adaptor 100. For example, FIGS. 79A-82 illustrate configurations of the concentrate adaptor 100 which provide improved vapor production and a reduction in the amount of time for producing vapor. These configurations and/or components thereof may be incorporated and/or applied to any of the concentrate adaptors 100, 500, 600 described herein, such as the concentrate adaptor shown in FIGS. 1-78 and 83A-87C.

Figure 79A:
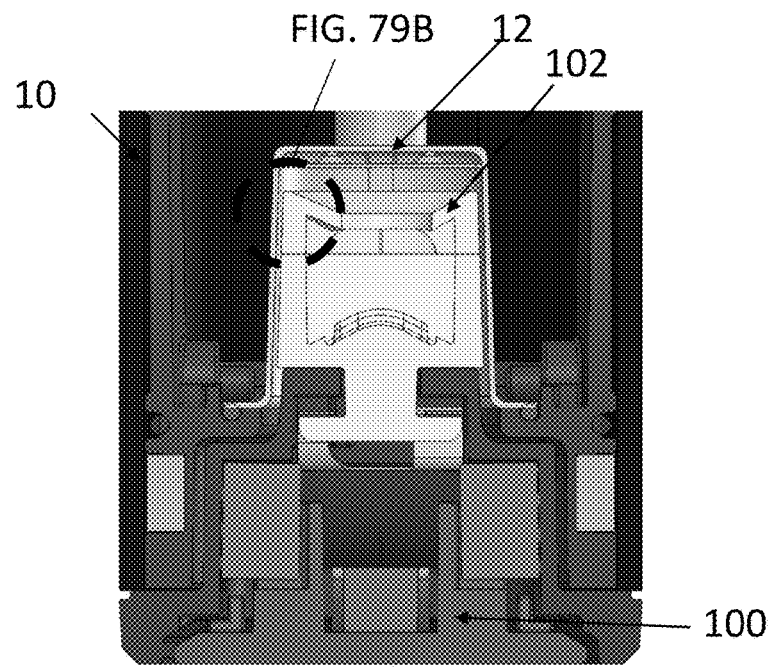
FIGS. 79A-79B illustrate an example concentrate adaptor and vaporizer device consistent with implementations of the current subject matter.
Figure 79B:
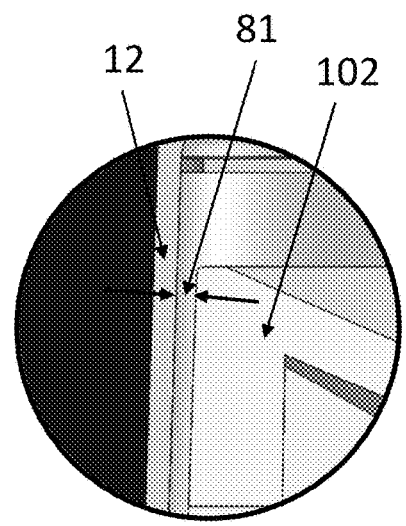

FIGS. 79A-79B illustrate an example of the concentrate adaptor 100 coupled to the vaporizer device 10 consistent with implementations of the current subject matter. As shown in FIGS. 79A and 79B, a gap 81 is formed between an exterior of the reservoir 102 of the concentrate adaptor 100 and an inner wall of the vessel 12. The air gap 81 may be approximately 0.2 mm, 0.1 mm, 0.3 mm, 0.5 mm, 0.6 mm, 0.7 mm, 0.8 mm, 0.9 mm, 1.0 mm or greater. The gap 81 may be desirably small to reduce the amount of time to heat the reservoir 102 and thus reduce the amount of time to aerosolize the vaporizable material contained within the reservoir and produce vapor.

Figure 80A:
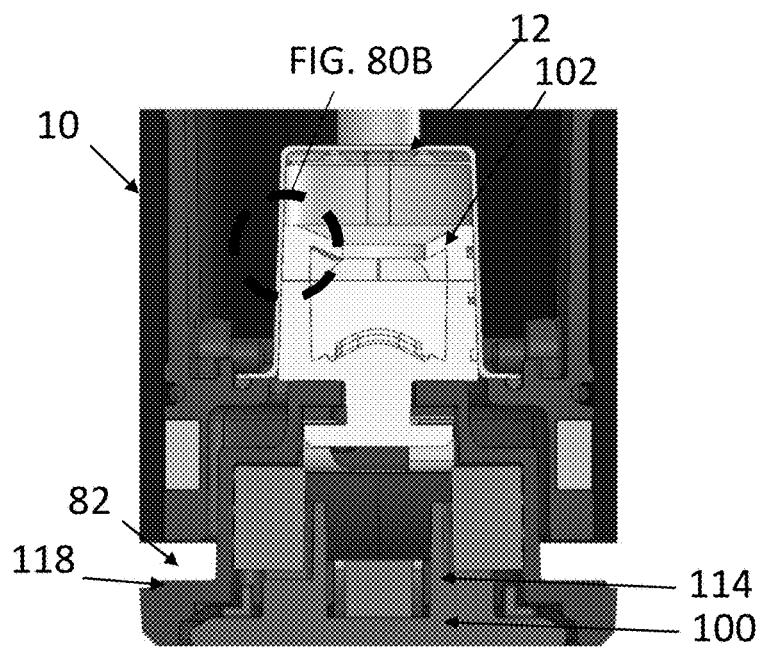
FIGS. 80A-80B illustrate an example concentrate adaptor and vaporizer device consistent with implementations of the current subject matter.
Figure 80B:
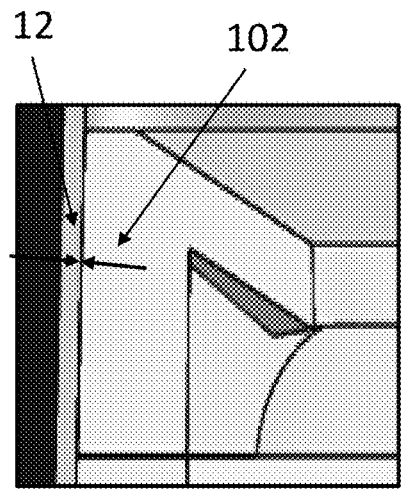

FIGS. 80A-80B illustrate an example of the concentrate adaptor 100 coupled to the vaporizer device 10 consistent with implementations of the current subject matter. As shown in FIGS. 80A and 80B, the gap 81 formed between an exterior of the reservoir 102 of the concentrate adaptor 100 and the inner wall of the vessel 12 has been eliminated. Rather, the exterior of the reservoir 102 directly contacts the inner wall of the vessel 12 on at least one (e.g., one, two, three, four or more) sides of the reservoir 102 to reduce the amount of time to heat the reservoir 102 and thus reduce the amount of time to aerosolize the vaporizable material contained within the reservoir and produce vapor. In this example, an air gap 82 is formed between a bottom surface of the vaporizer device 10 and a ledge 118 formed on an outer surface of the base 114 of the concentrate adaptor 100. The air gap may have a length of approximately 1.75 mm, 1.0 mm to 2.95 mm, 0.1 mm to 0.5 mm, 0.5 mm to 1.0 mm, 1.0 mm to 1.5 mm, 1.5 mm to 2.0 mm, 2.0 mm to 2.5 mm, 2.5 mm to 3.0 mm, 3.0 mm to 3.5 mm, and/or greater. This configuration allows for a greater amount of air to pass into the concentrate adaptor 100 through the air gap 82, which increases the amount of vapor produced by the concentrate adaptor 100 when the vaporizable material is aerosolized.

FIGS. 81A-81C illustrate an example of the concentrate adaptor 100 coupled to the vaporizer device 10 consistent with implementations of the current subject matter. As shown in FIGS. 81A-81C, the reservoir 102 is biased such that one side of the reservoir 102 contacts the vessel 12 and a gap 81 is formed between the opposing side of the reservoir 102 and the vessel. To bias the reservoir 102 such that one side of the reservoir 102 contacts the vessel 12 while a gap is formed between the opposing side of the reservoir 102 and the vessel 12, the concentrate adaptor 100 may include one or more magnets 170 of different sizes. For example, the concentrate adaptor 100 may include a first magnet 170A positioned on one side of the base 114 and having a first thickness that is greater than a second thickness of a second magnet 170A positioned on an opposing side of the base 114. The first magnet 170A having the greater thickness biases the concentrate adaptor 100 (e.g., the reservoir 102) to one side of the vessel 12 when the concentrate adaptor is inserted into the vaporizer device 10.

In some implementations, the top surface of the reservoir 102 may additionally and/or alternatively be flattened so that the top surface of the reservoir 102 also contacts the vessel 12. As described herein, direct contact between the reservoir 102 and the vessel 12 and/or the heating element of the vaporizer device 10 reduces the amount of time to heat the reservoir 102 and thus reduces the amount of time to aerosolize the vaporizable material contained within the reservoir and produce vapor.

In some implementations, reducing the mass of the reservoir 102 may additionally and/or alternatively improve vapor performance. As the mass of the reservoir 102 containing the vaporizable material is reduced, less material of the reservoir 102 needs to be heated. As a result, the amount of time to heat the reservoir 102 and the vaporizable material stored within the reservoir 102 may be reduced. As shown in FIG. 81B, portions of the connection feature 117 may be scalloped to remove material from the reservoir 102 and reduce the overall mass of the reservoir 102. Additionally and/or alternatively, as shown in FIG. 81C, the capillary structure from the base wall 193 of the reservoir 102 have been removed to reduce the mass of the reservoir 102. Additionally and/or alternatively, as shown in FIG. 81A, portions of the top surface of the reservoir 102 may be removed to form detents 79 in the top surface. This helps to reduce the mass of the reservoir 102 and reduce the amount of time to heat the reservoir 102.

Figure 82:
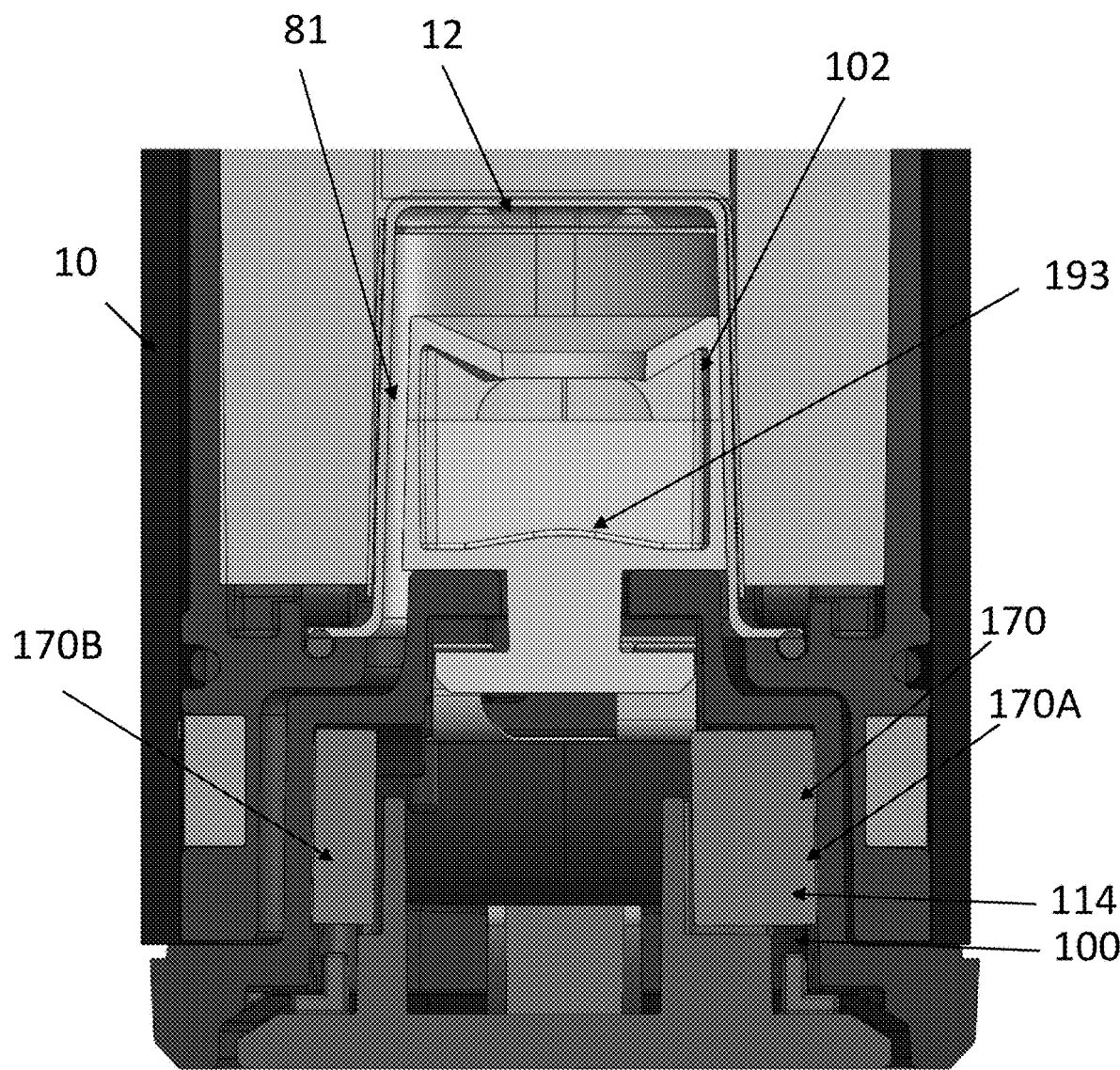
FIG. 82 illustrates an example concentrate adaptor and vaporizer device consistent with implementations of the current subject matter.

FIG. 82 illustrates another example of the concentrate adaptor 100 coupled to the vaporizer device 10 consistent with implementations of the current subject matter. As shown in FIG. 82, the reservoir 102 has a reduced mass to reduce the amount of time to heat the reservoir 102 and to improve vapor performance. Similar to the variation illustrated in FIGS. 81A-81C, portions of the connection feature 117, the capillary structure from the base wall 193 of the reservoir, and portions of the top surface of the reservoir 102 may be removed to reduce the overall mass of the reservoir 102. In this example, the height of the reservoir 102 may be reduced to further reduce the overall mass of the reservoir 102. This helps to reduce the amount of time to heat the reservoir 102 and improve vapor performance.

Consistent with implementations of the current subject matter, the reservoir 102 may receive a vaporizable material, such as the concentrate through the opening 112 in the top portion of the reservoir 102. For example, a user may use an accessory tool (e.g., an accessory tool shown in FIGS. 91-94B) to provide the vaporizable material to the concentrate adaptor 100. Upon insertion of the vaporizable material to the interior of the concentrate adaptor 100 through the opening 112, a portion of the vaporizable material may be left on one or more exterior surfaces of the concentrate adaptor 100, such as an outer surface of the top portion of the reservoir 102. In use, some vaporizable material may additionally and/or alternatively leak out of the interior of the reservoir 102, such as via the opening 112. During use of the concentrate adaptor 100, the reservoir 102 may be heated by the vaporizer device 10. This causes the vaporizable material to be heated, and in some instances liquefy.

In some implementations, the reservoir 102 includes an exterior channel defining a recess formed in at least one exterior surface of the reservoir of the concentrate adaptor. The exterior channel may collect vaporizable material remaining on and/or leaked onto the one or more exterior surfaces of the reservoir 102, redirect the vaporizable material back into the interior of the reservoir 102, such as via the opening 112, and/or prevent the vaporizable material from migrating to other exterior faces of the reservoir 102. Thus, the exterior channel may improve performance of the concentrate adaptor 100 by helping to ensure that all of the vaporizable material intended to be vaporized is actually vaporized.

In some implementations, the exterior channel serves as a collection feature to collect the vaporizable material remaining on the exterior surface of the reservoir. Additionally and/or alternatively, the exterior channel may be shaped and/or sized to direct the vaporizable material into the interior portion of the reservoir. For example, the exterior channel may be tapered, angled, sloped, and/or the like to direct the vaporizable material into the interior portion of the reservoir, such as via the opening 112 and/or through one or more other openings in the reservoir. Additionally and/or alternatively, the exterior channel may define a capillary channel. For example, the liquefied vaporizable material may be collected into the exterior channel when the vaporizable material liquefies and may be held within the exterior channel and/or drawn along the exterior channel towards the interior of the reservoir due to, for example, capillary action caused by shape and/or size of the exterior channel. For example, opposing side walls of the exterior channel can be desirably spaced to allow for fluid, such as the liquefied vaporizable material, to be transported from and/or drawn from an exterior surface of the reservoir into the exterior channel, and/or along the exterior channel into the interior of the reservoir, such as via capillary action. The size (e.g., length, width, etc.) of the space between opposing sidewalls of the exterior channel can be desirably narrow to maintain strong and/or sufficient capillary forces to draw along and/or otherwise retain the vaporizable material within the exterior channel.

FIGS. 83A-83F illustrate examples of various configurations of the exterior channel which may be incorporated and/or applied to any of the reservoirs of the concentrate adaptors 100, 500, 600 described herein, such as the reservoir 102, 502, 602 shown in FIGS. 1-82 and 84A-87C.

Referring to FIG. 83A, the reservoir 102 may include an exterior channel 83A. The exterior channel 83A may form a ring that extends about the opening 112. As shown, the exterior channel 83A may extend around all or a portion of a perimeter of a top surface of the top portion of the reservoir 102. The exterior channel 83A may be inset from an outer edge of the top surface of the top portion of the reservoir 102. The exterior channel 83A may be pill-shaped, rectangular, oval, and/or the like. The exterior channel 83A may include an outlet region 84 that directs the vaporizable material held within the exterior channel 83A through the opening 112 and into the interior portion of the reservoir 102. The outlet region 84 may be positioned on one or opposing sides of the opening 112. The position of the outlet region 84 may be desirably positioned at a loading interface, such as a portion of the top surface of the top portion of the reservoir 102 where the vaporizable material is most likely to remain after depositing the vaporizable material into the reservoir 102. The outlet region 84 may include one, two, three, four, or more outlet regions 84. The outlet region 84 may include a wide inlet 85 and narrow outlet 86 to funnel the vaporizable material through the opening 112. For example, the outlet region 84 may include opposing side walls that are tapered towards one another to direct the flow of the vaporizable material. Additionally and/or alternatively, all or a portion of the exterior channel 83A, including the outlet region 84 may be angled inwardly towards the opening 112. Thus, the exterior channel 83A may capture the vaporizable material and/or redirect the vaporizable material through the opening 112.

FIG. 83B illustrates another example configuration of the reservoir 102 consistent with implementations of the current subject matter. As shown in FIG. 83B, the reservoir 102 includes a plurality of exterior channels 83B positioned along the top surface of the top portion of the reservoir 102. For example, the reservoir 102 may include one, two, three, four, five, five to ten, ten to fifteen, fifteen to twenty, twenty to twenty-five or more exterior channels 83B. The exterior channels 83B may be positioned radially about the opening 112 to direct the vaporizable material towards the opening 112. The exterior channels 83B may extend from a portion of the top surface of the reservoir 102 inwardly towards the opening 112. For example, at least one exterior channel 83B may extend from an outer edge of the top surface of the reservoir 102 and/or a portion of the top surface inset from the outer edge to an edge of the opening 112 and/or to a portion of the top surface inset from the edge of the opening 112. In some implementations, the reservoir 102 includes a greater number of exterior channels 83B along one or both long sides of the reservoir than along one or both short sides of the reservoir 102. As shown in FIG. 83B, the reservoir 102 may include a plurality of adjacent exterior channels 83B that are spaced apart from one another along the long sides of the reservoir 102. The exterior channels 83B extend from the outer edge of the top surface of the reservoir 102 to the edge of the opening 112 along one long side of the reservoir 102 and extend from the outer edge of the top surface of the reservoir to a portion of the reservoir 102 inset from the opening 112. This helps to direct the vaporizable material towards the opening 112 in the region in which vaporizable material is most likely to remain after depositing the vaporizable material into the reservoir 102, and to prevent the vaporizable material from leaking to other exterior surfaces of the reservoir 102 at the opposing long side. In this example, the reservoir includes a single exterior channel positioned at opposing short sides of the reservoir 102 from a portion that is inset from the outer edge of the top surface of the reservoir 102 to the edge of the opening 112.

FIG. 83C illustrates another example configuration of the reservoir 102 consistent with implementations of the current subject matter. As shown in FIG. 83C, the reservoir 102 includes a plurality of parallel exterior channels 83C positioned along an outer surface of one or more sidewalls of the reservoir 102. For example, the exterior channels 83C may extend from an upper edge and/or from a lower edge of one or more sidewalls of the reservoir 102. In some implementations, a first plurality of exterior channels 83C extends from an upper edge of a sidewall of the reservoir 102 towards the lower edge of the sidewall and terminates at a region inset from the lower edge, and a second plurality of exterior channels 83C extends from the lower edge of the sidewall of the reservoir 102 towards the upper edge of the sidewall and terminates at a region inset from the upper edge. The first plurality of exterior channels 83C and the second plurality of exterior channels may be spaced apart from one another. This configuration may help to capture and/or retain vaporizable material positioned on one or more of the exterior sidewalls of the reservoir 102 and prevent or limit the vaporizable material from leaking into another portion of the vaporizer device and/or out of the vaporizer device.

FIG. 83D illustrates another example configuration of the reservoir 102 consistent with implementations of the current subject matter. As shown in FIG. 83D, the reservoir 102 includes a pair of exterior channels 83D positioned along a top surface of the reservoir 102. The pair of exterior channels 83D are positioned about opposing sides (e.g., opposing short sides) of the opening 112. The pair of exterior channels 83D include a curved shape to correspond to the shape of the reservoir 102 along the short sides of the reservoir 102. The pair of exterior channels 83D may be positioned inset from the outer edge of the top surface of the reservoir 102 and inset from the edge of the opening 112. Though the pair of exterior channels 83D are illustrated along opposing short sides of the top surface of the reservoir 102, the pair of exterior channels 83D may be positioned along opposing long sides of the top surface of the reservoir 102, and/or about all sides of the top surface of the reservoir surrounding the opening 112. The exterior channels 83D may be shaped and/or sized to capture the vaporizable material that remains on the top surface of the reservoir after depositing the vaporizable material into the interior portion of the reservoir 102 through the opening 112.

FIG. 83E illustrates another example configuration of the reservoir 102 consistent with implementations of the current subject matter. As shown in FIG. 83E, the reservoir 102 includes an exterior channel 83E positioned on at least one exterior sidewall of the reservoir 102. The exterior channel 83E may include one, two, three, four or more exterior channels 83E. The exterior channels 83E may be positioned parallel to one another. The exterior channels 83E may wrap around the exterior sidewalls of the reservoir 102. In this configuration, the exterior channels 83E may capture and/or retain vaporizable material positioned on one or more of the exterior sidewalls of the reservoir 102, and prevent or limit the vaporizable material from leaking onto another surface of the reservoir, into the vaporizer device and/or out of the vaporizer device.

FIG. 83F illustrates another example configuration of the reservoir 102 consistent with implementations of the current subject matter. As shown in FIG. 83F, the reservoir 102 includes an exterior channel 83F positioned along a portion of the opposing long sides and/or the opposing short sides of the reservoir 102. For example, the exterior channel 83F may be positioned along a portion of the outer edge of each of the long sides and short sides of the top surface of the reservoir. The exterior channel 83F may form a notch in the outer edge of the top surface of the reservoir 102. Thus, the exterior channel 83F captures the vaporizable material before the vaporizable material travels to another surface of the reservoir 102. This helps to prevent or limit the vaporizable material from leaking onto another surface of the reservoir, into the vaporizer device and/or out of the vaporizer device.

FIGS. 84A-85C illustrate an example of a concentrate adaptor 600 consistent with implementations of the current subject matter. The concentrate adaptor 600 illustrated in FIGS. 84A-85C includes the same and/or similar properties and/or components as the concentrate adaptor 100 illustrated in FIGS. 1-83F. For example, the concentrate adaptor 600 may be used with the vaporizer device 10 and includes a reservoir 602 and a base 614, which are the same or similar to the reservoir 102 and the base 114 described herein.

Figure 84A:
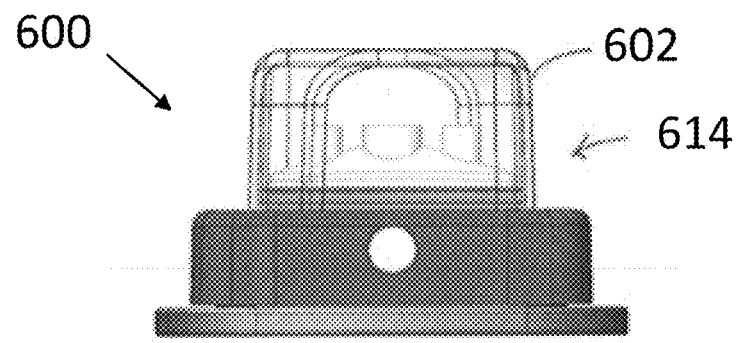
FIGS. 84A-84N illustrate an example concentrate adaptor consistent with implementations of the current subject matter.
Figure 84B:
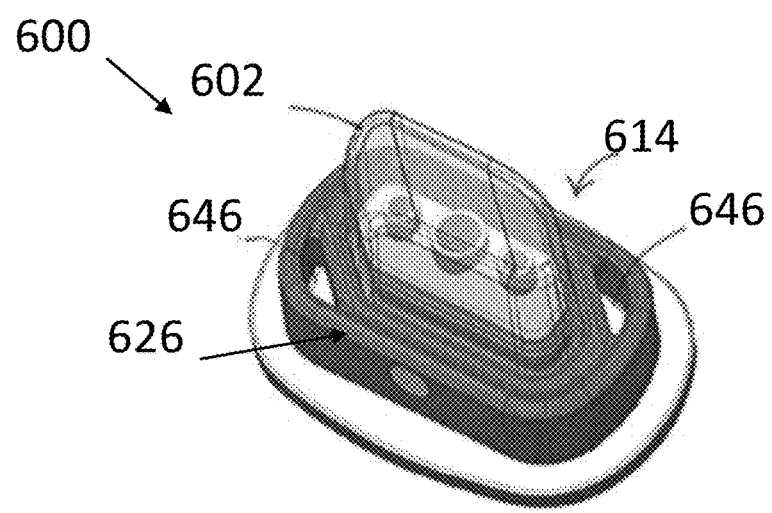
Figure 84C:
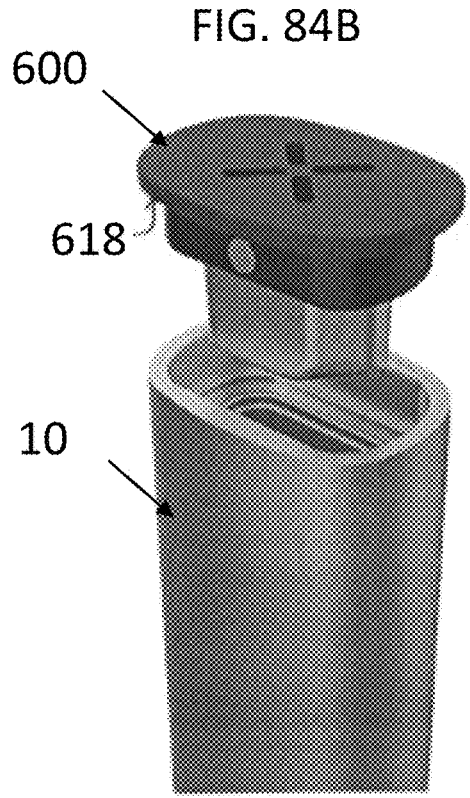
Figure 84D:
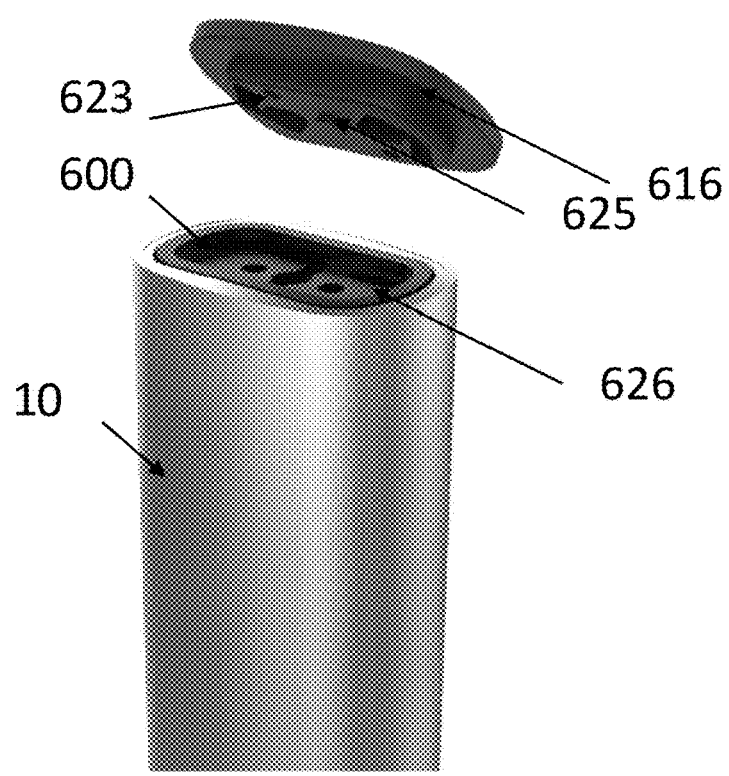
Figure 84E:
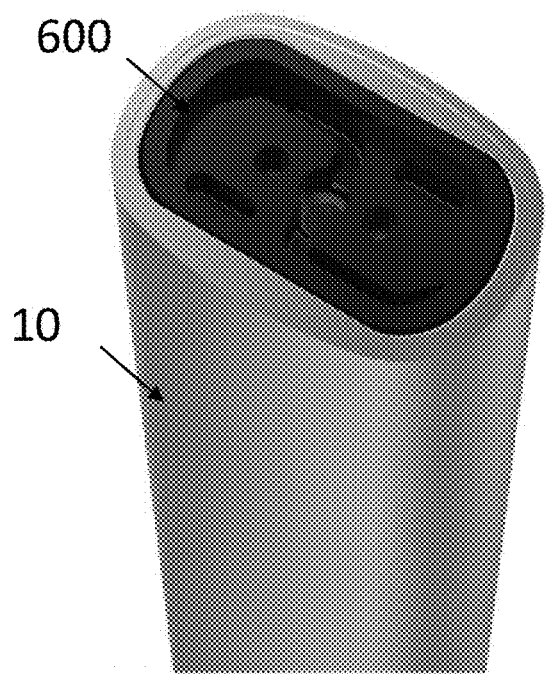
Figure 84F:
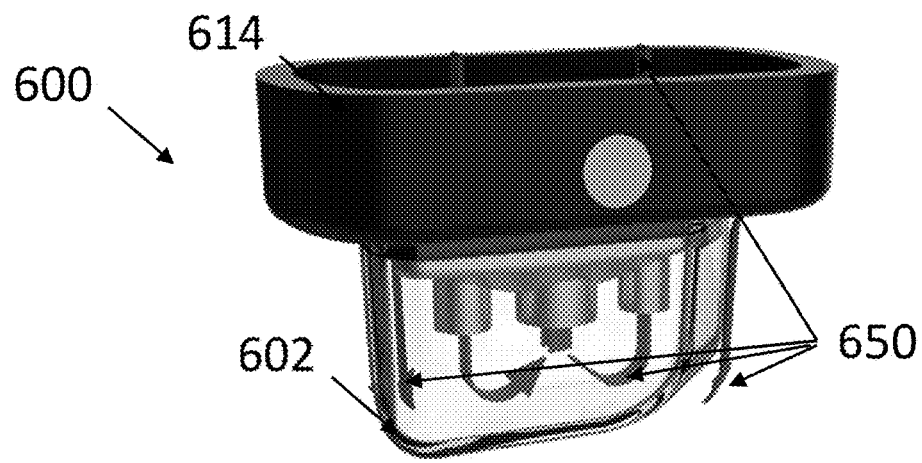
Figure 84G:
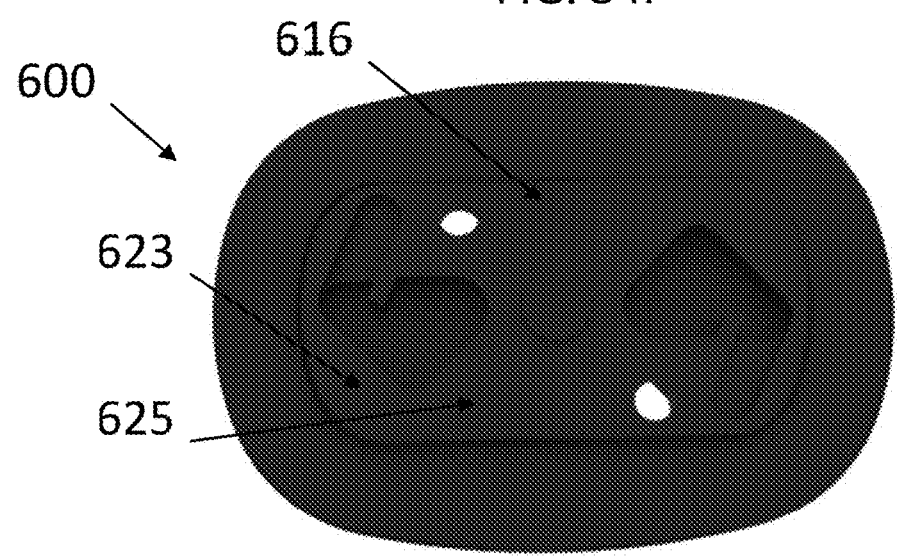
Figure 84H:
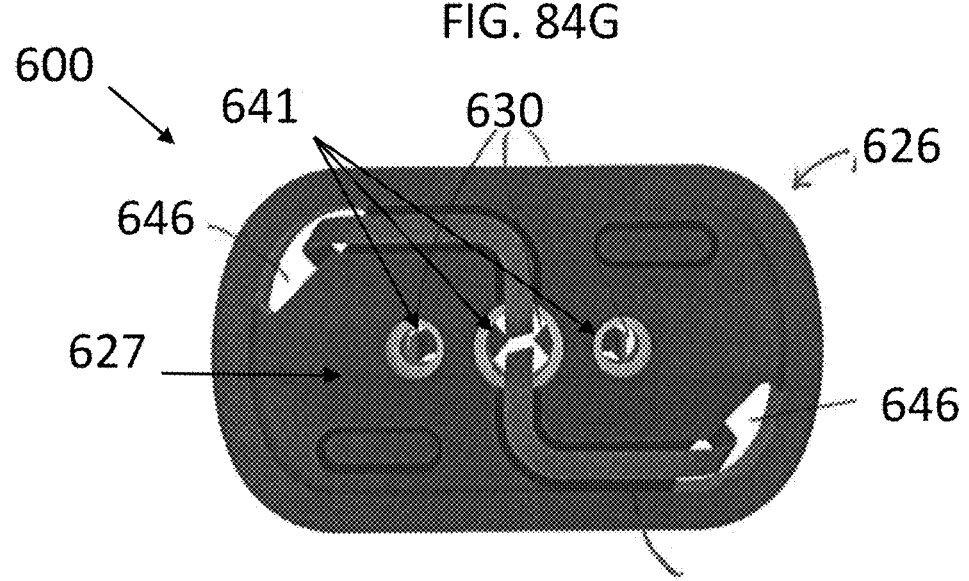
Figure 84I:
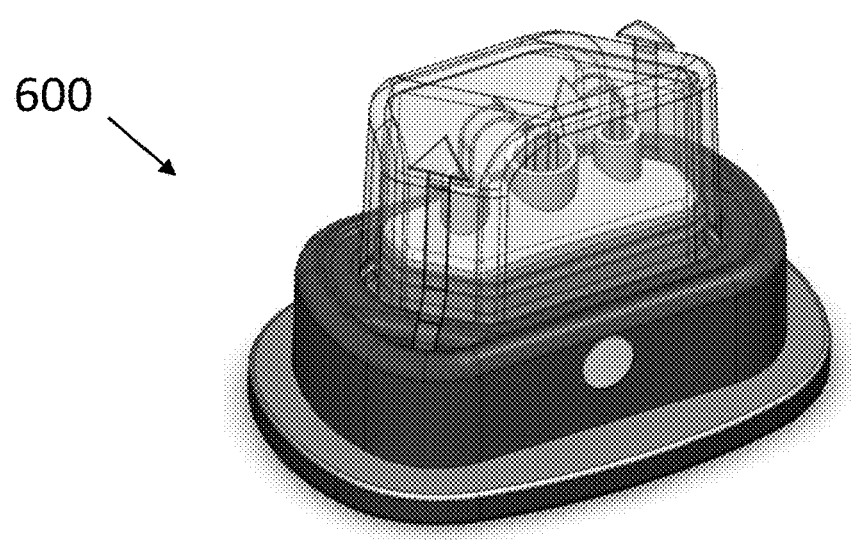
Figure 84J:
Figure 84K:
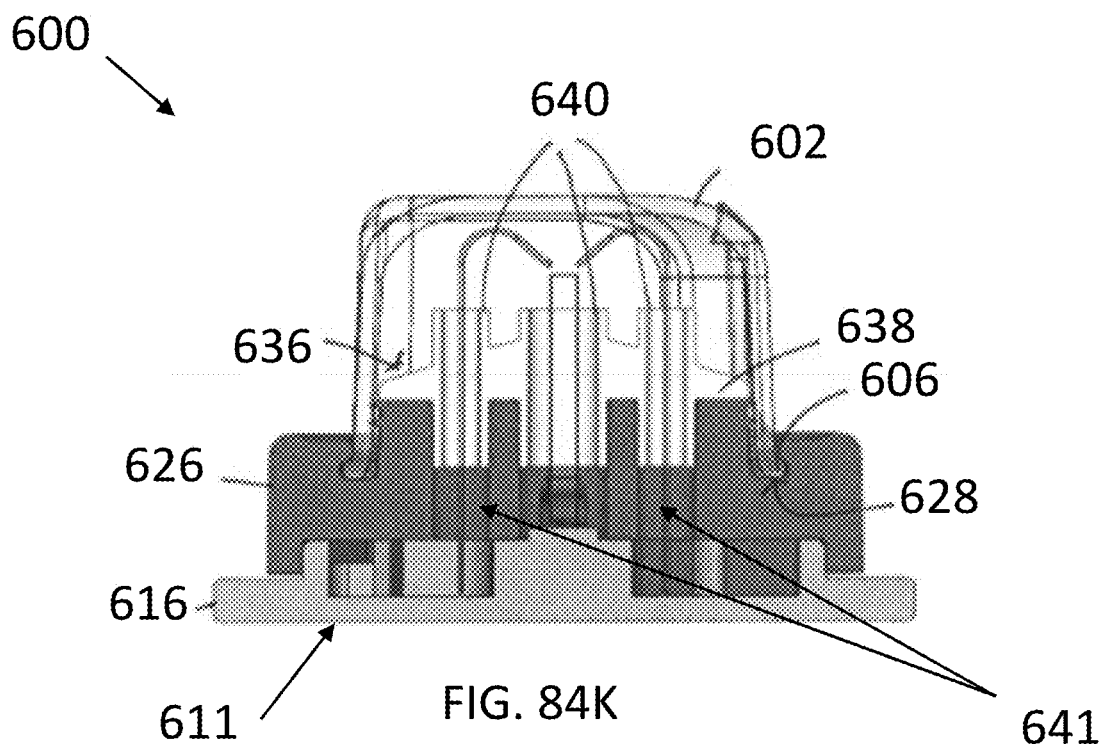
Figure 84L:
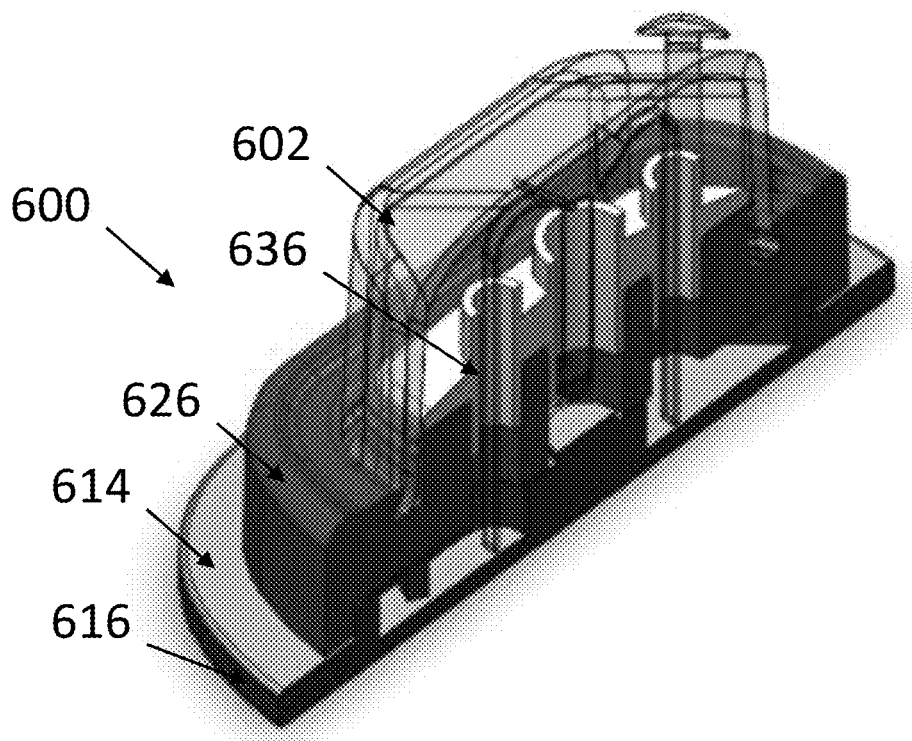
Figure 84M:
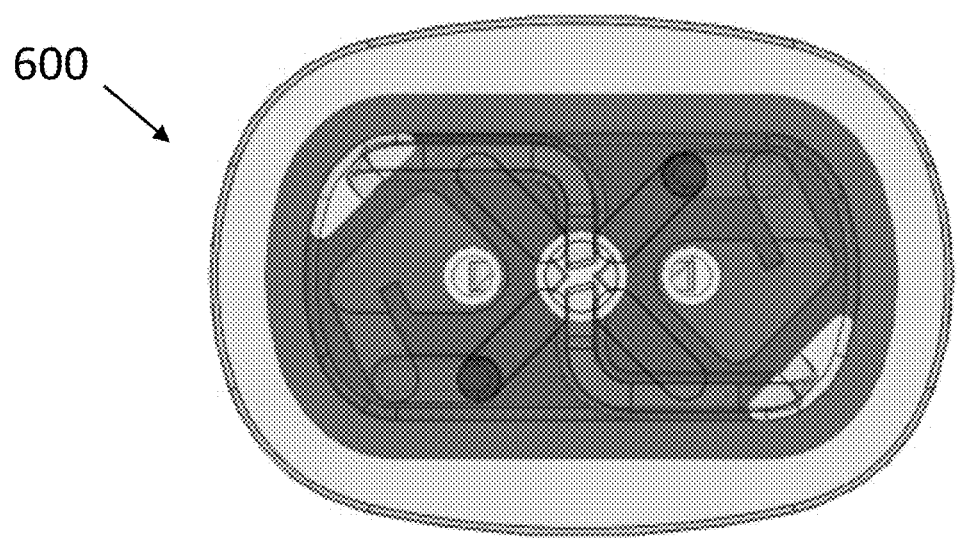
Figure 84N:
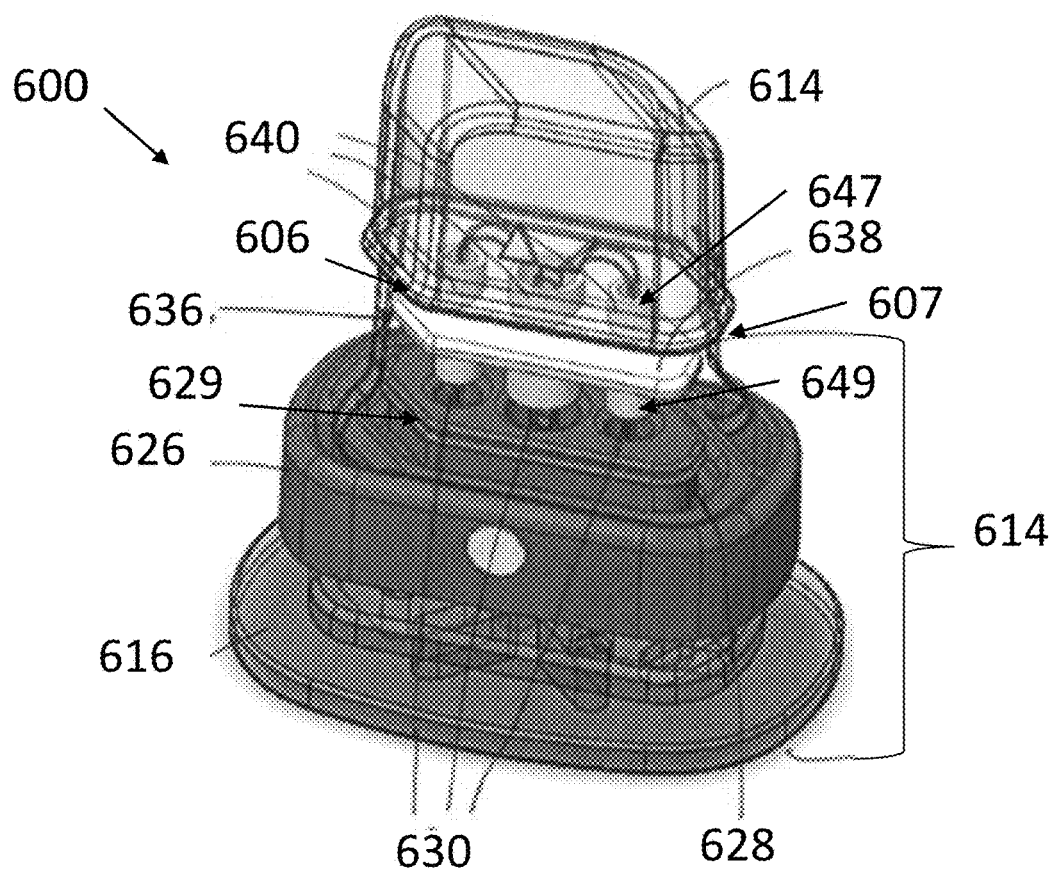
Figure 85A:
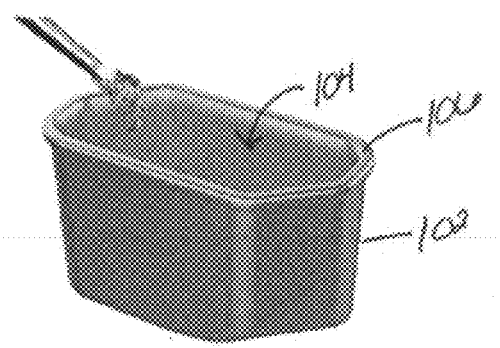
FIGS. 85A-85C illustrate an example method of assembling a concentrate adaptor consistent with implementations of the current subject matter.
Figure 85B:
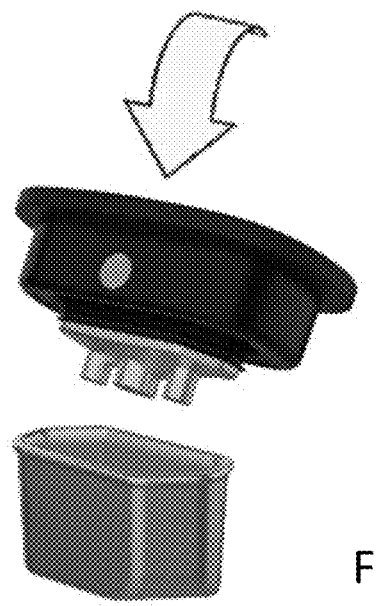
Figure 85C:
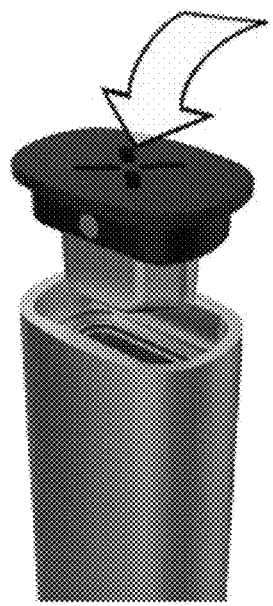

The reservoir 602 may include a lip 606 (see FIGS. 84K, 84N). The lip 606 may extend around an outer perimeter of a top side 607 (e.g., a top end of the sidewalls of the reservoir 602 may include a lip 606) of the reservoir 602. The lip 606 may engage with a first mating structure 628 on a top surface 629 of the base 614 (described in detail below), thereby attaching or otherwise connecting the reservoir 602 to the base 614 (FIGS. 84K, 84L, and 84N).

The base 614 includes a base support structure 616, a base mounting structure 626, and an airflow guider 636. A bottom surface of the base support structure 616 defines the bottom surface 611 of the base 614. The base mounting structure 626 connects or is otherwise attached to the base support structure 616. For example, a bottom surface 627 of the base mounting structure 626 connects or is otherwise attached to a top surface of the base support structure 616. The first mating structure 628 and a second mating structure 630 are formed on the base mounting structure 626. The first mating structure 628 is configured to engage with the lip 606 of the reservoir 602. The second mating structure 630 is configured to engage with the airflow guider 636. One or more apertures 646 are formed and extend through the base mounting structure 626 (see FIG. 84B) to allow air to pass through. The apertures may be of various sizes and shapes.

The first mating structure 628 may be one or more grooves or indentations formed on the top surface 629 of the base 614, where the one or more grooves or indentations are sized and shaped to securely hold therein (through for example a friction fit) the lip 606 of the reservoir 602. In some implementations, the first mating structure 628 is a groove formed on the top surface 629 of the base 614, where the size and shape of the groove generally and/or substantially correspond to that of the lip 606. The top surface 629 of the base 614 may be formed of a material that allows for the lip 606 to be fitted within the groove. For example, the material may include a material with some elasticity and/or flexibility. The reservoir 602 may engage with the first mating structure 628 by applying pressure to the reservoir 602 such that the lip 606 of the reservoir 602 engages with the first mating structure 628. For example, the lip 606 may be fitted within the groove. The reservoir 602 may disengage with the first mating structure 628 by applying pressure to the reservoir 602 such that the reservoir 602 is pulled out of the first mating structure 628. For example, the lip 606 may be pulled out of the groove.

Referring to FIG. 84N, the airflow guider 636 includes a plate 638 through which a plurality of airflow holes 640 are formed. The airflow holes 640 may include upper sidewalls 647 that extend above a top surface of the plate 638 and lower sidewalls 649 that extend below a bottom surface of the plate 638. Properties of the airflow holes 640 (e.g., diameter, placement with respect to one another, length) may vary and may be adjusted to account for total particulate matter, vapor density, vapor flow rate, airflow rate, desirable or undesirable presence of turbulence or vortices, or combinations thereof. The airflow holes 640 may have circular cross-sections, oval cross-sections, elliptical cross-sections, square cross-sections, rectangular cross-sections, or other polygonal cross-sections.

The second mating structure 630 of the base mounting structure 626 includes a plurality of through-holes 641 sized and shaped to receive respective ones of the airflow holes 640 of the airflow guider 636. For example, the airflow holes 640 securely and snugly fit within respective ones of the through-holes 641.

A cooling path 632 may be formed on the bottom surface 627 of the base mounting structure 626 (see FIGS. 84H, 84I, 84K, 84L, 84N). For example, the cooling path 632 may extend from one or more of the through-holes 641 formed through the base mounting structure 626 such that air is forced along the cooling path 632 and directed to the apertures 646 (FIG. 84H). The cooling path 632 provides a pathway through which the vapor may be cooled. The bottom surface 627 of the base mounting structure 626 may define a recess in which the cooling path 632, the through-holes 641, and the apertures 646 are contained (FIG. 84H). A top surface 623 of the base support structure 616 may include a complementary plate 625 that securely fits within the recess (FIG. 84D, FIG. 84G, FIG. 84M). When the base mounting structure 626 and the base support structure are connected, the complementary plate 625 is securely contained in the recess, forcing the airflow along the cooling path 632 before being directed to the apertures 640 (as further described below). Moreover, the top surface of the base mounting structure 626 may include one or more cavities in which leaked vaporizable material may collect to prevent or reduce leaking. The one or more cavities may be positioned adjacent portions of the cooling path 632, thus able to collect excess vaporizable material. When the concentrate adaptor 600 is an assembled form, the reservoir 602 encloses the airflow guider 636, and the apertures 646 are exposed (e.g., not covered by the reservoir 602) (FIG. 84B).

Referring to a bottom view of the base mounting structure 626 (e.g., the base mounting structure 626 without being connected to the base support structure 616), an airflow path 650 through the base mounting structure 626 is illustrated with reference to FIG. 84F, FIG. 84I, FIG. 84K, and FIG. 84N. First, air flows into the concentrate adaptor 600 from outside (e.g., through holes through the bottom surface of the base 614), entering the reservoir 602 through the airflow holes 640 and mixing with vapor produced from the vaporizable material contained in the reservoir 602. The air is then moved downward through the center airflow hole 640. The air is then moved along the cooling path 632 of the base mounting structure 626. The air is then forced to exit through the apertures 646. The apertures 646 may capitalize on the difference in velocity of air flowing into the concentrate adaptor 600 relative to air in other parts of the concentrate adaptor 600 and/or the vessel of the vaporizer device 10, and may similarly capitalize on the difference in pressure of those apertures.

The base 614 of the concentrate adaptor 600 may be formed of various materials. For example, the base support structure 616 may be made from a plastic, metal, or other resilient material. The base mounting structure 626 may be made from an elastomeric material that provides for sealing (e.g., sealing with the reservoir 600 and the airflow guider 636). The airflow guider 636 may be formed from a metal material, such as aluminum, stainless steel, and/or the like.

FIGS. 86A-87C illustrate an example of a concentrate adaptor 500 consistent with implementations of the current subject matter. The concentrate adaptor 500 illustrated in FIGS. 86A-87C includes the same and/or similar properties and/or components as the concentrate adaptor 100, 600 illustrated in FIGS. 1-85C. For example, the concentrate adaptor 500 may be used with the vaporizer device 10 and includes a reservoir 502 and a base 514, which are the same or similar to the reservoir 102, 602 and the base 114, 614 described herein.

As described herein, the reservoir 502 may include one or more materials, such as stainless steel, aluminum, glass, ceramic, titanium, and/or a conductive metal or combination thereof. For example, the material of the reservoir 502 may be capable of withstanding heat from the heating element of the vaporizer device 10. The reservoir 502 may include a glass material and may form a glass container. Glass may be desirable due at least in part to its inert properties, while also providing transparency to the user to allow the user to view the amount of concentrate remaining in the reservoir 502 during use, and/or during filling of the reservoir 502. The glass container may include sidewalls extending from and connected to a closed side 503. An opened side 505 is opposite the closed side 503 and forms an opening to allow access to an interior portion 504 of the reservoir 502 (e.g., for inserting concentrate and/or cleaning of the reservoir 502).

The reservoir 502 may include a lip 506. The lip 506 may extend around an outer perimeter of the open side 505 of the reservoir 502. For example, an outer end of the sidewalls of the reservoir 502 may include the lip 506. The lip 506 may engage with a mating structure 116 on a top surface of the base 514, thereby attaching or otherwise connecting the reservoir 502 to the base 514.

Figure 86A:
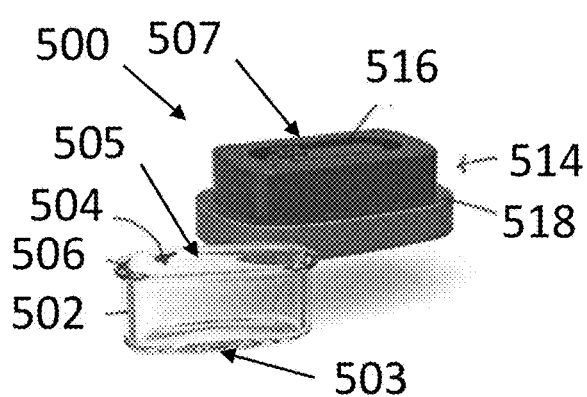
FIGS. 86A-86D illustrate an example concentrate adaptor consistent with implementations of the current subject matter.
Figure 86B:
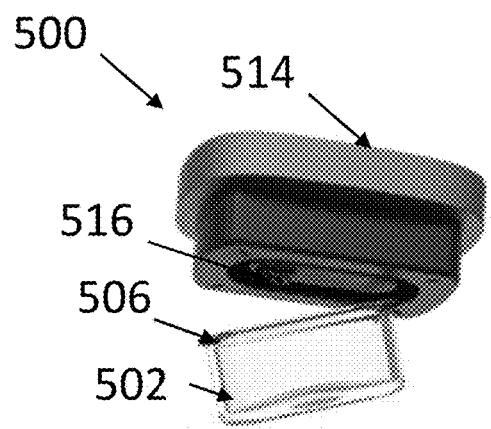
Figure 86C:
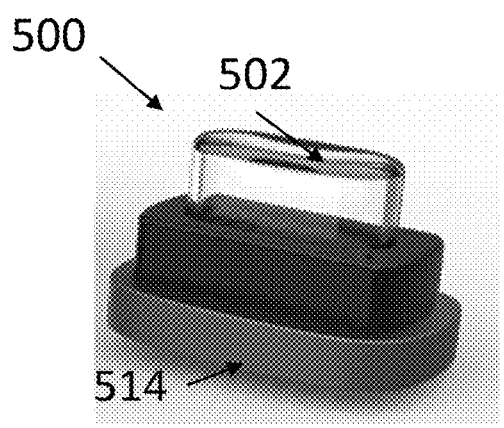

For example, as shown in FIGS. 86A-86C, the base 514 includes a top surface 507 and a bottom surface 518. The top surface 507 includes the mating structure 516 that engages with the lip 506 of the reservoir 502. The mating structure 516 may be one or more grooves or indentations formed on the top surface 507 of the base, where the one or more grooves or indentations are sized and shaped to securely hold therein (through for example a friction fit) the lip 506 of the reservoir 502. In some implementations, the mating structure 516 is a groove formed on the top surface 507 of the base 514, where the size and shape of the groove generally and/or substantially correspond to that of the lip 506. The top surface 507 of the base may be formed of a material that allows for the lip 506 to be fitted within the groove (e.g., a material with some elasticity and/or flexibility). The reservoir 502 may engage with the mating structure 516 by applying pressure to the reservoir 502 such that the lip 506 of the reservoir 502 engages with the mating structure 516 (e.g., the lip 506 is fitted within the groove). The reservoir 502 may disengage with the mating structure 516 by applying pressure to the reservoir 502 such that the reservoir 502 is pulled out of the mating structure 516 (e.g., the lip 506 is pulled out of the groove).

Figure 86D:
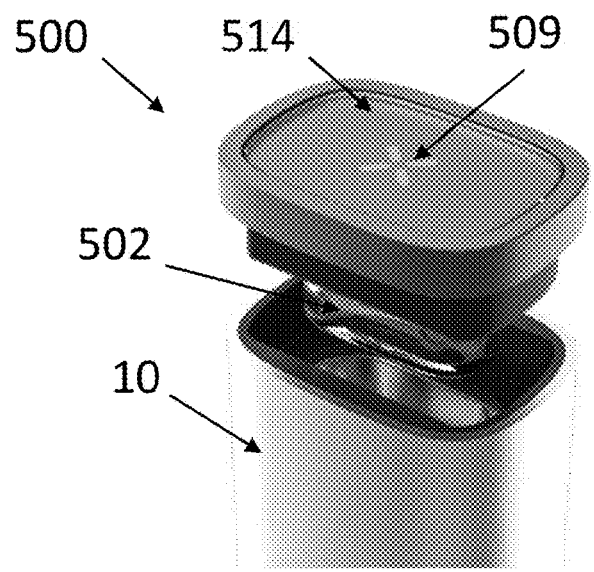

In some implementations, an outer surface 509 of the base 514 of the concentrate adaptor 500 may include a thermochromic pigment that is configured to change colors in response to the temperature of the heating element of the vaporizer device 10 to communicate a temperature to the user (see FIG. 86D). For example, the thermo-chromic pigment may turn orange or red when the heating element of the vaporizer device 10 is activated and/or is at a high temperature (e.g., an operating temperature for vaporization), serving as a potential warning or indication to the user that the concentrate adaptor 500 may be hot and/or heated. At or near room temperature, the thermo-chromic pigment may be a shade of green or blue. At temperatures in between room temperature and operating temperatures, the thermochromic pigment may be a yellow shade. The thermoschromic pigment may serve as an indicator or dynamic feedback to indicate if the concentrate adaptor 500 is too hot to handle by the user.

Figure 87A:
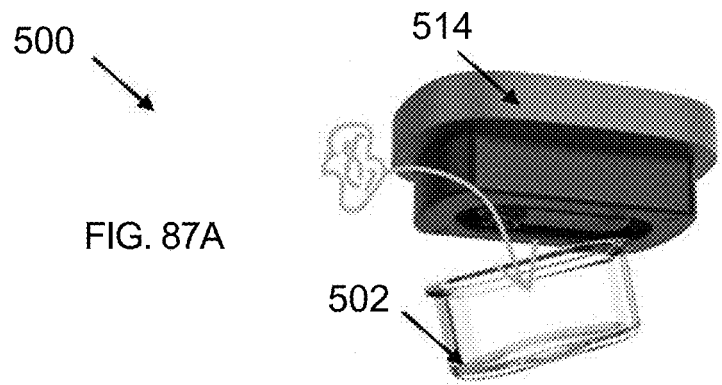
FIGS. 87A-87C illustrate an example method of assembling a concentrate adaptor consistent with implementations of the current subject matter.
Figure 87B:
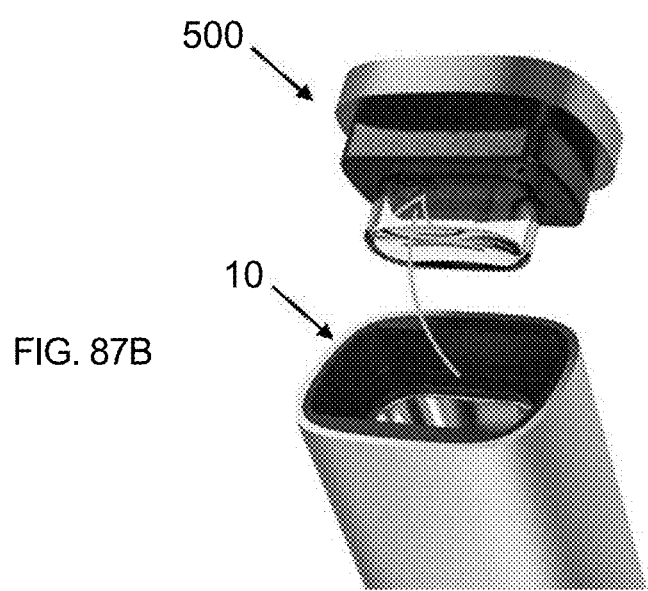
Figure 87C:
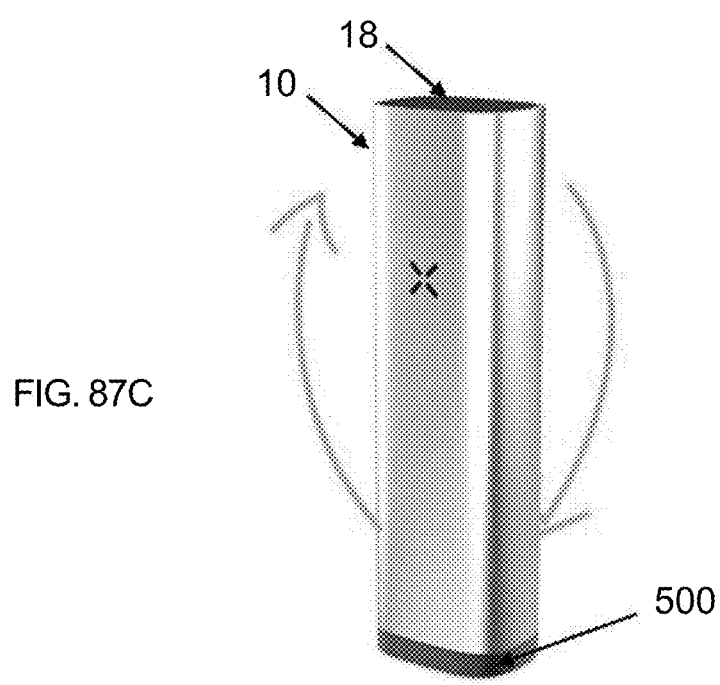

FIGS. 87A-87C illustrate a method of assembling the concentrate adaptor 500 and coupling the concentrate adaptor to the vaporizer device 10. For example, as shown in FIG. 87A, the reservoir 502 may receive a vaporizable material through the opening of the reservoir 502. The reservoir 502 and the base 114 may then be coupled. As shown in FIG. 87B, the concentrate adaptor 500 may be at least partially inserted into an open end of the vaporizer device 10. For example, the reservoir 502 may be inserted into the vessel of the vaporizer device 10. As shown in FIG. 87C, in use, the vaporizer device 10 may be flipped so that the user may take a puff via the mouthpiece 18 of the vaporizer device 10 and the concentrate adaptor 500 is coupled to the opposite end of the vaporizer device 10 away from the user.

FIGS. 88A-88B and 89A-89B illustrate an example of a case 200 that may be used with the concentrate adaptor 100 shown and described with respect to FIGS. 1-87C, consistent with implementations of the current subject matter. The case 200 may hold and secure the concentrate adaptor 100 when the concentrate adaptor 100 is not coupled with the vaporizer device 10 and/or is otherwise not in use. For example, the case 200 may include one or more magnets or magnetic material that magnetically secures the concentrate adaptor 100 within the case 200. In the example case shown in FIGS. 89A-89B, the case 200 may include one or more magnets 208 positioned on opposite sides of the case 200. The magnets 208 may magnetically secure the concentrate adaptor 100 within the case 200. In some implementations, the case 200 may include a material that is temperature resistant and/or chemical resistant. This allows the case 200 to be safely closed, and to secure the concentrate adaptor 100 while the concentrate adaptor 100 has a high temperature after use.

Figure 88A:
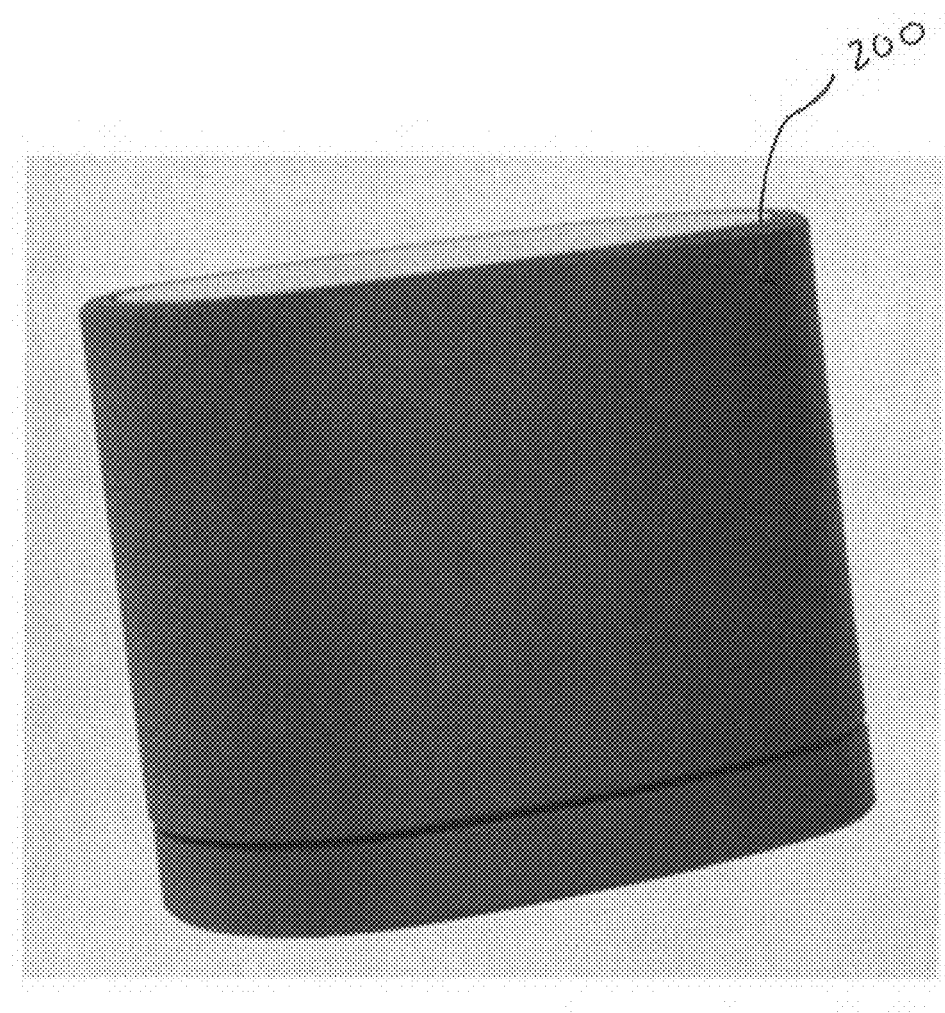
FIGS. 88A-88B illustrate an example case for a concentrate adaptor consistent with implementations of the current subject matter.
Figure 88B:
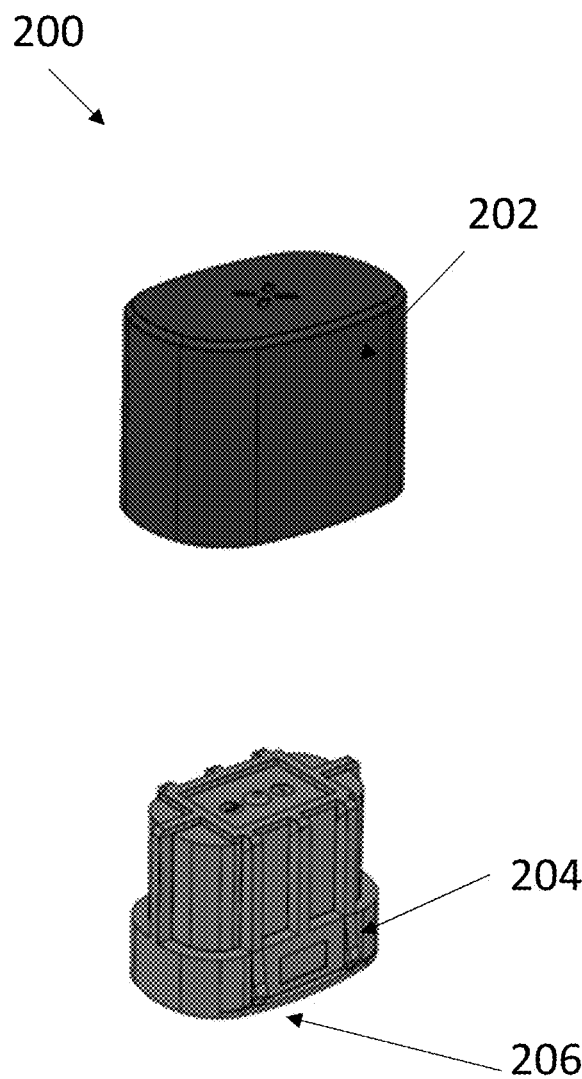
Figure 89A:
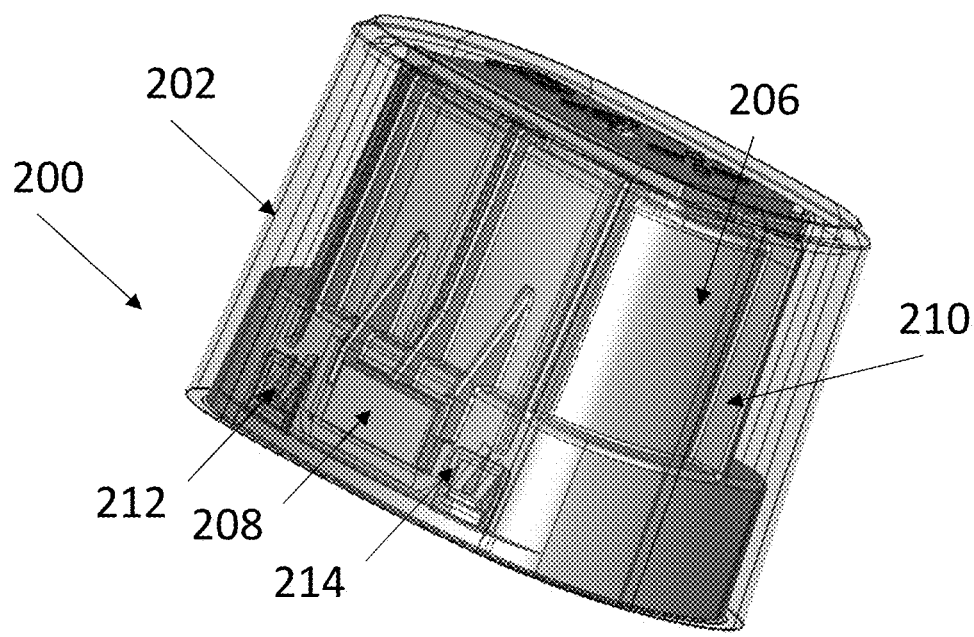
FIGS. 89A-89B illustrate an example case for a concentrate adaptor consistent with implementations of the current subject matter.
Figure 89B:
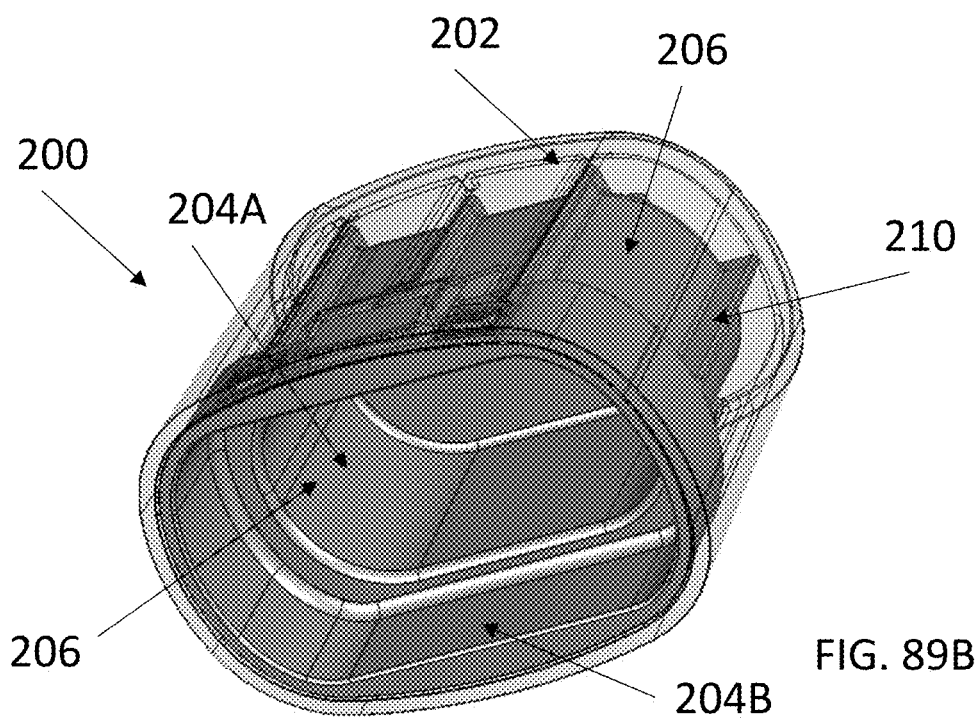

FIG. 88B illustrates an example exploded view of the case 200. FIGS. 89A-89B illustrate another example of the case 200, consistent with implementations of the current subject matter. The case 200 may include an outer shell 202 and an inner shell 204. The inner shell 204 may fit within and be secured to the outer shell 202, for example, via fasteners, a snap-fit arrangement, adhesive, and/or the like. For example, the inner shell 204 may include one or more protrusions 212 (e.g., two or more protrusions) positioned on opposing sides of the inner shell 204. The one or more protrusions 212 are configured to couple with and/or otherwise be secured to one or more corresponding recesses 214 on the interior of the outer shell 202.

The inner shell 204 may include an opening 206 through which the concentrate adaptor 100 is inserted into the case 200. In some implementations, the inner shell 204 includes a stepped portion along the interior of the inner shell 204. For example, the inner shell 204 may include an inner portion 204A and an outer portion 204B. The inner portion 204A may have a width that is narrower than a width of the outer portion 204B. This allows the reservoir 102 of the concentrate adaptor 100 to securely fit within the inner portion 204A and the base 114 of the concentrate adaptor 100 to securely fit within the outer portion 204B.

The multiple-component construction of the case 200 may help to improve the thermal resistivity of the case 200. This configuration may be especially useful when inserting the concentrate adaptor 100 into the case 200 to store the concentrate adaptor 100 when the concentrate adaptor 100 has a high temperature after use. For example, at least a portion of the concentrate adaptor 100, such as the reservoir 102 may be heated in use. The case 200 may be able to store the concentrate adaptor 100 and/or a component of the concentrate adaptor that is heated up to 260° F., 50° F. to 100° F., 100° F. to 150° F., 150° F. to 200° F., 200° F. to 250° F., 250° F. to 300° F., 300° F. to 400° F., 400° F. to 500° F., and/or the like. In some implementations, the inner shell 204 may include one or more struts 210 positioned along an exterior of the inner shell 204. The struts may extend along at least a portion of a height of the inner shell 204. For example, the struts 210 may extend along at least a portion of the inner shell 204 that is configured to secure the reservoir 102 of the concentrate adaptor 100. The struts 210 may provide additional rigidity to the case to help protect the concentrate adaptor 100 from impacts on the exterior of the case 200. In some implementations, the struts 210 help to space the inner shell 204 from the outer shell 202 to further improve thermal resistivity of the case 200 and allow the concentrate adaptor 100 to be positioned within the case 200 when the concentrate adaptor 100 is at a high temperature.

As noted above, the case 200 may include one or more magnets 208 positioned on opposite sides of the case 200. The magnets 208 may be secured within an interior of the case between the inner shell 204 and the outer shell 202. For example, the inner shell 204 may retain the magnets between the inner shell 204 and the outer shell 202.

In some implementations, the inner shell 204 and/or the outer shell 202 may be made of one or more materials such as acrylonitrile butadiene styrene, polypropyl sulfate ("PPS"), polyoxymethylene, polyketone, and/or other thermally resistant plastics, or other materials. In some implementations, the inner shell 204 may be made of acrylonitrile butadiene styrene and the outer shell 202 may be made of PPS. Such configurations may help to improve thermal resistance of the case 200. In some implementations, a size of the case may be the same or similar to the size of the concentrate adaptor 100 to desirably improve the portability and convenience of the case 200. For example, the case 200 may have a height and/or width of approximately 20 mm, 10 mm to 15 mm, 15 mm to 20 mm, 20 mm to 25 mm, and/or ranges therebetween.

Figure 90A:
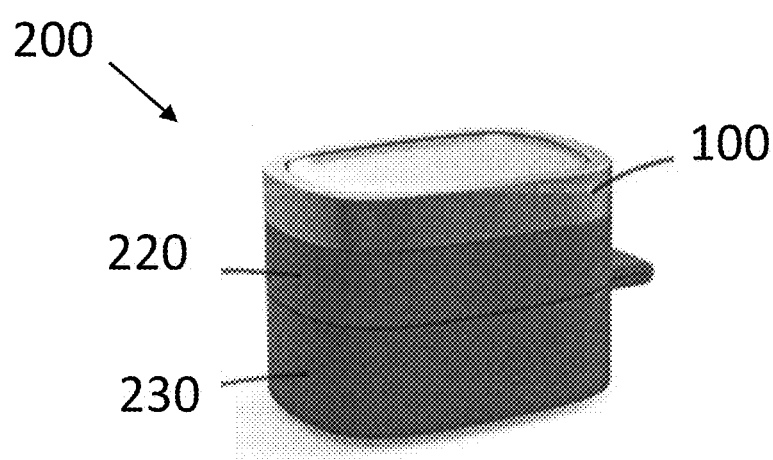
Figure 90B:
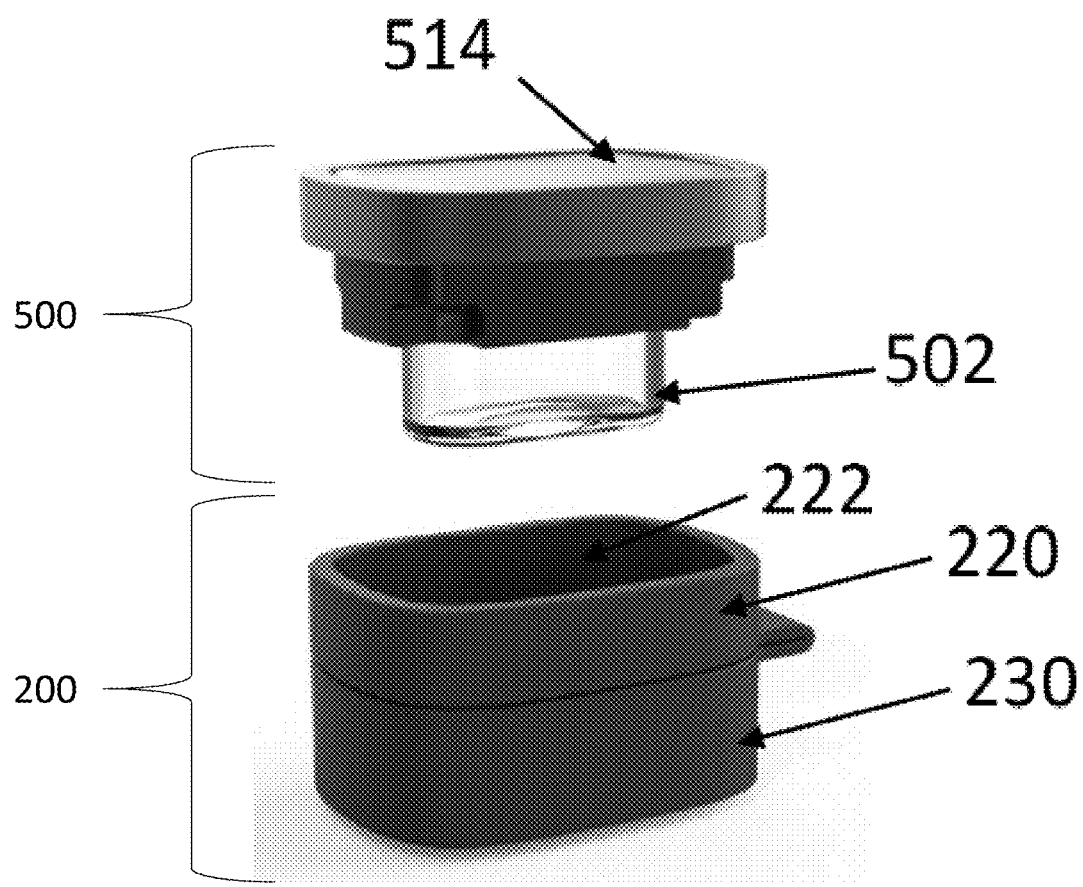
Figure 90C:
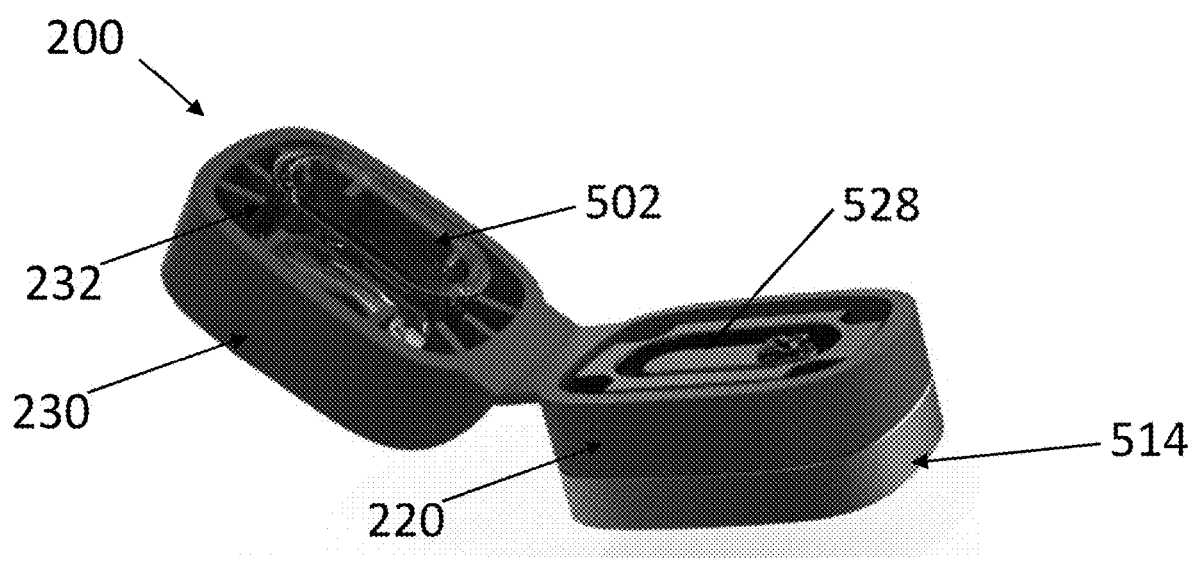
Figure 91:
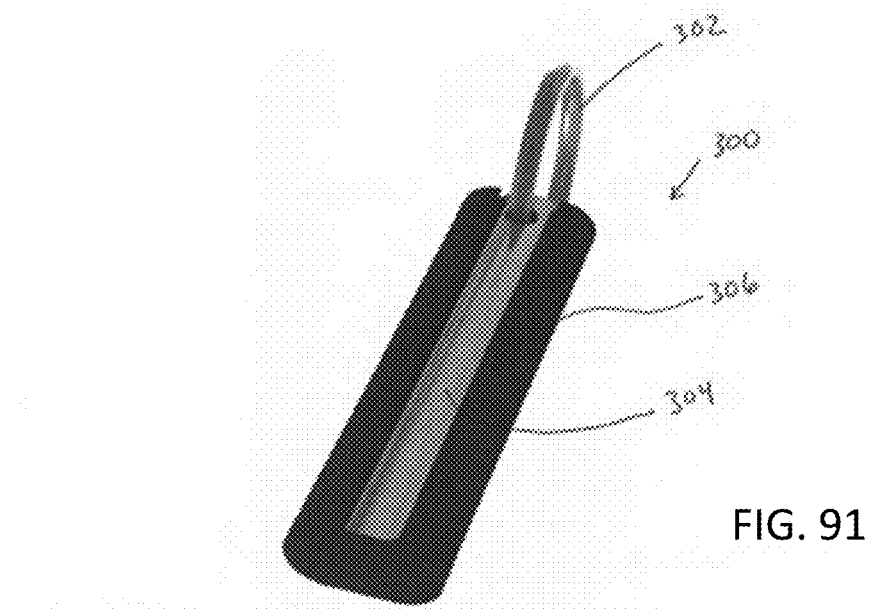
FIGS. 91-94B illustrate an example accessory tool for use with a concentrate adaptor consistent with implementations of the current subject matter.
Figure 92:
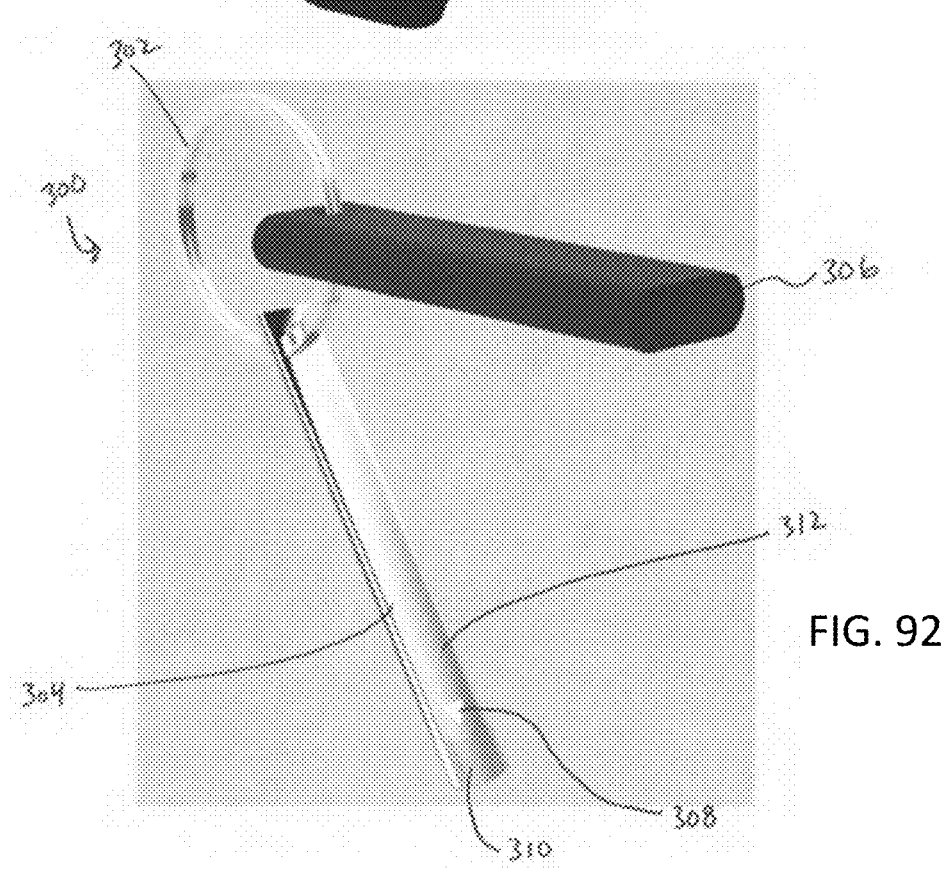
Figure 93A:
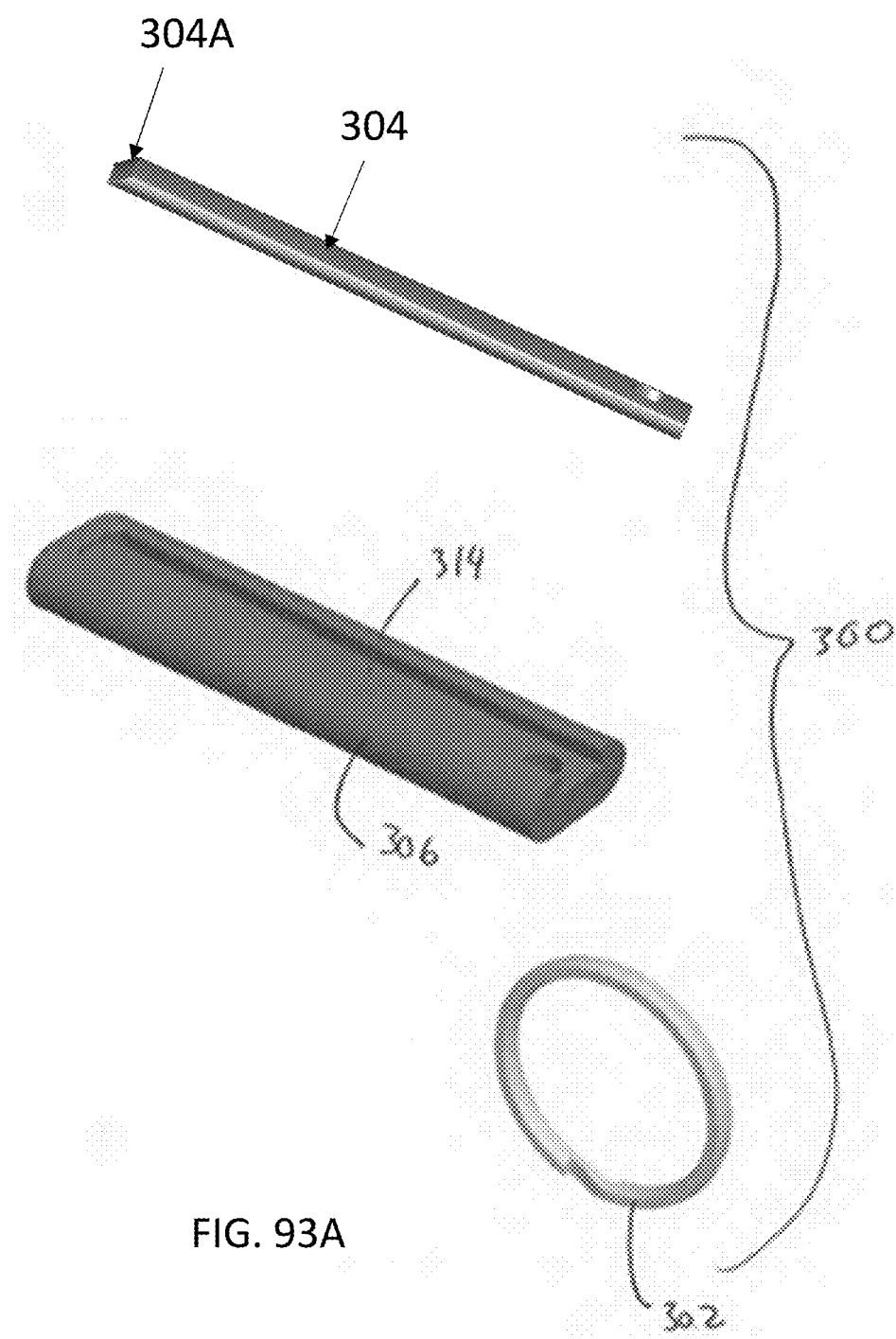
Figure 93B:
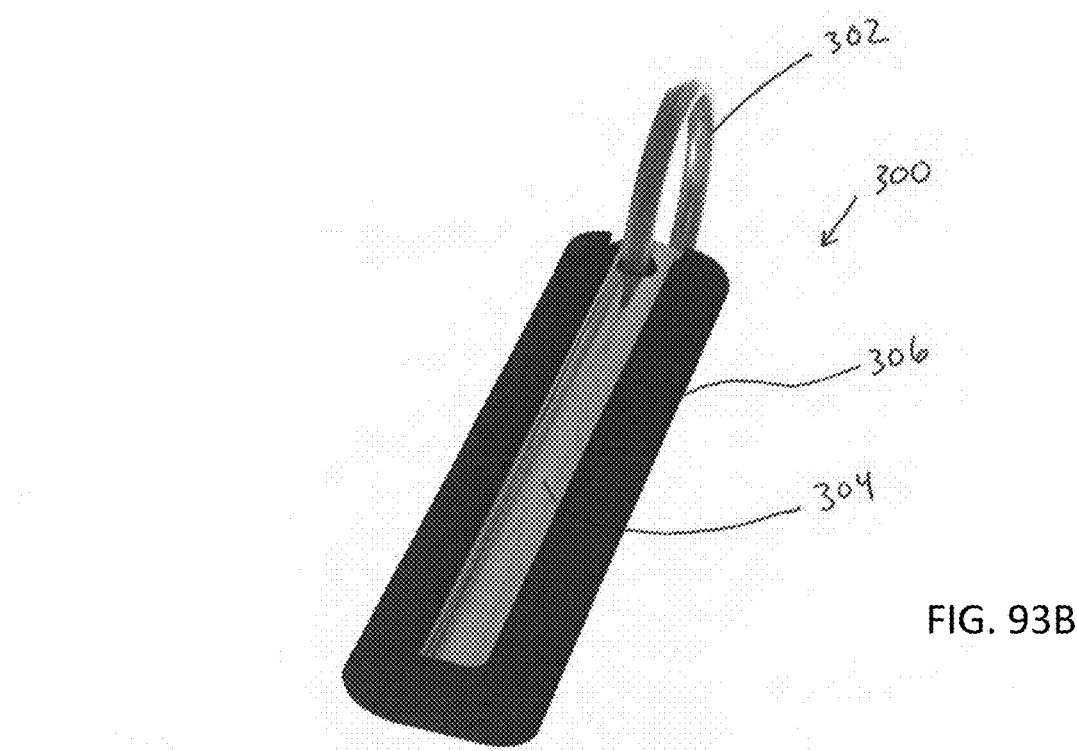
Figure 93C:
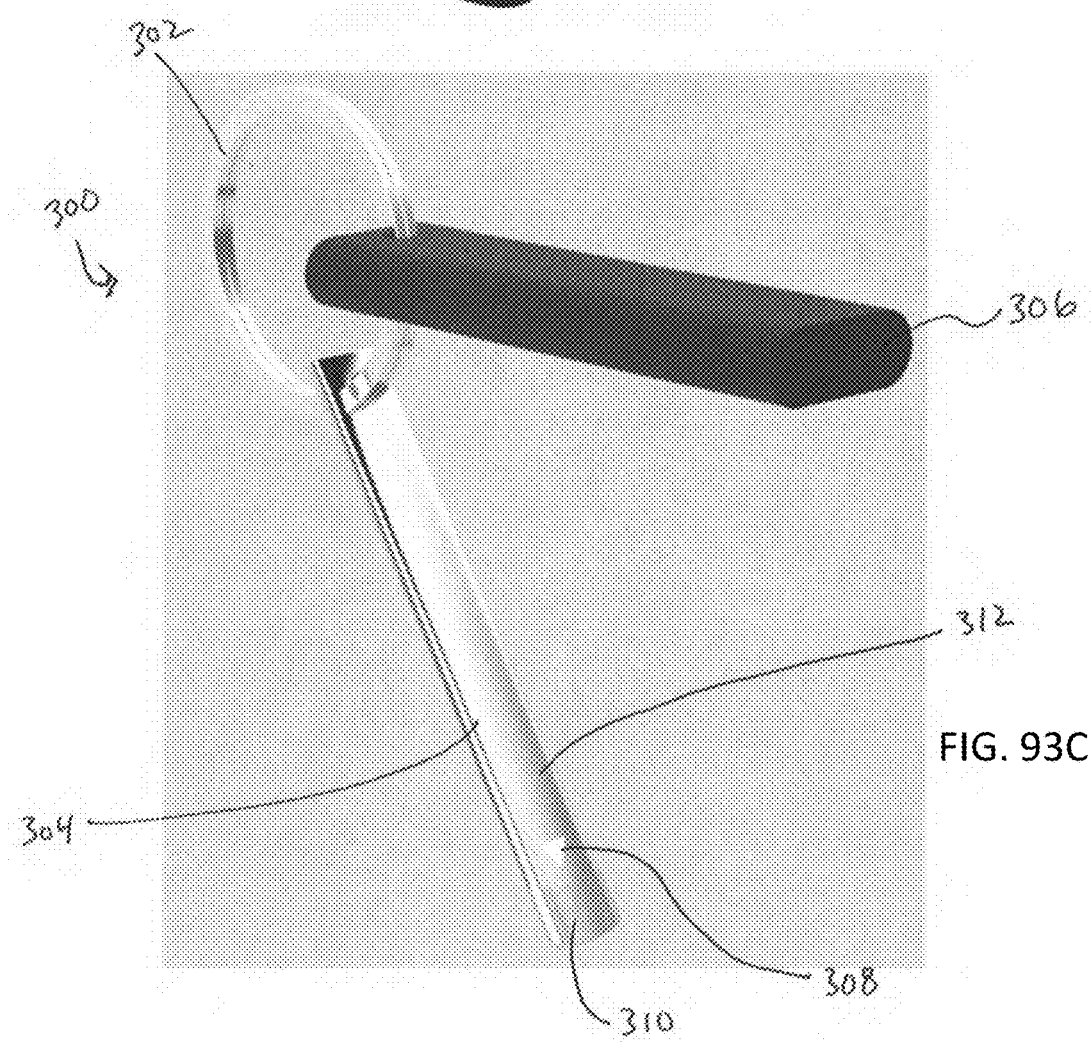
Figure 94A:
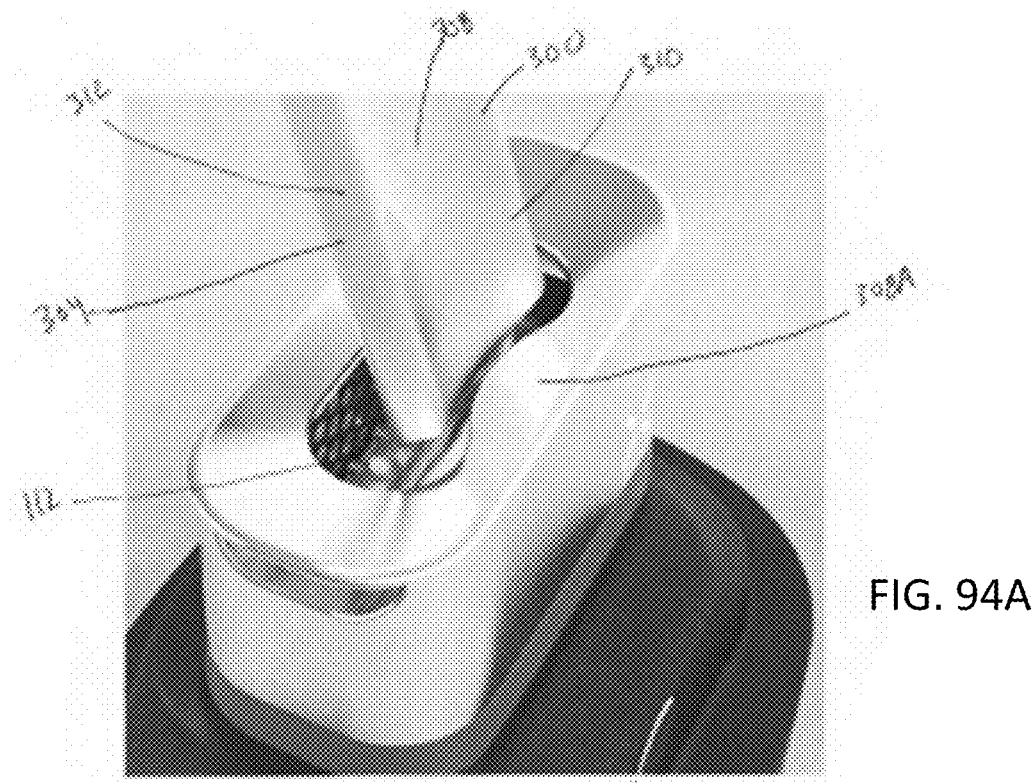
Figure 94B:
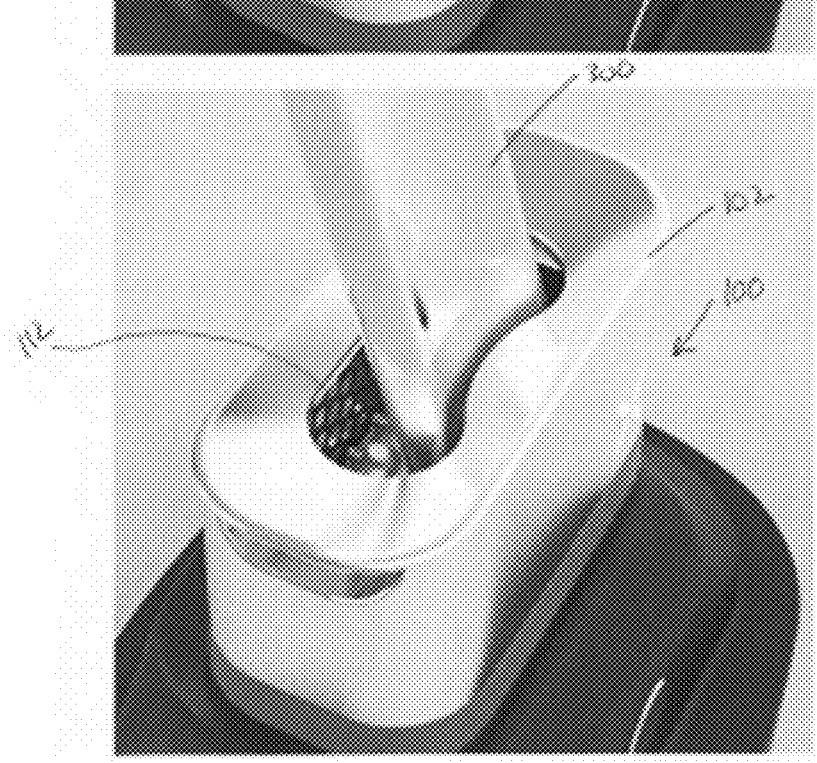

FIGS. 90A-90C illustrate another example of the case 200 consistent with implementations of the current subject matter. The case 200 shown in FIGS. 90A-90C may include a first component 220, such as a top component, and a second component 230, such as a bottom component. The first and second components 220, 230 may be coupled to one another via a hinge or other coupling mechanism. The hinge allows for the first component 220 and the second component 230 to be moved and/or rotated with respect to one another without decoupling the first component 220 from the second component 230 or vice versa. The first component 220 includes an opening 222. The opening 222 may be sized and/or shaped to receive the concentrate adaptor 100 described herein.

FIGS. 90A-90C illustrate the case 200 being used with the concentrate adaptor 500 shown in FIGS. 86A-87C. The second component 220 includes a connection component 232 configured to engage one or more sidewalls of the reservoir 502 of the concentrate adaptor 500. For example, the sidewalls of the reservoir 506 of the concentrate adaptor 500 engages with the connection component 232 when the concentrate adaptor 500 is placed within the opening 222 of the first component 220.

The connection component 232 may include one or more ribs or other structures configured to surround and engage the sidewalls of the reservoir 502, such as via a friction fit. When the case 200 is opened, such as via the hinge, the rotation of the first component 220 and/or the second component 230 with respect to one another may cause the reservoir 502 to disengage from the base 514 of the concentrate adaptor 500, resulting in the reservoir 502 being contained in the second component 230 of the case 200 and the base 514 being contained in the first component 220 (see FIG. 90C). The connection component 232 of the case 200 thus holds the reservoir 502 with a greater force than that of the mating structure 516 of the base 114. This causes the reservoir 502 to disconnect from the base 514 when the first component 220 and the second component 230 are rotated away from one another.

FIGS. 91-94B illustrate an example of an accessory tool 300 that may be used with the concentrate adaptor 100 shown and described with respect to FIGS. 1-87C, consistent with implementations of the current subject matter. The accessory tool 300 may assist with providing a vaporizable material, such as the concentrate, to the concentrate adaptor 100.

The accessory tool 300 includes an applicator 304, an applicator storage 306, and a connector such as a ring 302. The applicator 304 may be secured within a recess of the applicator storage 306 and may be coupled to the applicator storage 306 by the ring 302. The applicator 304 may help to guide a user when applying the vaporizable material to the interior of the reservoir 102 of the concentrate adaptor 100. In some implementations, the applicator 304 includes a beveled edge to help guide the vaporizable material into the concentrate adaptor 100. The applicator 304 may have a curved shape to help retain at least a portion of the vaporizable material so that the user may scoop the vaporizable material using the applicator 304. In some implementations, the curve has a circular or a U-shape (such as the shape shown in FIGS. 91-94B), to help the user more easily scoop vaporizable material using the applicator 304. In some implementations, the curve has a circular shape, oval shape, square shape, rectangular shape, trapezoidal shape, and/or the like. The curve of the applicator 304 may correspond to curve surrounding the opening 112 in the top portion of the reservoir 102. The corresponding curves of the applicator 304 and the opening 112 helps to guide the user to properly position at least an end portion of the applicator 304 within the concentrate adaptor 100. For example, the applicator 304 is in the proper position relative to the reservoir 102 when the curve of the applicator 304 aligns with the curve of the opening 112. In some implementations, the applicator 304 includes an applicator indicator 308 that matches a corresponding indicator 308A on the reservoir 102 (see FIG. 94A). In some implementations, a width of the applicator 304 may be approximately 7.0 mm, or 5.0 mm to 8.0 mm. The width of the applicator 304 may be desirably shaped and sized to scoop an optimal or particular amount of vaporizable material to be positioned by the applicator 304 into the interior of the reservoir 102. The width of the applicator 304 may also be sized to be easily gripped by the user in use. The width of the applicator 304 may be sized to be less than a width of the opening 112, so that at least a portion of the applicator 304 may slide into the opening 112 of the reservoir 102. Thus, in some implementations, the width of the applicator 304 may be less than approximately 12.0 mm to 14.0 mm, 10.0 mm to 12.0 mm, 8.0 mm to 10.0 mm, 6.0 mm to 8.0 mm, and/or other ranges therebetween.

In some implementations, the applicator 304 may help the user avoid overfilling the reservoir 102 of the concentrate adaptor 100. For example, the applicator 304 may include a proximal end portion 310 made of a material that is different from a material of a distal end portion 312 of the applicator 304. In some implementations, the proximal end portion 310 may have a different coating (e.g., polish) than the distal end portion 312 of the applicator 304. In some implementations, a length of the proximal end portion 310 provides a visual guide corresponding to a maximum amount, an optimal amount, and/or another amount of vaporizable material that may be positioned within the reservoir 102 of the concentrate adaptor 100. In some implementations, the applicator 304 enhances the user's experience using the concentrate adaptor 100, by for example, helping to limit overfilling the concentrate adaptor 100, providing an easier method to fill the concentrate adaptor 100 with vaporizable material, and/or providing an optimal amount of vaporizable material to the concentrate adaptor 100.

Figure 95:
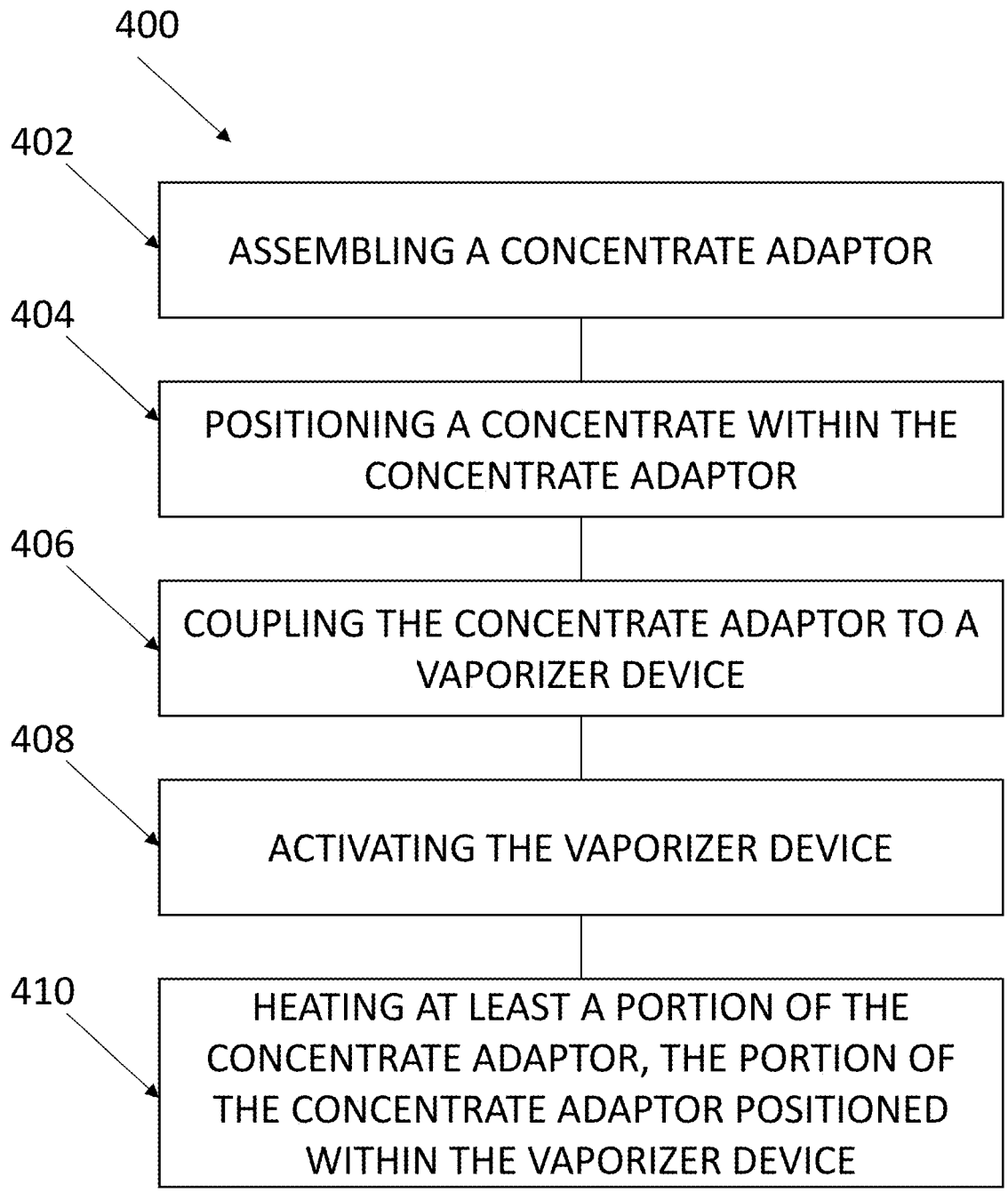
FIG. 95 illustrates an example method of vaporizing a concentrate held within a concentrate adaptor.

FIG. 95 illustrates an example process 400 for vaporizing a concentrate held within a concentrate adaptor, such as the concentrate adaptor 100 described herein. The concentrate adaptor may be coupled to a vaporizer device. The concentrate adaptor may include a capillary structure, such as the capillary structure 190 described herein.

At 402, the concentrate adaptor may be assembled. For example, assembling the concentrate adaptor may include coupling a reservoir (e.g., the reservoir 102) of the concentrate adaptor to a base (e.g., the base 114) of the concentrate adaptor. In some implementations, coupling the reservoir to the base may include inserting a portion of the reservoir into an opening in the base and turning the reservoir with respect to the base by 90 degrees. Turning the reservoir with respect to the base by 90 degrees may cause tactile feedback, such as via a retention feature, which indicates that the concentrate adaptor is properly assembled.

In some implementations, as described herein, the reservoir may include a first sidewall, a second side wall opposing the first sidewall, a third sidewall joining the first side wall to the second side wall, and a fourth sidewall opposing the third sidewall and joining the first sidewall to the second sidewall. The first sidewall and the second sidewall may be longer than the third sidewall and the fourth sidewall.

In some implementations, the reservoir also includes a connection feature and the base includes a base opening that is configured to receive the connection feature. In some implementations, the concentrate adaptor may be assembled by turning the reservoir relative to the base when the connection feature is positioned within the base opening is configured to secure the reservoir to the base. Turning the reservoir may include moving the reservoir from a first position to a second position. For example, in the first position, the first sidewall and the second sidewall of the reservoir may be positioned approximately perpendicular to long sides of the base and the connection feature may be positioned perpendicular to the first sidewall and the second sidewall. Additionally and/or alternatively, in the second position, the first sidewall and the second sidewall of the reservoir may be positioned parallel to the long sides of the base and the connection feature may be positioned perpendicular to the long sides of the base.

At 406, the concentrate adaptor may be coupled to the vaporizer device. For example, at least a portion of the concentrate adaptor may be inserted into and/or secured to an opening within an end of the vaporizer device. In some implementations, the concentrate adaptor is magnetically coupled to the vaporizer device.

At 408, the vaporizer device may be activated. For example, the vaporizer device may detect a user inhaling on a mouthpiece of the vaporizer device. In some implementations, power may otherwise be supplied to the vaporizer device.

At 410, at least a portion of the concentrate adaptor may be heated. For example, the vaporizer device may include a heating element that heats the concentrate adaptor. In some implementations, the portion of the concentrate adaptor may be positioned within the vaporizer device, such as the reservoir of the concentrate adaptor. The portion of the concentrate adaptor positioned within the vaporizer device may include a capillary structure. The capillary structure, as described herein, may include one or more capillary channels. The capillary structure may cause at least a portion of the concentrate to flow towards a sidewall of the concentrate adaptor to be vaporized more efficiently, and to help prevent leakage of the concentrate from the concentrate adaptor.

Although the disclosure, including the figures, described herein may described and/or exemplify these different variations separately, it should be understood that all or some, or components of them, may be combined.

In various implementations, the vaporizer device may be configured for use with liquid vaporizable material (e.g., a carrier solution in which an active and/or inactive ingredient(s) are suspended or held in solution or a liquid form of the vaporizable material itself) or solid vaporizable material. Solid vaporizable material may include a plant material that emits some part of the plant material as the vaporizable material (e.g., such that some part of the plant material remains as waste after the vaporizable material is emitted for inhalation by a user) or optionally may be a solid form of the vaporizable material itself such that all of the solid material may eventually be vaporized for inhalation. Liquid vaporizable material may likewise be capable of being completely vaporized or may include some part of the liquid material that remains after all of the material suitable for inhalation has been consumed.

Additionally and/or alternatively, the vaporizable material may include liquid and/or oil-type plant-based smokeable materials such as cannabis, a semi-solid like a wax, solid/liquid (e.g., suspensions, liquid-coated) materials, and/or a solid material, such as plant material including loose-leaf materials, leaves or flowers, either raw or processed. The vaporizable material may additionally and/or alternatively include concentrates (e.g., cannabis concentrates including wax, shatter, budder, butane hash oil, and the like).

In some examples, the vaporizable material may include a viscous liquid such as, for example a cannabis oil. In some variations, the cannabis oil comprises between 0.3% and 100% cannabis oil extract. The viscous oil may include a carrier for improving vapor formation, such as, for example, propylene glycol, glycerol, medium chain triglycerides (MCT) including lauric acid, capric acid, caprylic acid, caproic acid, etc., at between 0.01% and 25% (e.g., between 0.1% and 22%, between 1% and 20%, between 1% and 15%, and/or the like). In some variations the vapor-forming carrier is 1,3-Propanediol. A cannabis oil may include a cannabinoid or cannabinoids (natural and/or synthetic), and/or a terpene or terpenes derived from organic materials such as for example fruits and flowers. For example, any of the vaporizable materials described herein may include one or more (e.g., a mixture of) cannabinoid including one or more of: CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), CBGM (Cannabigerol Monomethyl Ether), Tetrahydrocannabinol, Cannabidiol (CBD), Cannabinol (CBN), Tetrahydrocannabinolic Acid (THCA), Cannabidioloc Acid (CBDA), Tetrahydrocannabivarinic Acid (THCVA), one or more Endocannabinoids (e.g., anandamide, 2-Arachidonoylglycerol, 2-Arachidonyl glyceryl ether, N-Arachidonoyl dopamine, Virodhamine, Lysophosphatidylinositol), and/or a synthetic cannabinoids such as, for example, one or more of: JWH-018, JWH-073, CP-55940, Dimethylheptylpyran, HU-210, HU-331, SR144528, WIN 55,212-2, JWH-133, Levonantradol (Nantrodolum), and AM-2201. The oil vaporization material may include one or more terpene, such as, for example, Hemiterpenes, Monoterpenes (e.g., geraniol, terpineol, limonene, myrcene, linalool, pinene, Iridoids), Sesquiterpenes (e.g., humulene, farnesenes, farnesol), Diterpenes (e.g., cafestol, kahweol, cembrene and taxadiene), Sesterterpenes, (e.g., geranylfarnesol), Triterpenes (e.g., squalene), Sesquarterpenes (e.g, ferrugicadiol and tetraprenylcurcumene), Tetraterpenes (lycopene, gamma-carotene, alpha- and beta-carotenes), Polyterpenes, and Norisoprenoids. For example, an oil vaporization material as described herein may include between 0.3-100% cannabinoids (e.g., 0.5-98%, 10-95%, 20-92%, 30-90%, 40-80%, 50-75%, 60-80%, etc.), 0-40% terpenes (e.g., 1-30%, 10-30%, 10-20%, etc.), and 0-25% carrier (e.g., medium chain triglycerides (MCT)).

In any of the oil vaporizable materials described herein (including in particular, the cannabinoid-based vaporizable materials), the viscosity may be within a predetermined range. The range may be between, at room temperature (23° C.) about 30 cP (centipoise) and 115 kcP (kilocentipoise), between 30 cP and 200 kcP, although higher viscosities and/or lower viscosities may be implemented as well. For example, the viscosity may be between 40 cP and 113 kcP at room temperature. Outside of this range, the vaporizable material may fail in some instances to wick appropriately to form a vapor as described herein. In particular, it is typically desired that the oil may be made sufficiently thin to both permit wicking at a rate that is useful with the apparatuses described herein, while also limiting leaking (e.g., viscosities below that of ~40 cP at room temperature might result in problems with leaking).

Although various illustrative embodiments are described above, any of a number of changes may be made to various embodiments. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. References to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as, for example, "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, are possible.

In the descriptions above and in the claims, phrases such as, for example, "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An insert for a vaporizer device, the insert comprising:
a reservoir comprising an interior volume configured to hold a vaporizable material, the reservoir configured to be positioned within a vessel of the vaporizer device and be heated by clement of the vaporizer device to transfer heat to the vaporizable material, thereby generating an aerosol for inhalation by a user, the reservoir comprising:
a sidewall surrounding the interior volume of the reservoir, the sidewall configured to be heated by the vaporizer device to transfer the heat to the vaporizable material; and
a capillary structure positioned along at least a portion of the sidewall and surrounding the interior volume, the capillary structure configured to direct the vaporizable material to the sidewall to be heated,.
wherein an airflow path extends into a reservoir opening in the reservoir, and wherein the airflow path is in fluid communication with a mouthpiece of the vaporizer device for delivery of the aerosol through the mouthpiece.

2. The insert of claim 1, further comprising a base coupled with the reservoir, wherein at least a portion of the base is positioned external to the vaporizer device when the reservoir is positioned within the vessel.

3. The insert of claim 1, wherein the capillary structure includes one or more channels formed across at least a portion of an interior of the sidewall.

4. The insert of claim 3, wherein the one or more channels extend in a first direction and a second direction that is perpendicular to the first direction.

5. The insert of claim 3, wherein the capillary structure further comprises one or more channels formed along a base wall of the reservoir.

6. The insert of claim 3, wherein at least one channel extends from a bottom of the interior of the sidewall to a top of the interior of the sidewall.

7. The insert of claim 3, wherein the one or more channels are formed as recesses between adjacent elongated bars and/or cylinders.

8. The insert of claim 1, wherein the capillary structure includes one or more openings.

9. The insert of claim 1, wherein the sidewall comprises:
a first sidewall;
a second sidewall opposing the first sidewall;
a third sidewall joining the first sidewall to the second sidewall; and
a fourth sidewall opposing the third sidewall and joining the first sidewall to the second sidewall,
wherein the first sidewall and the second sidewall are longer than the third sidewall and the fourth sidewall.

10. The insert of claim 9, further comprising a base coupled with the reservoir, wherein the reservoir further comprises a connection feature, wherein the base comprises a base opening configured to receive the connection feature, and wherein turning the reservoir relative to the base when the connection feature is positioned within the base opening is configured to secure the reservoir to the base.

11. The insert of claim 10, wherein the reservoir is secured to the base when the reservoir is moved from a first position to a second position, wherein in the first position, the first sidewall and the second sidewall of the reservoir are positioned approximately perpendicular to long sides of the base and the connection feature is positioned approximately perpendicular to the first sidewall and the second sidewall, and wherein in the second position, the first sidewall and the second sidewall of the reservoir are positioned approximately parallel to the long sides of the base and the connection feature is positioned approximately perpendicular to the long sides of the base.

12. The insert of claim 1, further comprising a base coupled with the reservoir, wherein the base comprises:
a base floor comprising an outer base surface exposed external to the vaporizer device when the reservoir is positioned within the vessel; and
a base housing configured to surround at least a portion of the base floor.

13. The insert of claim 12, wherein the base floor comprises a base floor connector, wherein the base housing comprises a slot, and wherein the base floor connector is configured to be positioned within the slot to secure the base housing to the base floor.

14. The insert of claim 13, wherein the base housing comprises an outer housing surface, and wherein the outer base surface is spaced apart from the outer housing surface to define an inlet for the airflow path, the inlet configured to allow air to flow into the base.

15. The insert of claim 1, further comprising a base coupled with the reservoir, wherein the airflow path extends between the base and the reservoir, wherein the airflow path is positioned between an inlet of the base and an outlet of the reservoir.

16. The insert of claim 1, further comprising a base coupled with the reservoir, wherein the airflow path extends between the base and the reservoir, wherein the airflow path extends through an external opening into the base, out of the base, and into a reservoir opening in the reservoir.

17. The insert of claim 1, further comprising a base coupled with the reservoir and a retention member, the retention member configured to provide tactile feedback to a user when the reservoir is coupled to the base, the retention member configured to provide a force that pulls the reservoir towards the base to form a seal between the reservoir and the base.

18. The insert of claim 1, wherein the reservoir comprises a reservoir top and a reservoir base, wherein a first portion of the capillary structure is positioned on the reservoir base, and wherein a second portion of the capillary structure is positioned on the reservoir top.

19. The insert of claim 1, further comprising one or more exterior channels formed along an exterior surface of the reservoir, the one or more exterior channels configured to capture vaporizable material remaining on the exterior surface of the reservoir.

20. A vaporizer device comprising:
a housing comprising a vessel;
a mouthpiece; and
an insert comprising:
    a reservoir comprising an interior volume configured to hold a vaporizable material, the reservoir configured to be positioned within the vessel and be heated by to transfer heat to the vaporizable material, thereby generating an aerosol for inhalation by a user, the reservoir comprising:
        a sidewall surrounding the interior volume of the reservoir, the sidewall configured to be heated by the vaporizer device to transfer the heat to the vaporizable material; and
        a capillary structure positioned along at least a portion of the sidewall and surrounding the internal volume, the capillary structure configured to direct the vaporizable material to the sidewall to be heated,
wherein an airflow path extends into a reservoir opening in the reservoir, and wherein the airflow path is in fluid communication with the mouthpiece for delivery of the aerosol through the mouthpiece.

\* \* \* \* \*

UNITED STATES PATENT AND TRADEMARK OFFICE
CERTIFICATE OF CORRECTION

| | |
|---|---|
| PATENT NO. | : 11,801,351 B2 |
| APPLICATION NO. | : 16/932548 |
| DATED | : October 31, 2023 |
| INVENTOR(S) | : Franklyn Bucknor, Jr. et al. |

It is certified that error appears in the above-identified patent and that said Letters Patent is hereby corrected as shown below:

In the Claims

Column 55, Claim 1, Line 47, delete "clement of".

Column 55, Claim 1, Line 58, delete "heated,." and insert -- heated, --.

Signed and Sealed this
Sixteenth Day of July, 2024

Katherine Kelly Vidal
*Director of the United States Patent and Trademark Office*